(12) United States Patent
Park

(10) Patent No.: US 12,023,133 B2
(45) Date of Patent: Jul. 2, 2024

(54) METHOD OF MEASURING PHYSIOLOGICAL PARAMETER OF SUBJECT IN CONTACTLESS MANNER

(71) Applicant: GB SOFT CO., LTD., Daegu (KR)

(72) Inventor: Ki Bum Park, Daegu (KR)

(73) Assignee: GB SOFT CO., LTD., Daegu (KR)

( * ) Notice: Subject to any disclaimer, the term of this patent is extended or adjusted under 35 U.S.C. 154(b) by 0 days.

(21) Appl. No.: 17/102,082

(22) Filed: Nov. 23, 2020

(65) Prior Publication Data

US 2021/0153752 A1    May 27, 2021

Related U.S. Application Data

(60) Provisional application No. 62/938,744, filed on Nov. 21, 2019.

(30) Foreign Application Priority Data

| Mar. 10, 2020 | (KR) | 10-2020-0029856 |
| Mar. 10, 2020 | (KR) | 10-2020-0029857 |
| Mar. 10, 2020 | (KR) | 10-2020-0029858 |

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0077* (2013.01); *A61B 5/02055* (2013.01);
(Continued)

(58) Field of Classification Search
CPC ................ A61B 5/0077; A61B 5/6898; G06T 2207/10024; G06T 2207/10016; G06K 9/00114; G06K 9/00234
See application file for complete search history.

(56) References Cited

U.S. PATENT DOCUMENTS

| 9,750,420 B1 | 9/2017 | Agrawal et al. |
| 10,383,532 B2 | 8/2019 | Kitajima et al. |

(Continued)

FOREIGN PATENT DOCUMENTS

| CN | 105147274 A | 12/2015 |
| JP | 2014168541 A | 9/2014 |

(Continued)

OTHER PUBLICATIONS

H. Ghanadian, M. Ghodratigohar and H. Al Osman, "A Machine Learning Method to Improve Non-Contact Heart Rate Monitoring Using an RGB Camera," in IEEE Access, vol. 6, pp. 57085-57094, 2018 (Year: 2018).*

(Continued)

*Primary Examiner* — Tse W Chen
*Assistant Examiner* — Michael A Catina
(74) *Attorney, Agent, or Firm* — WTA Patents

(57) ABSTRACT

Disclosed is a method of measuring a physiological parameter in a contactless manner. The method includes acquiring a plurality of image frames for a subject, acquiring a first color channel value, a second color channel value, and a third color channel value for at least one image frame included in the plurality of image frames. The method further includes calculating a first difference and a second difference on the basis of the first color channel value, the second color channel value, and the third color channel value for at least one image frame included in the plurality of image frames. The first difference represents a difference between the first color channel value and the second color channel value for the same image frame, and the second difference represents a difference between the first color channel value and the third color channel value for the same image frame.

12 Claims, 90 Drawing Sheets

(51) Int. Cl.
    *A61B 5/103*     (2006.01)
    *A61B 5/1455*     (2006.01)
    *A61B 5/16*     (2006.01)
    *G06N 20/00*     (2019.01)
    *G06T 7/00*     (2017.01)
    *G16H 30/40*     (2018.01)
    *G16H 50/30*     (2018.01)
    *A61B 5/021*     (2006.01)
    *A61B 5/024*     (2006.01)

(52) U.S. Cl.
    CPC ........ *A61B 5/1032* (2013.01); *A61B 5/14552* (2013.01); *A61B 5/165* (2013.01); *A61B 5/7246* (2013.01); *A61B 5/7267* (2013.01); *G06N 20/00* (2019.01); *G06T 7/0012* (2013.01); *G16H 30/40* (2018.01); *G16H 50/30* (2018.01); *A61B 5/02125* (2013.01); *A61B 5/02427* (2013.01); *A61B 5/7425* (2013.01); *A61B 2576/00* (2013.01); *G06T 2207/10016* (2013.01); *G06T 2207/10024* (2013.01); *G06T 2207/20081* (2013.01); *G06T 2207/20084* (2013.01); *G06T 2207/30048* (2013.01); *G06T 2207/30076* (2013.01); *G06T 2207/30201* (2013.01)

(56) References Cited

U.S. PATENT DOCUMENTS

| | | | |
|---|---|---|---|
| 10,624,586 | B2 | 4/2020 | Noguchi et al. |
| 2006/0062548 | A1 | 3/2006 | Low |
| 2010/0234747 | A1 | 9/2010 | Hatakeyama |
| 2014/0180132 | A1 | 6/2014 | Shan et al. |
| 2014/0192177 | A1* | 7/2014 | Bartula ................. G06T 7/0012 348/77 |
| 2014/0206965 | A1 | 7/2014 | De Haan et al. |
| 2014/0221781 | A1 | 8/2014 | Schrauf et al. |
| 2014/0303454 | A1 | 10/2014 | Clifton et al. |
| 2014/0378779 | A1 | 12/2014 | Freeman et al. |
| 2015/0148687 | A1 | 5/2015 | Kitajima et al. |
| 2015/0366456 | A1 | 12/2015 | Takamori et al. |
| 2015/0379370 | A1 | 12/2015 | Clifton et al. |
| 2016/0000343 | A1 | 1/2016 | Matsui et al. |
| 2016/0343135 | A1* | 11/2016 | De Haan ............... G06K 9/4652 |
| 2017/0065230 | A1* | 3/2017 | Sinha .................... G16H 50/20 |
| 2017/0238805 | A1 | 8/2017 | Addison et al. |
| 2018/0089856 | A1 | 3/2018 | Sato |
| 2019/0380807 | A1 | 12/2019 | Addison et al. |
| 2021/0121084 | A1 | 4/2021 | Hong et al. |

FOREIGN PATENT DOCUMENTS

| | | |
|---|---|---|
| JP | 2016187430 A | 11/2016 |
| KR | 20100023021 A | 3/2010 |
| KR | 20160016263 A | 2/2016 |
| KR | 20160065702 A | 6/2016 |
| KR | 20170056232 A | 5/2017 |

OTHER PUBLICATIONS

International Search Report of PCT Application No. PCT/KR2020/006144, Sep. 4, 2020.
Written Opinion of PCT Application No. PCT/KR2020/006144, Sep. 4, 2020.
Screen shot of YouTube Video "rPPG: Lab test with baseline measurements", Source: https://www.youtube.com/watch?v=4RKor-O5bQ8, Sep. 18, 2016.
Office Action of Korean Patent Application No. 10-2020-0029859, Jun. 20, 2021.
Office Action of Korean Patent Application No. 10-2020-0029858, Sep. 13, 2021.
Notice of Allowance of U.S. Appl. No. 17/102,090, Mar. 19, 2021.
Second Notice of Allowance of U.S. Appl. No. 17/102,090, Jul. 13, 2021.

* cited by examiner

FIG. 5
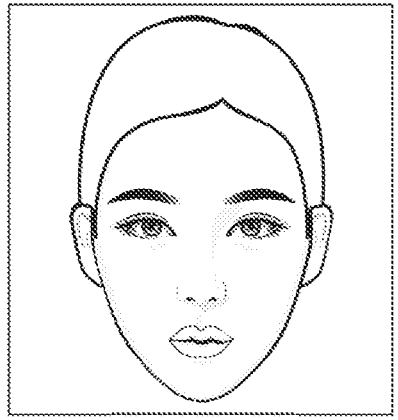
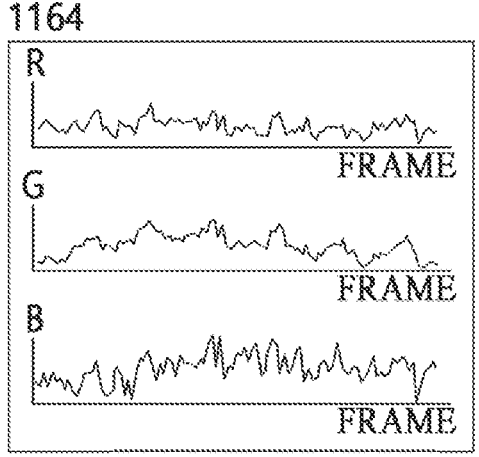
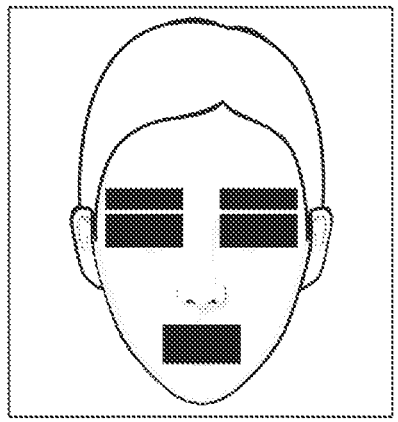
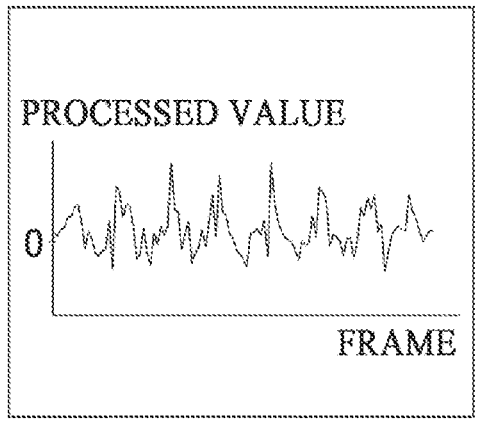
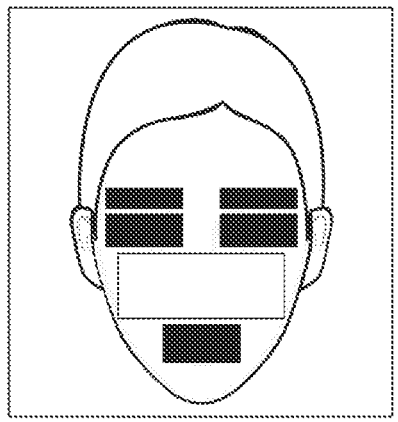

FIG. 19
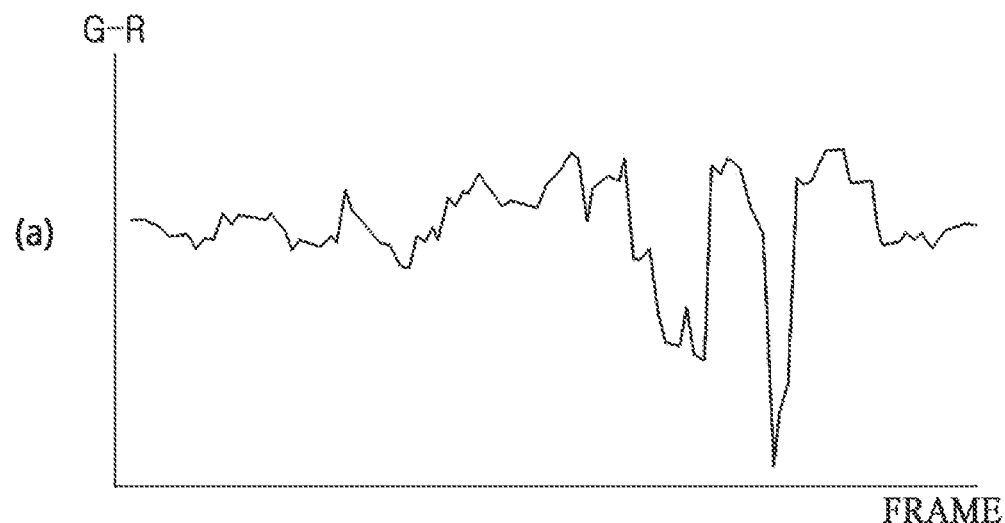
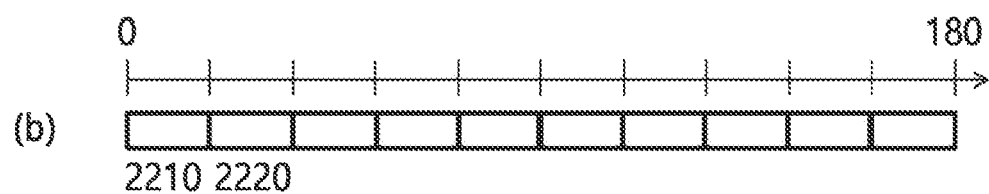
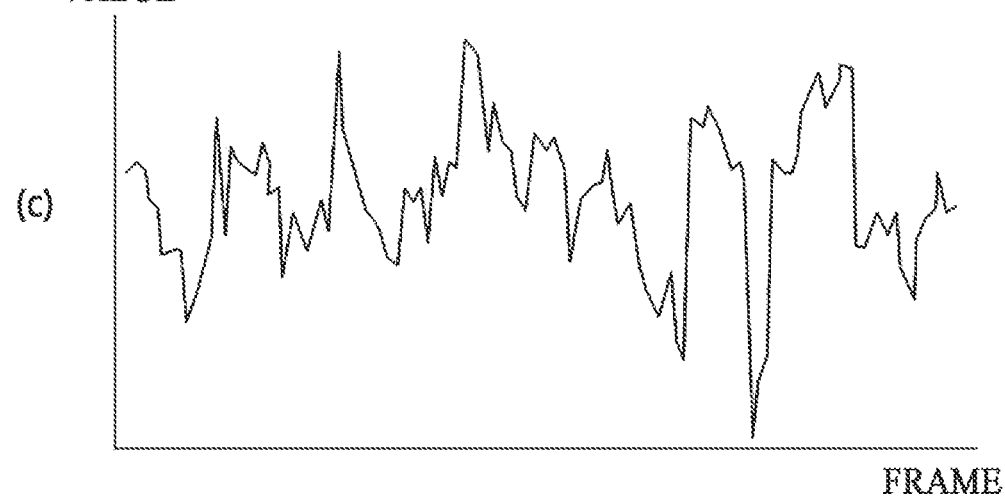

FIG. 76
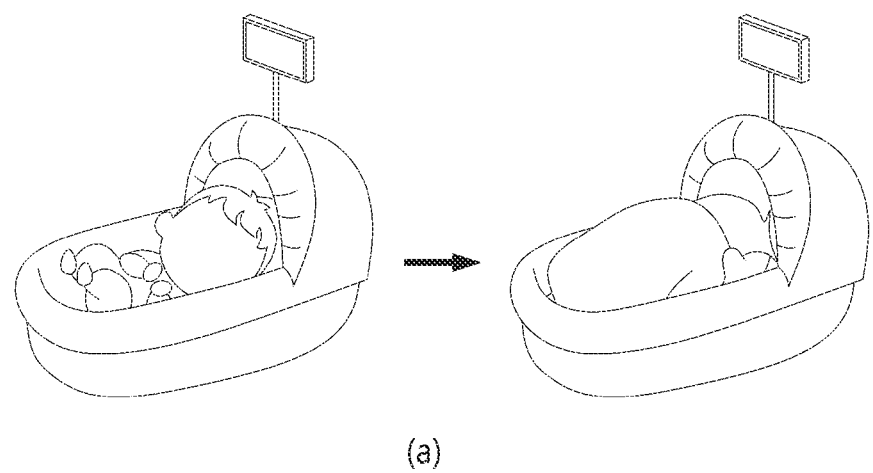
(a)
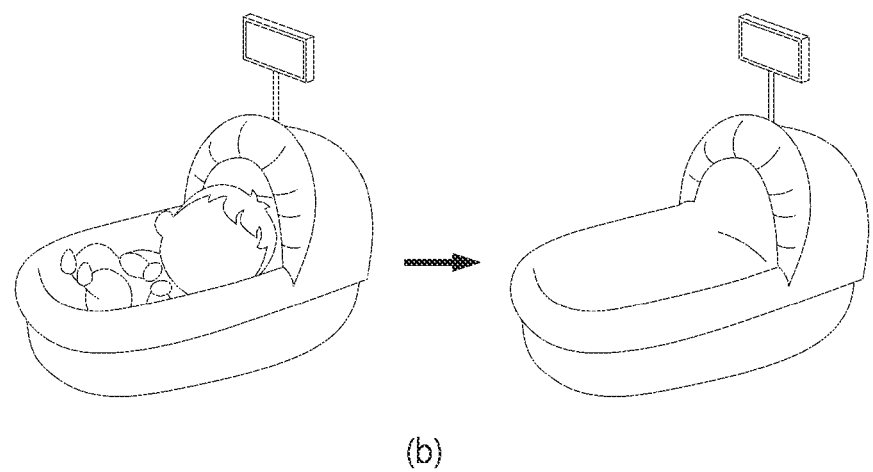
(b)

METHOD OF MEASURING PHYSIOLOGICAL PARAMETER OF SUBJECT IN CONTACTLESS MANNER

CROSS-REFERENCE TO RELATED APPLICATION

This application claims priority to and the benefit of U.S. Patent Application No. 62/938,744, filed on Nov. 21, 2019, Korean Patent Application No. 2020-0029856, filed on Mar. 10, 2020, Korean Patent Application No. 2020-0029857, filed on Mar. 10, 2020, Korean Patent Application No. 2020-0029858, filed on Mar. 10, 2020 and Korean Patent Application No. 2020-0029859, filed on Mar. 10, 2020 the disclosure of which is incorporated herein by reference in its entirety.

BACKGROUND

1. Field of the Invention

Plethysmography is a technique for measuring and analyzing natural changes in shape or form when the volume of human tissues such as human organs or blood vessels changes according to the flow of blood vessels.

2. Discussion of Related Art

The most common technique for measuring photoplethysmography (PPG) using light uses a method of analyzing the amount of transmitted light with respect to the amount of light emitted to a human body, and this is explained by the Beer-Lambert law in which light absorbance is proportional to the concentration of absorbing material and the thickness of an absorbing layer. According to this law, the change in transmitted light results in a signal proportional to the change in the volume of light-transmitting material, and thus it is possible to check a state of a human heart by using PPG even when the absorbance of the material is not known.

Recently, a technique using remote photoplethysmography (rPPG), which is one step evolved from the technique using PPG, has emerged. As the most popular technique to check a signal related to a heartbeat using PPG; there is a technique for acquiring PPG by bringing a device having a camera and a light that are close to each other and attached thereto, such as a smartphone, into direct contact with a human body, emitting light, and measuring transmitted light. Recently, a technology related to remote photoplethysmography (rPPG) to check a change in the volume of a blood vessel in a signal acquired from an image captured by a camera is continuously being researched and developed.

The technique using rPPG can be variously applied to devices and places equipped with cameras, such as airport immigration offices and remote medical treatments, in that no contact between a subject and a measurement instrument is required.

However, in the technique related to rPPG noise that is caused by ambient light and subject movement while a subject is captured with a camera has a large effect on a signal, and thus a technique for extracting only a signal related to the change in volume of a subject to be measured from the captured image can be regarded as a core technique for a technique for measuring a physiological signal using rPPG.

SUMMARY OF THE INVENTION

A problem to be solved according to an embodiment is to acquire a physiological parameter in a contactless manner.

A problem to be solved according to another embodiment is to reduce noise caused by subject movement in order to acquire a physiological parameter.

A problem to be solved according to still another embodiment is to reduce noise caused by a change in intensity of external light in order to acquire a physiological parameter.

A problem to be solved according to still another embodiment is to acquire various physiological parameters at the same time.

A problem to be solved according to still another embodiment is to acquire physiological information based on various physiological parameters.

A problem to be solved according to still another embodiment is to acquire various physiological parameters in association with each other at the same time.

A problem to be solved according to still another embodiment is to detect drowsiness on the basis of an LF/HF ratio of a heartbeat signal and a heart rate of a subject.

A problem to be solved according to still another embodiment is related to a smart mirror device for acquiring at least two associated physiological parameters.

A problem to be solved according to still another embodiment is related to a smart mirror device operating method to acquire at least two associated physiological parameters.

A problem to be solved according to still another embodiment is related to a smart mirror device including a switch device.

According to an aspect of the present invention, there is provided a method of measuring a physiological parameter in a contactless manner, the method including acquiring a plurality of image frames for a subject, acquiring a first color channel value, a second color channel value, and a third color channel value for at least one image frame included in the plurality of image frames, calculating a first difference and a second difference on the basis of the first color channel value, the second color channel value, and the third color channel value for at least one image frame included in the plurality of image frames, wherein the first difference represents a difference between the first color channel value and the second color channel value for the same image frame, and the second difference represents a difference between the first color channel value and the third color channel value for the same image frame, acquiring a first characteristic value on the basis of the first difference for at least one image frame included in a first image frame group acquired during a first preset time period and the mean of first differences for the first image frame group, acquiring a second characteristic value on the basis of the second difference for at least one image frame included in the first image frame group and the mean of second differences for the first image frame group, and determining a physiological parameter of the subject on the basis of the first characteristic value and the second characteristic value, wherein the first color channel value may represent an average pixel value of a first color channel for one image frame, the second color channel value may represent an average pixel value of a second color channel for one image frame, and the third color channel value may represent an average pixel value of a third color channel for one image frame.

According to an aspect of the present invention, there is provided a method of measuring a physiological parameter using an infrared camera, the method including acquiring a plurality of image frames for a subject using an infrared camera, acquiring a first region value, a second region value, and a third region value for at least one image frame included in the plurality of image frames, calculating a first difference and a second difference on the basis of the first region value, the second region value, and the third region value for at least one image frame included in the plurality of image frames, acquiring a first characteristic value on the basis of the first difference for at least one image frame included in a first image frame group acquired during a first preset time period and the mean of first differences for the first image frame group, acquiring a second characteristic value on the basis of the second difference for at least one image frame included in the first image frame group and the mean of second differences for the first image frame group, and determining a physiological parameter of the subject on the basis of the first characteristic value and the second characteristic value, wherein the first region value may be an average pixel value of a first region of interest for one image frame, the second region value may be an average pixel value of a second region of interest for one image frame, the third region value may be an average pixel value of a third region of interest for one image frame, the first difference may be a difference between the first region value and the second region value for the same image frame, and the second difference may be a difference between the first region value and the third region value for the same image frame.

According to an aspect of the present invention, there is provided a physiological parameter acquisition device including an image acquisition unit for acquiring an image frame for a subject and a control unit for acquiring a physiological parameter using the image frame, wherein the control unit is configured to acquire a first color channel value, a second color channel value, and a third color channel value for at least one image frame included in a plurality of acquired image frames, calculate a first difference and a second difference on the basis of the first color channel value, the second color channel value, and the third color channel value for at least one image frame included in the plurality of image frames, acquire a first characteristic value on the basis of the first difference for at least one image frame included in a first image frame group acquired during a first preset time period and the mean of first differences for the first image frame group, acquire a second characteristic value on the basis of the second difference for at least one image frame included in the first image frame group and the mean of second differences for the first image frame group, and determine a physiological parameter of the subject on the basis of the first characteristic value and the second characteristic value, wherein the first color channel value may be an average pixel value of a first color channel for one image frame, the second color channel value may be an average pixel value of a second color channel for one image frame, the third color channel value may be an average pixel value of a third color channel for one image frame, the first difference may be a difference between the first color channel value and the second color channel value for the same image frame, and the second difference may be a difference between the first color channel value and the third color channel value for the same image frame.

According to an aspect of the present invention, there is provided a method of providing a physiological parameter in a contactless manner, the method including acquiring a plurality of image frames for a subject, acquiring a first color channel value, a second color channel value, and a third color channel value for at least one image frame included in the plurality of image frames, acquiring a first characteristic value on the basis of a first color channel value, a second color channel value, and a third color channel value for at least one image frame included in a first image frame group acquired during a first preset time period, acquiring a second characteristic value on the basis of a first color channel value, a second color channel value, and a third color channel value for at least one image frame included in a second image frame group acquired during a second preset time period, and determining a physiological parameter on the basis of the first characteristic value and the second characteristic value, wherein the first image frame group and the second image frame group may partially overlap each other, and a first characteristic value for a first image frame included in the first image frame group but not included in the second image frame group, a first characteristic value and a second characteristic value for a second image frame included in both of the first image frame group and the second image frame group, and a second characteristic value for a third image frame included in the second image frame group but not included in the first image frame group may be used in order to determine the physiological parameter.

According to an aspect of the present invention, there is provided a method of measuring a physiological parameter in a contactless manner, the method including acquiring a plurality of image frames including a first image frame group and a second image frame group at least partially overlapping the first image frame group, acquiring a physiological parameter on the basis of the first image frame group, outputting the physiological parameter at a first time point, acquiring a first physiological parameter on the basis of the second image frame group, and outputting the physiological parameter at a second time point later than the first time point, wherein the physiological parameter output at the first time point may be a physiological parameter acquired based on the first image frame group, the physiological parameter output at the second time point may be the first physiological parameter when a difference between the first physiological parameter and the physiological parameter output at the first time point is less than or equal to a reference value and may be a physiological parameter obtained by correcting the physiological parameter output at the first time point when the difference between the first physiological parameter and the physiological parameter output at the first time point is greater than the reference value.

According to an aspect of the present invention, there is provided a method of measuring a physiological parameter, the method including acquiring a plurality of image frames for a subject, setting a first region and a second region for at least one image frame included in the plurality of image frames, determining an oxygen saturation level of the subject on the basis of a first feature acquired based on at least two of a first color channel value, a second color channel value, and a third color channel value for the first region, determining a heart rate of the subject on the basis of a second feature acquired based on a first difference, which is a difference between the first color channel value and the second color channel value for the first region, determining a blood pressure of the subject on the basis of a third feature acquired based on the first difference and a second difference, which is a difference between a first color channel value and a second color channel value for the second region, and outputting the oxygen saturation level, the heart rate, and the blood pressure, wherein the first feature may be acquired based on a first image frame group acquired during a first time period, the second feature may be acquired based on a second image frame group acquired during a second time period, the third feature may be acquired based on a third image frame group acquired during a third time period, and the first image frame group, the second image frame group, and the third image frame group may include a plurality of image frames in common to acquire the oxygen saturation level, the heart rate, and the blood pressure in association with each other.

According to another aspect of the present invention, there is provided a method of measuring a physiological parameter, the method including acquiring a plurality of image frames for a subject, setting a first region, a second region, and a third region for at least one image frame included in the plurality of image frames, determining an oxygen saturation level of the subject on the basis of a first feature acquired based on at least two of a first color channel value, a second color channel value, and a third color channel value for the first region, determining a heart rate of the subject on the basis of a second feature acquired based on a first difference, which is a difference between the first color channel value and the second color channel value for the first region, determining a blood pressure of the subject on the basis of a third feature acquired based on a second difference, which is a difference between a first color channel value and a second color channel value for the second region, and a third difference, which is a difference between a first color channel value and a second color channel value for the third region, and outputting the oxygen saturation level, the heart rate, and the blood pressure, wherein the first feature may be acquired based on a first image frame group acquired during a first time period, the second feature may be acquired based on a second image frame group during a second time period, the third feature may be acquired based on a third image frame group during a third time period, and the first image frame group, the second image frame group, and the third image frame group may include a plurality of image frames in common to acquire the oxygen saturation level, the heart rate, and the blood pressure in association with each other.

According to still another aspect of the present invention, there is provided a method of measuring a physiological parameter, the method including acquiring a plurality of image frames for a subject, acquiring a first color channel value, a second color channel value, and a third color channel value for at least one image frame included in the plurality of image frames, determining an oxygen saturation level of the subject on the basis of a first feature acquired based on at least two of the first color channel value, the second color channel value, and the third color channel value, determining a heart rate of the subject on the basis of a second feature acquired based on a first difference, which is a difference between the first color channel value and the second color channel value, and a second difference, which is a difference between the first color channel value and the third color channel value, determining a blood pressure of the subject on the basis of a third feature acquired based on the first difference and the second difference, and outputting the oxygen saturation level, the heart rate, and the blood pressure, wherein the first feature may be acquired based on a first image frame group acquired during a first time period, the second feature may be acquired based on a second image frame group acquired during a second time period, the third feature may be acquired based on a third image frame group acquired during a third time period, and the first image frame group, the second image frame group, and the third image frame group may include a plurality of image frames in common to acquire the oxygen saturation level, the heart rate, and the blood pressure in association with each other.

According to still another aspect of the present invention, there is provided a method of measuring a physiological parameter, the method including acquiring a plurality of image frames for a subject, setting at least two regions for at least one image frame included in the plurality of image frames, acquiring a first color channel value, a second color channel value, a third color channel value, a fourth color channel value, and a fifth color channel value for at least one image frame included in the plurality of image frames, determining an oxygen saturation level of the subject on the basis of a first feature acquired based on at least two of the first color channel value, the second color channel value, and the third color channel value, determining a heart rate of the subject on the basis of a second feature acquired based on at least two of the first color channel value, the second color channel value, and the third color channel value, determining a blood pressure of the subject on the basis of a third feature acquired based on at least two of the first color channel value, the second color channel value, and the third color channel value, determining a core temperature of the subject on the basis of a fourth feature acquired based on the fourth color channel value, and outputting the oxygen saturation level, the heart rate, the core temperature, and the blood pressure, wherein the first color channel value may be a green channel value, the second channel value may be a red channel value, the third color channel value may be a blue channel value, the fourth color channel value may be a saturation channel value, and the fifth color channel value may be a hue channel value.

According to still another aspect of the present invention, there is provided a method of measuring a physiological parameter, the method including acquiring a plurality of image frames for a subject, acquiring N preliminary heart rates on the basis of at least one image frame included in the plurality of image frames, acquiring M preliminary oxygen saturation levels on the basis of at least one image frame included in the plurality of image frames, acquiring K preliminary blood pressures on the basis of at least one image frame included in the plurality of image frames, acquiring a heart rate on the basis of the N preliminary heart rates, acquiring an oxygen saturation level on the basis of the M preliminary oxygen saturation levels, acquiring a blood pressure on the basis of the K preliminary blood pressures, and outputting the heart rate, the oxygen saturation level, and the blood pressure, wherein when an image frame acquired when the subject is in a first state is a first image frame, the first image frame may be included in common in the image frames used to obtain the N preliminary heart rates, the NI preliminary oxygen saturation levels, and the K blood pressures.

According to an aspect of the present invention, there is provided a method of acquiring physiological information, the method including acquiring a plurality of image frames for a subject, acquiring a first physiological parameter on the basis of a first image frame group including at least one image frame included in the plurality of image frames, acquiring a second physiological parameter on the basis of a second image frame group including at least one image frame included in the plurality of image frames, acquiring physiological information on the basis of at least one of the first physiological parameter and the second physiological parameter, and outputting the first physiological parameter, the second physiological parameter, and the physiological information, wherein the first image frame group and the second image frame group may at least partially overlap each other in order to acquire physiological information in response to a specific state of the subject.

According to an aspect of the present invention, there is provided a method of detecting drowsiness based on a heart rate, the method being performed by at least one processor and including acquiring a heart rate of a subject, acquiring a comparison result obtained by comparing the heart rate to a reference heart rate, acquiring a duration for which the heart rate is less than or equal to the reference heart rate on the basis of the comparison result, and a drowsiness detection operation for determining a drowsiness state of the subject on the basis of whether the duration reaches a reference duration.

According to an aspect of the present invention, there is provided a method of detecting drowsiness based on a heart rate and a low frequency (LF)/high frequency (HF) ratio, the method being performed by at least one processor and including acquiring a heart rate of a subject, acquiring a comparison result obtained by comparing the heart rate to a reference heart, rate, acquiring a first drowsiness parameter on the basis of the comparison result, acquiring an LF/HF ratio representing a ratio of a sympathetic nerve activity and a parasympathetic nerve activity of the subject, acquiring a second drowsiness parameter on the basis of the LF/HF ratio of the subject, and a drowsiness detection operation for determining a drowsiness state of the subject using at least one of the first drowsiness parameter and the second drowsiness parameter.

According to an aspect of the present invention, there is provided a smart mirror device including a reflective mirror surface, an image acquisition unit for acquiring a plurality of image frames for a subject, a display unit placed behind the reflective mirror surface and configured to display visual information through the reflective mirror surface, and a control unit configured to control the operation of the image acquisition unit and the display unit and acquire a physiological parameter in a contactless manner, wherein the control unit may control the display unit so that a first physiological parameter acquired based on a first image frame group included in the plurality of image frames at a first time point is displayed and control the display unit so that a second physiological parameter acquired based on a second image frame group included in the plurality of image frames at a second time point is displayed, the first image frame group and the second image frame group may include at least one image frame in common to associate the first physiological parameter and the second physiological parameter with each other, and the at least one image frame included in the first image frame group and the second image frame group in common may include an image frame acquired in a first state of the subject observed by the subject through the reflective mirror surface before the first time point and the second time point.

According to an aspect of the present invention, there is provided a method of operating a smart mirror device, the method including acquiring an on-trigger, acquiring a plurality of image frames for a subject, acquiring a first physiological parameter on the basis of a first image frame group included in the plurality of image frames, acquiring a second physiological parameter on the basis of a second image frame group included in the plurality of image frames, displaying the first physiological parameter and the second physiological parameter, acquiring an off-trigger, and stopping the acquisition of the plurality of image frames for the subject, wherein the first image frame group and the second image frame group may include at least one image frame in common to associate the first physiological parameter and the second physiological parameter with each other, the on-trigger may be acquired from at least one sensor, and the off-trigger may be acquired from an image sensor for acquiring the plurality of image frames.

According to another aspect of the present invention, there is provided a smart mirror device including a reflective mirror surface, an image acquisition unit for acquiring a plurality of image frames, a display unit placed behind the reflective mirror surface and configured to display visual information through the reflective mirror surface, a switch unit placed in front of the image acquisition unit and configured to switch a field of view of the image acquisition unit, and a control unit configured to control operations of the image acquisition unit and the display unit and acquire a physiological parameter, wherein the switch unit may have a surface formed as a reflective mirror, and when the switch unit is open, the control unit may control the display unit so that the physiological parameter and at least one piece of visual information are displayed through the display unit, and when the switch unit is closed, the control unit may control the display unit so that at least one piece of visual information is displayed through the display unit.

Solutions of the present invention are not limited to the above-mentioned solutions, and solutions that have not been mentioned will be clearly understood by those skilled in the art from the following description and the accompanying drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 5 is a diagram showing a physiological parameter acquisition method according to an embodiment;

FIG. 19 is a diagram illustrating a characteristic value acquisition method according to an embodiment;

FIG. 76 is a diagram illustrating the occurrence of an event in relation to an infant;

DETAILED DESCRIPTION OF EXEMPLARY EMBODIMENTS

Figure 1:
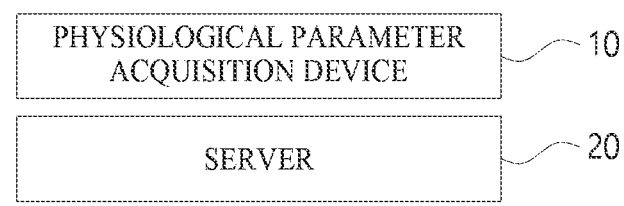
FIG. 1 is a diagram showing a physiological-parameter and physiological-information management system according to an embodiment.

Embodiments described in this specification are intended to clearly explain the spirit of the invention to those skilled in the art. Therefore, the present invention is not limited by the embodiments, and the scope of the present invention should be interpreted as encompassing modifications and variations without departing from the spirit of the invention.

Terms used in this specification are selected from among general terms, which are currently widely used, in consideration of functions in the present invention and may have meanings varying depending on intentions of those skilled in the art, customs in the field of art, the emergence of new technologies, or the like. If a specific term is used with a specific meaning, the meaning of the term will be described specifically. Accordingly, the terms used in this specification should not be defined as simple names of the components but should be defined on the basis of the actual meaning of the terms and the whole context throughout the present specification.

The accompanying drawings are for facilitating the explanation of the present invention, and the shape in the drawings may be exaggerated for the purpose of convenience of explanation, so the present invention should not be limited by the drawings.

When it is determined that detailed descriptions of well-known elements or functions related to the present invention may obscure the subject matter of the present invention, detailed descriptions thereof will be omitted herein as necessary.

According to an embodiment, there may be provided a method of measuring a physiological parameter in a contactless manner, the method including acquiring a plurality of image frames for a subject, acquiring a first color channel value, a second color channel value, and a third color channel value for at least one image frame included in the plurality of image frames, calculating a first difference and a second difference on the basis of the first color channel value, the second color channel value, and the third color channel value for at least one image frame included in the plurality of image frames, wherein the first difference represents a difference between the first color channel value and the second color channel value for the same image frame, and the second difference represents a difference between the first color channel value and the third color channel value for the same image frame, acquiring a first characteristic value on the basis of the first difference for at least one image frame included in a first image frame group acquired during a first preset time period and the mean of first differences for the first image frame group, acquiring a second characteristic value on the basis of the second difference for at least one image frame included in the first image frame group and the mean of second differences for the first image frame group, and determining a physiological parameter of the subject on the basis of the first characteristic value and the second characteristic value, wherein the first color channel value may represent an average pixel value of a first color channel for one image frame, the second color channel value may represent an average pixel value of a second color channel for one image frame, and the third color channel value may represent an average pixel value of a third color channel for one image frame.

Here, the physiological parameter may include at least one of a heart rate and a blood pressure.

Here, the first color channel, the second color channel, and the third color channel may be color channels of an RGB color space.

Here, the first color channel may be set to a green channel, the second color channel may be set to a red channel, and the third color channel may be set to a blue channel in order to reduce noise in consideration of the absorbance of hemoglobin and oxyhemoglobin.

Here, the first characteristic value may be acquired based on a first deviation of the first difference for at least one image frame included in the first image frame group, the second characteristic value may be acquired based on a second deviation of the second difference for at least one image frame included the first image frame group, the first deviation may be calculated based on the first difference for the at least one image frame and the mean of first differences for the first image frame group, and the second deviation may be calculated based on the second difference for the at least one image frame and the mean of second differences for the first image frame group.

Here, the first characteristic value and the second characteristic value may be normalized values.

Here, the first characteristic value may be a value normalized by a first standard deviation, the second characteristic value may be a value normalized by a second standard deviation, the first standard deviation may be the standard deviation of the first difference for the first image frame group, and the second standard deviation may be the standard deviation of the second difference for the first image frame group.

Here, the physiological parameter of the subject may be determined based on a third characteristic value acquired by summing the first characteristic value and the second characteristic value.

Here, the method may further include outputting the physiological parameter of the subject, the determined physiological parameter may include a first physiological parameter and a second physiological parameter, and the output physiological parameter may be determined based on the first physiological parameter and the second physiological parameter.

Here, the first physiological parameter may be determined based on a second image frame group, the second physiological parameter may be determined based on a third image frame group, the number of image frames included in the first image frame group may be smaller than the number of image frames included in the second image frame group and the third image frame group, and the first image frame group may be included in the second image frame group.

Here, the number of image frames included in the second image frame group may be equal to the number of image frames included in the third image frame group.

Here, the method may further include outputting the physiological parameter based on the determined physiological parameter, the determined physiological parameter may include at least four preliminary physiological parameters, and the output physiological parameter may be determined based on the four preliminary physiological parameters.

Here, the method may further include outputting the physiological parameter based on the determined physiological parameter, the output physiological parameter may include a first physiological parameter and a second physiological parameter, the second physiological parameter may be a physiological parameter of the same type as the first physiological parameter, the second physiological parameter may be output after the first physiological parameter is output, and when a difference between the second physiological parameter and the first physiological parameter exceeds a reference value, the second physiological parameter may be corrected and output.

According to another embodiment, there is provided a method of measuring a physiological parameter in a contactless manner using an infrared camera, the method including acquiring a plurality of image frames for a subject using an infrared camera, acquiring a first region value, a second region value, and a third region value for at least one image frame included in the plurality of image frames, calculating a first difference and a second difference on the basis of the first region value, the second region value, and the third region value for at least one image frame included in the plurality of image frames, acquiring a first characteristic value on the basis of the first difference for at least one image frame included in a first image frame group acquired during a first preset time period and the mean of first differences for the first image frame group, acquiring a second characteristic value on the basis of the second difference for at least one image frame included in the first image frame group and the mean of second differences for the first image frame group, and determining a physiological parameter of the subject on the basis of the first characteristic value and the second characteristic value, wherein the first region value may be an average pixel value of a first region of interest for one image frame, the second region value may be an average pixel value of a second region of interest for one image frame, the third region value may be an average pixel value of a third region of interest for one image frame, the first difference may be a difference between the first region value and the second region value for the same image frame, and the second difference may be a difference between the first region value and the third region value for the same image frame.

Here, the physiological parameter may include at least one of a heart rate and a blood pressure.

Here, the first characteristic value may be acquired based on a first deviation of the first difference for at least one image frame included in the first image frame group, the second characteristic value may be acquired based on a second deviation of the second difference for at least one image frame included the first image frame group, the first deviation may be calculated based on the first difference for the at least one image frame and the mean of first differences for the first image frame group, and the second deviation may be calculated based on the second difference for the at least one image frame and the mean of second differences for the first image frame group.

According to still another embodiment, there may be provided a physiological parameter measurement device for measuring a physiological parameter in a contactless manner, the physiological parameter measurement device including an image acquisition unit for acquiring an image frame for a subject and a control unit for acquiring a physiological parameter using the image frame, wherein the control unit is configured to acquire a first color channel value, a second color channel value, and a third color channel value for at least one image frame included in a plurality of acquired image frames, calculate a first difference and a second difference on the basis of the first color channel value, the second color channel value, and the third color channel value for at least one image frame included in the plurality of image frames, acquire a first characteristic value on the basis of the first difference for at least one image frame included in a first image frame group acquired during a first preset time period and the mean of first differences for the first image frame group, acquire a second characteristic value on the basis of a second difference for at least one image frame included in the first image frame group and the mean of second differences for the first image frame group, and determine a physiological parameter of the subject on the basis of the first characteristic value and the second characteristic value, wherein the first color channel value may be an average pixel value of a first color channel for one image frame, the second color channel value may be an average pixel value of a second color channel for one image frame, the third color channel value may be an average pixel value of a third color channel for one image frame, the first difference may be a difference between the first color channel value and the second color channel value for the same image frame, and the second difference may be a difference between the first color channel value and the third color channel value for the same image frame.

Here, the first color channel, the second color channel, and the third color channel may be color channels of an RGB color space, and the first color channel may be set to a green channel, the second color channel may be set to a red channel, and the third color channel may be set to a blue channel in order to reduce noise in consideration of the absorbance of hemoglobin and oxyhemoglobin.

Here, the first characteristic value may be acquired based on a first deviation of the first difference for at least one image frame included in the first image frame group, the second characteristic value may be acquired based on a second deviation of the second difference for at least one image frame included the first image frame group, the first deviation may be calculated based on the first difference for the at least one image frame and the mean of first differences for the first image frame group, and the second deviation may be calculated based on the second difference for the at least one image frame and the mean of second differences for the first image frame group.

Here, the control unit may acquire physiological information on the basis of the determined physiological parameter, and the physiological information may include at least one of emotion information, drowsiness information, stress information, and excitement information.

According to still another embodiment, there may be provided a method of measuring a physiological parameter in a contactless manner, the method including acquiring a plurality of image frames for a subject, acquiring a first color channel value, a second color channel value, and a third color channel value for at least one image frame included in the plurality of image frames, acquiring a first characteristic value on the basis of a first color channel value, a second color channel value, and a third color channel value for at least one image frame included in a first image frame group acquired during a first preset time period, acquiring a second characteristic value on the basis of a first color channel value, a second color channel value, and a third color channel value for at least one image frame included in a second image frame group acquired during a second preset time period, and determining a physiological parameter on the basis of the first characteristic value and the second characteristic value, wherein the first image frame group and the second image frame group may partially overlap each other, and a first characteristic value for a first image frame included in the first image frame group but not included in the second image frame group, a first characteristic value and a second characteristic value for a second image frame included in both of the first image frame group and the second image frame group, and a second characteristic value for a third image frame included in the second image frame group but not included in the first image frame group may be used in order to determine the physiological parameter.

Here, the method may further include calculating a first difference on the basis of at least some of the first color channel value, the second color channel value, and the third color channel value for the at least one image frame included in the plurality of image frames, wherein the first characteristic value may be acquired based on the first difference for the at least one image frame included in the first image frame group and the mean of first differences for the first image frame group, the second characteristic value may be acquired based on the first difference for the at least one image frame included in the second image frame group and the mean of second differences for the second image frame group, the first difference may be a difference between a first color channel value and a second color channel value for the same image frame, and the second difference may be a difference between a first color channel value and a third color channel value for the same image frame.

Here, the first characteristic value may be acquired based on a first deviation of the first difference for at least one image frame included in the first image frame group, the second characteristic value may be acquired based on a second deviation of the first difference for at least one image frame included the second image frame group, the first deviation may be calculated based on the first difference for the at least one image frame included in the first image frame group and the mean of first differences for the first image frame group, and the second deviation may be calculated based on the first difference for the at least one image frame included in the second image frame group and the mean of first differences for the second image frame group.

According to still another embodiment, there may be provided a physiological parameter output method for acquiring and outputting a physiological parameter in a contactless manner, the physiological parameter output method including acquiring a plurality of image frames including a first image frame group and a second image frame group at least partially overlapping the first image frame group, acquiring a physiological parameter on the basis of the first image frame group, outputting the physiological parameter at a first time point, acquiring a first physiological parameter on the basis of the second image frame group, and outputting the physiological parameter at a second time point later than the first time point, wherein the physiological parameter output at the first time point may be a physiological parameter acquired based on the first image frame group, the physiological parameter output at the second time point may be the first physiological parameter when a difference between the first physiological parameter and the physiological parameter output at the first time point is less than or equal to a reference value and may be a physiological parameter obtained by correcting the physiological parameter output at the first time point when the difference between the first physiological parameter and the physiological parameter output at the first time point is greater than the reference value.

Here, the corrected physiological parameter may be a physiological parameter corrected by adding a preset value to the physiological parameter output at the first time point when the first physiological parameter is greater than the physiological parameter output at the first time point and may be a physiological parameter corrected by subtracting a preset value from the physiological parameter output at the first time when the first physiological parameter is smaller than the physiological parameter output at the first time point.

According to an embodiment, there may be provided a method of measuring various physiological parameters including a heart rate, an oxygen saturation level, and a blood pressure at the same time, the method including acquiring a plurality of image frames for a subject, setting a first region and a second region for at least one image frame included in the plurality of image frames, determining an oxygen saturation level of the subject on the basis of a first feature acquired based on at least two of a first color channel value, a second color channel value, and a third color channel value for the first region, determining a heart rate of the subject on the basis of a second feature acquired based on a first difference, which is a difference between the first color channel value and the second color channel value for the first region, determining a blood pressure of the subject on the basis of a third feature acquired based on the first difference and a second difference, which is a difference between a first color channel value and a second color channel value for the second region, and outputting the oxygen saturation level, the heart rate, and the blood pressure, wherein the first feature may be acquired based on a first image frame group acquired during a first time period, the second feature may be acquired based on a second image frame group acquired during a second time period, the third feature may be acquired based on a third image frame group acquired during a third time period, and the first image frame group, the second image frame group, and the third image frame group may include a plurality of image frames in common to acquire the oxygen saturation level, the heart rate, and the blood pressure in association with each other.

Here, the first color channel value may be a green channel value, the second color channel value may be a red channel value, and the third color channel value may be a blue channel value.

Here, the first feature may be acquired based on the second color channel value for a second color channel in which the absorbance of oxyhemoglobin is lower than the absorbance of hemoglobin and the third color channel value for a third color channel in which the absorbance of oxyhemoglobin is higher than the absorbance of hemoglobin.

Here, the second feature may be acquired based on the first difference and a third difference, which is a difference between the first color channel value and the second color channel value for the first region.

Here, in order to reduce noise caused by external light, the first color channel value may be a green channel value, the second color channel value may be a red channel value, and the third color channel value may be a blue channel value.

Here, the second feature may include a frequency component value of time-series data acquired based on the first difference.

Here, the third feature may include a pulse transit time (PTT) acquired based on the first difference and the second difference.

Here, the fourth feature may be acquired based on the first difference, the second difference, the third difference, and a fourth difference, which is a difference between the first color channel value and the third color channel value for the second region.

Here, the first region and the second region may include a face region of the subject, and the center of the second region may have a different vertical position from the center of the first region.

According to another embodiment, there may be provided a method of measuring various physiological parameters including a heart rate, an oxygen saturation level, and a blood pressure at the same time, the method including acquiring a plurality of image frames for a subject, setting a first region, a second region, and a third region for at least one image frame included in the plurality of image frames, determining an oxygen saturation level of the subject on the basis of a first feature acquired based on at least two of a first color channel value, a second color channel value, and a third color channel value for the first region, determining a heart rate of the subject on the basis of a second feature acquired based on a first difference, which is a difference between the first color channel value and the second color channel value for the first region, determining a blood pressure of the subject on the basis of a third feature acquired based on a second difference, which is a difference between a first color channel value and a second color channel value for the second region, and a third difference, which is a difference between a first color channel value and a second color channel value for the third region, and outputting the oxygen saturation level, the heart rate, and the blood pressure, wherein the first feature may be acquired based on a first image frame group acquired during a first time period, the second feature may be acquired based on a second image frame group during a second time period, the third feature may be acquired based on a third image frame group during a third time period, and the first image frame group, the second image frame group, and the third image frame group may include a plurality of image frames in common to acquire the oxygen saturation level, the heart rate, and the blood pressure in association with each other.

Here, the first feature may be acquired based on the second color channel value for a second color channel in which the absorbance of oxyhemoglobin is lower than the absorbance of hemoglobin and the third color channel value for a third color channel in which the absorbance of oxyhemoglobin is higher than the absorbance of hemoglobin.

Here, the second feature may be acquired based on the first difference and a third difference, which is a difference between the first color channel value and the second color channel value for the first region.

Here, the third feature may include a pulse transit time (PTT) acquired based on the first difference and the second difference.

According to still another embodiment, there may be a method of measuring various physiological parameters including a heart rate, an oxygen saturation level, and a blood pressure at the same time, the method including acquiring a plurality of image frames for a subject, acquiring a first color channel value, a second color channel value, and a third color channel value for at least one image frame included in the plurality of image frames, determining an oxygen saturation level of the subject on the basis of a first feature acquired based on at least two of the first color channel value, the second color channel value, and the third color channel value, determining a heart rate of the subject on the basis of a second feature acquired based on a first difference, which is a difference between the first color channel value and the second color channel value, and a second difference, which is a difference between the first color channel value and the third color channel value, determining a blood pressure of the subject on the basis of a third feature acquired based on the first difference and the second difference, and outputting the oxygen saturation level, the heart rate, and the blood pressure, wherein the first feature may be acquired based on a first image frame group acquired during a first time period, the second feature may be acquired based on a second image frame group acquired during a second time period, the third feature may be acquired based on a third image frame group acquired during a third time period, and the first image frame group, the second image frame group, and the third image frame group may include a plurality of image frames in common to acquire the oxygen saturation level, the heart rate, and the blood pressure in association with each other.

Here, the first feature may be acquired based on the second color channel value for a second color channel in which the absorbance of oxyhemoglobin is lower than the absorbance of hemoglobin and the third color channel value for a third color channel in which the absorbance of oxyhemoglobin is higher than the absorbance of hemoglobin.

Here, the second feature may include a frequency component value of time-series data acquired based on the first difference and the second difference.

Here, the third feature may include at least one of a gradient component value, a maximum value, a minimum value, a local maximum value, a local minimum value, the mean of local maximum values, and the mean of local minimum values, a difference between the mean of local maximum values and the mean of local minimum values, and an average value of time-series data acquired based on the first difference and the second difference.

According to still another embodiment, there may be provided a method of measuring various physiological parameters including a heart rate, an oxygen saturation level, a blood pressure, and a core temperate at the same time, the method including acquiring a plurality of image frames for a subject, setting at least two regions for at least one image frame included in the plurality of image frames, acquiring a first color channel value, a second color channel value, a third color channel value, a fourth color channel value, and a fifth color channel value for at least one image frame included in the plurality of image frames, determining an oxygen saturation level of the subject on the basis of a first feature acquired based on at least two of the first color channel value, the second color channel value, and the third color channel value, determining a heart rate of the subject on the basis of a second feature acquired based on at least two of the first color channel value, the second color channel value, and the third color channel value, determining a blood pressure of the subject on the basis of a third feature acquired based on at least two of the first color channel value, the second color channel value, and the third color channel value, determining a core temperature of the subject on the basis of a fourth feature acquired based on the fourth color channel value, and outputting the oxygen saturation level, the heart rate, the core temperature, and the blood pressure, wherein the first color channel value may be a green channel value, the second channel value may be a red channel value, the third color channel value may be a blue channel value, the fourth color channel value may be a saturation channel value, and the fifth color channel value may be a hue channel value.

Here, the first feature may be acquired based on the second color channel value for a second color channel in which the absorbance of oxyhemoglobin is lower than the absorbance of hemoglobin and the third color channel value for a third color channel in which the absorbance of oxyhemoglobin is higher than the absorbance of hemoglobin.

Here, the second feature may be acquired based on a first difference, which is a difference between the first color channel value and the second color channel value, and a second difference, which is a difference between the first color channel value and the third color channel value.

Here, the second feature may include a frequency component value of time-series data acquired based on the first difference and the second difference.

Here, the third feature may be acquired based on a first difference, which is a difference between the first color channel value and the second color channel value, and a second difference, which is a difference between the first color channel value and the third color channel value.

Here, the third feature may include at least one of a gradient component value, a maximum value, a minimum value, a local maximum value, a local minimum value, the mean of local maximum values, and the mean of local minimum values, a difference between the mean of local maximum values and the mean of local minimum values, and an average value of time-series data acquired based on the first difference and the second difference.

Here, the fourth feature may be acquired based on the fourth color channel value and the fifth color channel value.

Here, the fourth feature may include a skin temperature of the subject.

According to still another embodiment, there may be provided a method of measuring various physiological parameters including a heart rate, an oxygen saturation level, and a blood pressure at the same time, the method including acquiring a plurality of image frames for a subject, acquiring N preliminary heart rates on the basis of at least one image frame included in the plurality of image frames, acquiring M preliminary oxygen saturation levels on the basis of at least one image frame included in the plurality of image frames, acquiring K preliminary blood pressures on the basis of at least one image frame included in the plurality of image frames, acquiring a heart rate on the basis of the N preliminary heart rates, acquiring an oxygen saturation level on the basis of the M preliminary oxygen saturation levels, acquiring a blood pressure on the basis of the K preliminary blood pressures, and outputting the heart rate, the oxygen saturation level, and the blood pressure, wherein when an image frame acquired when the subject is in a first state is a first image frame, the first image frame may be included in common in the image frames used to obtain the N preliminary heart rates, the M preliminary oxygen saturation levels, and the K blood pressures.

According to still another embodiment, there may be provided a method of acquiring physiological information using various physiological parameters, the method including acquiring a plurality of image frames for a subject, acquiring a first physiological parameter on the basis of a first image frame group including at least one image frame included in the plurality of image frames, acquiring a second physiological parameter on the basis of a second image frame group including at least one image frame included in the plurality of image frames, acquiring physiological information on the basis of at least one of the first physiological parameter and the second physiological parameter, and outputting the first physiological parameter, the second physiological parameter, and the physiological information, wherein the first image frame group and the second image frame group may at least partially overlap each other in order to acquire physiological information in response to a specific state of the subject.

Here, the method may further include acquiring personal statistical data for the subject, and the physiological information may be acquired based on the first physiological parameter, the second physiological parameter, and the acquired personal statistical data.

Here, the first physiological parameter and the second physiological parameter may include at least one of a heart rate, an oxygen saturation level, a blood pressure, and a core temperature, and the physiological information may include at least one of drowsiness information, stress information, excitement information, and emotion information.

According to an embodiment, there may be provided a method of detecting drowsiness on the basis of a heart rate, the method being performed by at least one processor and including acquiring a heart rate of a subject, acquiring a comparison result obtained by comparing the heart rate to a reference heart rate, acquiring a duration for which the heart rate is less than or equal to the reference heart rate on the basis of the comparison result, and a drowsiness detection operation for determining a drowsiness state of the subject on the basis of whether the duration reaches a reference duration, wherein the reference duration may include a first reference duration, a second reference duration, and a third reference duration, the second reference duration may be longer than the first reference duration, and the third reference duration may be longer than the second reference duration, and the drowsiness state of the subject includes a normal state, a first drowsiness state, a second drowsiness state, and a third drowsiness state, and the first drowsiness state may represent a state in which the subject is more likely to enter a sleep state than the normal state, the second drowsiness state may represent a state in which the subject is more likely to enter a sleep state than the first drowsiness state, and the third drowsiness state may represent a state in which the subject is more likely to enter a sleep state than the second drowsiness state.

Here, the drowsiness detection operation may include determining that the drowsiness state of the subject is the first drowsiness state when the duration is longer than the first reference duration and shorter than the second reference duration, determining that the drowsiness state of the subject is the second drowsiness state when the duration is longer than the second reference duration and shorter than the third reference duration, and determining that the drowsiness state is the second drowsiness state when the duration is longer than the third reference duration.

Here, the drowsiness detection operation may further include determining that the drowsiness state of the subject is the normal state when the duration for which the heart rate of the subject is less than or equal to the reference heart rate is shorter than the first reference duration.

Here, the first drowsiness state may represent a state in which the subject is not aware of drowsiness but physically likely to enter a sleep state.

Here, the heart rate of the subject may represent the mean of a plurality of heart rates during a predetermined time period including a time point at which the heart rate is acquired.

Here, the method may further include acquiring a recovery duration for which the heart rate is greater than or equal to the reference heart rate when the drowsiness state of the subject is one of the first to third drowsiness states and a recovery detection operation of determining the drowsiness state of the subject on the basis of whether the recovery duration reaches a reference recovery duration.

Here, the reference recovery duration may include a first reference recovery duration, a second reference recovery duration, and a third reference recovery duration. When it is assumed that the drowsiness state of the subject is the third drowsiness state, the recovery detection operation may include determining that the drowsiness state of the subject is the second drowsiness state when the recovery duration is longer than the first reference recovery duration and shorter than the second reference recovery duration, determining that the drowsiness state of the subject is the first drowsiness state when the recovery duration is longer than the second reference recovery duration and shorter than the third reference recovery duration, and determining that the drowsiness state of the object is the normal state when the recovery duration is longer than the third reference recovery duration. When it is assumed that the drowsiness state of the subject is the second drowsiness state, the recovery detection operation may include determining that the drowsiness state of the subject is the first drowsiness state when the recovery duration is longer than the first reference recovery duration and shorter than the second reference recovery duration, determining that the drowsiness state of the subject is the normal state when the recovery duration is longer than the second reference recovery duration and shorter than the third reference recovery duration. When it assumed that the drowsiness state of the subject is the first drowsiness state, the recovery detection operation may include determining that the drowsiness state of the object is the normal state when the recovery duration is longer than the first reference recovery duration and shorter than the second reference recovery duration.

Here, one of the first reference duration, the second reference duration, and the third reference duration may be the same as at least one of the first reference recovery duration, the second reference recovery duration, and the third reference recovery duration.

Here, the first reference duration, the second reference duration, and the third reference duration may be different from the first reference recovery duration, the second reference recovery duration, and the third reference recovery duration.

According to an embodiment, there may be provided a method of detecting drowsiness based on a heart rate and a low frequency (LF)/high frequency (HF) ratio, the method being performed by at least one processor and including acquiring a heart rate of a subject, acquiring a comparison result obtained by comparing the heart rate to a reference heart rate, acquiring a duration for which the heart rate is changed on the basis of the comparison result, acquiring a first drowsiness parameter (a drowsiness level determined based on a heart rate) on the basis of the duration, acquiring an LF/HF ratio of the subject representing a ratio of a sympathetic nerve activity and a parasympathetic nerve activity of the subject, acquiring a second drowsiness parameter on the basis of the LF/HF ratio of the subject, and a drowsiness detection operation for determining the drowsiness state of the subject using at least one of the first drowsiness parameter and the second drowsiness parameter.

Here, the acquiring of the duration may include acquiring the duration on the basis of the length of the duration for which the heart rate is less than or equal to the reference heart rate on the basis of the comparison result.

Here, the drowsiness state may include a first drowsiness state and a second drowsiness state. The second drowsiness state is a state in which the subject is more likely to enter a sleep state than the first drowsiness state. The drowsiness state may be determined according to a first drowsiness parameter acquired based on a result of comparing the duration to a first reference duration and a second reference duration and a second drowsiness parameter acquired based on a result of comparing the LF/HF of the subject to a first reference value and a second reference value. The drowsiness state may be determined as the first drowsiness state when the duration is longer than the first reference duration and the LF/HF of the subject is smaller than the first reference value and may be determined as the second drowsiness state when the duration is longer than the second reference duration or when the LF/HF of the subject is smaller than the second reference value.

Here, the drowsiness state may further include a third drowsiness state. The first drowsiness state may be a state in which the subject is not aware of drowsiness but physically has a possibility of entering the sleep state, and the second drowsiness state and the third drowsiness state may be states in which the subject is aware of drowsiness and physically has a possibility of entering the sleep state. The third drowsiness state may be a state in which the subject is more likely to enter the sleep state than the second drowsiness state.

Here, the drowsiness state may include a normal state, a first-level drowsiness state, a second-level drowsiness state, and a third-level drowsiness state. The first-level drowsiness state may represent a state in which the subject is more likely to enter the sleep state than the normal state, the second-level drowsiness state may represent a state in which the subject is more likely to enter the sleep state than the first-level drowsiness state, and the third-level drowsiness state may represent a state in which the subject is more likely to enter the sleep state than the second drowsiness state. As the first drowsiness parameter and the second drowsiness parameter increase, the possibility of the subject entering the sleep state may increase. When the first drowsiness parameter and the second drowsiness parameter have the same value, the value may be acquired, and the drowsiness state may be determined as one of the first-level drowsiness state, the second-level drowsiness state, and the third-level drowsiness state on the basis of the value.

Here, the drowsiness state may include a normal state, a first-level drowsiness state, a second-level drowsiness state, and a third-level drowsiness state. The first-level drowsiness state may represent a state in which the subject is more likely to enter the sleep state than the normal state, the second-level drowsiness state may represent a state in which the subject is more likely to enter the sleep state than the first-level drowsiness state, and the third-level drowsiness state may represent a state in which the subject is more likely to enter the sleep state than the second drowsiness state. As the first drowsiness parameter and the second drowsiness parameter increase, the possibility of the subject entering the sleep state may increase. When the first drowsiness parameter and the second drowsiness parameter have different values, the larger value between the first drowsiness parameter and the second drowsiness parameter may be acquired, and the drowsiness state may be determined as one of the normal state, the first-level drowsiness state, the second-level drowsiness state, and the third-level drowsiness state on the basis of the larger value.

Here, the drowsiness state may include a normal state, a first-level drowsiness state, a second-level drowsiness state, and a third-level drowsiness state. The first-level drowsiness state may represent a state in which the subject is more likely to enter the sleep state than the normal state, the second-level drowsiness state may represent a state in which the subject is more likely to enter the sleep state than the first-level drowsiness state, and the third-level drowsiness state may represent a state in which the subject is more likely to enter the sleep state than the second drowsiness state. As the first drowsiness parameter and the second drowsiness parameter increase, the possibility of the subject entering the sleep state may increase. When the first drowsiness parameter and the second drowsiness parameter have different values, the smaller value between the first drowsiness parameter and the second drowsiness parameter may be acquired, and the drowsiness state may be determined as one of the normal state, the first-level drowsiness state, the second-level drowsiness state, and the third-level drowsiness state on the basis of the smaller value.

Here, the drowsiness state may include a normal state, a first-level drowsiness state, a second-level drowsiness state, and a third-level drowsiness state. The first-level drowsiness state may represent a state in which the subject is more likely to enter the sleep state than the normal state, the second-level drowsiness state may represent a state in which the subject is more likely to enter the sleep state than the first-level drowsiness state, and the third-level drowsiness state may represent a state in which the subject is more likely to enter the sleep state than the second drowsiness state. As the first drowsiness parameter and the second drowsiness parameter increase, the possibility of the subject entering the sleep state may increase. When the first drowsiness parameter and the second drowsiness parameter have different values, an average value of the first drowsiness parameter and the second drowsiness parameter may be acquired, and the drowsiness state may be determined as one of the normal state, the first-level drowsiness state, the second-level drowsiness state, and the third-level drowsiness state on the basis of the average value.

Here, the method may be performed through a recording medium on which a program for performing the method is recorded.

According to still another embodiment, there may be provided a smart mirror device configured to display at least two physiological parameters among a heart rate, an oxygen saturation level, a blood pressure, and a core temperature at the same time, the smart mirror device including a reflective mirror surface, an image acquisition unit for acquiring a plurality of image frames for a subject, a display unit placed behind the reflective mirror surface and configured to display visual information through the reflective mirror surface, and a control unit configured to control the operation of the image acquisition unit and the display unit and acquire a physiological parameter in a contactless manner, wherein the control unit may control the display unit so that a first physiological parameter acquired based on a first image frame group included in the plurality of image frames at a first time point is displayed and control the display unit so that a second physiological parameter acquired based on a second image frame group included in the plurality of image frames at a second time point is displayed, the first image frame group and the second image frame group may include at least one image frame in common to associate the first physiological parameter and the second physiological parameter with each other, and the at least one image frame included in the first image frame group and the second image frame group in common may include an image frame acquired in a first state of the subject observed by the subject through the reflective mirror surface before the first time point and the second time point.

Here, the first physiological parameter and the second physiological parameter may include at least one physiological parameter among a heart rate, an oxygen saturation level, a blood pressure, and a core temperature.

Here, the first image frame group may be identical to the second image frame group.

Here, the first image frame group may be different from the second image frame group.

Here, the first time point and the second time point may be the same time point.

Here, the first time point may be earlier than the second time point, and the at least one image frame included in the first image frame group and the second image frame group in common may include an image frame acquired in a second state of the subject which is observed by the subject through the reflective mirror surface before the first time point.

Here, the control unit may control the display unit so that a third physiological parameter acquired based on a third image frame group included in the plurality of image frames at a third time point is displayed, the first image frame group, the second image frame group, and the third image frame group may include at least one image frame in common to associate the first physiological parameter, the second physiological parameter, and the third physiological parameter with each other, and at least one image frame included in the first image frame group, the second image frame group, and the third image frame group in common may include an image frame acquired in a first state of the subject which is observed by the subject through the reflective mirror surface before; the first time point, the second time point, and the third time point.

Here, the control unit may acquire the first physiological parameter and the second physiological parameter on the basis of at least some of the plurality of image frames during a first time period and recognize the subject on the basis of at least one of the plurality of image frames during a second time period. The second time period may be shorter than the first time period and may be included in the first time period. The control unit may display information on the recognized subject before the first physiological parameter and the second physiological parameter are displayed.

Here, the information on the subject may be the first physiological parameter and the second physiological parameter which are previously measured and stored.

Here, the control unit may control the display unit so that first information is displayed at a fourth time point and control the display unit so that second information is displayed at a fifth time point. The first information may include weather information and time information, the second information may include the information on the subject, the fourth time point may be earlier than the fifth time point, and the fifth time point may be earlier than the first time point and the second time point.

Here, the second information may include at least one of schedule information, medication information, recognition information, messenger information, and information of interest of the subject.

Here, the control unit may control the display unit so that the first information is displayed at the fourth time point, control the display unit so that the first information and the second information are displayed at the fifth time point, and control the display unit so that the first information, the second information, the first physiological parameter, and the second physiological parameter are displayed at the second time point.

Here, the control unit may operate to acquire the first physiological parameter and the second physiological parameter on the basis of at least three color channel values for the plurality of image frames and may operate so that the first physiological parameter and the second physiological parameter are displayed within 10 seconds after a first image frame included in the first image frame group is acquired.

Here, when an image of a plurality of people is included in an image frame acquired through the image acquisition unit, the control unit may acquire the first physiological parameter and the second physiological parameter on the basis of an image of one person selected from among the plurality of people according to priority and may control the display unit so that the acquired first and second physiological parameters are displayed and so that information on the person selected from among the plurality of people is displayed.

Here, when an image frame including a first subject and a second subject is acquired after an image frame including the first subject is acquired, the control unit may acquire the first physiological parameter and the second physiological parameter on the basis of an image of the first subject and may control the display unit so that information on the first subject is displayed.

Here, the control unit may prioritize the plurality of people on the basis of the acquired image frame.

Here, when an image of the first subject and the second subject is included in an image frame acquired through the image acquisition unit, the control unit may operate to acquire a first physiological parameter of the first subject on the basis of a fourth image frame group included in the plurality of image frames, acquire a second physiological parameter of the first subject on the basis of a fifth image frame group included in the plurality of image frames, acquire a first physiological parameter of the second subject on the basis of a sixth image frame group included in the plurality of image frames, and acquire a second physiological parameter of the second subject on the basis of a seventh image frame group included in the plurality of image frames. The fourth image frame group and the fifth image frame group may include at least one image frame in common, and the sixth image frame group and the seventh image frame group may include at least one image frame in common.

Here, the control unit may acquire physiological information on the basis of the first physiological parameter and control the display unit so that the physiological information is displayed at a third time point. The physiological information displayed at the third time point may be acquired based on the first physiological parameter displayed at the first time point in order to display the first physiological parameter and the physiological information in real time, and the first time point may be earlier than the third time point.

Here, the control unit may acquire the physiological information on the basis of the first physiological parameter and the second physiological parameter. The physiological information displayed at the third time point may be acquired based on the first physiological parameter displayed at the first time point and the second physiological parameter displayed at the second time point in order to increase the accuracy of the physiological information. The third time point may be later than the first time point and the second time point.

Here, the physiological information may include at least one of condition information, concentration information, drowsiness information, and emotion information.

Here, the control unit may acquire physiological information on the basis of the first physiological parameter and control the display unit so that the physiological information is displayed at a third time point. The physiological information displayed at the third time point may be acquired based on first physiological parameters displayed up to the third time point in order to accurately display the physiological information, and the third time point may be later than the first time point.

Here, the physiological information displayed at the third time point may be acquired on the basis of an average value of the first physiological parameters displayed up to the third time point.

Here, the control unit may acquire the physiological information on the basis of the first physiological parameter and the second physiological parameter, and the physiological information displayed at the third time point may be acquired based on first physiological parameters displayed up to the third time point and second physiological parameters displayed up to the third time point. The third time point may be later than the first time point and the second time point.

Here, a cycle in which the first physiological parameter is updated may be different from a cycle in which the second physiological parameter is updated.

Here, the control unit may determine an information provision situation, control the display unit so that first information is displayed in the case of a first situation, and control the display unit so that second information is displayed in the case of a second situation. The first information may include the first physiological parameter and the second physiological parameter. The second information may not include the first physiological parameter and the second physiological parameter.

Here, the control unit may determine the information provision situation on the basis of a movement direction of the subject.

Here, the smart mirror device may further include an operation detection sensor for detecting the direction of the movement of the subject.

Here, the control unit may determine the information provision situation on the basis of the plurality of acquired image frames.

Here, the first information may include at least one of external weather information, schedule information of the subject, and time information, and the second information may include at least one of internal temperature information, internal humidity information, internal air information, security information, and activity time information.

Here, the first information may include at least two physiological parameters, and the second information may include at least one of weather information, time information, news information, schedule information, and medication information.

Here, the control unit may acquire at least three color channel values for at least one image frame included in the plurality of image frames, acquire a first difference and a second difference on the basis of the at least three color channel values, and acquire the first physiological parameter and the second physiological parameter on the basis of the first difference and the second difference.

According to still another embodiment, there may be provided a method of operating a smart mirror device configured to display at least two physiological parameters among a heart rate, an oxygen saturation level, a blood pressure, and a core temperature at the same time, the method including acquiring an on-trigger, acquiring a plurality of image frames for a subject, acquiring a first physiological parameter on the basis of a first image frame group included in the plurality of image frames, acquiring a second physiological parameter on the basis of a second image frame group included in the plurality of image frames, displaying the first physiological parameter and the second physiological parameter, acquiring an off-trigger, and stopping the acquisition of the plurality of image frames for the subject, wherein the first image frame group and the second image frame group may include at least one image frame in common to associate the first physiological parameter and the second physiological parameter with each other, the on-trigger may be acquired from at least one sensor, and the off-trigger may be acquired from an image sensor for acquiring the plurality of image frames.

Here, the on-trigger may be acquired from at least one of an operation detection sensor, a touch sensor, a mouse, and a keyboard.

According to still another embodiment, there may be provided a smart mirror device configured to display at least one physiological parameter among a heart rate, an oxygen saturation level, a blood pressure, and a core temperature, the smart mirror device including a reflective mirror surface, an image acquisition unit for acquiring a plurality of image frames, a display unit placed behind the reflective mirror surface and configured to display visual information through the reflective mirror surface, a switch unit placed in front of the image acquisition unit and configured to switch a field of view of the image acquisition unit, and a control unit configured to control operations of the image acquisition unit and the display unit and acquire a physiological parameter, wherein the switch unit may have a surface formed as a reflective mirror, and when the switch unit is open, the control unit may control the display unit so that the physiological parameter and at least one piece of visual information are displayed through the display unit, and when the switch unit is closed, the control unit may control the display unit so that at least one piece of visual information is displayed through the display unit.

Here, when the switch unit is changed from the closed state to the open state, the control unit may control the image acquisition unit so that an image frame is acquired from the image acquisition unit, and when the switch unit is changed from the open state to the closed state, the control unit may control the image acquisition unit so that the image acquisition unit cannot acquire the image frame.

0. Definition of Terms

The term "measurement" used herein can be understood as a concept including direct measurement, speculative measurement, and measurement of amounts relative to a certain amount.

The term "heart rate" used herein can be understood as a heart rate, which can be understood as a concept including both of a heart rate, which may refer to the number of beats measured near a heart due to heartbeats, and a pulse rate, which may refer to vibration generated due to heartbeats and propagated to peripheral blood vessels.

The term "blood pressure" used herein can be understood as a pressure generated in blood vessels when blood is pushed from a heart and can be understood as a value that can be estimated as a value that can be understood as typical blood pressure regardless of the measurement site (e.g., a value measured in the artery in an upper arm).

The terms "oxygen saturation level" used herein can be understood as the degree of saturation of oxygen in blood, and more specifically, it can be understood as the fraction of oxyhemoglobin to total hemoglobin in blood.

The term "core temperature" used herein can be understood as the body temperature of people or animals and may be different from skin temperature which may be measured on skin.

The term "skin temperature" used herein can be understood as the surface temperature of skin being measured.

The term "image" used herein can be understood as a concept including one image or a plurality of images included in a video.

The term "color channel" used herein can be understood as each axis constituting color space. For example, a red channel, a green channel, and a blue channel may refer to a red axis, a green axis, and a blue axis constituting RGB color space. Such a color channel may be formed in two dimensions, three dimensions, or four dimensions.

The term "image of a subject" used herein can be understood as an image including a measurement position of a subject. For example, when the measurement position is a subject's face, it can be understood as an image including a face region of the subject.

The term "personal statistical data" used herein may refer to collectible personal statistical data of a subject such as age, gender, height, and weight, observable personal statistical data such as facial expressions, wrinkles, and face color of a subject, or quantifiable personal statistical data such as statistical data the average blood pressure of people in their 20s, the average skin color of Asian people, the average height of men in their 30s, the average weight of Korean men, etc.) calculated for a group including or relating to a subject.

The term "time series data" used herein may refer to data listed along a time axis, but the present invention is not limited thereto. This term may refer to data listed along an image frame axis that may correspond to time, may refer to data that can be sorted along a time axis or an image frame axis, and can be understood as typical time series data.

1. Physiological-Parameter and Physiological-Information Management System

The term "physiological parameter" may refer to a result of a measurable or estimable human physiological activity, for example, heart rate, oxygen saturation level, blood pressure, core temperature, blood flow, etc. However, the present invention is not limited thereto, and this term may refer to other results of measurable or estimable human physiological activities.

The term "physiological information" may refer to information that may be calculated in consideration of at least some results of human physiological activities such as a physiological parameter and personal statistical data such as facial expressions, postures, and age and may include drowsiness information, stress information, excitement information, emotion information, etc., but the present invention is not limited thereto.

The term "physiological-parameter and physiological-information management system" may refer to a management system capable of storing, sharing, or analyzing measurable or estimable physiological parameters and calculable physiological information and comprehensively managing individuals' health or the like by using the physiological parameters and physiological information.

Figure 2:
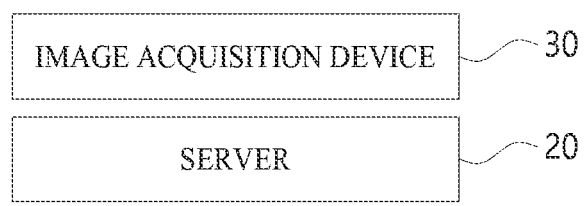
FIG. 2 is a diagram showing a physiological-parameter and physiological-information management system according to another embodiment.

FIGS. 1 and 2 are diagrams showing a physiological-parameter and physiological-information management system according to an embodiment.

Referring to FIG. 1, a physiological-parameter and physiological-information management system 100 according to an embodiment may include a physiological parameter acquisition device 10 and a server 20.

In this case, the physiological parameter acquisition device 10 may measure a physiological parameter of a subject. In detail, the physiological parameter acquisition device 10 may measure a physiological parameter of a subject in an invasive manner, in a non-invasive and contact manner, or in a contactless manner.

For example, the physiological parameter acquisition device 10 may analyze a video or image of the subject and measure a physiological parameter, such as a heart rate, an oxygen saturation level, and a blood pressure, of the subject, but the present invention is not limited thereto.

Also, the physiological parameter acquisition device 10 may calculate physiological information on the basis of the measured physiological parameter. In detail, the physiological parameter acquisition device 10 may calculate physiological information on the basis of the measured physiological parameter and may calculate physiological information in consideration of the measured physiological parameter and personal statistical data such as a facial expression, a posture, and an age.

For example, the physiological parameter acquisition device 10 may calculate physiological information, such as emotion information and drowsiness information, of the subject on the basis of the measured physiological parameter such as a heart rate, an oxygen saturation level, and a blood pressure, but the present invention is not limited thereto.

Also, the physiological parameter acquisition device 10 may store the measured physiological parameter and the calculated physiological information. For example, the physiological parameter acquisition device 10 may store the measured physiological parameter and the calculated physiological information of the subject in an internal memory, but the present invention is not limited thereto.

Also, the physiological parameter acquisition device 10 may display the measured physiological parameter and the calculated physiological information. For example, the physiological parameter acquisition device 10 may further include a display and may display the measured physiological parameter and the calculated physiological information of the subject using the display, but the present invention is not limited thereto. The physiological parameter acquisition device 10 may transmit the corresponding information to an external display so that the information can be displayed through the external display.

Also, the physiological parameter may be displayed once through the display, and a physiological parameter changing in real time may be continuously displayed.

Also, the physiological parameter acquisition device 10 may transmit the physiological parameter and the physiological information of the subject to the server 20.

In this case, the physiological parameter and the physiological information transmitted to the server 20 may be stored in the server 20 as personal data. For example, a measured physiological parameter and calculated physiological information of a subject A may be stored in the server 20 as data on the subject A, and a measured physiological parameter and calculated physiological information of a subject B may be stored in the server 20 as data on the subject B.

Also, when necessary, the server 20 may communicate with an external terminal to transmit a physiological parameter and physiological information of a subject. For example, when the subject A whose physiological parameter and physiological information are stored in the server 20 visits a hospital to receive treatment, a doctor who will treat the subject A may need the physiological parameter and physiological information of the subject A. In this case, when the server 20 receives a request for transmission of the physiological parameter and physiological information of the subject A from an external terminal placed in the hospital, the server 20 may communicate with the external terminal to transmit the physiological parameter and physiological information of the subject A.

As described above, the physiological-parameter and physiological-information management system 100 may serve as a basis for providing a continuous and comprehensive management service for an individual's health. In addition to the above example, it is obvious that the physiological-parameter and physiological-information management system 100 can serve as a basis for providing various comprehensive management services using physiological parameters and physiological information which are continuously measured, stored, and managed.

Also, referring to FIG. 2, a physiological-parameter and physiological-information management system 100 according to an embodiment may include an image acquisition device 30 and a server 20.

In this case, the image acquisition device 30 may acquire a video or image of a subject.

Also, the server 20 may acquire a video or image of a subject from the image acquisition device 30.

Also, the server 20 may acquire personal statistical data of the subject from an input device, an external terminal, or the like.

Also, the server 20 may measure a physiological parameter of the subject on the basis of the acquired video or image. For example, the server 20 may analyze the acquired video or image to measure the heart rate, oxygen saturation level, blood pressure, and the like of the subject, but the present invention is not limited thereto.

Also, the server 20 may calculate physiological information on the basis of the measured physiological parameter. In detail, the server 20 may calculate the physiological information on the basis of the measured physiological parameter and may calculate the physiological information in comprehensive consideration of the measured physiological parameter and personal statistical data such as facial expression, posture, and age.

For example, the server may calculate the physiological information, such as emotion information and drowsiness information, of the subject on the basis of the measured physiological parameter such as the heart rate, the oxygen saturation level, and the blood pressure, but the present invention is not limited thereto.

Also, the server 20 may store the measured physiological parameter and the calculated physiological information.

Also, since it is apparent that the physiological-parameter and physiological-information management system 100 including the image acquisition device 30 and the server 20 can perform the functions of the physiological-parameter and physiological-information management system that has been described with reference to FIG. 1, a redundant description thereof will be omitted here.

2. Various Embodiments of Physiological Parameter Acquisition Device

Figure 3:
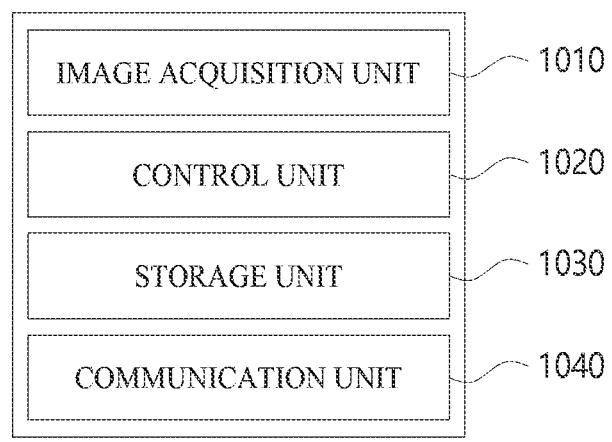
FIG. 3 is a diagram illustrating a physiological parameter acquisition device according to an embodiment.

FIG. 3 is a diagram illustrating a physiological parameter acquisition device according to an embodiment.

Referring to FIG. 3, a physiological parameter acquisition device 1000 according to an embodiment may include an image acquisition unit 1010, a control unit 1020, a storage unit 1030, and a communication unit 1040. However, the physiological parameter acquisition device 1000 may include at least some of the image acquisition unit 1010, the control unit 1020, the storage unit 1030, and the communication unit 1040. For example, the physiological parameter acquisition device 1000 may include only the image acquisition unit 1010 and the control unit 1020. However, the present invention is not limited thereto and may be implemented in various ways.

Also, the image acquisition unit 1010 may acquire a video or image of a subject. In detail, the image acquisition unit 1010 may include a photographing device and may acquire a video or image of the subject using the photographing device or a photographing device placed outside the physiological parameter acquisition device 1000, but the present invention is not limited thereto.

Also, when the image acquisition unit 1010 acquires a video or image of a subject from the photographing device, the photographing device may be provided as a visible camera for acquiring a visible light image, an infrared (IR) camera for acquiring an infrared image, and the like. However, the present invention is not limited thereto, and a hybrid-type camera for acquiring a visible light image and an infrared image may be provided.

Also, when the photographing device acquires a visible light image, the acquired visible light image may be acquired as at least one color channel value. For example, the acquired visible light image may be acquired as a color channel value of an RGB color space, which is represented using red, green, and blue or a color channel value of an HSV color space, which is represented using hue, saturation, and brightness (value). However, the present invention is not limited thereto, and the acquired visible light image may be acquired as color channel values of various color spaces such as YCrCb and YiQ.

Also, when the photographing device acquires an infrared image, the photographing device may acquire an infrared image through an infrared light source placed inside or outside the photographing device. In this case, the infrared light source may emit near-infrared light in a wavelength range of 750 nm to 3000 nm. However, the present invention is not limited thereto, and the infrared light source may emit middle-infrared light, far-infrared light, and extreme-infrared light.

Also, the control unit 1020 may acquire a physiological parameter using an image of a subject acquired from the image acquisition unit 1010.

For example, the control unit 1020 may analyze the image of the subject acquired from the image acquisition unit 1010 to acquire a physiological parameter, such as a heart rate, an oxygen saturation level, a blood pressure, and a core temperature, of the subject. However, the present invention is not limited thereto, and the control unit 1020 may acquire various physiological parameters.

Also, the control unit 1020 may calculate physiological information on the basis of the acquired physiological parameter.

For example, the control unit 1020 may calculate physiological information, such as emotion information and drowsiness information, of the subject on the basis of the acquired physiological parameter such as the heart rate, the oxygen saturation level, the blood pressure, and the core temperature. However, the present invention is not limited thereto, and the control unit 1020 may calculate various pieces of physiological information.

Also, the control unit 1020 may control the operation of at least some of the image acquisition unit 1010, the storage unit 1030, and the communication unit 1040.

Also, the storage unit 1030 may store the physiological parameter and physiological information acquired by the control unit 1020. In detail, the storage unit 1030 may store a physiological parameter and physiological information of one subject and also may store a physiological parameter and physiological information of each of several subjects.

Also, the communication unit 1040 may transmit the physiological parameter and physiological information acquired by the control unit 1020. In detail, the communication unit 1040 may transmit the physiological parameter and physiological information acquired by the control unit 1020 to a management server or to a user terminal.

3. Various Embodiments of Method of Acquiring Physiological Parameter and Physiological Information 3.1 Physiological Parameter Acquisition Method FIG. 4 is a flowchart showing a physiological parameter acquisition method according to an embodiment.

Figure 4:
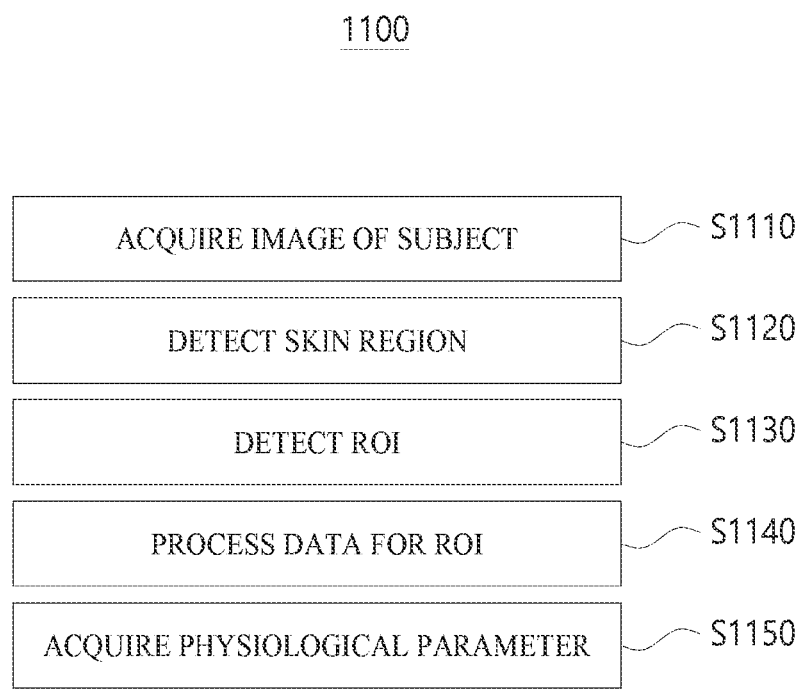
FIG. 4 is a flowchart showing a physiological parameter acquisition method according to an embodiment.

Referring to FIG. 4, a physiological parameter acquisition method 1100 according to an embodiment may include acquiring an image of a subject (S1110).

In this case, as described above, the image of the subject may be acquired using various cameras such as a visible light camera and an infrared light camera or using various other cameras, and thus a detailed description thereof will be omitted.

Also, the physiological parameter acquisition method 1100 according to an embodiment may include detecting a skin region (S1120).

In this case, the skin region may refer to a region that can be estimated as a skin region of the subject in the image of the subject.

Also, the skin region may well reflect changes in blood vessels due to heartbeats. The detection of the skin region in this way can increase the accuracy of the acquisition of the physiological parameter.

Also, according to an embodiment, in order to detect the skin region, non-skin regions such as the eyes and hair of the subject rather than the skin region, which can reflect a change in color due to the dilation of blood vessels, may be removed. For example, the hue values of the non-skin regions such as the eyes and hair of the subject may be replaced with a meaningless value such as black, but the present invention is not limited thereto.

Also, according to an embodiment, a specific color space may be used to detect the skin region. For example, the detecting of the skin region (S1120) may include replacing the acquired image of the subject with a value in the YCrCb color space and detecting the skin region on the basis of an image represented in the YCrCb color space, but the present invention is not limited thereto.

Also, it is obvious that the skin region can be detected using various well-known techniques.

Also, the physiological parameter acquisition method 1110 according to an embodiment may include setting a region of interest (ROI) (S1130).

In this case, the ROI may refer to a region of interest for data processing in the acquired image of the subject and also may refer to a region to be used for data processing so as to acquire a physiological parameter, but the present invention is not limited thereto.

Also, according to an embodiment, in order to set the ROI, a face region of the subject may be set. For example, in order to set an ROI included in the subject's face, a face region of the subject may be set.

In detail, a region having a certain proportion from the center of the set face region of the subject may be set as an ROI.

For example, a region corresponding to 80% in length and 60% in width on the basis of the center of the face region of the subject may be cropped, but the present invention is not limited thereto.

Also, according to an embodiment, a feature point may be used to set the ROI. For example, a feature point of a nose region of the subject may be extracted from the acquired image of the subject, and an ROI may be set based on the extracted feature point. However, the present invention is not limited thereto.

In detail, a region with a certain size from the center of the extracted feature point may be set as an ROI in the set face region, but the present invention is not limited thereto.

Also, according to an embodiment, a plurality of feature points may be used to set the ROI. For example, feature points of an eye region and a noise region of the subject may be extracted from the acquired image of the subject, and the ROI may be set based on the extracted feature points.

Also, when an ROI is set for each of a plurality of images that are consecutively acquired, the ROIs may be set for the plurality of images individually or in association with each other.

For example, in order to set the ROIs of the plurality of images in association with each other, a face region of the subject may be set for each of the plurality of images. When the difference between the center of a face region set for a first image frame and the center of a face region set for a second image frame, which is acquired after the first image frame, does not exceed a threshold, the face region of the second image frame may be set to be the same as the face region set for the first image frame, but the present invention is not limited thereto.

Also, when the difference between the center of the face region set in the first image frame and the center of the face region set in the second image frame exceeds the threshold, the face region of the second image frame may be set to be different from the face region set in the first image frame, but the present invention is not limited thereto.

Also, an ROI according to an embodiment may be set to include a portion of a body part or a portion of a face depending on a physiological parameter to be acquired and may include at least one ROI.

For example, the ROI may be set to include at least a portion of a cheek region in order to acquire a heart rate as the physiological parameter. In detail, the ROI may be set to include a cheek region which can well reflect the degree of the dilation of blood vessels according to blood flow and from which a heart rate is easy to acquire, but the present invention is limited thereto.

Also, for example, at least two such ROIs may be set to acquire a blood pressure as the physiological parameter, and specifically, may include an ROI including an upper face region and an ROI including a lower face region in order to reflect blood flow.

Also, for example, at least two such ROIs may be set to acquire a blood pressure as the physiological parameter, and specifically, may be set as two or more ROIs spaced different distances from a heart. For example, the ROIs may be set to include an ROI including a hand region and an ROI including a face region, but the present invention is not limited thereto.

Also, the physiological parameter acquisition method 1110 according to an embodiment may include processing data for the ROI (S1140).

Also, a color channel value for the ROI may be extracted to process the data for the ROI. In this case, the color channel value may be the mean of color channel values of pixels included in the ROI and may be referred to as an average pixel value.

For example, when color channel values corresponding to the RGB color space are extracted, a red channel pixel value, a green channel pixel value, and a blue channel pixel value of each pixel included in the ROI may be extracted. A red channel value, which is the mean of red channel pixel values included in the ROI, a blue channel value, which is the mean of blue channel pixel values included in the ROI, and a green channel value, which is the mean of green channel pixel values included in the ROI, may be extracted. However, the present invention is not limited thereto, and color channel values corresponding to various color spaces such as the HSV color space and the YCrCb color space may be extracted.

Also, a color channel value extracted according to a specific color space may be converted into another color space. For example, a color channel value extracted according to the RGB color space may be converted into color channel values corresponding to various color spaces such as the HSV color space and the YCrCb color space.

A color channel value extracted to process the data for the ROI may be a color channel value obtained by weighting at least some of the color channel values extracted according to various color spaces and combining the color channel values.

Also, the color channel value may be extracted for each of a plurality of image frames that are consecutively acquired or may be extracted from at least some of the image frames.

Also, color channel values extracted from one image frame may be processed through a mathematical operation or the like. In detail, a plurality of channel values acquired from one image frame may be processed through a mathematical operation such as addition or subtraction. For example, a green channel value and a red channel value acquired from one image frame may be processed through a subtraction operation. However, the present invention is not limited thereto, and various channel values may be processed through various mathematical operations.

Also, color channel values extracted from each of the plurality of image frames or processed values of the color channel values may be processed through a mathematical operation or the like. In detail, color channel values extracted from each of the plurality of image frames or processed values of the color channel values may be processed through a mathematical operation such as by obtaining an average or a deviation in a certain section. However, the present invention is not limited thereto, and the color channel values or the processed values may be processed by obtaining the difference between the maximum values and minimum values for a certain section and through various mathematical operations.

Also, the color channel values extracted from each of the plurality of image frames and the processed values of the color channel values may be processed to acquire at least one piece of time-series data.

Also, a characteristic value for acquiring a physiological parameter may be extracted based on at least some of the color channel values, the processed values, and the time-series data. For example, a frequency component for acquiring a heart rate may be extracted based on a frequency component of the time-series data, but the present invention is not limited thereto.

Also, the physiological parameter acquisition method 1110 according to an embodiment may include acquiring a physiological parameter (S1150).

Also, a characteristic value extracted from the ROI may be used to acquire the physiological parameter. For example, a heart rate based on the frequency component of the time-series data extracted from the ROI may be acquired, but the present invention is not limited thereto.

Also, the processing of the data for the ROI (S1140) and the acquiring of the physiological parameter (S1150) may vary depending on each physiological parameter, and a detailed description thereof will be described in detail in corresponding sections.

FIG. 5 is a diagram showing a physiological parameter acquisition method according to an embodiment.

Referring to FIG. 5, an image 1161 of a subject may include a face region. A skin region may be detected (1162), and an ROI may be detected (1163). A detailed description thereof is redundant and will be omitted.

Also, referring to FIG. 5, a color channel value for the ROI may be extracted (1164), the extracted color channel value may be processed (1165), and a physiological parameter may be acquired based on the processed color channel value (1166).

However, this will be described in detail in the corresponding section below.

3.2 Physiological Information Acquisition Method

Figure 6:
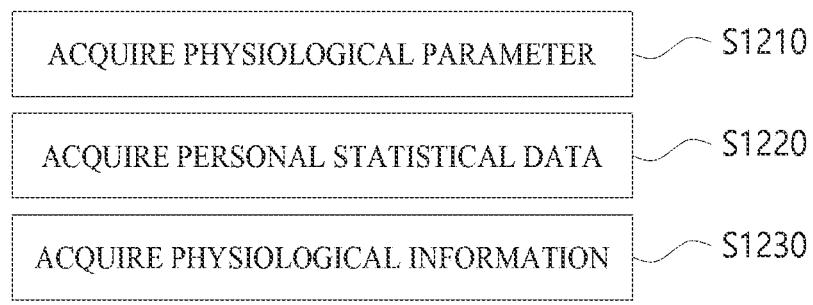
FIG. 6 is a flowchart showing a physiological information acquisition method according to an embodiment.

FIG. 6 is a flowchart showing a physiological information acquisition method according to an embodiment.

Referring to FIG. 6, the physiological information acquisition method according to an embodiment may include acquiring a physiological parameter (S1210).

In this case, the physiological parameter may be acquired by the above-described physiological parameter acquisition method. However, the present invention is not limited thereto, and the physiological parameter may be acquired by an external sensor such as an electrocardiography (ECG) sensor.

Also, a redundant description of the physiological parameter will be omitted.

Also, the physiological information acquisition method according to an embodiment may include acquiring personal statistical data (S1220).

In this case, the personal statistical data may refer to collectible personal statistical data, such as age and gender, of the subject and also may refer to observable personal statistical data, such as facial expression and wrinkles, of the subject. However, the present invention is not limited thereto, and the personal statistical data may be various types of personal statistical data other than the physiological parameter for acquiring the physiological information.

Also, the physiological information acquisition method according to an embodiment may include acquiring physiological information (S1230).

In this case, the physiological information may be drowsiness information, emotion information, or the like of the subject, but the present invention is not limited thereto.

Also, the physiological parameter may be used to acquire the physiological information. For example, a heart rate may be used as a physiological parameter to acquire the drowsiness information. In detail, when the heart rate of the subject is less than or equal to a reference heart rate, the subject may be regarded as being drowsy. The drowsiness level of the subject may be acquired according to a time period for which the heart rate is less than or equal to the reference heart rate.

Also, for example, a heart rate and a blood pressure may be used as physiological parameters to acquire the emotion information. In detail, when the heart rate and blood pressure of the subject are greater than or equal to a reference heart rate and a reference blood pressure, the subject may be regarded as being excited.

Also, the physiological parameter and the personal statistical data may be used to acquire the physiological information. For example, a heart rate and personal statistical data, such as age and gender, of the subject may be used to acquire the drowsiness information.

Also, for example, a heart, rate, a blood pressure, and personal statistical data, such as facial expression, age, and gender, of the subject may be used to acquire the emotion information.

Also, the physiological parameter and the personal statistical data may be weighted to acquire the physiological information. For example, in order to acquire the physiological information, different weights may be assigned to the physiological parameter and the personal statistical data, and different weights may be assigned depending on the subject.

Figure 7:
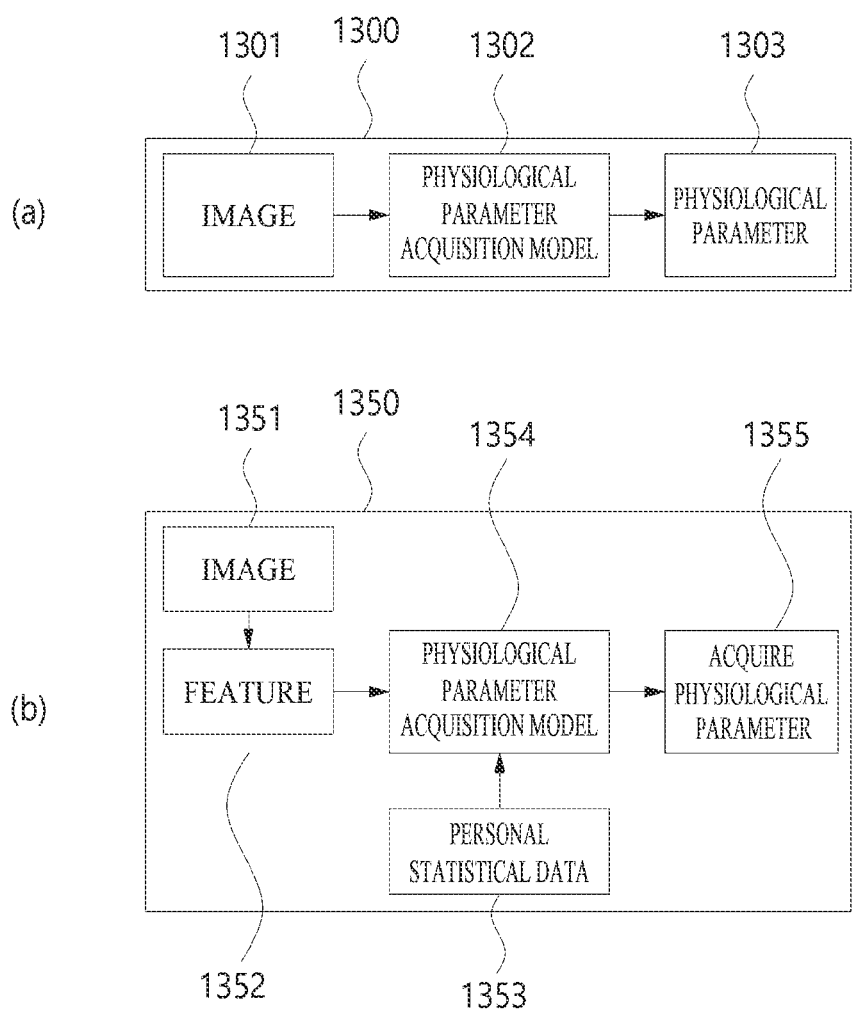
FIGS. 7 and 8 are diagrams illustrating a physiological parameter acquisition method using a physiological parameter acquisition model.
Figure 8:
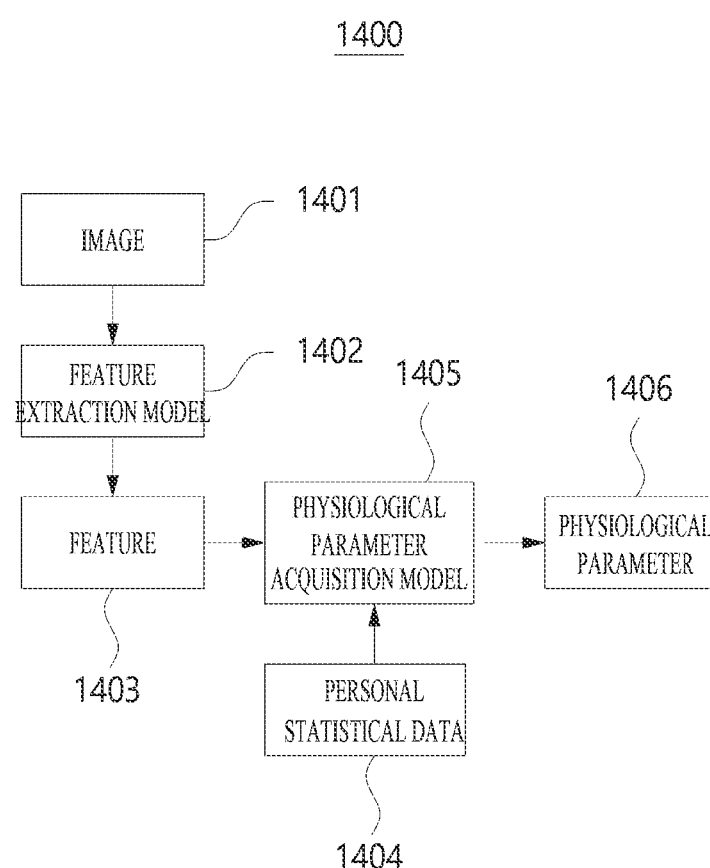

3.3 Physiological Parameter Acquisition Method Using Physiological Parameter Acquisition Model FIGS. 7 and 8 are diagrams illustrating a physiological parameter acquisition method using a physiological parameter acquisition model.

FIG. 7A shows a physiological parameter acquisition method 1300 using a physiological parameter acquisition model 1302 according to an embodiment.

In this case, the physiological parameter acquisition model 1302 according to an embodiment may be implemented in a machine learning method. For example, the physiological parameter acquisition model 1302 may be a model implemented through supervised learning. However, the present invention is not limited thereto, and the physiological parameter acquisition model 1302 may be a model implemented through unsupervised learning, semi-supervised learning, reinforcement learning, and the like.

Also, the physiological parameter acquisition model 1302 according to an embodiment may be implemented as an artificial neural network (ANN). For example, the physiological parameter acquisition model 1302 may be implemented as a feedforward neural network, a radial basis function network, a Kohonen self-organizing network, or the like, but the present invention is not limited thereto.

Also, the physiological parameter acquisition model 1302 according to an embodiment may be implemented as a deep neural network (DNN). For example, the physiological parameter acquisition model 1302 may be implemented as a convolutional neural network (CNN), a recurrent neural network (RNN), a long short-term memory network (LSTM), or gated recurrent units (GRUs), but the present invention is not limited thereto.

Also, an image 1301 input to the physiological parameter acquisition model 1302 may be acquired image data itself.

Also, an image 1301 input to the physiological parameter acquisition model 1302 may be pre-processed image data. For example, the image 1301 may be subject to the Eulerian video magnification. However, the present invention is not limited thereto, and various pre-processes such as a process of obtaining the mean of acquired RGB values may be performed.

Also, the acquired physiological parameter 1303 may include a heart rate, an oxygen saturation level, a blood pressure, a core temperature, or the like.

Also, the acquired physiological parameter 1303 may have one physiological parameter or have a plurality of physiological parameters acquired at the same time. For example, a heart rate may be acquired as a result of the physiological parameter acquisition model 1302. However, the present invention is not limited thereto, and both of a heart rate and a blood pressure may be acquired as a result of the physiological parameter acquisition model 1302.

Also, FIG. 7B shows a physiological parameter acquisition method 1350 using a physiological parameter acquisition model 1354 according to another embodiment.

In this case, the physiological parameter acquisition model 1354 may acquire personal statistical data 1353 and a feature 1352 extracted from an image 1351 as an input value. For example, time-series data for a color channel value may be extracted from the image 1351 as a feature, and the physiological parameter acquisition model 1354 may acquire the time-series data for the color channel value and personal statistical data as an input value and may calculate a physiological parameter 1355 as a result.

Also, the personal statistical data may refer to collectible personal statistical data, such as age, gender, height, and weight, of the subject, observable personal statistical data, such as facial expression, wrinkles, and face color, of the subject, or quantifiable personal statistical data such as an average blood pressure, an average color, an average height, and an average weight.

Also, the description of the physiological parameter acquisition model 1302 may be applied to the physiological parameter acquisition model 1354, and thus a redundant description thereof will be omitted.

Also, FIG. 8 shows a physiological parameter acquisition method 1400 using a physiological parameter acquisition model 1405 according to still another embodiment.

In this case, the physiological parameter acquisition method 1400 may include a feature extraction model 1402, and the feature extraction model 1402 according to an embodiment may be implemented in a machine learning method. For example, the feature extraction model 1402 may be a model implemented through supervised learning. However, the present invention is not limited thereto, and the feature extraction model 1402 may be a model implemented through unsupervised learning, semi-supervised learning, reinforcement learning, and the like.

Also, the feature extraction model 1402 according to an embodiment may be implemented as an artificial neural network (ANN). For example, the feature extraction model 1402 may be implemented as a feedforward neural network, a radial basis function network, a Kohonen self-organizing network, or the like, but the present invention is not limited thereto.

Also, the feature extraction model 1402 according to an embodiment may be implemented as a deep neural network (DNN). For example, the feature extraction model 1402 may be implemented as a convolutional neural network (CNN), a recurrent neural network (RNN), a long short-term memory network (LSTM), or gated recurrent units (GRUs), but the present invention is not limited thereto.

Also, the physiological parameter acquisition model 1405 may acquire personal statistical data 1404 and a feature 1403 extracted by the feature extraction model 1402 as an input value and may calculate a physiological parameter 1406 as a result on the basis of the input value.

Also, the description of the physiological parameter acquisition model 1302 may be applied to the physiological parameter acquisition model 1405, and thus a redundant description thereof will be omitted.

Machine learning, an artificial neural network, or a deep neural network model may be used to acquire a physiological parameter like an example that has been described with reference to FIGS. 7 and 8.

4. Various Embodiments of Physiological Parameter Acquisition

4.1 Various Embodiments of Heart Rate Measurement Method

When a heart beats in the body of a living organism, blood can be carried throughout the body by the heartbeats. In this case, the blood flows through blood vessels. The volume of the blood vessels may change over time, and the amount of blood contained in the blood vessels may change.

Accordingly, when the change in the volume of the blood vessels or the change in the amount of blood is measured, a heart rate may be acquired. For example, when the amount of blood included in the blood vessels changes, the amounts of hemoglobin and oxyhemoglobin contained in the blood may change, and thus the amount of light reflected by the blood may change. Accordingly, when the change in the amount of light reflected by the blood is measured, a heart rate may be acquired.

Also, it is obvious that, in addition to the above-described exemplary principle, various principles for measuring a heart rate with light are applicable.

Figure 9:
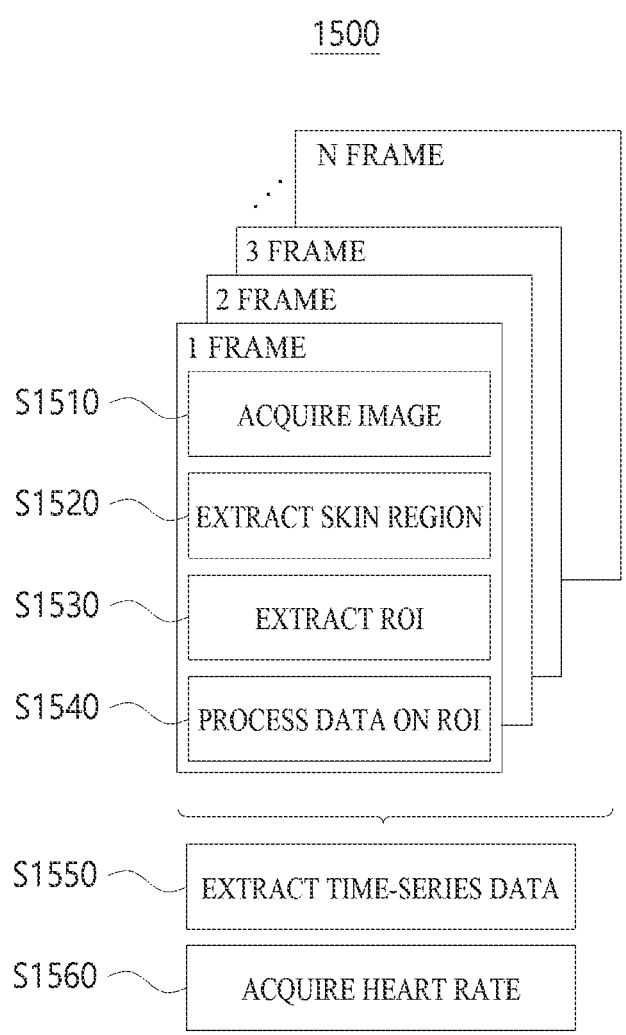
FIG. 9 is a flowchart illustrating a heart rate measurement method according to an embodiment.

FIG. 9 is a flowchart illustrating a heart rate measurement method according to an embodiment.

Referring to FIG. 9, a heart rate measurement method 1500 according to an embodiment may include at least some of an operation of acquiring an image for at least one of a plurality of acquired image frames (S1510), an operation of detecting a skin region (S1520), an operation of detecting an ROI (S1530), and an operation of processing data for the ROI (S1540), but the present invention is not limited thereto.

Also, the operation of acquiring the image (S1510), the operation of detecting the skin region (S1520), and the operation of detecting the ROI (S1530) have been described above, and thus a redundant description thereof will be omitted.

Also, the operation of processing the data for the ROI (S1540) may be performed on at least one of a plurality of acquired image frames.

Also, a color channel value for the ROI may be extracted for the at least one of the plurality of acquired image frames in order to process the data for the ROI. In this case, the color channel value may be the mean of color channel values of pixels included in the ROI and may be referred to as an average pixel value.

Also, the operation of processing the data for the ROI (S1540) has been described in detail above, and thus a redundant description thereof will be omitted.

Also, the heart rate measurement method 1500 according to an embodiment may include at least some of an operation of extracting time-series data for an image frame group including at least some of the plurality of acquired image frames (S1550) and an operation of acquiring a heart rate (S1560), but the present invention is not limited thereto.

Also, the operation of extracting the time-series data (S1550) may be performed on the image frame group including at least some of the plurality of acquired image frames.

In this case, the image frame group may be a group of a plurality of consecutive or nonconsecutive image frames. For example, the image frame group may refer to a group of consecutive image frames starting from a first image frame up to a $180^{th}$ image frame. However, the present invention is not limited thereto, and the image frame group may refer to a group of at least some of the image frames starting from the first image frame up to the $180^{th}$ image frame.

Also, the operation of acquiring the heart rate (S1560) may be performed on the image frame group including at least some of the plurality of acquired image frames.

In this case, a frequency component of the acquired time-series data may be extracted to acquire the heart rate. For example, in order to acquire the heart rate, the time-series data may be transformed by a Fourier transform (FT) to extract the frequency component. However, the present invention is not limited thereto, and the time-series data may be transformed by a fast Fourier transform (FFT), a discrete Fourier transform (DFT), the short-time Fourier transform (STFT)), or the like. However, the present invention is not limited thereto, and the time-series data may be subject to various processes for extracting frequency components.

Also, the heart rate may be acquired based on one heartbeat and may be acquired based on at least two heartbeats. For example, one heartbeat may be acquired based on one piece of time-series data, and another heart heat may be acquired based on another piece of time-series data. A final heartbeat may be acquired based on at least two acquired heart rates, but the present invention is not limited thereto.

4.2 Various Embodiments of Oxygen Saturation Level Measurement Method

Oxygen saturation level (SpO2) may refer to the amount of oxygen combined with hemoglobin and may indicate a ratio of oxyhemoglobin to a total amount of hemoglobin in blood.

Also, hemoglobin and oxyhemoglobin may have the same or different absorbances for light with one wavelength. For example, hemoglobin and oxyhemoglobin may have different absorbances for light in a wavelength range of 700 nm, may have different absorbances for light in a wavelength range of 1000 nm, and may have similar absorbances for light in a wavelength range of 800 nm.

Also, when the amount of blood included in blood vessels changes, the amounts of hemoglobin and oxyhemoglobin contained in the blood may change.

Accordingly, an oxygen saturation level may be acquired by using extinction coefficients of hemoglobin and oxyhemoglobin for light in a first wavelength range, extinction coefficients of hemoglobin and oxyhemoglobin for light in a second wavelength range, the degree of change of light in the first wavelength range due to a change in the amount of blood, and the degree of change of light in the second wavelength range due to a change in the amount of blood.

For example, when it is assumed that the extinction coefficient of oxyhemoglobin for light in the first wavelength range is $\varepsilon_1$, that the extinction coefficient of hemoglobin for light in the first wavelength range is $\varepsilon_2$, that the extinction coefficient of oxyhemoglobin for light in the second wavelength range is $\varepsilon_3$, that the extinction coefficient of hemoglobin for light in the second wavelength range is $\varepsilon_4$, and that the proportion of oxyhemoglobin is S, Equation 1 may be obtained as follows:

$$\frac{S*\varepsilon_1 + (1-S)*\varepsilon_2}{S*\varepsilon_3 + (1-S)*\varepsilon_4} = \frac{AC_{\lambda 1}/DC_{\lambda 1}}{AC_{\lambda 2}/DC_{\lambda 2}}. \quad \text{[Equation 1]}$$

Here, the oxygen saturation level may be represented as S*100(%) but the present invention is not limited thereto.

Also, it is obvious that, in addition to the above-described exemplary principle, various principles for measuring oxygen saturation levels with light are applicable.

Figure 10:
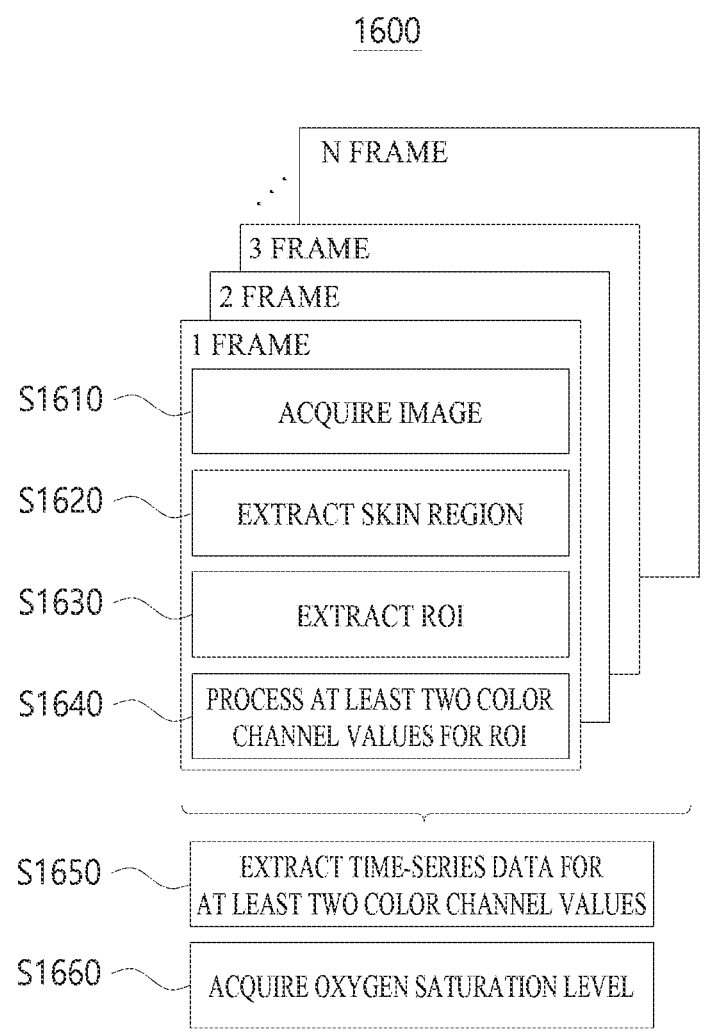
FIG. 10 is a flowchart illustrating an oxygen saturation level measurement method according to an embodiment.

FIG. 10 is a flowchart illustrating an oxygen saturation level measurement method according to an embodiment.

Referring to FIG. 10, an oxygen saturation level measurement method 1600 according to an embodiment may include at least some of an operation of acquiring an image for at least one of a plurality of acquired image frames (S1610), an operation of detecting a skin region (S1620), an operation of detecting an ROI (S1630), and an operation of processing at least two color channel values for the ROI (S1640), but the present invention is not limited thereto.

Also, the operation of acquiring the image (S1610), the operation of detecting the skin region (S1620), and the operation of detecting the ROI (S1630) have been described above, and thus a redundant description thereof will be omitted.

Also, the operation of processing the at least two color channel values for the ROI (S1640) may include the above-described operations for processing the data for the ROI, and thus a redundant description thereof will be omitted.

Also, the two color channels may be selected in consideration of the absorbance of hemoglobin and the absorbance of oxyhemoglobin. For example, when the RGB color space is used, a red channel in which the absorbance of hemoglobin is higher than the absorbance of oxyhemoglobin and a blue channel in which the absorbance of oxyhemoglobin is higher than the absorbance of hemoglobin may be selected, but the present invention is not limited thereto.

Also, the oxygen saturation level measurement method 1600 according to an embodiment may include at least some of an operation of extracting time-series data for the at least two color channel values for an image frame group including at least some of the plurality of acquired image frames (S1650) and acquiring an oxygen saturation level (S1660), but the present invention is not limited thereto.

Also, the operation of extracting the time-series data for the at least two color channel values (S1650) may be performed on the image frame group including the at least some of the plurality of acquired image frames.

In this case, the image frame group may be a group of a plurality of consecutive or nonconsecutive image frames. For example, the image frame group may refer to a group of consecutive image frames starting from a first image frame up to a $180^{th}$ image frame. However, the present invention is not limited thereto, and the image frame group may refer to a group of at least some of the image frames starting from the first image frame up to the $180^{th}$ image frame.

Also, the operation of acquiring the oxygen saturation level (S1660) may be performed on the image frame group including at least some of the plurality of acquired image frames.

In this case, an alternating current (AC) component and a direct current (DC) component of the at least two acquired pieces of time-series data may be used to acquire the oxygen saturation level. In this case, the AC component may refer to a difference between the maximum value and the minimum value of the time-series data and also may refer to a difference between the mean of maximum values and the mean of minimum values. However, the present invention is not limited thereto, and the AC component may be understood as a typical AC component. Also, the DC component may be understood as an average value of time-series data. However, the present invention is not limited thereto, and the DC component may be understood as a typical DC component.

Also, an equation may be used to acquire the oxygen saturation level.

For example, when it is assumed that the absorbance of oxyhemoglobin in the red channel is $\varepsilon_1$, that the absorbance of hemoglobin in the red channel is $\varepsilon_2$, that the absorbance of oxyhemoglobin in the blue channel is $\varepsilon_3$, that the absorbance of hemoglobin in the blue channel is $\varepsilon_4$, and that the proportion of oxyhemoglobin is S, Equation 2 may be obtained as follows:

$$\frac{S*\varepsilon_3 + (1-S)*\varepsilon_4}{S*\varepsilon_1 + (1-S)*\varepsilon_2} = \frac{AC_{Blue}/DC_{Blue}}{AC_{Red}/DC_{Red}}. \quad \text{[Equation 2]}$$

Here, the oxygen saturation level may be represented as S*100(%), but the present invention is not limited thereto.

Also, it is obvious that various equations, other than the above-described exemplary equation for obtaining an oxygen saturation level using at least two color channel values, are possible.

Also, the oxygen saturation level may be acquired based on one oxygen saturation level and may be acquired based on at least two oxygen saturation levels. For example, one oxygen saturation level may be acquired based on at least two pieces of time-series data, another oxygen saturation level may be acquired based on at least two other pieces of time-series data. A final oxygen saturation level may be acquired based on at least two acquired oxygen saturation levels, but the present invention is not limited thereto.

Also, the finally acquired oxygen saturation level and an oximeter may be used to more accurately acquire the oxygen saturation level.

Figure 11:
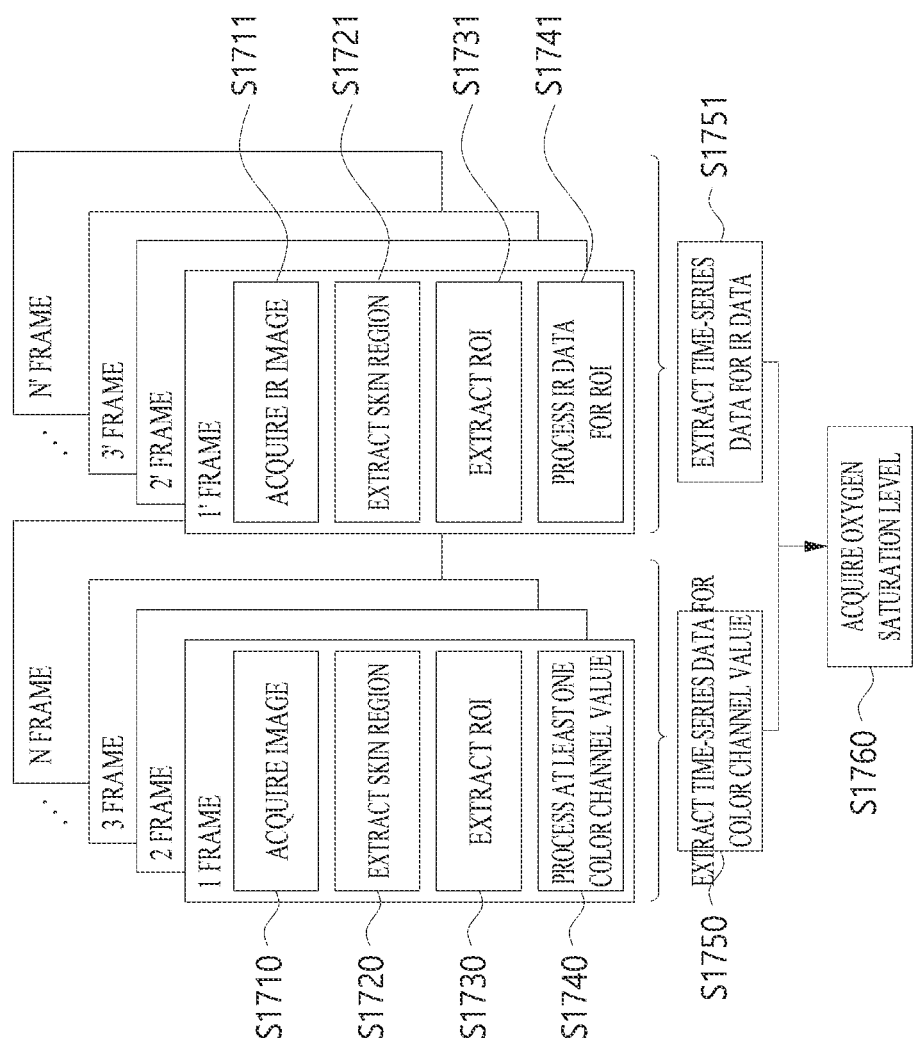
FIG. 11 is a flowchart illustrating an oxygen saturation level measurement method according to another embodiment.

FIG. 11 is a flowchart illustrating an oxygen saturation level measurement method according to another embodiment.

Referring to FIG. 11, an oxygen saturation level measurement method 1700 according to an embodiment may include at least some of an operation of acquiring an image for at least one of a plurality of acquired image frames (S1710), an operation of detecting a skin region (S1720), an operation of detecting an ROI (S1730), and an operation of processing at least one color channel value for the ROI (S1740), but the present invention is not limited thereto.

Also, a plurality of infrared (IR) image frames may be acquired through the oxygen saturation level measurement method 1700 according to an embodiment. The oxygen saturation level measurement method 1700 may include at least some of an operation of acquiring an IR image for at least one of the acquired IR image frames (S1711), an operation of detecting a skin region (S1721), an operation of detecting an ROI (S1731), and an operation of processing IR data for the ROI (S1751), but the present invention is not limited thereto.

Also, the operation of acquiring the image (S1710, S1711), the operation of detecting the skin region (S1720, S1721), and the operation of detecting the ROI (S1730, S1731) have been described above, and thus a redundant description thereof will be omitted.

Also, the operation of processing the at least one color channel value for the ROI (S1740) and the operation of processing the IR data for the ROI (S1741) may include the above-described operations for processing the data for the ROI, and thus a redundant description thereof will be omitted.

Also, the at least one color channel value and the wavelength range of the IR may be selected in consideration of the absorbance of hemoglobin and the absorbance of oxyhemoglobin. For example, when the RGB color space is used, a red channel in which the absorbance of hemoglobin is higher than the absorbance of oxyhemoglobin may be selected, and an 880-nm IR wavelength range in which the absorbance of oxyhemoglobin is higher than the absorbance of hemoglobin may be selected, but the present invention is not limited thereto.

Also, the oxygen saturation level measurement method 1700 according to an embodiment may include at least some of an operation of extracting time-series data for a color channel value for an image frame group including at least some of the plurality of acquired image frames (S1750), an operation of extracting time-series data for the IR data (S1751), and an operation of acquiring an oxygen saturation level (S1760), but the present invention is not limited thereto.

Also, the above-described operations for extracting the time-series data are applicable to the operation of extracting the time-series data for the color channel value (S1750) and the operation of extracting the time-series data for the IR data (S1751), and thus a redundant description thereof will be omitted.

Also, the operation of acquiring the oxygen saturation level (S1760) may be performed on the image frame group including at least some of the plurality of acquired image frames and the IR image frame group including at least some of the plurality of acquired IR image frames.

In this case, the image frame group including at least some of the plurality of acquired image frames may be identical to or different from the IR image frame group including at least some of the plurality of acquired IR image frames.

For example, the image frame group and the IR image frame group may be different from each other when the image frames and the IR image frames are acquired in different sequences, and the image frame group and the IR image frame group may be identical to each other when the image frames and the IR image frames are acquired in the same sequence.

Also, an equation may be used to acquire the oxygen saturation level.

For example, when it is assumed that the absorbance of oxyhemoglobin in the red channel is $\varepsilon_1$, that the absorbance of hemoglobin in the red channel is $\varepsilon_2$, that the absorbance of oxyhemoglobin in a wavelength of 880 nm is $\varepsilon_3$, that the absorbance of hemoglobin oxyhemoglobin in a wavelength of 880 nm is $\varepsilon_4$, and that the proportion of oxyhemoglobin is S, Equation 3 may be obtained as follows:

$$\frac{S*\varepsilon_3 + (1-S)*\varepsilon_4}{S*\varepsilon_1 + (1-S)*\varepsilon_2} = \frac{AC_{880\,nm}/DC_{880\,nm}}{AC_{Red}/DC_{Red}}. \quad \text{[Equation 3]}$$

Here, the oxygen saturation level may be represented as S*100(%), but the present invention is not limited thereto.

Also, it is obvious that various equations other than the above-described exemplary equation for obtaining an oxygen saturation level using at least one color channel value and IR data are available.

Also, the oxygen saturation level may be acquired based on one oxygen saturation level and may be acquired based on at least two oxygen saturation levels. For example, one oxygen saturation level may be acquired based on at least two pieces of time-series data, another oxygen saturation level may be acquired based on at least two other pieces of time-series data. A final oxygen saturation level may be acquired based on at least two acquired oxygen saturation levels, but the present invention is not limited thereto.

Also, the finally acquired oxygen saturation level and oximeter may be used to more accurately acquire the oxygen saturation level.

4.3 Various Embodiments of Blood Pressure Measurement Method

Blood pressure may refer to a pressure that blood flowing through a blood vessel exerts against the wall of the blood vessel.

Accordingly, the blood pressure may be affected by the speed of blood flow, the thickness of the blood vessel wall, and waste products accumulated in blood vessels.

Also, when blood flows through a blood vessel, the volume of the blood vessel may change, and the amount of blood contained in the blood vessel may change.

Accordingly, when a rate of change in the volume of the blood vessel and a rate of change in the amount of blood are measured, the blood pressure may be acquired.

For example, when a change in a blood vessel is measured at two points at different distances from a heart, a blood pressure may be obtained based on a difference between the changes at the two points in the blood vessel, and a blood pressure may be obtained by extracting a feature that can represent a change with time in the blood vessel, but the present invention is not limited thereto.

Also, it is obvious that, in addition to the above-described exemplary principle, various principles for measuring blood pressures with light are applicable.

Figure 12:
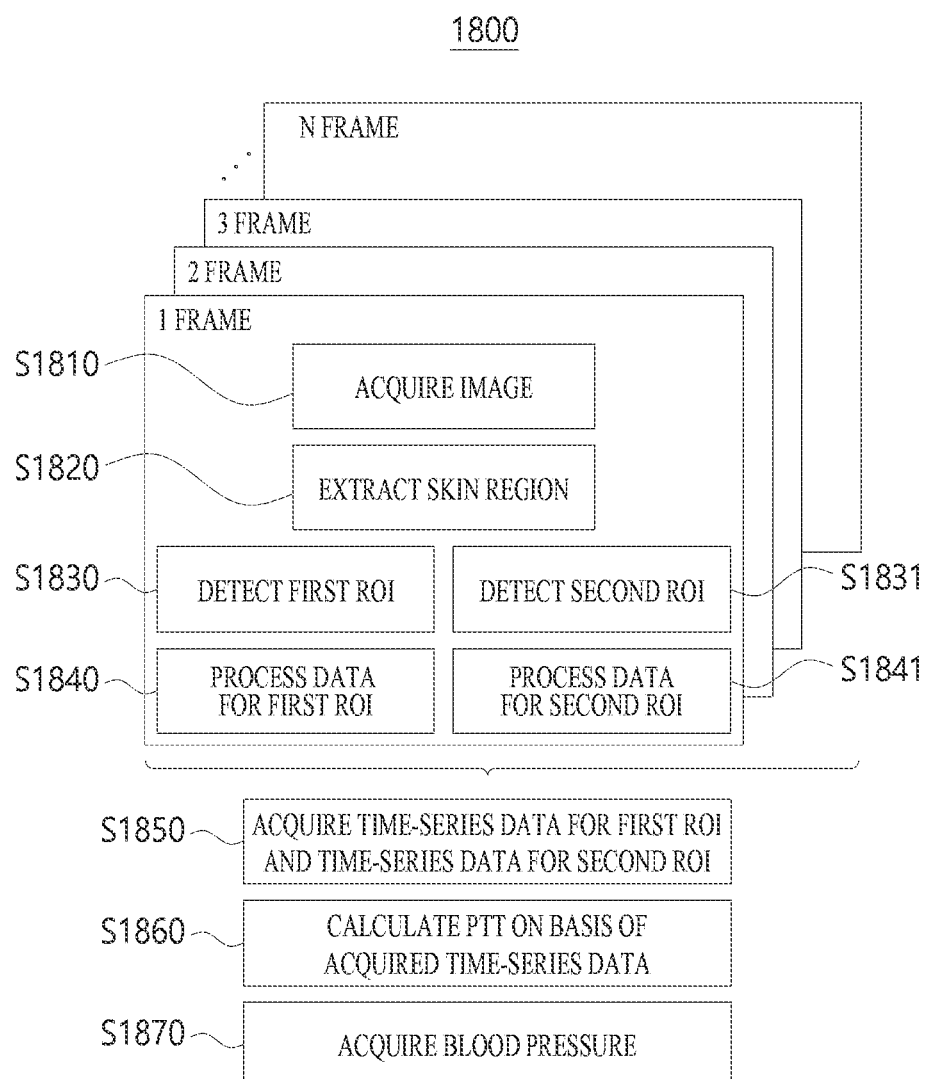
FIG. 12 is a flowchart illustrating a blood pressure measurement method according to an embodiment.

FIG. 12 is a flowchart illustrating a blood pressure measurement method according to an embodiment.

Referring to FIG. 12, a blood pressure measurement method 1800 according to an embodiment may include at least some of an operation of acquiring an image for at least one of a plurality of acquired image frames (S1810), an operation of detecting a skin region (S1820), an operation of detecting a first ROI (S1830), an operation of detecting a second ROI (S1831), an operation of processing data for the first ROI (S1840), and an operation of processing data for the second ROI (S1841), but the present invention is not limited thereto.

Also, the operation of acquiring the image (S1810) and the operation of detecting the skin region (S1820) have been described above, and thus a redundant description thereof will be omitted.

Also, the operation of detecting the first ROI (S1830) and the operation of detecting the second ROI (S1831) have been described in detail above, and thus a redundant description thereof will be omitted.

In this case, the first ROI and the second ROI may be set as two regions at different distances from a subject's heart. For example, the first ROI may be set as an upper region of the subject's face, and the second ROI may be set as a lower region of the subject's face, but the present invention is not limited thereto. The first ROI may be set as a face region of the subject, and the second ROI may be set as a back-of-hand region of the subject.

Also, the operation of processing the data for the first ROI (S1840) and the operation of processing the data for the second ROI (S1841) may include the above-described operations for processing the data for the ROI, and thus a redundant description thereof will be omitted.

Also, the blood pressure measurement method 1800 according to an embodiment may include at least some of an operation of extracting time-series data for the first ROI and time-series data for the second ROI for an image frame group including at least some of the plurality of acquired image frames (S1850), calculating a pulse transit time (PTT) on the basis of the acquired time-series data (S1860), and acquiring a blood pressure (S1870), but the present invention is not limited thereto.

Also, the above-described operations for extracting the time-series data are applicable to the operation of extracting the time-series data for the first ROI and the second ROI (S1850), and thus a redundant description thereof will be omitted.

Also, the operation of calculating the PTT on the basis of the acquired time-series data (S1860) may be performed on an image frame group including at least some of the plurality of acquired image frames.

In this case, the PTT may be calculated based on local extremum values of the time-series data for the first ROI and the time-series data for the second ROI. For example, the PTT may be calculated based on the time difference between a local maximum value of the time-series data for the first ROI and a local maximum value of the time-series data for the second ROI. However, the present invention is not limited thereto, and the PTT may be calculated based on the time difference between a local minimum value of the time-series data for the first ROI and a local minimum value of the time-series data for the second ROI.

Also, the PTT may be calculated based on inflection points of the time-series data for the first ROI and the time series data for the second ROI. For example, the PTT may be calculated based on the time difference between the inflection point of the time-series data for the first ROI and the inflection point of the time-series data for the second ROI, but the present invention is not limited thereto.

Also, the PTT may be calculated based on various points of the time-series data for each ROI other than the local extremism values and the inflection points.

Also, the time difference between the time-series data for the first ROI and the time-series data for the second ROI may be calculated based on frames acquired at points such as the local extremum values and the inflection points. For example, when a local maximum value is acquired at a tenth frame in the time-series data for the first ROI and a local maximum value is acquired at a twelfth frame in the time-series data for the second ROI, the time difference between the time-series data for the first ROI and the time series data for the second ROI may be the time required to acquire two frames, and the PTT may be calculated based on the time difference.

Also, the operation of acquiring the blood pressure (S1870) may be performed on the image frame group including at least some of the plurality of acquired image frames.

Also, the PTT may be used to acquire the blood pressure. For example, a function for the PTT may be used to acquire the blood pressure. In detail, a function such as Equation 4 is available, and various functions, such as a linear function, a quadratic function, a logarithmic function, and an exponential function, which have the PTT as a variable are available, but the present invention is not limited thereto.

$$BP=f(PTT) \quad \text{[Equation 4]}$$

Also, the PTT and personal statistical data may be used to acquire the blood pressure. For example, a function for the PTT and a function for the personal statistical data such as age, weight, and height may be used to acquire the blood pressure. In detail, Equation 5 below is available, and various functions, such as a linear function, a quadratic function, a logarithmic function, and an exponential function, which have the PTT, the weight, the height, and the age as variables are available, but the present invention is not limited thereto.

$$BP=af_1(\text{weight})+bf_2(\text{height})+cf_3(\text{age})+df_4(PTT) \quad \text{[Equation 5]}$$

Also, a regression analysis method using the above-described function may be used to acquire the blood pressure, but the present invention is not limited thereto.

Also, a machine learning method using the above-described function may be used to acquire the blood pressure, but the present invention is not limited thereto.

Also, it is obvious that various equations other than the above-described exemplary equation for obtaining a blood pressure using a PTT are available.

Also, the blood pressure may be acquired based on one blood pressure and may be acquired based on at least two blood pressures. For example, one blood pressure may be acquired based on a first PTT calculated based on time-series data for the first ROI and the second ROI, and another blood pressure may be acquired based on a second PTT calculated based on other time-series data for the first ROI and the second ROI. A final blood pressure may be acquired based on at least two acquired blood pressures, but the present invention is not limited thereto.

Figure 13:
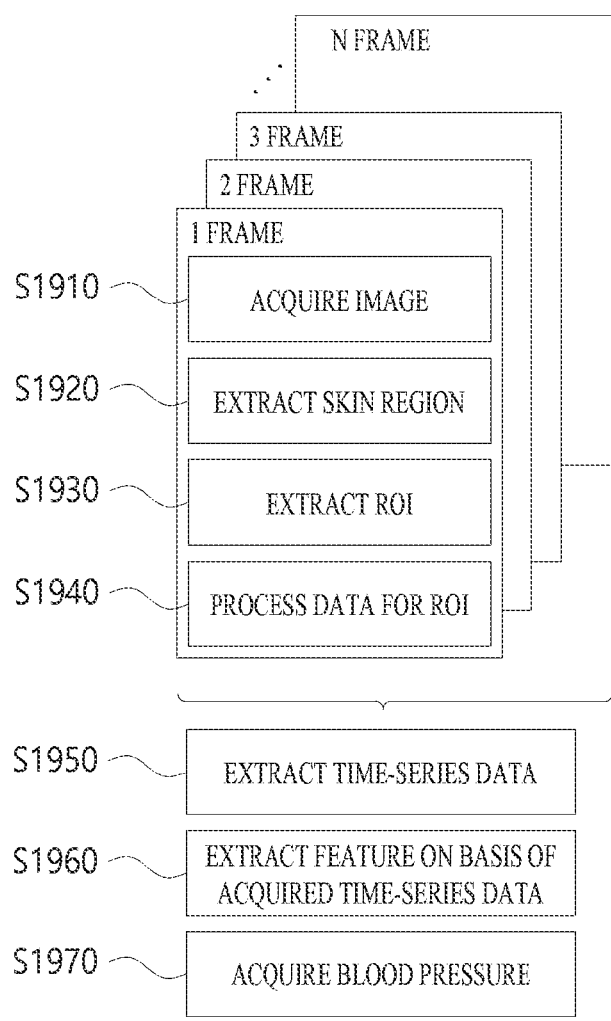
FIG. 13 is a flowchart illustrating a blood pressure measurement method according to another embodiment.

FIG. 13 is a flowchart illustrating a blood pressure measurement method according to another embodiment.

Referring to FIG. 13, a blood pressure measurement method 1900 according to an embodiment may include at least some of an operation of acquiring an image for at least one of a plurality of acquired image frames (S1910), an operation of detecting a skin region (S1920), an operation of detecting an ROI (S1930), and an operation of processing data for the ROI (S1940), but the present invention is not limited thereto.

In this case, the operation of acquiring the image (S1910), the operation of detecting the skin region (S1920), the operation of detecting the ROI (S1930), and the operation of processing data for the ROI (1940) have been described above, and thus a redundant description thereof will be omitted.

Also, the blood pressure measurement method 1900 according to an embodiment may include at least some of an operation of extracting time-series data for an image frame group including at least some of the plurality of acquired image frames (S1950), an operation of extracting a feature on the basis of the acquired time-series data (S1960), and an operation of acquiring a blood pressure (S1970), but the present invention is not limited thereto.

Also, the above-described operations for extracting the time-series data are applicable to the operation of extracting the time-series data (S1950), and thus a redundant description thereof will be omitted.

Also, the operation of extracting the feature on the basis of the acquired time-series data (S1960) may be performed on the image frame group including the at least some of the plurality of acquired image frames.

In this case, the feature may refer to a mathematical or physical feature of the acquired time-series data. For example, the feature may refer to a mathematical feature of the acquired time-series data such as a local maximum value, the mean of local maximum values, a local minimum value, the mean of local minimum values, a difference between a local maximum value and a local minimum value, an average, an inflection point, first-order differential data, second-order differential data, and a slope at a specific point or a physical feature of the acquired time-series data such as a blood variation, a blood change rate, a blood vessel variation, and a blood vessel change rate, but the present invention is not limited thereto.

Also, it is obvious that the feature may include various features for acquiring a blood pressure in addition to the above-described exemplary features.

Also, the operation of acquiring the blood pressure (S1970) may be performed on the image frame group including at least some of the plurality of acquired image frames.

Also, the feature may be used to acquire the blood pressure. For example, a function for the feature may be used to acquire the blood pressure. In detail, a function such as Equation 6 is available, and various functions, such as a linear function, a quadratic function, a logarithmic function, and an exponential function, which have the feature as a variable are available, but the present invention is not limited thereto.

$$BP=f(\text{feature}) \quad \text{[Equation 6]}$$

Also, the feature and personal statistical data may be used to acquire the blood pressure. For example, a function for the feature and a function for the personal statistical data such as age, weight, and height may be used to acquire the blood pressure. In detail, Equation 7 below is available, and various functions, such as a linear function, a quadratic function, a logarithmic function, and an exponential function, which have the feature, the weight, the height, and the age as variables are available, but the present invention is not limited thereto.

$$BP = af_1(\text{weight}) + bf_2(\text{height}) + cf_3(\text{age}) + df_4(\text{feature}) \quad [\text{Equation 7}]$$

Also, a regression analysis method using the above-described function may be used to acquire the blood pressure, but the present invention is not limited thereto.

Also, a machine learning method using the above-described function may be used to acquire the blood pressure, but the present invention is not limited thereto.

Also, it is obvious that in addition to the above-described exemplary equation, an equation for obtaining a blood pressure using a feature is available.

Also, the blood pressure may be acquired based on one blood pressure and may be acquired based on at least two blood pressures. For example, one blood pressure may be acquired based on a first feature calculated based on time-series data, and another blood pressure may be acquired based on a second feature calculated based on other time-series data. A final blood pressure may be acquired based on at least two acquired blood pressures, but the present invention is not limited thereto.

4.4 Various Embodiments of Core Temperature Measurement Method

Figure 14:
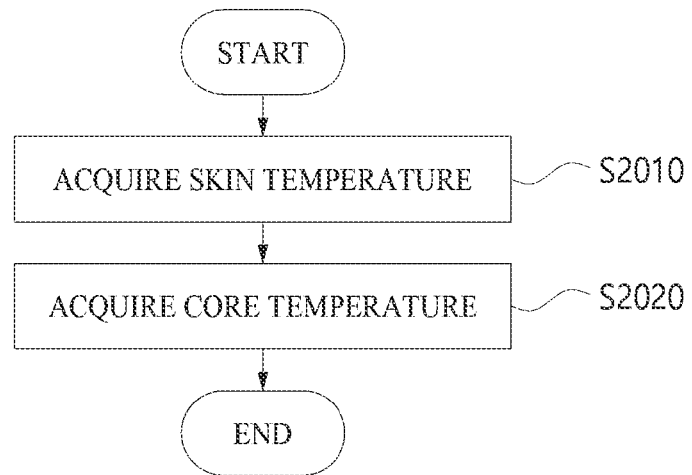
FIG. 14 is a flowchart strafing a core temperature measurement method according to an embodiment.

FIG. 14 is a flowchart illustrating a core temperature measurement method according to an embodiment.

Referring to FIG. 14, a core temperature measurement method 2000 according to an embodiment may include at least some of an operation of acquiring a skin temperature (S2010) and an operation of acquiring a core temperature (S2020), but the present invention is not limited thereto.

Also, the operation of acquiring the skin temperature (S2010) may be performed in a contactless manner.

For example, an image sensor such as a camera may be used to acquire the skin temperature. In detail, at least one color channel value of an image acquired from the image sensor such as a camera may be used to acquire the skin temperature. As an example, when the HSV color space is used, the skin temperature may be acquired using a saturation (S) value, but the present invention is not limited thereto.

Also, for example, a sensor such as a thermal imaging camera may be used to acquire the skin temperature. An image sensor such as an infrared camera is available, but the present invention is not limited thereto.

Also, the operation of acquiring the core temperature (S2020) may be performed in a contactless manner.

For example, the skin temperature may be used to acquire the core temperature. In detail, the core temperature may be acquired based on the skin temperature using the relationship between the core temperature and a portion where the skin temperature is measured.

In this case, the skin temperature may be acquired in the operation of acquiring the skin temperature (S2010) and may also be acquired by another external sensor.

Also, for example, an image sensor such as a camera may be used to acquire the core temperature. In detail, an image acquired by an image sensor such as a camera may be used to acquire the skin temperature. As an example, the core temperature may be acquired by applying the image acquired by the image sensor such as a camera to a machine learning model for core temperature measurement as data, but the present invention is not limited thereto.

A method of acquiring a skin temperature and a method of acquiring a core temperature will be described in detail below.

First, a method of acquiring a skin temperature using an image sensor such as a camera will be described.

According to an embodiment, a brightness value of an acquired image may be used to acquire a skin temperature. For example, a function for the brightness value may be used to acquire the skin temperature. In detail, Equation 8 below is available, and various functions, such as a linear function, a quadratic function, a logarithmic function, and an exponential function, which have the brightness value as a variable are available, but the present invention is not limited thereto.

$$\text{Skin Temperature} = Af_1(S) \quad [\text{Equation 8}]$$

Also, according to an embodiment, a brightness value of an acquired image and personal statistical data may be used to acquire a skin temperature. For example, a function for the brightness value and a function for the personal statistical data such as age, race, and gender may be used to acquire the skin temperature. In detail, Equation 9 below is available, and various functions, such as a linear function, a quadratic function, a logarithmic function, and an exponential function, which have the brightness value, the age, the race, and the gender as variables are available, but the present invention is not limited thereto.

$$\text{Skin Temperature} = Af_1(S) + Bf_2(\text{age}) + Cf_3(\text{race}) + Df_4(\text{gender}) \quad [\text{Equation 9}]$$

Also, according to an embodiment, a brightness value and a hue value of an acquired image may be used to acquire a skin temperature. For example, a function for the brightness value and a function for the hue value may be used to acquire the skin temperature. In detail. Equation 10 below is available, and various functions, such as a linear function, a quadratic function, a logarithmic function, and an exponential function, which have the brightness value and the hue value as variables are available, but the present invention is not limited thereto.

$$\text{Skin Temperature} = Af_1(S) + Bf_2(H) \quad [\text{Equation 10}]$$

Also, according to an embodiment, a brightness value and a hue value of an acquired image and personal statistical data may be used to acquire a skin temperature. For example, a function for the brightness value, a function for the hue value, and a function for the personal statistical data such as age, race, and gender may be used to acquire the skin temperature. In detail, Equation 11 below is available, and various functions, such as a linear function, a quadratic function, a logarithmic function, and an exponential function, which have the brightness value, the hue value, the age, the race, and the gender as variables are available, but the present invention is not limited thereto.

$$\text{Skin Temperature} = Af_1(S) + Bf_2(H) + Cf_3(\text{age}) + Df_4(\text{race}) + Ef_5(\text{gender}) \quad [\text{Equation 11}]$$

Also, according to an embodiment, a brightness value, a hue value, and a brightness variation of an acquired image may be used to acquire a skin temperature. For example, a function for the brightness value, a function for the hue value, and a function for the brightness variation may be used to acquire the skin temperature. In detail, Equation 12 below is available, and various functions, such as a linear function, a quadratic function, a logarithmic function, and an exponential function, which have the brightness value, the hue value, and the brightness variation as variables are available, but the present invention is not limited thereto. Also, when such a variation is used, it is possible to reduce measurement noise caused by an external environment.

$$\text{Skin Temperature} = Af_1(S) + Bf_2(H) + Cf_3(\Delta S) \quad \text{[Equation 12]}$$

Also, according to an embodiment, a brightness value, a hue value, and a brightness variation of an acquired image and personal statistical data may be used to acquire a skin temperature. For example, a function for the brightness value, a function for the hue value, a function for the brightness variation, and a function for the personal statistical data such as age, race, and gender may be used to acquire the skin temperature. In detail, Equation 13 below is available, and various functions, such as a linear function, a quadratic function, a logarithmic function, and an exponential function, which have the brightness value, the hue value, the brightness variation, the age, the race, and the gender as variables are available, but the present invention is not limited thereto.

$$\text{Skin Temperature} = Af_1(S) + Bf_2(H) + Cf_3(\Delta S) + Df_4(\text{age}) + Ef_5(\text{race}) + Ff_6(\text{gender}) \quad \text{[Equation 13]}$$

Also, according to an embodiment, a brightness value, a hue value, a brightness variation, and a hue variation of an acquired image may be used to acquire a skin temperature. For example, a function for the brightness value, a function for the hue value, a function for the brightness variation, and a function for the hue variation may be used to acquire the skin temperature. In detail, Equation 14 below is available, and various functions, such as a linear function, a quadratic function, a logarithmic function, and an exponential function, which have the brightness value, the hue value, the brightness variation, and the hue variation as variables are available, but the present invention is not limited thereto. Also, when such a variation is used, it is possible to reduce measurement noise caused by an external environment.

$$\text{Skin Temperature} = Af_1(S) + Af_2(H) + Cf_3(\Delta S) + Df_4(\Delta H) \quad \text{[Equation 14]}$$

Also, according to an embodiment, a brightness value, a hue value, a brightness variation, and a hue variation of an acquired image and personal statistical data may be used to acquire a skin temperature. For example, a function for the brightness value, a function for the hue value, a function for the brightness variation, a function for the hue variation, and a function for the personal statistical data such as age, race, and gender may be used to acquire the skin temperature. In detail, Equation 15 below is available, and various functions, such as a linear function, a quadratic function, a logarithmic function, and an exponential function, which have the brightness value, the hue value, the brightness variation, the hue variation, the age, the race, and the gender as variables are available, but the present invention is not limited thereto.

$$\text{Skin Temperature} = Af_1(S) + Bf_2(H) + Cf_3(\Delta S) + Df_4(\Delta H) + Ef_5(\text{age}) + Ff_6(\text{race}) + Gf_7(\text{gender}) \quad \text{[Equation 15]}$$

Also, a regression analysis method using the above-described function may be used to acquire the skin temperature, but the present invention is not limited thereto.

Also, a deep learning method or a machine learning method using the above-described function may be used to acquire the skin temperature, but the present invention is not limited thereto.

Also, it is obvious that various equations other than the above-described exemplary equation are available. For example, an equation using at least some of the brightness value, the hue value, the brightness variation, the hue variation, and the personal statistical data such as age, race, and gender is available, and also an equation using other data is available.

Subsequently, a method of acquiring a core temperature using an image sensor such as a camera will be described.

According to an embodiment, an acquired skin temperature may be used to acquire a core temperature. For example, a function for the skin temperature may be used to acquire the core temperature. In detail, Equation 16 below is available, and various functions, such as a linear function, a quadratic function, a logarithmic function, and an exponential function, which have the skin temperature as a variable are available, but the present invention is not limited thereto.

$$\text{Core Temperature} = Af(\text{Skin Temp.}) \quad \text{[Equation 16]}$$

According to an embodiment, when a core temperature is acquired indoors, the acquired skin temperature and indoor temperature may be used to acquire the core temperature. For example, a function for the skin temperature and a function for the indoor temperature may be used to acquire the core temperature. In detail, Equation 17 below is available, and various functions, such as a linear function, a quadratic function, a logarithmic function, and an exponential function, which have the skin temperature and the indoor temperature as variables are available, but the present invention is not limited thereto.

$$\text{Core Temperature} = Af(\text{Skin Temp.}) + Bf(\text{Room Temp.}) \quad \text{[Equation 17]}$$

Also, according to an embodiment, when a core temperature is acquired indoors, the acquired skin temperature and indoor temperature and a heart rate may be used to acquire the core temperature. For example, a function for the skin temperature, a function for the indoor temperature, and a function for the heart rate may be used to acquire the core temperature. In detail, Equation 18 below is available, and various functions, such as a linear function, a quadratic function, a logarithmic function, and an exponential function, which have the skin temperature, the indoor temperature, and the heart rate as variables are available, but the present invention is not limited thereto.

$$\text{Core Temperature} = Af(\text{Skin Temp.}) + Bf(\text{Room Temp.}) + Cf(\text{Heartrate}) \quad \text{[Equation 18]}$$

Also, according to an embodiment, various skin temperatures may be used at the same time. For example, when a core temperature is acquired indoors, a first skin temperature acquired at a first body part, a second skin temperature acquired at a second body part, an acquired indoor temperature, and an acquired heart rate may be used to acquire the core temperature. For example, a function for the first skin temperature, a function for the second skin temperature, a function for the indoor temperature, and a function for the heart rate may be used to acquire the core temperature. In detail, Equation 19 below is available, and various functions, such as a linear function, a quadratic function, a logarithmic function, and an exponential function, which have the first skin temperature, the second skin temperature, the indoor temperature, and the heart rate as variables are available, but the present invention is not limited thereto.

$$\text{Core Temperature} = Af(\text{Skin Temp.1}) + Bf(\text{Skin Temp.2}) + Cf(\text{Room Temp.}) + df(\text{Heartrate}) \quad \text{[Equation 19]}$$

Also, a regression analysis method using the above-described function may be used to acquire the core temperature, but the present invention is not limited thereto.

Also, a deep learning method or a machine learning method using the above-described function may be used to acquire the core temperature, but the present invention is not limited thereto.

Also, it is obvious that various equations other than the above-described exemplary equation are available. For example, an equation using at least some of the first skin temperature, the second skin temperature, the indoor temperature, and the heart rate is available, and also an equation using personal statistical data such as age, gender, race, height, and weight is available.

5. Various Embodiments of Heart Rate Measurement Method

Figure 15:
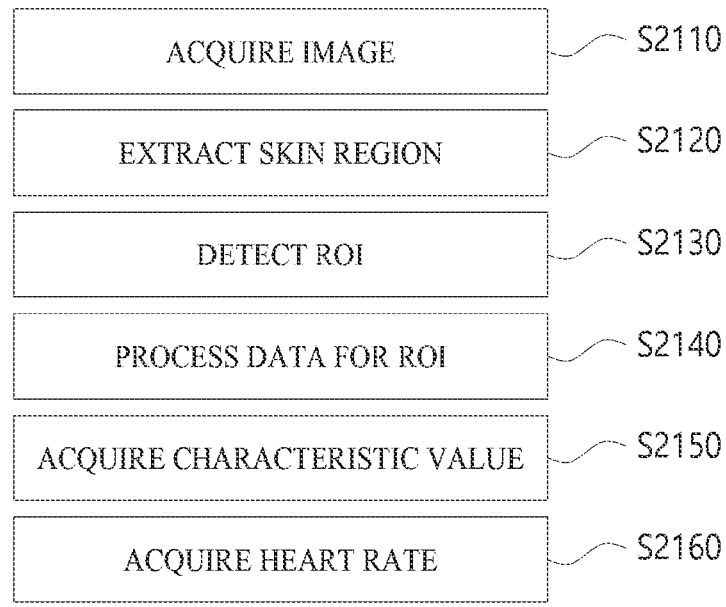
FIG. 15 is a flowchart illustrating a heart rate acquisition method according to an embodiment.

FIG. 15 is a flowchart illustrating a heart rate acquisition method according to an embodiment.

Referring to FIG. 15, a heart rate acquisition method 2100 according to an embodiment may include at least some of an operation of acquiring an image (S2110), an operation of detecting a skin region (S2120), an operation of detecting an ROI (S2130), an operation of processing data for the ROI (S2140), an operation of acquiring a characteristic value (S2150), and an operation of acquiring a heart rate (S2160), but the present invention is not limited thereto.

In this case, the operation of acquiring the image (S2110), the operation of detecting the skin region (S2120), and the operation of detecting the ROI (S2130) have been described above, and thus a redundant description thereof will be omitted.

Also, the operation of processing the data for the ROI (S2140) may be performed on at least one of a plurality of acquired image frames.

Also, the operation of processing the data for the ROI (S2140) may be performed to reduce noise caused by motion (motion artifact), noise caused by external light, or the like.

Also, the operation of acquiring the characteristic value (S2150) may be performed on an image frame group including at least some of the plurality of acquired image frames.

Also, the operation of acquiring the characteristic value (S2150) may be performed to reduce noise caused by motion, noise caused by external light, or the like.

Also, the operation of acquiring the heart rate (S2160) may be performed on an image frame group including at least some of the plurality of acquired image frames.

In this case, the image frame group for acquiring the heart rate may be identical to or different from the image frame group for acquiring the characteristic value. For example, the image frame group for acquiring the characteristic value may include 18 image frames, and the image frame group for acquiring the heart rate may include 180 image frames, but the present invention is not limited thereto.

The operation of processing the data for the ROI (S2140), the operation of acquiring the characteristic value (S2150), and the operation of acquiring the heart rate (S2160) will be described in detail below.

Figure 16:
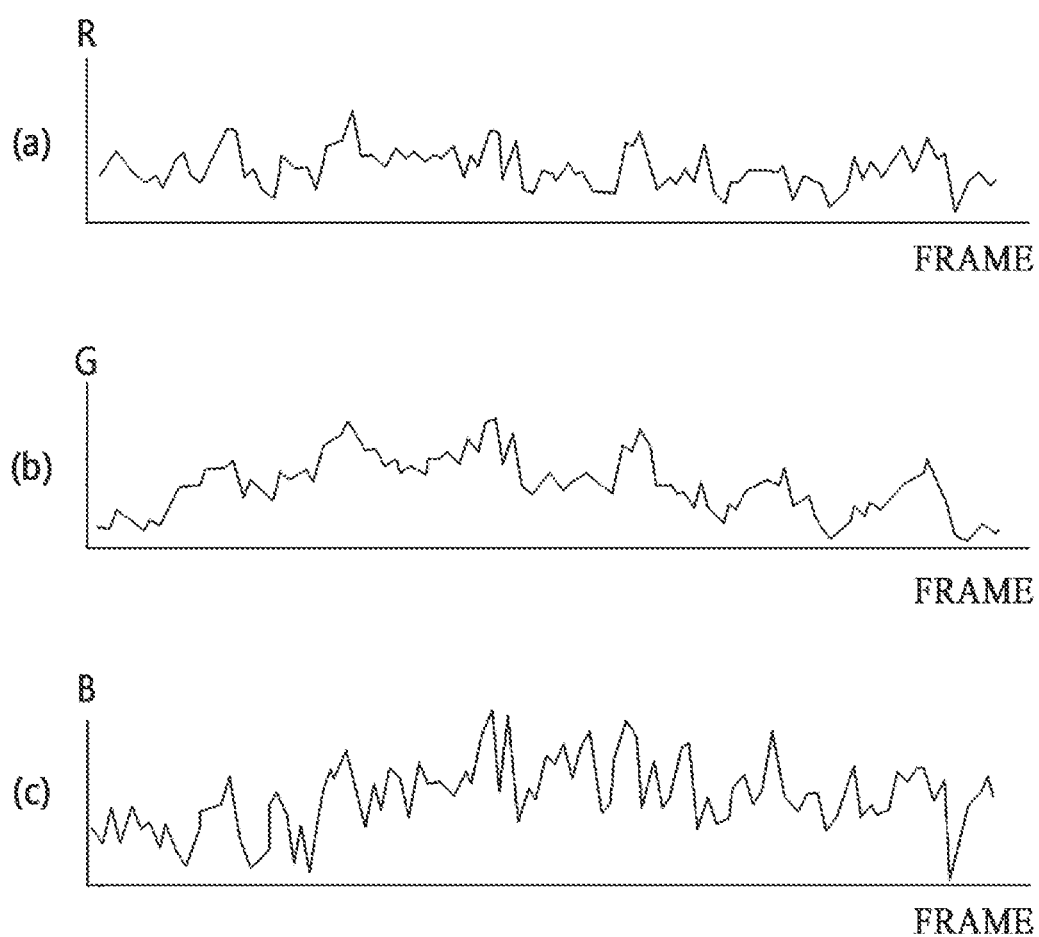
FIG. 16 is a graph of color channel values according to an embodiment.

FIG. 16 is a graph of color channel values according to an embodiment.

According to an embodiment, a color channel value for the ROI may be extracted to process the data for the ROI. In this case, the color channel value may be the mean of color channel values of pixels included in the ROI and may be referred to as an average pixel value.

Referring to FIG. 16, a color channel value for the ROI corresponding to the RGB color space may be extracted to process the data for the ROI. In detail, a red channel value, which is the mean of red channel pixel values, a blue channel value, which is the mean of blue channel pixel values, and a green channel value, which is the mean of green channel pixel values, may be extracted.

For example, when color channel values corresponding to the RGB color space are extracted, a red channel pixel value, a green channel pixel value, and a blue channel pixel value of each pixel included in the ROI may be extracted. A red channel value, which is the mean of red channel pixel values included in the ROI, a blue channel value, which is the mean of blue channel pixel values included in the ROI, and a green channel value, which is the mean of green channel pixel values included in the ROI, may be extracted. However, the present invention is not limited thereto, and color channel values corresponding to various color spaces such as the HSV color space and the YCrCb color space may be extracted.

Also, a color channel value extracted according to a specific color space may be converted into another color space. For example, a color channel value extracted according to the RGB color space may be converted into color channel values corresponding to various color spaces such as the HSV color space and the YCrCb color space.

A color channel value extracted to process the data for the ROI may be a color channel value obtained by weighting at least some of the color channel values extracted according to various color spaces and combining the color channel values.

Also, the color channel value may be extracted for each of a plurality of image frames that are consecutively acquired or may be extracted from at least some of the image frames.

The following description is based on a color channel value extracted according to the RGB color space. However, the present invention is not limited thereto, and it is obvious that various color channel values are available.

FIG. 16A is a graph showing a red channel value extracted according to the RGB color space, FIG. 16B is a graph showing a green channel value extracted according to the RGB color space, and FIG. 16C is a graph showing a blue channel value extracted according to the RCB color space.

As shown in FIG. 16, each color channel value may vary depending on the heartbeat.

However, each color channel value may vary due to subject movement or a change in intensity of external light while varying due to a heartbeat.

Accordingly, in order to acquire a heart rate using an extracted color channel value, there may be a need for an operation of reducing the variation due to subject movement or the variation due to the change in intensity of external light and maximizing the variation due to the heartbeat.

5.1 Various Embodiments of Method of Processing Data for ROI

It is obvious that the above description is applicable to the method of processing the data for the RGI, and thus a redundant description thereof will be omitted.

Figure 17:
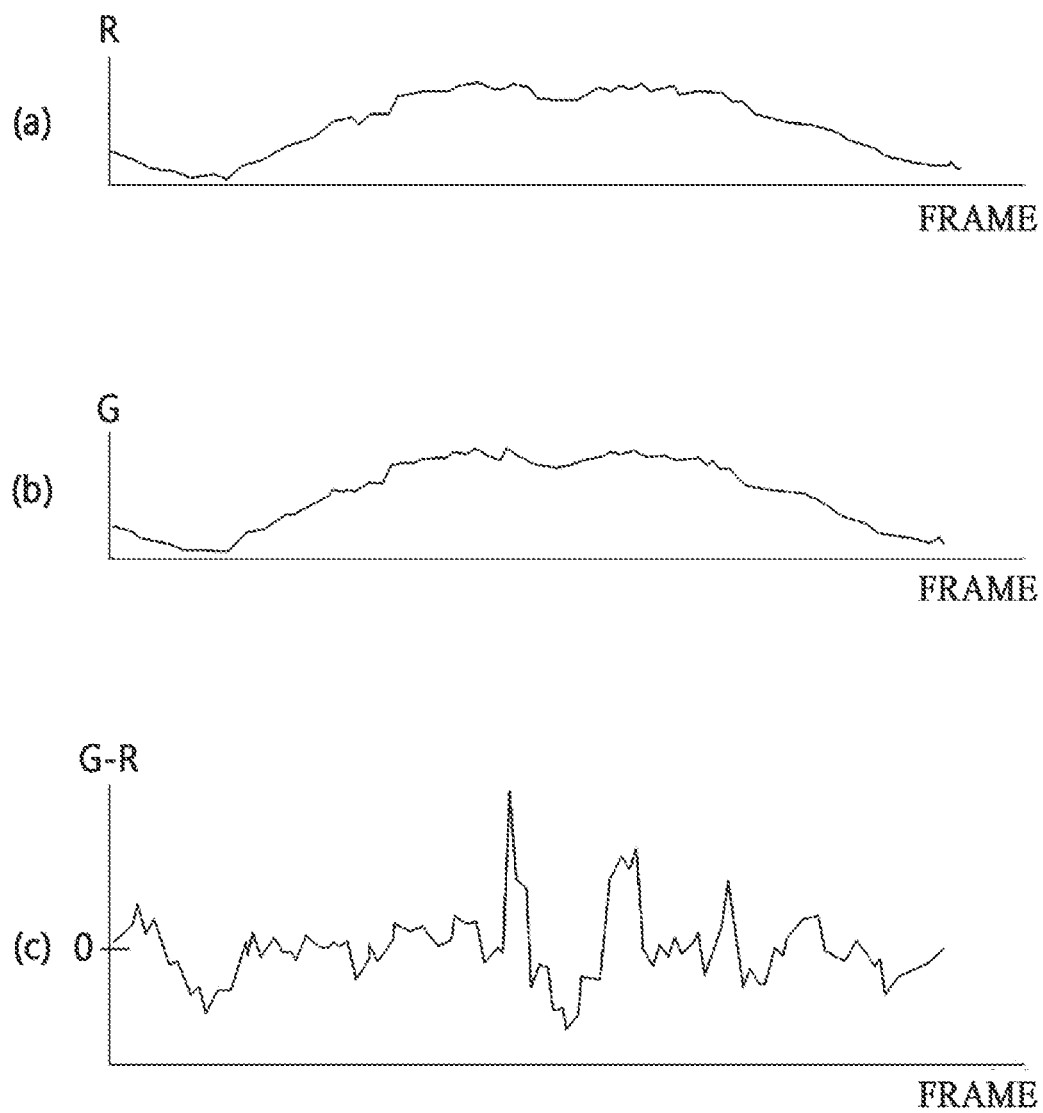
FIG. 17 is a graph showing a noise reduction method according to an embodiment.

FIG. 17 is a graph illustrating a noise reduction method according to an embodiment.

FIG. 17A is a graph showing a red channel value extracted according to the RGB color space, and FIG. 17B is a graph showing a green channel value extracted according to the RGB color space.

Referring to FIGS. 17A and 17B, it can be seen that the extracted color channel values vary with time.

In this case, the extracted color channel values may vary depending on a heartbeat, subject movement, or a change in intensity of external light.

In detail, the variation of the color channel value being large and slow may mean that the variation is more affected by subject movement or a change in intensity of external light, and the variation of the color channel value being small and quick may mean that the variation is more affected by a subject's heartbeat.

Therefore, the variation due to subject movement or the change in intensity of external light are greater than the variation due to the heartbeat, and thus a relative difference between at least two color channel values may be used to reduce the variation.

As an example, a difference between a green channel value and a red channel value may be used to reduce noise. In detail, a green channel value and a red channel value acquired from the same image frame may reflect the same motion and the same intensity of external light. A difference between the green channel value and the red channel value of the same frame may reduce noise due to the subject's motion, the change in intensity of external light, and the like. However, the present invention is not limited thereto, and noise may be reduced using a relative difference between at least two color channel values.

FIG. 17C is a graph showing a difference between the green channel value and the red channel value.

As shown in FIG. 17C, the difference between the green channel value and the red channel value may reduce noise due to subject movement, the change in intensity of external light, and the like.

Also, the above-described noise reduction method may be performed on at least one of a plurality of acquired image frames or may be performed on each of a plurality of consecutive image frames.

Also, although not shown in FIG. 17C, noise may be reduced using a difference between the green channel value and the blue channel value, and noise may be reduced using a difference between the red channel value and the blue channel value.

Also, in order to reduce noise using a relative difference between at least two color channel values as described above, at least two color channel values may be selected to obtain the difference.

In this case, the at least two color channel values may be selected in consideration of the absorbance of blood.

Figure 18:
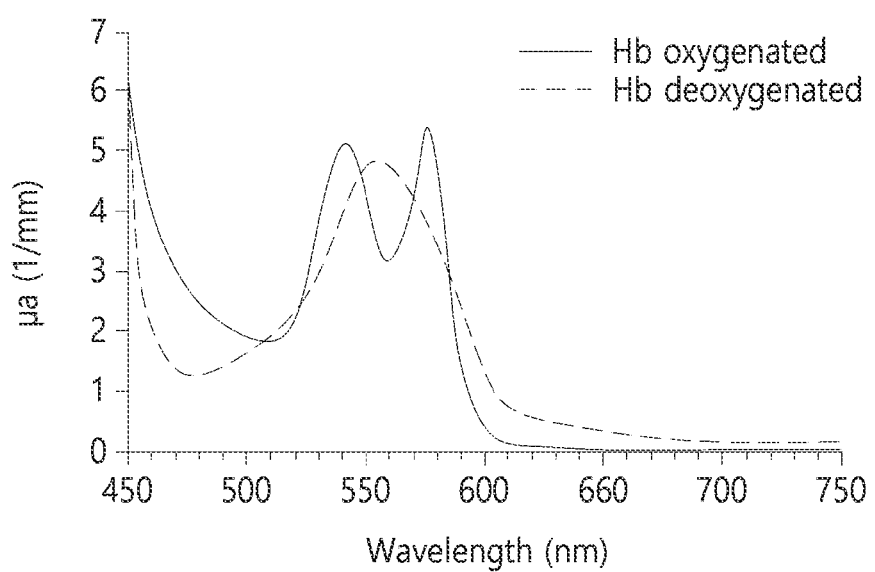
FIG. 18 is a diagram showing the absorbance of hemoglobin and oxyhemoglobin in a visible light range.

FIG. 18 is a diagram showing the absorbance of hemoglobin and oxyhemoglobin in a visible light range.

According to an embodiment, a red channel may be a channel including at least a portion of a wavelength range from 620 nm to 750 nm, a green channel may be a channel including at least a portion of a wavelength range from 495 nm to 570 nm, and a blue channel may be a channel including at least a portion of a wavelength range from 450 nm to 495 nm. However, the present invention is not limited thereto, and each of the red channel, the green channel, and the blue channel may be color channels that are generally understandable.

Referring to FIG. 18, the absorbance of hemoglobin and oxyhemoglobin according to the wavelength range of light can be seen. For example, as shown in FIG. 18, the absorbance of hemoglobin and oxyhemoglobin for light in a wavelength range of 500 nm, which is included in the green channel, may be higher than the absorbance of hemoglobin and oxyhemoglobin for light in a wavelength range of 650 nm, which is included in the red channel.

Also, for example, as shown in FIG. 18, the absorbance of hemoglobin and oxyhemoglobin for light in a wavelength range of 550 nm, which is included in the green channel, may be higher than the absorbance of hemoglobin and oxyhemoglobin for light in a wavelength range of 470 nm, which is included in the blue channel.

Also, when blood is transported throughout a body by a heartbeat, the volume of a blood vessel or the amount of blood contained in a blood vessel may change due to the flow of blood.

Accordingly, a color channel value including a wavelength range of light that is absorbed relatively more by hemoglobin and oxyhemoglobin contained in blood may vary relatively greatly due to a change in the amount of blood caused by a heartbeat.

On the contrary, a color channel value including a wavelength range of light that is absorbed relatively less by hemoglobin and oxyhemoglobin contained in blood may vary relatively little due to a change in the amount of blood caused by a heartbeat.

Accordingly, according to an embodiment, at least two color channels may be selected to reduce noise in consideration of the absorbance of hemoglobin and oxyhemoglobin.

For example, according to an embodiment, a difference between a green channel value, which is absorbed relatively more by hemoglobin and oxyhemoglobin, and a red channel value, which is absorbed relatively less by hemoglobin and oxyhemoglobin, may be used to reduce noise.

Also, for example, according to an embodiment, a difference between a green channel value, which is absorbed relatively more by hemoglobin and oxyhemoglobin, and a blue channel value, which is absorbed relatively less by hemoglobin and oxyhemoglobin, may be used to reduce noise.

Also, for example, according to an embodiment, a difference between a blue channel value, which is absorbed relatively more by hemoglobin and oxyhemoglobin, and a red channel value, which is absorbed relatively less by hemoglobin and oxyhemoglobin, may be used to reduce noise.

Also, for example, according to an embodiment, the difference between the green channel value and the red channel value and the difference between the green channel value and the blue channel value may be used at the same time.

Also, the above examples have been described based on a difference, but a processed value obtained by applying a weight to each channel value, other than the difference, may be used to reduce noise caused by subject movement and noise caused by external light or the like.

For example, a processed value obtained by applying a weight to each channel value may be used as shown in Equation 20 below:

$$\text{Processed Value} = a * \text{Red Channel Value} + b * \text{Blue Channel Value} + c * \text{Green Channel Value}. \quad \text{[Equation 20]}$$

Also, a, b, and c may be determined so that a+b+c=0 in order to efficiently remove noise caused by subject movement and noise caused by external light. In this case, each channel value may contain similar levels of noise caused by motion and noise caused by external light in one image frame, and this can be advantageous in effectively reducing noise.

5.2 Various Embodiments of Acquisition of Characteristic Value

A characteristic value may be acquired to reduce noise caused by subject movement and noise caused by the intensity of external light or the like.

In this case, the characteristic value may be acquired for an image frame group including at least some of a plurality of acquired image frames.

Also, the characteristic value may be a value indicating a feature of an acquired color channel value or a processed value. For example, the characteristic value may refer to the mean, the deviation, the standard deviation, and the like of color channel values or processed values included in an image frame group, but the present invention is not limited thereto.

FIG. 19 is a diagram illustrating a characteristic value acquisition method according to an embodiment.

FIG. 19A is a graph showing a color channel value acquired according to an embodiment, and more particularly, a graph showing a difference between a green channel value and a red channel value. However, the difference between the green channel value and the red channel value is just specified for convenience of description, and the present invention is not limited thereto. Therefore, various color channel values, differences, processed values, and the like are available.

Referring to FIG. 19A, it can be seen that the difference between the green channel value and the red channel value (hereinafter referred to as a "G-R value") may not change constantly over time.

In this case, the G-R value may not be constant due to subject movement. For example, the change in the G-R value may be small when the subject movement is small and may be large when the subject movement is large, but the present invention is not limited thereto.

Also, the G-R value may not be constant due to the intensity of external light. For example, the change in the G-R value may be small when the intensity of external light is small and may be large when the intensity of external light is large, but the present invention is not limited thereto.

Accordingly, a characteristic value may be extracted to reduce noise caused by subject movement, the intensity of external light, or the like.

Also, a window for the characteristic value may be set to extract the characteristic value.

In this case, the window for the characteristic value may refer to a predetermined time period and also may refer to the predetermined number of frames. However, the present invention is not limited thereto, and the window for the characteristic value may refer to a window for setting a frame group including at least some of a plurality of frames in order to acquire the characteristic value.

FIG. 19B is a schematic diagram illustrating a window for a characteristic value, and more particularly, a schematic diagram illustrating a window for a characteristic value by which 180 image frames are set as ten equal parts, each of which includes 18 image frames. However, for convenience of description, there is shown a window for a characteristic value by which 180 image frames are set as ten equal parts, each of which includes 18 image frames, but the present invention is not limited thereto, and the window for the characteristic value may be set in various ways and numbers.

Referring to FIG. 19B, a plurality of acquired image frames may be grouped by the window for the characteristic value. For example, referring to FIG. 19B, 180 image frames may be set as groups, each of which includes 18 image frames, by the window for the characteristic value. In detail, $1^{st}$ to $18^{th}$ image frames may be included in a first image frame group 2210, and $19^{th}$ to $36^{th}$ image frames may be included in a second image frame group 2220, but the present invention is not limited thereto.

In this case, the characteristic value may be acquired for an image frame group which is set by the window for the characteristic value. For example, the characteristic value may be acquired for color channel values for the first image frame group 2210 and may also be acquired for color channel values for the second image frame group 2220.

Also, for example, when the characteristic value is an average value, the mean of color channel values for an image frame group may be acquired. In detail, the mean of G-R values for the $1^{st}$ to $18^{th}$ image frames included in the first image frame group 2210 may be acquired, and the mean of G-R values for the $19^{th}$ to $36^{th}$ image frames included in the second image frame group 2220 may be acquired, but the present invention is not limited thereto.

Also, for example, when the characteristic value is a standard deviation, the standard deviation of color channel values for an image frame group may be acquired. In detail, the standard deviation of G-R values for the $1^{st}$ to $18^{th}$ image frames included in the first image frame group 2210 may be acquired, and the standard deviation of G-R values for the $19^{th}$ to $36^{th}$ image frames included in the second image frame group 2220 may be acquired, but the present invention is not limited thereto.

However, the present invention is not limited to the above examples, and various characteristic values may be acquired for an image frame group.

Also, the characteristic value may be acquired for at least some image frames included in an image frame group obtained through division by the window for the characteristic value. For example, the characteristic value may be acquired for color channel values for at least some of the 18 image frames included in the first image frame group 2210, and the characteristic value may be acquired for color channel values for at least some of the 18 image frames included in the second image frame group 2220.

Also, for example, when the characteristic value is a deviation, the deviation of color channel values for at least some image frames included in an image frame group may be acquired. In detail, the deviation of the G-R value of the first image frame included in the first image frame group 2210 from the mean of G-R values of the first image frame group 2210 may be acquired, and the deviation of the G-R value of the ninth image frame included in the second image frame group 2220 from the mean of G-R values of the second image frame group 2220 may be acquired, but the present invention is not limited thereto.

Also, for example, when the characteristic value is a deviation, the deviation of color channel values for at least some image frames included in an image frame group may be acquired. In detail, the deviation of the G-R value of the first image frame included in the first image frame group 2210 from the mean of G-R values of the first image frame group 2210 may be acquired, and the deviation of the G-R value of the second image frame included in the first image frame group 2210 from the mean of G-R values of the first image frame group 2210 may be acquired, but the present invention is not limited thereto.

Also, the acquired characteristic value may be normalized.

For example, when the characteristic value is a deviation, the deviation may be normalized by the standard deviation. In detail, when the deviation of the G-R value of the first image frame included in the first image frame group 2210 from the mean of G-R values of the first image frame group 2210 is acquired, the deviation of the G-R value of the first image frame may be normalized by the standard deviation of the first image frame group 2210. However, the present invention is not limited thereto, and the deviation may be normalized in various ways.

Also, when the normalization is performed, the magnitude of variation may be normalized. Thus, it is possible to better reflect a change due to a heartbeat, and also it is possible to effectively reduce noise caused by subject movement and noise caused by a change in the intensity of external light or the like.

FIG. 19C is a graph showing a characteristic value acquired according to an embodiment, and more particularly, a graph showing a deviation acquired based on a G-R value. However, the deviation acquired based on the G-R value is just specified for convenience of description, and the present invention is not limited thereto. Therefore, various characteristic values acquired based on various color channel values, differences, and processed values are available.

Referring to FIG. 19C, it can be seen that the variation is constant compared to FIG. 19A.

Accordingly, by acquiring a characteristic value in the above-described way, it is possible to reduce noise caused by subject movement and noise caused by a change in the intensity of external light or the like, and also it is possible to better reflect a change due to a heartbeat.

Figure 20:
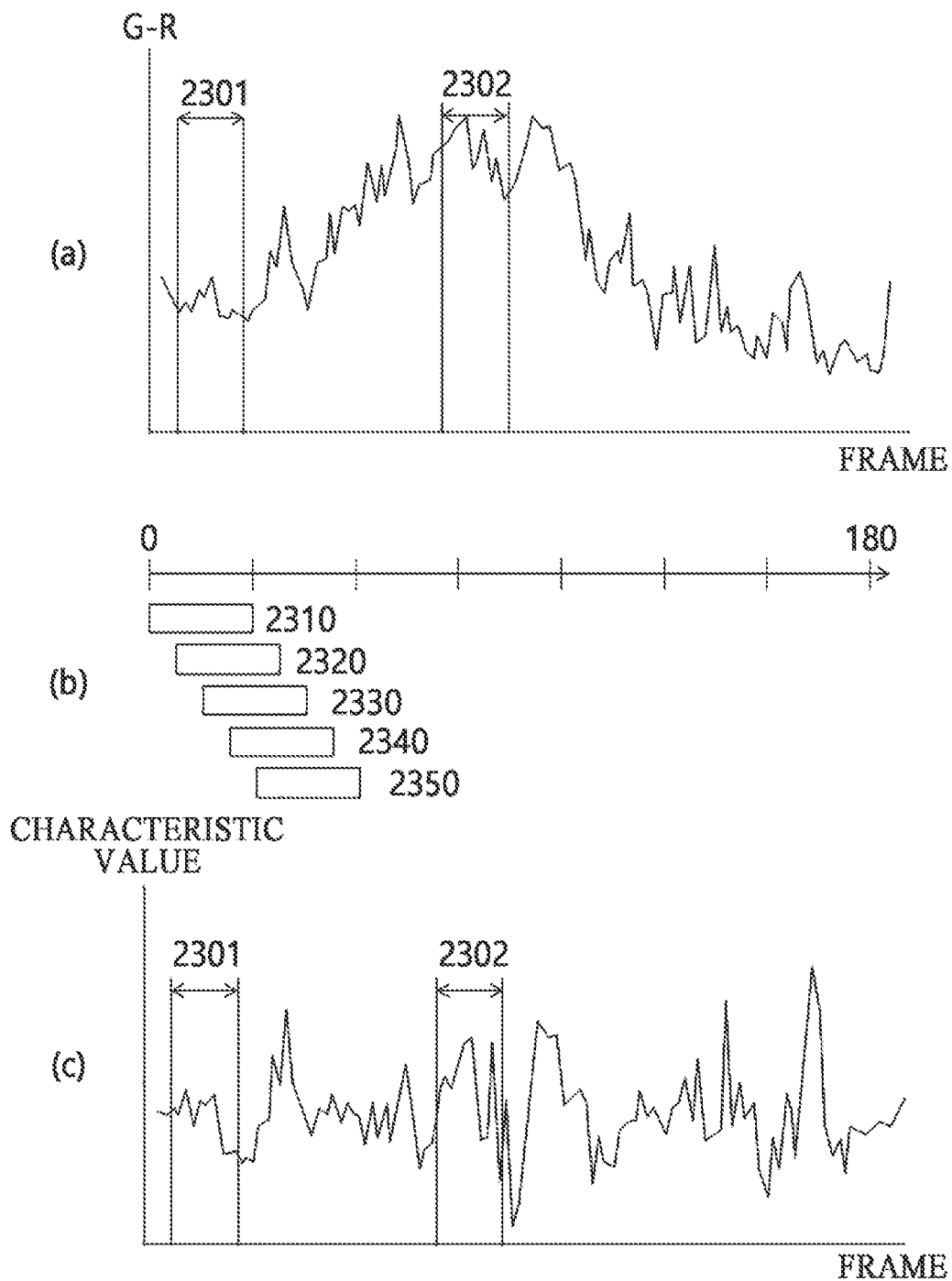
FIG. 20 is a diagram illustrating a characteristic value acquisition method according to another embodiment.

FIG. 20 is a diagram illustrating a characteristic value acquisition method according to another embodiment.

FIG. 20A is a graph showing a color channel value acquired according to an embodiment, and more particularly, a graph showing a difference between a green channel value and a red channel value. However, the difference between the green channel value and the red channel value is just specified for convenience of description, and the present invention is not limited thereto. Therefore, various color channel values, differences, processed values, and the like are available.

Referring to FIG. 20A, it can be seen that the difference between the green channel value and the red channel value (hereinafter referred to as a "G-R value") may not change constantly over time.

In this case, the G-R value may not be constant due to subject movement. For example, the overall G-R value may be small in a time period 2301 in which a subject is positioned in a first state, and the overall G-R value may be large in a time period 2302 in which a subject is positioned in a second state different from the first state, but the present invention is not limited thereto.

Also, the G-R value may not be constant due to the intensity of external light. For example, the intensity of external light in the time period 2301 in which the subject is positioned in the first state may be different from the intensity of external light in the time period 2302 in which the subject is positioned in the second state. Thus, a difference may occur in the overall G-R value, but the present invention is not limited thereto.

Accordingly, a characteristic value may be extracted to reduce noise caused by subject movement, the intensity of external light, or the like.

Also, a window for the characteristic value may be set to extract the characteristic value.

In this case, the window for the characteristic value may refer to a predetermined time period and also may refer to the predetermined number of frames. However, the present invention is not limited thereto, and the window for the characteristic value may refer to a window for setting frame groups each including at least some of a plurality of frames in order to acquire the characteristic value.

Also, the frame groups that are set by the window may at least partially overlap each other.

FIG. 20B is a schematic diagram illustrating a window for a characteristic value, and more particularly, a schematic diagram illustrating a window for a characteristic value by which 180 image frames are set as eight equal parts. However, for convenience of description, there is shown a window for a characteristic value by which 180 image frames are set as eight equal parts, but the present invention is not limited thereto, and the window for the characteristic value may be set in various ways and numbers.

Also, referring to FIG. 20B, a plurality of acquired image frames may be grouped by the window for the characteristic value. For example, referring to FIG. 20B, 180 image frames may be set as groups, each of which includes 22 or 23 image frames, by the window for the characteristic value. In detail, $1^{st}$ to $22^{nd}$ image frames may be included in a first image frame group 2310.

Also, referring to FIG. 20B, the image frame groups set by the window for the characteristic value may at least partially overlap each other. For example, as shown in FIG. 20B, $1^{st}$ to $22^{nd}$ image frames may be included in a first image frame group 2310, $6^{th}$ to $28^{th}$ image frames may be included in a second image frame group 2320, $12^{th}$ to $33^{rd}$ image frames may be included in a third image frame group 2330, and $17^{th}$ to $39^{th}$ image frames may be included in a fourth image frame group 2340, but the present invention is not limited thereto.

Also, referring to FIG. 20B, the image frame groups set by the window for the characteristic value may not overlap each other. For example, as shown in FIG. 20B, the $1^{st}$ to $22^{nd}$ image frames may be included in the first image frame group 2310, and $23^{rd}$ to $45^{th}$ image frames may be included in a fifth image frame group 2350, but the present invention is not limited thereto.

In this case, the characteristic value may be acquired for an image frame group set by the window for the characteristic value or may be acquired for at least some image frames included in the image frame group. However, the above description is applicable to this case, and thus a redundant description thereof will be omitted.

However, the processing of characteristic values acquired for the image frames included in the at least partially overlapping image frame groups will be described in detail below.

A plurality of characteristic values may be acquired for image frames included in a region where at least two image frame groups overlap each other.

For example, at least two characteristic values may be acquired for the $6^{th}$ to $22^{nd}$ image frames in a region where the first image frame group 2310 and the second image frame group 2320 overlap each other.

In detail, a first deviation, which is the deviation of a G-R value of the sixth image frame from the mean of G-R values of the first image frame group 2310, may be acquired, and a second deviation, which is the deviation of a G-R value of the $6^{th}$ image frame from the mean of G-R values of the second image frame group 2320, may be acquired, but the present invention is not limited thereto.

Also, a plurality of acquired characteristic value may be acquired as one characteristic value through a mathematical operation. For example, the deviation of the sixth image frame may be obtained by adding the first deviation and the second deviation, but the present invention is not limited thereto.

Also, the above operations are applicable to acquire a characteristic value for an image frame included in a region where multiple, e.g., three or four, image frame groups overlap each other.

Also, in addition to the above-described operation, a sliding window scheme, which can be typically understood, is available.

FIG. 20C is a graph showing a characteristic value acquired according to an embodiment, and more particularly, a graph showing a deviation acquired based on a G–R value. However, the deviation acquired based on the G–R value is just specified for convenience of description, and the present invention is not limited thereto. Therefore, various characteristic values acquired based on various color channel values, differences, and processed values are available.

Referring to FIG. 20C, it can be seen that values are more uniform than those FIG. 19A as a whole.

In detail, the overall characteristic value in the time period 2301 in which a subject is positioned in the first state may become similar to the overall characteristic value in the time period 2302 in which a subject is positioned in the second state.

Accordingly, by acquiring a characteristic value in the above-described way, it is possible to reduce noise caused by subject movement and noise caused by a change in the intensity of external light or the like, and also it is possible to better reflect a change due to a heartbeat.

5.3 Various Embodiments of Method of Using Plurality of Characteristic Values A characteristic value acquired in the above-described methods may be influenced by a color channel value, a difference, and a processed value which are to be used as a basis. Accordingly, by acquiring a plurality of characteristic values on the basis of various color channel values, differences, and processed values and using the plurality of characteristic values, it is possible to accurately acquire a physiological parameter.

Figure 21:
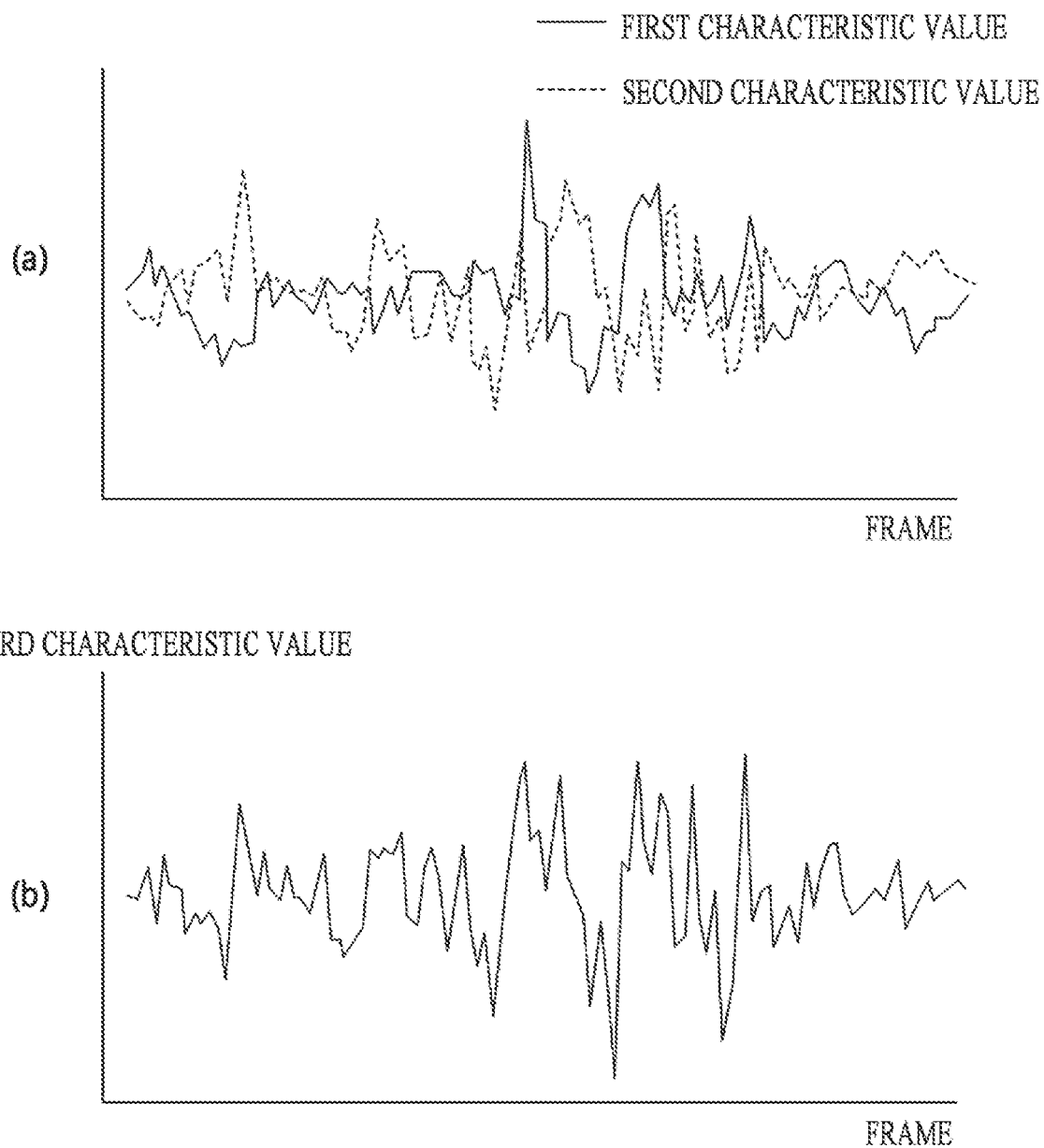
FIG. 21 is a diagram illustrating a method of using a plurality of characteristic values.

FIG. 21 is a diagram illustrating a method of using a plurality of characteristic values.

FIG. 21A is a graph showing two characteristic values acquired according to an embodiment, and more particularly, a graph showing a first characteristic value acquired based on a G–R value and a second characteristic value acquired based on a G–B value. However, the first characteristic value and the second characteristic value are just specified for convenience of description, and the present invention is not limited thereto. Therefore, characteristic values acquired based on various color channel values, differences, and processed values are available.

In this case, the first characteristic value acquired based on the G–R value may be influenced by the G–R value. For example, when external light is close to a blue channel, the G–R value may not reflect a change in blood due to a heartbeat well.

Alternatively, for example, the G–R value may be influenced by a difference between the absorbance of a green channel and the absorbance of a red channel and thus may reflect a change in blood due to a heartbeat.

Also, the second characteristic value acquired based on the G–B value may be influenced by the G–B value. For example, when external light is close to a red channel, the G–B value may not reflect a change in blood due to a heartbeat well.

Alternatively, for example, the G–B value may be influenced by a difference between the absorbance of a green channel and the absorbance of a blue channel and thus may reflect a change in blood due to a heartbeat.

Also, referring to FIG. 21A, the first characteristic value and the second characteristic value may have a complementary relationship. For example, the second characteristic value may reflect a change due to a heartbeat well in a period in which the first characteristic value does not reflect a change due to a heartbeat well, and vice versa.

Accordingly, the first characteristic value and the second characteristic value may be used to reduce noise caused by a change in wavelength of external light or to reflect a change in blood due to a heartbeat better.

FIG. 21B is a graph showing a third characteristic value acquired using the first characteristic value and the second characteristic value, and more particularly, a graph showing a third characteristic value acquired by adding the first characteristic value and the second characteristic value. However, this is just specified for convenience of description, and the present invention is not limited thereto.

Also, the third characteristic value may be acquired based on a mathematical operation between the first characteristic value and the second characteristic value. For example, the third characteristic value may be acquired based on an addition operation between the first characteristic value and the second characteristic value. However, the present invention is not limited thereto, and the third characteristic value may be acquired based on various mathematical operations such as a difference operation and a multiplication operation.

Also, the third characteristic value may be acquired by assigning various weights to the first characteristic value and the second characteristic value. For example, the third characteristic value may be acquired based on Equation 21 below, but the present invention is not limited thereto.

$$\text{Third Characteristic value} = a*\text{First Characteristic value} + b*\text{Second Characteristic value} \quad \text{[Equation 21]}$$

Also, referring to FIGS. 21A and 21B, the third characteristic value may reflect a change in blood due to a heartbeat better than the first characteristic value and the second characteristic value and may reduce noise caused by a change in wavelength of external light.

5.4 Various Embodiments of Heart Rate Acquisition Method

In order to obtain a heart rate from data obtained by the above-described methods, it may be necessary to detect a periodic change due to a heartbeat. For example, in order to acquire a heart rate from an acquired characteristic value, there is a need to acquire a wavelength or frequency component most often included in the characteristic value.

Figure 22:
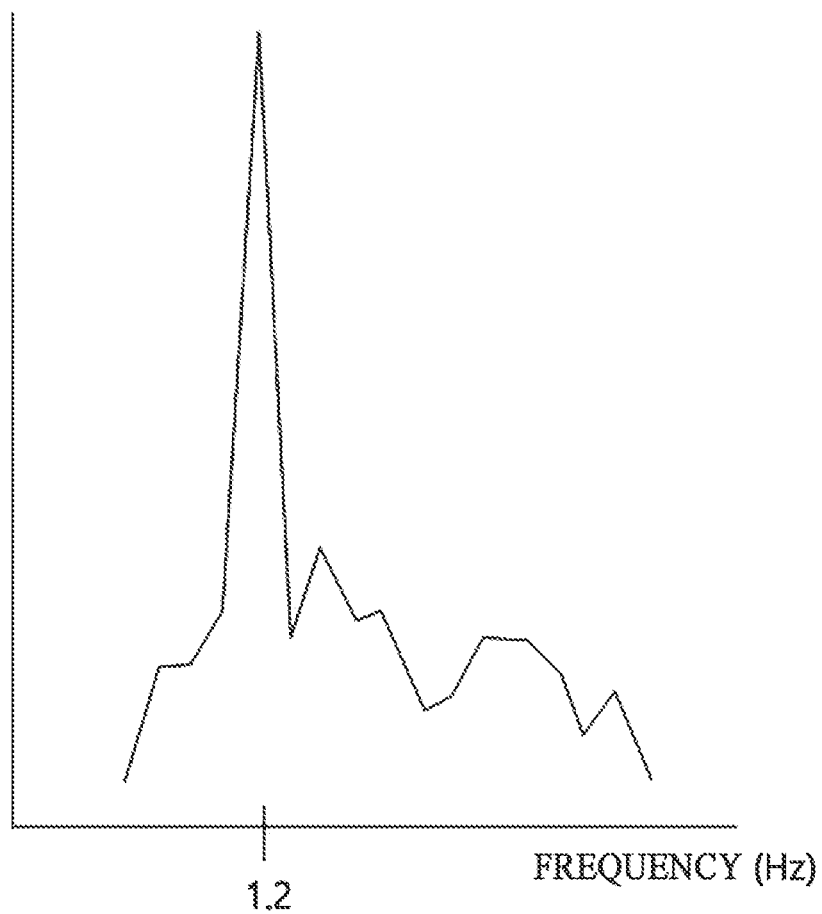
FIG. 22 is a graph showing a frequency component extracted from a graph for a characteristic value.

FIG. 22 is a graph showing a frequency component extracted from the graph for the characteristic value shown in FIG. 21B. In detail, FIG. 22 is a graph in which the graph for the characteristic value is Fast Fourier transformed into a frequency domain. However, the Fast Fourier transform is just specified for convenience of description, and the present invention is not limited thereto. The graph for the characteristic value may be transformed according to the Fast Fourier transform (FFT), discrete Fourier transform (DFT), short time Fourier transform (STFT), or the like.

Also, the graph for the characteristic value may be transformed into a frequency domain as shown in FIG. 22.

In this case, a frequency index with the highest intensity may be acquired, and a heart rate may be acquired using Equation 22 below:

Heart Rate=Frequency Index*60. [Equation 22]

For example, as shown in FIG. 22, when the frequency index with the highest intensity is 1.2 Hz, the heart rate may be equal to 72 bpm.

Also, although not shown in FIG. 22, the graph for the characteristic value may be transformed into a frequency*measurement time domain.

In this case, a wavelength index with the highest intensity may be acquired, and a heart rate may be acquired using Equation 23 below:

Heart Rate Index/Measurement Time*60. [Equation 23]

For example, although not shown in FIG. 22, when the wavelength index with the highest intensity is 8 and the measurement time is 6.6 seconds, the heart rate may be equal to 8/6.6*60, i.e., 72 bpm.

Also, various equations for acquiring a heart rate other than the above-described exemplary equation are available.

Also, a preliminary heart rate may be acquired to acquire a heart rate. In this case, the preliminary heart rate may be a heart rate which is calculated as a basis for acquiring the heart rate.

Figure 23:
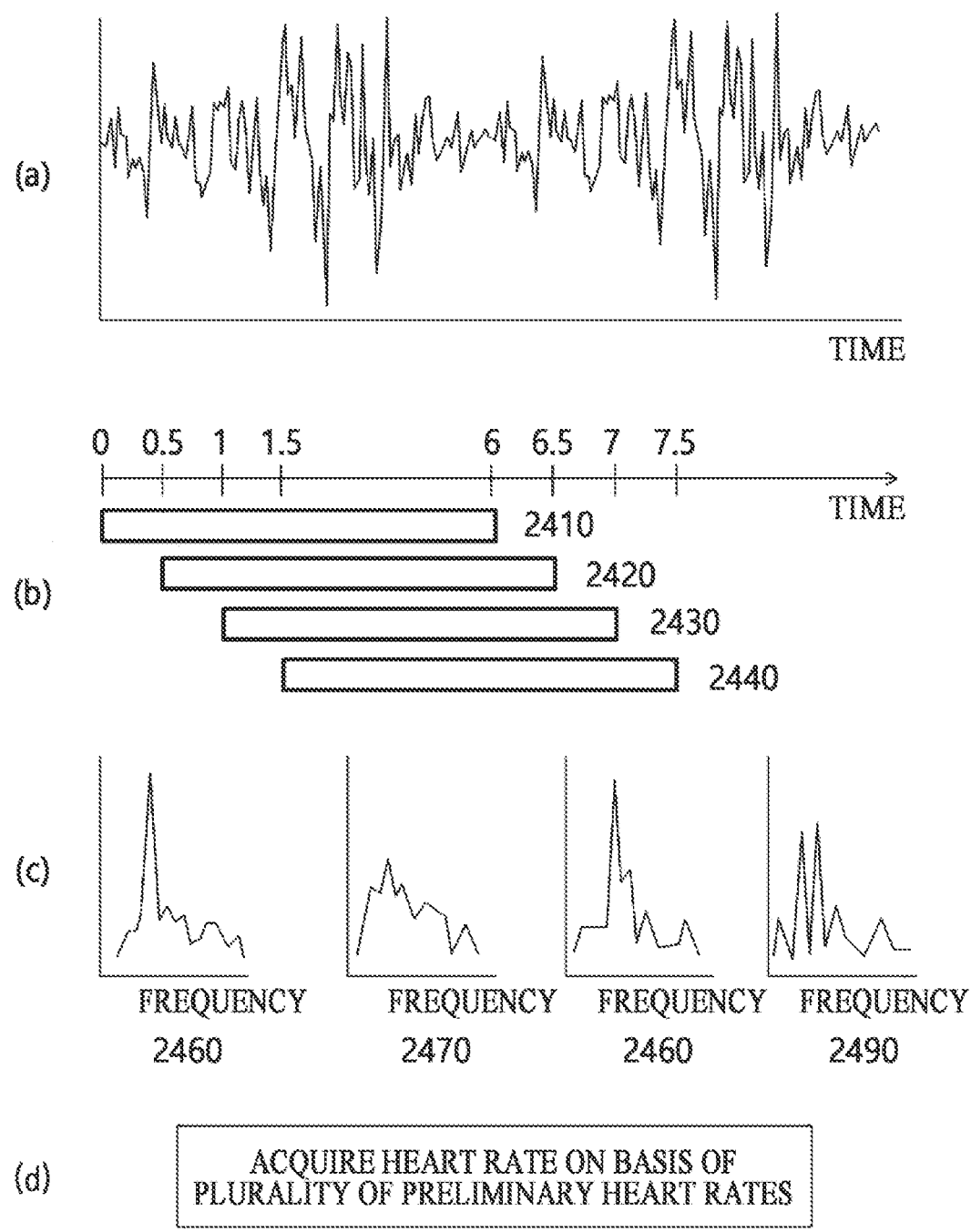
FIG. 23 is a diagram illustrating a heart rate acquisition method according to an embodiment.

FIG. 23 is a diagram illustrating a heart rate acquisition method according to an embodiment.

Prior to the description, the term "preliminary heart rate" used herein may refer to a heart rate acquired in the heart rate acquisition method and may be a heart rate to be used as a basis for acquiring one heart rate. For example, at least two heart rates acquired in the above-described heart rate acquisition method may be a first preliminary heart rate and a second preliminary heart rate to be used as a basis for acquiring one final heart rate, but the present invention is not limited thereto.

Also, a preliminary heart rate may itself be a final heart rate, and a final heart rate may be acquired based on a plurality of preliminary heart rates.

FIG. 23A is a graph showing a value acquired as time-series data. For example, the value shown in FIG. 23A may refer to a color channel value acquired as time-series data, but the present invention is not limited thereto. The value shown in FIG. 23A may refer to a difference or a processed value acquired as time-series data or may refer to a characteristic value acquired as time-series data.

The above description is applicable to a method of transforming a graph showing a value acquired as time-series data as shown in FIG. 23A into a wavelength domain or a frequency domain, and thus a redundant description thereof will be omitted.

FIG. 23B is a schematic diagram illustrating a window for a preliminary heart rate, and more particularly, a schematic diagram illustrating a window for a preliminary heart rate with a period of six seconds. However, this is just specified for convenience of description, and the present invention is not limited thereto. The window may be set in various sizes.

In this case, the window for the preliminary heart rate may refer to a predetermined time period and also may refer to the predetermined number of frames. However, the present invention is not limited thereto, and the window for the preliminary heart rate may refer to a window for setting a frame group including at least some of a plurality of frames in order to acquire the preliminary heart rate.

Also, referring to FIG. 23B, a plurality of acquired image frames may be grouped by the window for the preliminary heart rate. For example, as shown in FIG. 20B, image frames acquired between zero and six seconds may be included in a first image frame group 2410, but the present invention is not limited thereto.

Also, referring to FIG. 23B, the image frame groups set by the window for the preliminary heart rate may at least partially overlap each other. For example, as shown in FIG. 23B, image frames acquired between zero and six seconds may be included in a first image frame group 2410, image frames acquired between 0.5 and 6.5 seconds may be included in a second image frame group 2420, image frames acquired between one and seven seconds may be included in a third image frame group 2430, and image frames acquired between 1.5 and 7.5 seconds may be included in a fourth image frame group 2440, but the present invention is not limited thereto.

In this case, the preliminary heart rate may be acquired for an image frame group which is set by the window for the preliminary heart rate. For example, a first preliminary heart rate may be acquired based on characteristic values acquired from image frames included in the first image frame group 2410.

Also, a value acquired as time-series data from each image frame group in order to acquire the preliminary heart rate may be transformed into a wavelength domain or a frequency domain. For example, a value acquired as time series data from the first image frame group may be transformed into first frequency data 2460, a value acquired as time series data from the second image frame group may be transformed into second frequency data 2470, a value acquired as time series data from the third image frame group may be transformed into third frequency data 2480, and a value acquired as time series data from the fourth image frame group may be transformed into fourth frequency data 2490, but the present invention is not limited thereto.

Also, the above-described heart rate acquisition method may be applied to the acquisition of first to fourth preliminary heart rates from the first to fourth frequency data 2460, 2470, 2480, and 2490, and thus a redundant description thereof will be omitted.

Also, a heart rate may be acquired based on a plurality of preliminary heart rates. For example, a heart rate may be acquired by performing a mathematical operation on a plurality of preliminary heart rates, and more particularly, may be acquired by performing a mathematical operation of extracting the mean, the maximum, the minimum, or the like of the first to fourth preliminary heart rates, but the present invention is not limited thereto.

Also, a heart rate may be acquired based on a plurality of preliminary heart rates. For example, a heart rate may be acquired by performing a mathematical operation on some of a plurality of acquired preliminary heart rates which have the same tens digit (excluding preliminary heart rates having different tens digits from the preliminary heart rates).

In detail, when it is assumed that the first preliminary heart rate is 72 bpm, that the second preliminary heart rate is 80 bpm, that the third preliminary heart rate is 85 bpm, and that the fourth preliminary heart rate is 73 bpm, a mathematical operation may be performed on the first, third, and fourth preliminary heart rates (excluding the second preliminary heart rate which has a different tens digit) to acquire a heart rate. In this case, the mathematical operation may be a mathematical operation for extracting the mean, the maximum, the minimum, or the like.

Also, a heart rate may be acquired based on a plurality of preliminary heart rates. For example, when four acquired preliminary heart rates are paired in two pairs which have different tens digits from each other, a mathematical operation may be performed on the pair of preliminary heart rates which have the same tens digit as a previously acquired heart rate (excluding the pair of preliminary heart rates which have different tens digits) to acquire a heart rate.

In detail, when it is assumed that the first preliminary heart rate is 72 bpm, that the second preliminary heart rate is 80 bpm, that the third preliminary heart rate is 75 bpm, that the fourth preliminary heart rate is 73 bpm, and that a previously acquired heart rate is 75 bpm, a mathematical operation may be performed on the first and fourth preliminary heart rates (excluding the second and third preliminary heart rates) to acquire a heart rate.

Also, when a heart rate is acquired using a plurality of preliminary heart rates as described above, it is possible to increase robustness against noise, and also it is possible to acquire an accurate heart rate.

5.5 Various Embodiments of Output of Heart Rate

A heart rate acquired by the above-described methods may be output through a display or the like or may be transmitted to a terminal or server using a communication unit. For convenience of description, such an operation will be described below as an output of a heart rate.

When a heart rate is continuously measured in real time, an output heart rate may be corrected to provide stability and reliability to the measured heart rate.

Also, when an output heart rate is corrected, it is possible to provide stability and reliability to an acquired and output heart rate even if a bad image is acquired from some of a plurality of acquired image frames.

Figure 24:
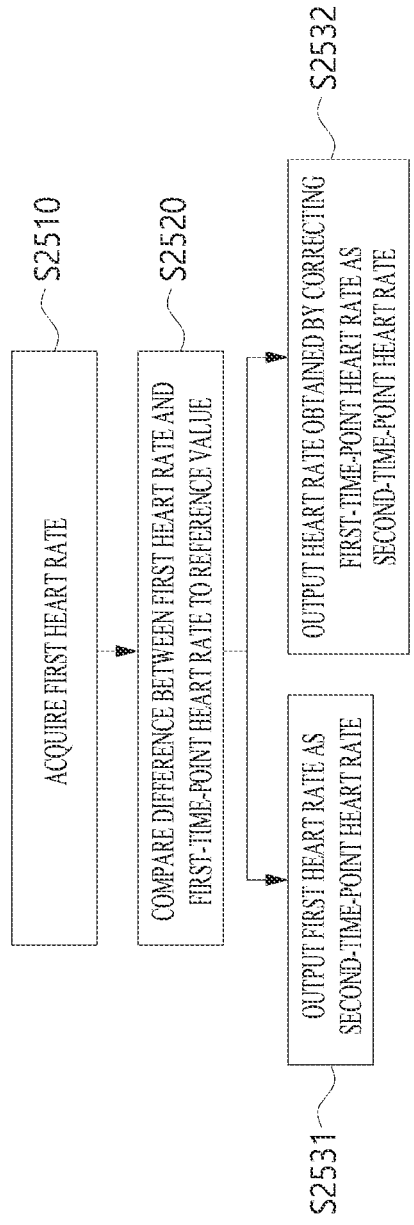
FIG. 24 is a flowchart illustrating an output heart rate correction method according to an embodiment.

FIG. 24 is a flowchart illustrating an output heart rate correction method according to an embodiment.

Referring to FIG. 24, an output heart rate correction method 2500 according to an embodiment may include an operation of acquiring a first heart rate (S2510) and an operation of comparing a difference between the first heart rate and a first-time-point heart rate to a reference value (S2520), but the present invention is not limited thereto.

The above-described heart rate acquisition methods may be applied to the operation of acquiring the first heart rate (S2510), and thus a redundant description thereof will be omitted.

In the operation of comparing the difference between the first heart rate and the first-time-point heart rate to the reference value (S2520), the first-time-point heart rate may refer to a heart rate which is acquired or output before the first heart rate. For example, when the first heart rate is acquired at 6.5 seconds, the first-time-point heart rate may be a heart rate acquired at six seconds or a heart rate output at six seconds, but the present invention is not limited thereto.

Also, the reference value may be determined as a certain numerical value or a certain ratio. For example, the reference value may be set to ten. In this case, it may be determined whether the difference between the first heart rate and the first-time-point heart rate exceeds ten, but the present invention is not limited thereto.

Also, when the difference between the first heart rate and the first-time-point heart rate is less than or equal to the reference value, an operation of outputting the first heart rate as a second-time-point heart rate (S2531) may be performed. In this case, the second time point may be later than the first time point.

For example, when it is assumed that the first-time-point heart rate is 72 bpm, that the first heart rate is 75 bpm, and that the reference value is ten, the heart rate output at the second time point may be 75 bpm, but the present invention is not limited thereto.

Also, when the difference between the first heart rate and the first-time-point heart rate exceeds the reference value, an operation of outputting a heart rate obtained by correcting the first-time-point heart rate as a second-time-point heart rate (S2532) may be performed. In this case, the second time point may be later than the first time point.

Also, in order to acquire a heart rate obtained by correcting the first-time-point heart rate, a mathematical operation may be performed on the first-time-point heart rate. For example, a mathematical operation such as addition or subtraction of a certain value to or from the first-time-point heart rate may be performed, but the present invention is not limited thereto.

For example, when it is assumed that the first-time-point heart rate is 72 bpm, that the first heart rate is 85 bpm, and that the reference value is ten, the heart rate output at the second time point may be 75 bpm, which is the first-time-point heart rate plus 3 bpm, but the present invention is not limited thereto.

Also, for example, when it is assumed that the first-time-point heart rate is 72 bpm, that the first heart rate is 61 bpm, and that the reference value is ten, the heart rate output at the second time point may be 69 bpm, which is the first-time-point heart rate minus 3 bpm, but the present invention is not limited thereto.

5.6 Various Embodiments of Extraction of Heartbeat Signal

A heartbeat signal may refer to a signal varying depending on a heartbeat and also may refer to a signal to be estimated as varying depending on a heartbeat.

Also, a heartbeat signal may be extracted based on a plurality of acquired image frames.

Figure 25:
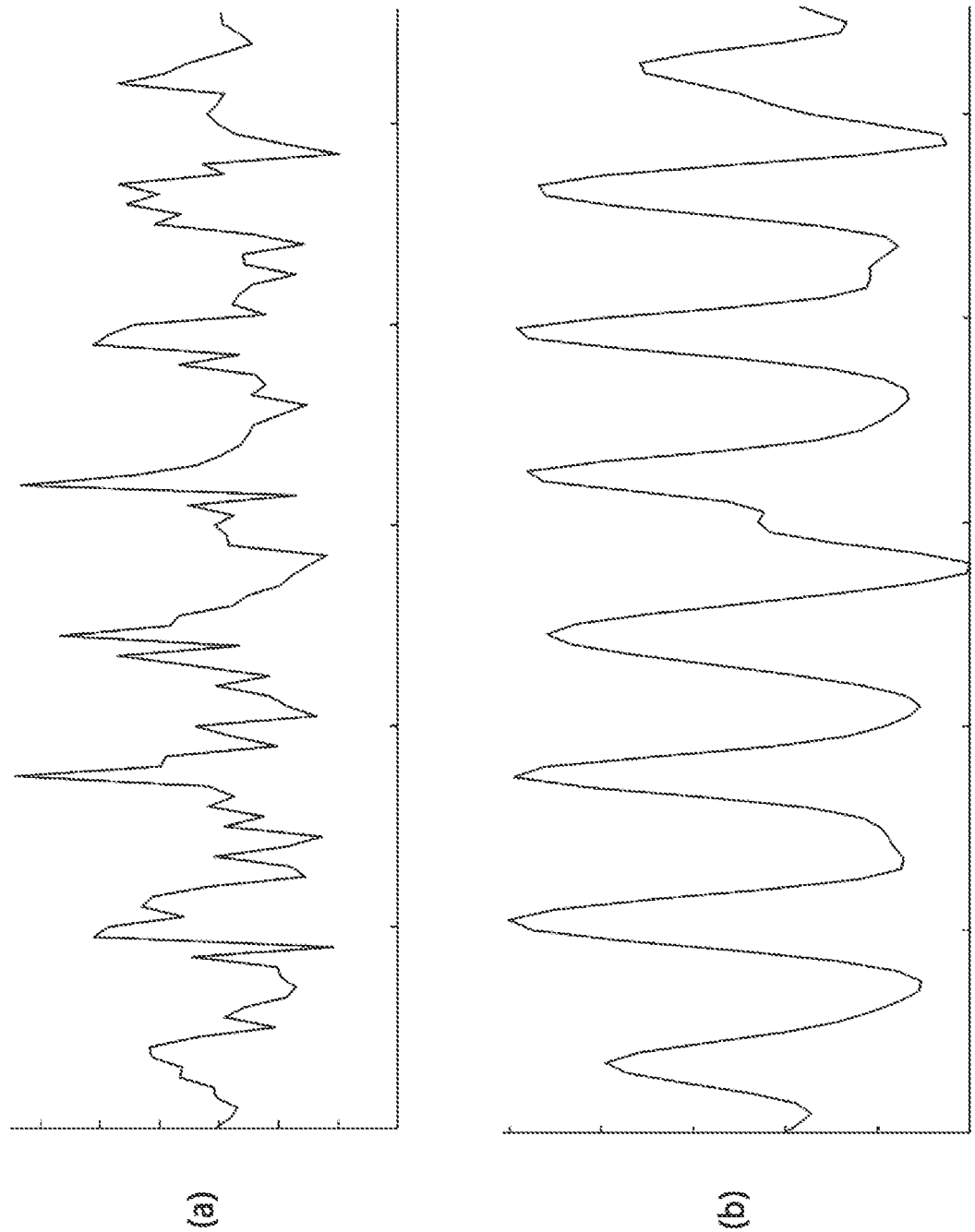
FIG. 25 is a diagram illustrating a heartbeat signal extraction method according to an embodiment.

FIG. 25 is a diagram illustrating a heartbeat signal extraction method according to an embodiment.

First, FIG. 25A is a graph showing a value acquired as time-series data. For example, the value shown in FIG. 25A may refer to a color channel value acquired as time-series data, but the present invention is not limited thereto. The value shown in FIG. 23A may refer to a difference or a processed value acquired as time-series data or may refer to a characteristic value acquired as time-series data.

In this case, the value acquired as the time-series data may be extracted as a heartbeat signal through a band-pass filter. In detail, the value acquired as the time-series data may be extracted as a heartbeat signal through a band-pass filter for a frequency band or wavelength band corresponding to a heartbeat.

Also, the frequency band or wavelength band corresponding to the heartbeat may be a frequency band or wavelength band that can be generally understood, but the present invention is not limited thereto. The frequency band or wavelength band may be a frequency band or wavelength band that is determined based on a heartbeat acquired by the above-described methods.

For example, a typical heart rate may be 60 to 100 bpm, a corresponding frequency band may be 1 to 1.67 Hz, and a corresponding band-pass filter may be used. However, the present invention is not limited thereto.

Also, for example, when an acquired heart rate is 72 bpm, a corresponding frequency is 1.2 and a frequency band may be set based on the corresponding frequency. In detail, when a frequency band of 0.5 Hz is set, the frequency band may be set to range from 0.95 Hz to 1.45 Hz, and a corresponding band-pass filter may be used, but the present invention is not limited thereto.

FIG. 25B is a heartbeat signal graph in which the value acquired as time-series data and shown in FIG. 25A is extracted as a heartbeat signal through a band-pass filter.

Referring to FIG. 25B, it can be seen that a value acquired as time-series data may be extracted as a heartbeat signal through a band-pass filter.

5.7 Various Embodiments of Heart Rate Measurement Method Using Infrared Light Basically, for a heart rate measurement method using infrared light, the above-described heart rate measurement methods may be used.

Figure 26:
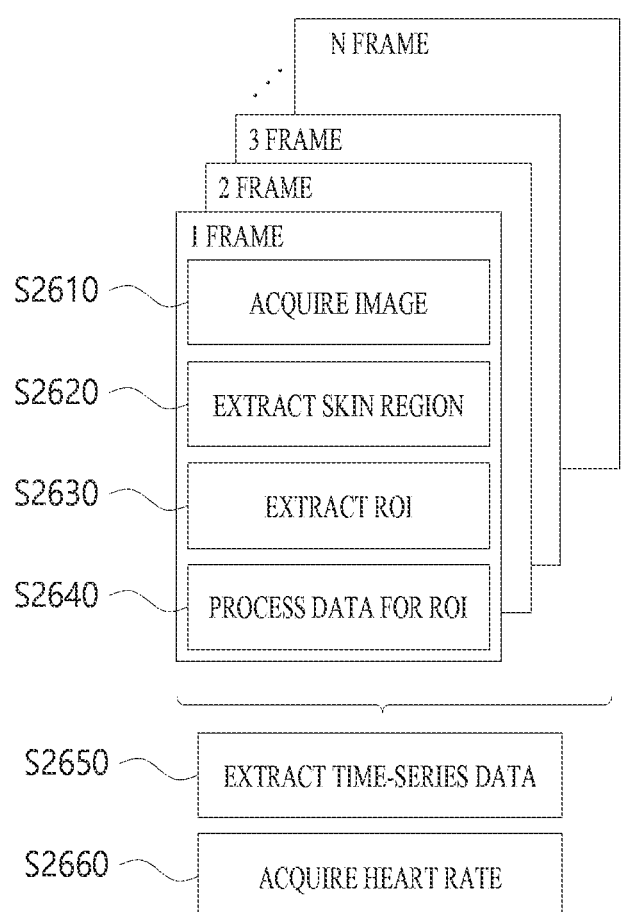
FIG. 26 is a diagram illustrating a heart rate acquisition method using infrared light according to an embodiment.

FIG. 26 is a diagram illustrating a heart rate acquisition method using infrared light according to an embodiment.

In this case, near-infrared light in a wavelength band of 750 nm to 3000 may be used as the infrared light. However, the present invention is not limited thereto, and middle-infrared light, far-infrared, light, and extreme-infrared light may be used.

Referring to FIG. 26, a heart rate acquisition method 2600 using infrared light according to an embodiment may include at least some of an operation of acquiring an image for at least one of a plurality of acquired image frames (S2610), an operation of detecting a skin region (S2620), an operation of detecting an ROI (S2630), and an operation of processing data for the ROI (S2640), but the present invention is not limited thereto.

Also, the above description is applicable to the operation of acquiring the image (S2610) and the operation of detecting the skin region (S2620), and thus a redundant description thereof will be omitted.

Also, the above-described methods of detecting the ROI are applicable to details of the operation of detecting the ROI (S2630), and thus a redundant description thereof will be omitted.

Also, the operation of detecting the ROI (S2630) may include an operation of detecting a first ROI, a second ROI, and a third ROI and may be performed on at least one of the plurality of acquired image frames.

Also, the first ROI, the second ROI, and the third ROI may at least partially overlap each other. For example, the first ROI may be set to be included in the second ROI and the third ROI, and the second ROI may be set to be included in the third ROI. However, the present invention is not limited thereto, and the first to third ROIs may be set to at least partially overlap each other.

Also, the first ROI, the second ROI, and the third ROI may be set not to overlap each other. For example, the first ROI and the second ROI may be positioned in an upper portion and a lower portion with respect to the left cheek of a subject and the third ROI may be positioned on the right cheek of the subject. However, the present invention is not limited thereto, and the first to third ROIs may be set not to overlap each other.

Also, the above-described methods of processing the data for the ROI are applicable to details of the operation of processing the data for the first, second, and third ROIs (S2640), and thus a redundant description thereof will be omitted.

Also, the operation of processing the data for the ROI (S2640) may be performed on at least one of the plurality of acquired image frames.

Also, the operation of processing the data for the ROI (S2640) may be performed on the first, second, and third ROIs.

Also, in order to process the data for the first to third ROIs, IR intensity values for the first to third ROIs may be extracted for at least one of the plurality of acquired image frames. In this case, each of the IR intensity values may be the mean of IR intensity values of pixels included in the first, second, or third ROI and may be referred to as an average pixel value.

Also, when the above-described method of processing the data for the ROI is used, the IR intensity value for each ROI may correspond to the above-described color channel value. For example, the IR intensity value of the first ROI may correspond to a red channel value, the IR intensity value of the second ROI may correspond to a green channel value, and the IR intensity value of the third ROI may correspond to a blue channel value, but the present invention is not limited thereto.

Also, for example, the above-described G-R value may correspond to the difference between the IR intensity value of the second ROI and the IR intensity value of the first ROI, and the above-described G-B value may correspond to the difference between the IR intensity value of the second ROI and the IR intensity value of the third ROI.

Accordingly, data may be processed based on the IR intensity value for each ROI, and the details may follow the above-described data processing method for the ROI.

Also, the heart rate acquisition method 2600 using infrared light according to an embodiment may include at least some of an operation of extracting time-series data for an image frame group including at least some of a plurality of acquired image frames (S2650) and an operation of acquiring a heart rate (S2660), but the present invention is not limited thereto.

In this case, the above description is applicable to the operation of extracting the time-series data (S2650) and the operation of acquiring the heart rate (S2660), and thus a redundant description thereof will be omitted.

Figure 27:
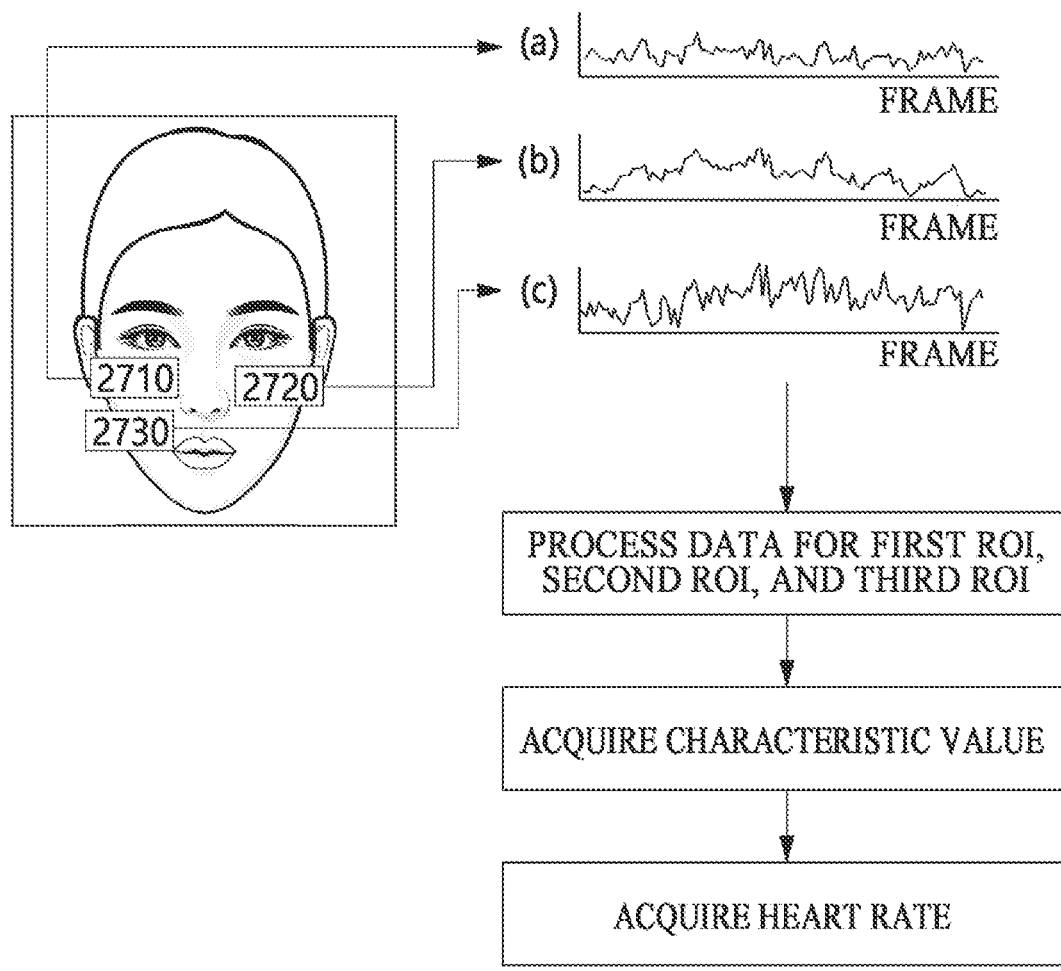
FIG. 27 is a diagram illustrating a heart rate acquisition method using infrared light according to an embodiment.

FIG. 27 is a diagram illustrating a heart rate acquisition method using infrared light according to an embodiment.

Referring to FIG. 27, at least two ROIs may be set in a face region of a subject. In detail, a first ROI 2710, a second ROI 2720, and a third ROI 2730 may be set in the face region of the subject, but the present invention is not limited thereto.

Also, IR intensity values for the first to third ROIs 2710, 2720, and 2730 may be extracted.

For example, the IR intensity value for the first ROI 2710 may be extracted (see FIG. 27A), the IR intensity value for the second ROI 2720 may be extracted (see FIG. 27B), and the IR intensity value for the third ROI 2730 may be extracted (see FIG. 27C), but the present invention is not limited thereto.

Also, data for the first to third ROIs 2710, 2720, and 2730 may be processed based on the IR intensity values extracted for the first to third ROIs 2710, 2720, and 2730. However, details thereof have been described above, and thus a redundant description thereof will be omitted.

Also, a characteristic value may be acquired based on the data processed for the first to third ROIs 2710, 2720, and

2730. However, details thereof have been described above, and thus a redundant description thereof will be omitted.

Also, a heart rate may be acquired using the characteristic value acquired based on the IR intensity values extracted for the first to third ROIs 2710, 2720, and 2730. However, details thereof have been described above, and thus a redundant description thereof will be omitted.

6. Physiological Parameter Acquisition Method According to Embodiment

Figure 28:
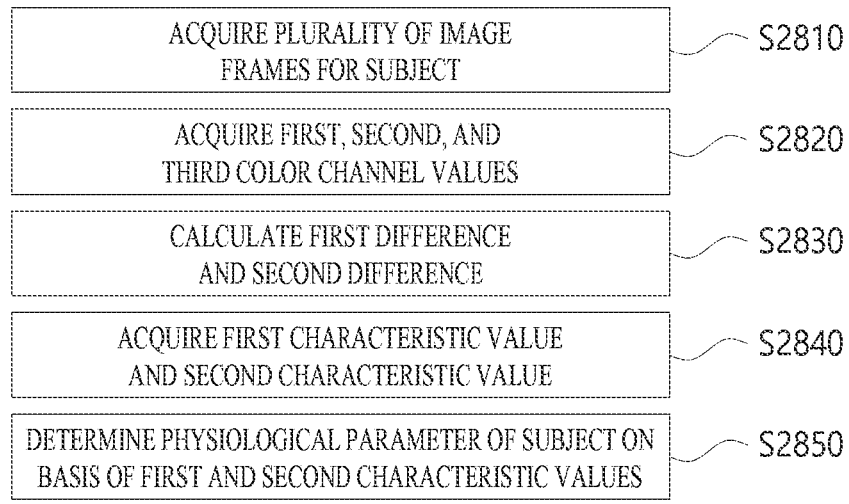
FIG. 28 is a flowchart illustrating a physiological parameter acquisition method according to an embodiment.

FIG. 28 is a flowchart illustrating a physiological parameter acquisition method according to an embodiment.

Referring to FIG. 28, the physiological parameter acquisition method according to an embodiment may include at least some of an operation of acquiring a plurality of image frames for a subject (S2810), an operation of acquiring first, second, and third color channel values (S2820), an operation of calculating a first difference and a second difference (S2830), an operation of acquiring a first characteristic value and a second characteristic value (S2840), and an operation of determining a physiological parameter of the subject on the basis of the first and second characteristic values (S2850).

In this case, a plurality of images may be acquired by a camera. For example, the plurality of images may be acquired by a camera such as a visible light camera and an IR camera.

Also, the plurality of images may be acquired from a camera placed outside. For example, the plurality of images may be images acquired from a camera such as a visible light camera or an IR camera placed outside.

Also, the operation of acquiring the first, second, and third color channel values (S2820) may be performed on at least one of the plurality of acquired image frames.

In this case, the first color channel value may refer to an average pixel value for a first color channel of the image frame on which the acquisition operation is performed, the second color channel value may refer to an average pixel value for a second color channel of the image frame, and the third color channel value may refer to an average pixel value for a third color channel of the image frame.

For example, the first color channel value may be a green channel value, the second color channel value may be a red channel value, and the third color channel value may be a blue channel value, but the present invention is not limited thereto.

Also, the operation of calculating the first difference and the second difference (S2830) may be performed on at least one of the plurality of acquired image frames.

In this case, the first difference may refer to a difference between the first color channel value and the second color channel value. For example, the first difference may refer to a difference between the first color channel value and the second color channel value for the same image frame, but the present invention is not limited thereto.

In detail, when the first color channel value is a green channel value and the second color channel value is a red channel value, the first difference may be a G–R value, but the present invention is not limited thereto.

Also, the second difference may refer to a difference between the first color channel value and the third color channel value. For example, the second difference may refer to a difference between the first color channel value and the third color channel value for the same image frame, but the present invention is not limited thereto.

In detail, when the first color channel value is a green channel value and the second color channel value is a blue channel value, the second difference may be a G–B value, but the present invention is not limited thereto.

Also, the operation of acquiring the characteristic value and the second characteristic value (S2840) may be performed on an image frame group including at least some of the plurality of acquired image frames.

For example, the first characteristic value may be acquired for a first image frame group, and the first image frame group may refer to an image frame group acquired during a predetermined time.

Also, for example, the second characteristic value may be acquired for a second image frame group, and the second image frame group may refer to an image frame group acquired during a predetermined time.

Also, the first characteristic value may be acquired based on the mean of first differences for the first image frame group and a first difference of an image frame included in the first image frame group.

For example, the first characteristic value may be a deviation acquired based on the mean of G–R values for the first image frame group and a G–R value for an image frame included in the first image frame group, but the present invention is not limited thereto.

Also, the second characteristic value may be acquired based on the mean of first differences for the second image frame group and a second difference of an image frame included in the second image frame group.

For example, the second characteristic value may be a deviation acquired based on the mean of G–B values for the second image frame group and a G–B value for an image frame included in the second image frame group, but the present invention is not limited thereto.

Here, the first image frame group may be identical to the second image frame group. However, the present invention is not limited thereto, and the first image frame group may be different from the second image frame group.

Also, the first characteristic value may be the mean, standard deviation, or the like of the first image frame group, but the present invention is not limited thereto.

Also, the first characteristic value may be the deviation or the like of at least some image frames included in the first image frame group, but the present invention is not limited thereto.

Also, the second characteristic value may be the mean, standard deviation, or the like of the second image frame group, but the present invention is not limited thereto.

Also, the second characteristic value may be the deviation or the like of at least some image frames included in the second image frame group, but the present invention is not limited thereto.

Also, the first characteristic value and the second characteristic value may be normalized. For example, the first characteristic value may be normalized using the standard deviation of the first image frame group, but the present invention is not limited thereto.

Also, for example, the second characteristic value may be normalized using the standard deviation of the second image frame group, but the present invention is not limited thereto.

Also, the operation of determining the physiological parameter of the subject on the basis of the first and second characteristic values (S2850) may be performed on an image frame group including at least some of the plurality of acquired image frames.

In this case, the physiological parameter may be a heart rate, a blood pressure, an oxygen saturation level, a core temperature, or the like, but the present invention is not limited thereto.

Also, the physiological parameter may be acquired based on the first characteristic value and the second characteristic value.

For example, the physiological parameter may be acquired based on a third characteristic value obtained by adding the first characteristic value and the second characteristic value, but the present invention is not limited thereto.

7. Various Embodiments of Method of Acquiring Plurality of Physiological Parameters and Plurality of Pieces of Physiological Information FIG. 29 is a diagram illustrating a method of acquiring a plurality of physiological parameters and a plurality of pieces of physiological information according to an embodiment.

Figure 29:
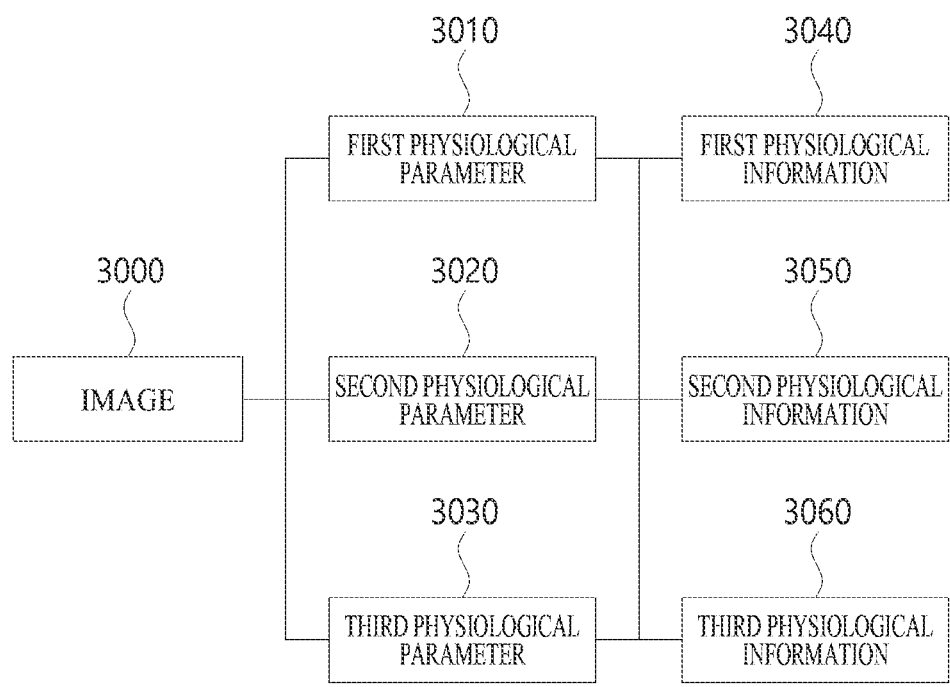
FIG. 29 is a diagram illustrating a method of acquiring a plurality of physiological parameters and a plurality of pieces of physiological information according to an embodiment.

Referring to FIG. 29, the method of acquiring a plurality of physiological parameters and a plurality of pieces of physiological information according to an embodiment may include acquiring a plurality of physiological parameters on the basis of an acquired image 3000. In detail, as shown in FIG. 29, a first physiological parameter 3010, a second physiological parameter 3020, and a third physiological parameter 3030 may be acquired based on the acquired image 3000. However, the present invention is not limited thereto, and at least two physiological parameters may be acquired. For example, four physiological parameters may be acquired.

In this case, the acquired image 3000 may be a visible light image which is acquired using a visible light camera or which is acquired from a visible light camera placed outside.

Also, the acquired image 3000 may be an infrared image which is acquired using an infrared camera or which is acquired from an infrared camera placed outside.

Also, the first to third physiological parameters 3010, 3020, and 30303 may include at least one of a heart rate, an oxygen saturation level, a blood pressure, and a core temperature, but the present invention is not limited thereto.

Also, the first to third physiological parameters 3010, 3020, and 3030 may be acquired in association with each other. For example, the first to third physiological parameters 3010, 3020, and 3030 may be physiological parameters acquired in the same or similar states of the subject, but the present invention is not limited thereto.

Also, the first to third physiological parameters 3010, 3020, and 3030 may be acquired independently of each other. For example, the first to third physiological parameters 3010, 3020, and 3030 may be physiological parameters acquired in different states of the subject, but the present invention is not limited thereto.

Also, the first to third physiological parameters 3010, 3020, and 3030 may be output at the same time. For example, the first to third physiological parameters 3010, 3020, and 3030 may be output at the same time when measured in real time, but the present invention is not limited thereto.

Also, the first to third physiological parameters 3010, 3020, and 3030 may be output at different times. For example, the second physiological parameter may be output after the first physiological parameter is output, and the third physiological parameter may be output after the second physiological parameter is output.

Also, Referring to FIG. 29, the method of acquiring a plurality of physiological parameters and a plurality of pieces of physiological information according to an embodiment may include acquiring a plurality of pieces of physiological information on the basis of the plurality of acquired physiological parameters.

In detail, as shown in FIG. 29, first physiological information 3040, second physiological information 3050, and third physiological information 3060 may be acquired on the acquired first to third physiological parameters 3010, 3020, and 3030, but the present invention is not limited thereto.

In this case, the first to third physiological information 3040, 3050, and 3060 may include at least one of drowsiness information, stress information, excitement information, and emotion information, but the present invention is not limited thereto.

Also, the first to third physiological information 3040, 3050, and 3060 may be acquired based on at least one of the first to third physiological parameters 3010, 3020, and 3030, but the present invention is not limited thereto.

Also, the first to third physiological information 3040, 3050, and 3060 may be acquired in consideration of personal statistical data in addition to the first to third physiological parameters 3010, 3020, and 3030. In this case, the term "personal statistical data" may refer to collectible personal statistical data of a subject such as age, gender, height, and weight, observable personal statistical data such as facial expressions, wrinkles, and face color of a subject, or quantifiable personal statistical data such as statistical data (e.g., the average blood pressure of people in their 20s, the average skin color of Asian people, the average height of men in their 30s, the average weight of Korean men, etc.) calculated for a group including or relating to a subject.

Also, the first to third physiological information 3040, 3050, and 3060 may be acquired based on independent physiological parameters. For example, the first to third physiological information 3040, 3050, and 3060 may be acquired based on the first to third physiological parameters 3010, 3020, and 3030 acquired independently of each other.

Also, the first to third physiological information 3040, 3050, and 3060 may be acquired based on associated physiological parameters. For example, the first to third physiological information 3040, 3050, and 3060 may be acquired based on the first to third physiological parameters 3010, 3020, and 3030 acquired in association with each other.

Also, when the first to third physiological information 3040, 3050, and 3060 are acquired based on associated physiological parameters, it is possible to improve the accuracy of the physiological information. For example, when a heart rate and a blood pressure to be included in the first to third physiological parameters 3010, 3020, and 3030 are used to acquire hypertension information be included in the first to third physiological information 3040, 3050, and 3060, the hypertension information may be more accurate when the heart rate and the blood pressure are associated with each other.

In detail, when it is assumed that a blood pressure is measured when a subject is exercising or excited, that a heart rate is measured when the subject is stable, and that hypertension information is acquired based on the blood pressure and the heart rate, the subject may be detected as having hypertension even if the subject is not hypertensive. However, on the contrary, when it is assumed that a blood pressure and a heart rate are measured when a subject is exercising or excited and that hypertension information is acquired based on the blood pressure and the heart rate, the hypertension information may be accurately acquired.

The method of acquiring a plurality of physiological parameters and a plurality of pieces of physiological information will be described below in detail.

Figure 30:
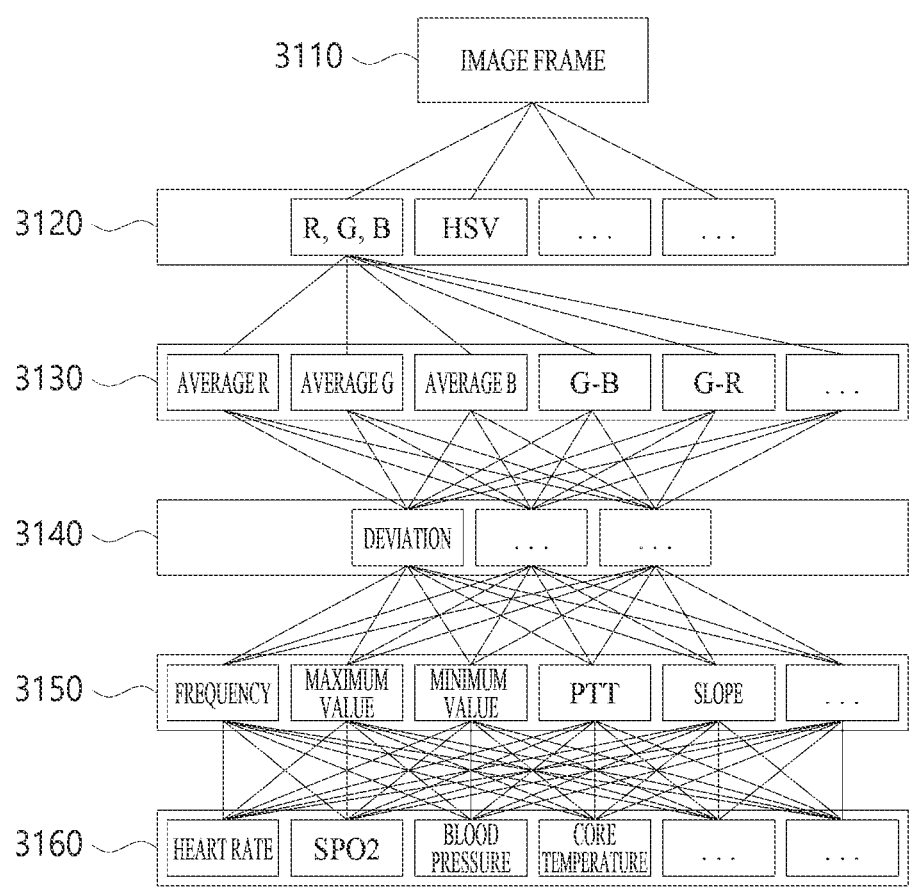
FIG. 30 is a diagram illustrating a method of acquiring a plurality of physiological parameters according to an embodiment.

FIG. 30 is a diagram illustrating a method of acquiring a plurality of physiological parameters according to an embodiment.

Referring to FIG. 30, an image frame 3110 may be acquired to acquire a plurality of physiological parameters according to an embodiment.

In this case, the image frame 3110 may be an image frame acquired from a visible light image, an infrared image, etc., but the present invention is not limited thereto.

Also, the image frame 3110 may include a plurality of image frames, but the present invention is not limited thereto.

Also, referring to FIG. 30, at least one pixel value 3120 may be acquired to acquire a plurality of physiological parameters according to an embodiment.

In this case, the pixel value 3120 may refer to an intensity value of at least one pixel included in an image frame, and particularly, an intensity value of at least one pixel for at least one color channel. For example, when the image frame is a 640*480 image, the image frame may include 640*480 pixels, and a red channel pixel value, a green channel pixel value, and a blue channel pixel value for each pixel may be acquired. However, the present invention is not limited thereto, and pixel values for color channels corresponding to various color spaces may be acquired.

Also, the pixel value 3120 may be acquired only for at least some of a plurality of pixels included in the image frame.

Also, referring to FIG. 30, at least one color channel value 3130 may be acquired to acquire a plurality of physiological parameters according to an embodiment.

In this case, the color channel value 3130 may refer to the mean of color channel pixel values. For example, the red channel value may refer to the mean of red channel pixel values, the green channel value may refer to the mean of green channel pixel values, and the blue channel value may refer to the mean of blue channel pixel values, but the present invention is not limited thereto.

Although the color channel value and the processed value have been separately described throughout the specification, the processed value may be described below as a concept included in the color channel value in order to describe a method of acquiring a plurality of physiological parameters.

Also, the color channel value 3130 may be described including a processed value. For example, the color channel value may be described including a G–R value, which is a difference between the red channel value and the green channel value, but the present invention is not limited thereto.

Also, the color channel value 3130 may be acquired for at least one of the plurality of acquired image frames.

Also, the color channel value 3130 may be acquired based on one color channel pixel value and may also be acquired based on a plurality of color channel pixel values. For example, a red channel value may be acquired based on a red channel pixel value, and a G–R value may be acquired based on a green channel pixel value and a red channel pixel value, but the present invention is not limited thereto.

Also, referring to FIG. 30, at least one piece of time-series data may be acquired to acquire a plurality of physiological parameters according to an embodiment.

In this case, time-series data 3140 may be acquired based on the acquired at least one color channel value 3130 and may also be acquired for an image frame group including at least some of the plurality of acquired image frames.

In this case, when the time-series data 3140 is acquired based on at least one color channel value 3130 acquired for a first image frame, the time-series data may be acquired for an image frame group including the first image frame.

Also, the time-series data 3140 may be time-series data of the color channel value 3130. For example, the time-series data 3140 may include time-series data of a red channel value, time-series data of a green channel value, time-series data of a blue channel value, time-series data of a hue channel value, time-series data of a G–R value, or time-series data of a G–B value, but the present invention is not limited thereto.

Also, the time-series data 3140 may be time-series data of a characteristic value acquired based on the color channel value 3130. For example, the time-series data may include the deviation, standard deviation, or mean of color channel values for at least some image frames included in an image frame group, but the present invention is not limited thereto.

For example, the time-series data 3140 may be time-series data of a red channel value and may also be time-series data of a G–R value, but the present invention is not limited thereto.

Also, for example, the time-series data 3140 may be time-series data for the deviation of color channel values for at least some image frames included in an image frame group, but the present invention is not limited thereto.

Also, the time-series data 3140 may be time-series data acquired based on a plurality of pieces of time-series data. For example, the time-series data 3140 may be first time-series data for a first image frame group including a first image frame and may also be second time-series data for a second image frame group including a second image frame, but the present invention is not limited thereto.

In detail, for example, when the time-series data 3140 is time-series data for an image frame group including 180 image frames, the time-series data 3140 may be acquired based on first time-series data acquired for a first image frame group including $1^{st}$ to $18^{st}$ image frames, second time-series data acquired for a second image frame group including $19^{th}$ to $36^{th}$ image frames, third time-series data acquired for a third image frame group including $37^{th}$ to $54^{th}$ image frames, fourth time-series data acquired for a fourth image frame group including $55^{th}$ to $72^{nd}$ image frames, fifth image-series data acquired for a fifth image frame group including $73^{rd}$ to $90^{th}$ image frames, sixth time-series data acquired for a sixth image frame group including $91^{st}$ to $108^{th}$ image frames, seventh time-series data acquired for a seventh image frame group including $109^{th}$ to $126^{th}$ image frames, eighth time-series data acquired for an eighth image frame group including $127^{th}$ to $144^{th}$ image frames, ninth time-series data acquired for a ninth image frame group including $145^{th}$ to $162^{nd}$ image frames, and tenth time-series data acquired for a tenth image frame group including $163^{rd}$ to $180^{th}$ image frame.

Also, referring to FIG. 30, a feature 3150 may be acquired to acquire a plurality of physiological parameters according to an embodiment.

In this case, the feature 3150 may refer to a mathematical or physical feature of the acquired time-series data. For example, the feature may refer to a mathematical feature of the acquired time-series data such as a frequency component, a maximum value, the mean of maximum values, a minimum value, the mean of minimum values, a difference between a maximum value and a minimum value, a difference between the mean of maximum values and the mean of minimum values, an alternating current (AC) value, a direct current (DC) value, an average value, an inflection point, first-order differential data, second-order differential data, and a slope at a specific point or a physical feature of the acquired time-series data such as a blood variation, a blood change rate, a blood vessel variation, and a blood vessel change rate, but the present invention is not limited thereto.

Also, the feature 3150 may refer to a mathematical or physical feature between a plurality of pieces of time-series data. For example, the feature may refer to a mathematical feature between the plurality of acquired time-series data such as a time difference therebetween, a time difference between local maximum values, a time difference between local minimum values, a time difference between inflection points, and the like or a physical feature between the plurality of acquired time-series data such as a pulse transit time (PTT), a difference between blood change rates, a time difference between blood vessel changes caused by blood, but the present invention is not limited thereto.

Also, the feature 3150 may be acquired for an image frame group including at least some of the plurality of acquired image frames.

Also, the feature 3150 may be acquired based on at least one piece of time-series data 3140. For example, the feature 3150 may be acquired based on one piece of time-series data and may also be acquired based on at least two pieces of time-series data, but the present invention is not limited thereto.

Also, referring to FIG. 30, a physiological parameter 3160 may be acquired to acquire a plurality of physiological parameters according to an embodiment.

In this case, the physiological parameter 3160 may be a heart rate, an oxygen saturation level, a blood pressure, a core temperature, or the like, but the present invention is not limited thereto.

Also, the physiological parameter 3160 may be acquired based on different features. For example, a heart rate may be acquired based on a frequency component of time-series data, a blood pressure may be acquired based on a PTT value between two pieces of time-series data, and an oxygen saturation level may be acquired based on AC values and DC values of two pieces of time-series data, but the present invention is not limited thereto.

Also, the physiological parameter 3160 may include a plurality of physiological parameters. For example, a heart rate, an oxygen saturation level, and a blood pressure may be acquired, but the present invention is not limited thereto.

Also, the physiological parameter 3160 may be acquired for an image frame group including at least some of the plurality of acquired image frames.

Also, the same image frame group may be used as a basis to acquire the plurality of physiological parameters 3160. For example, a heart rate, an oxygen saturation level, and a blood pressure may be acquired based on an image frame group including $1^{st}$ to $180^{th}$ image frames, but the present invention is not limited thereto.

Also, different image frame groups may be used as a basis to acquire the plurality of physiological parameters 3160. For example, a heart rate may be acquired based on a first image frame group including $1^{st}$ to $90^{th}$ image frames, an oxygen saturation level may be acquired based on a second image frame group including $91^{st}$ to $180^{th}$ image frames, and a blood pressure may be acquired based on a third image frame including $181^{st}$ to $270^{th}$ image frames, but the present invention is not limited thereto.

Also, image frame groups used as a basis to acquire the plurality of physiological parameters 3160 may at least partially overlap each other. For example, a heart rate may be acquired based on a first image frame group including $1^{st}$ to $180^{th}$ image frames, an oxygen saturation level may be acquired based on a second image frame group including $30^{th}$ to $100^{th}$ image frames, and a blood pressure may be acquired based on a third image frame including $10^{th}$ to $180^{th}$ image frames, but the present invention is not limited thereto.

Also, image frames included in image frame groups used as a basis to acquire the plurality of physiological parameters 3160 may be the same or different in number.

Figure 31:
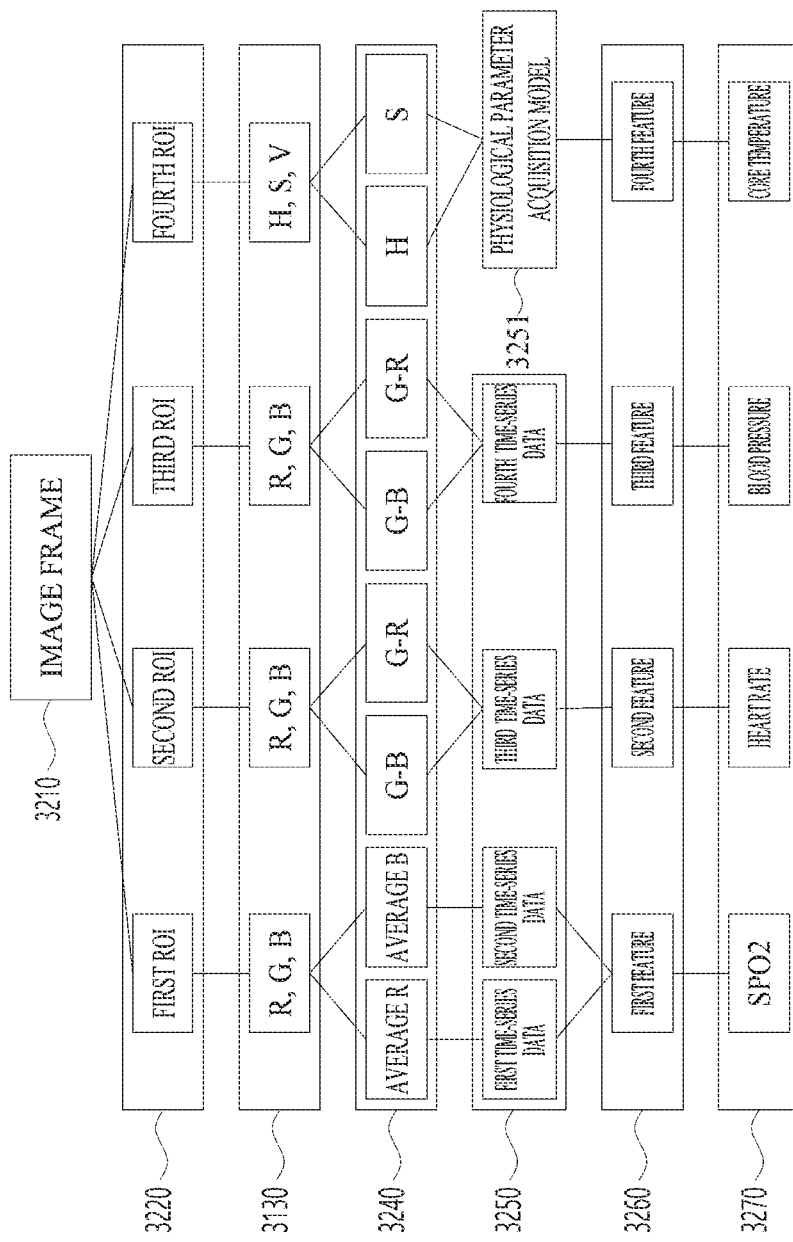
FIG. 31 is a diagram illustrating a method of acquiring a plurality of physiological parameters according to an embodiment.

7.1 Method of Acquiring Plurality of Physiological Parameters According to Embodiment FIG. 31 is a diagram illustrating a method of acquiring a plurality of physiological parameters according to an embodiment.

Referring to FIG. 31, an image frame 3210 may be acquired to acquire a plurality of physiological parameters according to an embodiment.

In this case, the image frame 3210 may be an image frame acquired from a visible light image, an infrared image, etc., but the present invention is not limited thereto.

Also, the image frame 3210 may include a plurality of image frames, but the present invention is not limited thereto.

Also, referring to FIG. 31, at least one ROI 3220 may be set to acquire a plurality of physiological parameters according to an embodiment. In detail, a first ROI, a second ROI, a third ROI, and a fourth ROI may be set.

In this case, the first ROI may be an ROI for acquiring an oxygen saturation level, the second ROI may be an ROI for acquiring a heart rate, the third ROI may be an ROI for acquiring a blood pressure, and the fourth ROI may be an ROI for acquiring a core temperature, but the present invention is not limited thereto.

Also, the first to fourth ROIs may be the same or different from each other.

Also, the first to fourth ROIs may at least partially overlap each other.

Also, the sizes and areas of the first to fourth ROIs may be set based on a physiological parameter to be acquired. For example, the second ROI for acquiring a heart rate may be set to be large enough to include a cheek region of a subject so as to detect a change in blood caused by a heartbeat well, and the third ROI for acquiring a blood pressure may be set to be vertically small and horizontally long enough to include a cheek region of a subject so as to detect a fine blood flow rate well, but the present invention is not limited thereto.

Also, referring to FIG. 31, at least one pixel value 3230 may be acquired to acquire a plurality of physiological parameters according to an embodiment.

Also, the pixel value 3230 may be acquired for at least one of the plurality of acquired image frames.

In detail, at least some of a red channel pixel value, a green channel pixel value, and a blue channel pixel value, which correspond to an RGB color space, may be acquired for the first ROI, at least some of a red channel pixel value, a green channel pixel value, and a blue channel pixel value, which correspond to an RGB color space, may be acquired for the second ROI, at least some of a red channel pixel value, a green channel pixel value, and a blue channel pixel value, which correspond to an RGB color space, may be acquired for the third ROI, and a hue channel pixel value, a saturation channel pixel value, and a value channel pixel value corresponding to an HSV color space may be acquired for the fourth ROI, but the present invention is not limited thereto.

Also, referring to FIG. 31, at least one color channel value 3240 may be acquired to acquire a plurality of physiological parameters according to an embodiment.

In this case, the color channel value 3240 may refer to the mean of color channel pixel values and also may refer to a processed value. However, this has been described in detail above, and thus a redundant description thereof will be omitted.

Also, the color channel value 3240 may be acquired in consideration of a physiological parameter to be acquired.

In detail, at least two color channel values may be acquired for the first ROI for acquiring an oxygen saturation level.

For example, at least two of a red channel value, a green channel value, and a blue channel value, which correspond to an RGB color space, a hue channel value, a saturation channel value, and a value channel value, which correspond to an HSV color space, and the like may be acquired for the first ROI for acquiring an oxygen saturation level, but the present invention is not limited thereto.

Also, for example, at least two of a G–R value, which is a difference between a red channel value and a green channel value, a G–B value, which is a difference between a green channel value and a blue channel value, an H–V value, which is a difference between a hue channel value and a value channel value, and the like may be acquired for the first ROI for acquiring an oxygen saturation level, but the present invention is not limited thereto.

Also, the at least two color channel values may be selected in consideration of the absorbance of hemoglobin and oxyhemoglobin.

For example, a blue channel in which the absorbance of oxyhemoglobin is higher than the absorbance of hemoglobin and a red channel in which the absorbance of oxyhemoglobin is lower than the absorbance of hemoglobin may be selected, and thus the at least two color channel values may be selected as a red channel value and a blue channel value, but the present invention is not limited thereto.

Also, at least two color channel values may be acquired for the second ROI for acquiring a heart rate.

For example, at least two of a red channel value, a green channel value, and a blue channel value, which correspond to an RGB color space, a hue channel value, a saturation channel value, and a value channel value, which correspond to an HSV color space, and the like may be acquired for the second ROI for acquiring a heart rate, but the present invention is not limited thereto.

Also, for example, at least two of a G–R value, which is a difference between a red channel value and a green channel value, a G–B value, which is a difference between a green channel value and a blue channel value, an H–V value, which is a difference between a hue channel value and a value channel value, and the like may be acquired for the first ROI for acquiring a heart rate, but the present invention is not limited thereto.

Also, the at least two color channel values may be selected to reduce noise caused by motion and noise caused by external light or the like.

For example, a G–R value, which is a difference between a green channel value absorbed relatively more by hemoglobin and oxyhemoglobin and a red channel value absorbed relatively less by hemoglobin and oxyhemoglobin, and a G–B value, which is a difference between a green channel value absorbed relatively more by hemoglobin and oxyhemoglobin and a blue channel value absorbed relatively less by hemoglobin and oxyhemoglobin, may be selected to reduce the noise, but the present invention is not limited thereto.

Also, for example, a G–R value and a G–B value, which are differences between a green channel value reflecting relatively more of a change caused by a heartbeat and red and blue channel values reflecting relatively less of a change caused by a heartbeat, may be selected to reduce the noise, but the present invention is not limited thereto.

Also, at least two color channel values may be acquired for the third ROI for acquiring a blood pressure.

For example, at least two of a red channel value, a green channel value, and a blue channel value, which correspond to an RGB color space, a hue channel value, a saturation channel value, and a value channel value, which correspond to an HSV color space, and the like may be acquired for the third ROI for acquiring a blood pressure, but the present invention is not limited thereto.

Also, for example, at least two of a G–R value, which is a difference between a red channel value and a green channel value, a G–B value, which is a difference between a green channel value and a blue channel value, an H–V value, which is a difference between a hue channel value and a value channel value, and the like may be acquired for the third ROI for acquiring a blood pressure, but the present invention is not limited thereto.

Also, the at least two color channel values may be selected to reduce noise caused by motion and noise caused by external light or the like.

For example, a G–R value, which is a difference between a green channel value absorbed relatively more by hemoglobin and oxyhemoglobin and a red channel value absorbed relatively less by hemoglobin and oxyhemoglobin, and a G–B value, which is a difference between a green channel value absorbed relatively more by hemoglobin and oxyhemoglobin and a blue channel value absorbed relatively less by hemoglobin and oxyhemoglobin, may be selected to reduce the noise, but the present invention is not limited thereto.

Also, for example, a G–R value and a G–B value, which are differences between a green channel value reflecting relatively more of a change caused by a heartbeat and red and blue channel values reflecting relatively less of a change caused by a heartbeat, may be selected to reduce the noise, but the present invention is not limited thereto.

Also, at least two color channel values may be acquired for the fourth ROI for acquiring a core temperature.

For example, at least two of a red channel value, a green channel value, and a blue channel value, which correspond to an RGB color space, a hue channel value, a saturation channel value, and a value channel value, which correspond to an HSV color space, and the like may be acquired for the fourth ROI for acquiring a core temperature, but the present invention is not limited thereto.

Also, for example, at least two of a G–R value, which is a difference between a red channel value and a green channel value, a G–B value, which is a difference between a green channel value and a blue channel value, an H–V value, which is a difference between a hue channel value and a value channel value, and the like may be acquired for the fourth ROI for acquiring a core temperature, but the present invention is not limited thereto.

Also, the at least two color channel values may be selected in consideration of a feature of a core temperature and a subject's skin color.

For example, a saturation channel value associated with a subject's core temperature and a hue channel value associated with a subject's skin color may be selected, but the present invention is not limited thereto.

Also, referring to FIG. 31, at least one piece of time-series data 3250 may be acquired to acquire a plurality of physiological parameters according to an embodiment.

Also, the time-series data 3250 may be acquired in consideration of a physiological parameter to be acquired.

In detail, at least two pieces of time-series data may be acquired for the first ROI for acquiring an oxygen saturation level. For example, first time-series data and second time-series data may be acquired for the first ROI for acquiring an oxygen saturation level.

In this case, the first time-series data may be acquired based on a color channel value acquired for the first ROI. For example, when the color channel value acquired for the first ROI for acquiring an oxygen saturation level is a red channel value, the first time-series data may be acquired based on the red channel value, but the present invention is not limited thereto.

Also, the first time-series data may be acquired for an image frame group including at least some of a plurality of acquired image frames.

For example, when the first time-series data is acquired based on a red channel value acquired for a first image frame, the first time-series data may be acquired for a first image frame group including the first image frame, but the present invention is not limited thereto.

Also, the second time-series data may be acquired based on a color channel value acquired for the first ROI. For example, when the color channel value acquired for the first ROI for acquiring an oxygen saturation level is a blue channel value, the second time-series data may be acquired based on the blue channel value, but the present invention is not limited thereto.

Also, the second time-series data may be acquired for an image frame group including at least some of a plurality of acquired image frames.

For example, when the second time-series data is acquired based on a blue channel value acquired for a second image frame, the second time-series data may be acquired for a second image frame group including the second image frame, but the present invention is not limited thereto.

Also, the first and second image frame groups may be the same, different, or at least partially overlapping each other.

Also, at least one piece of time-series data may be acquired for the second ROI for acquiring a heart rate. For example, third time-series data may be acquired for the second ROI for acquiring a heart rate.

In this case, the third time-series data may be acquired based on a color channel value acquired for the second ROI. For example, when the color channel value acquired for the second ROI for acquiring a heart rate includes a G–R value and a G–B value, the third time-series data may be acquired based on the G–R value and the G–B value, but the present invention is not limited thereto.

Also, the third time-series data may be acquired for an image frame group including at least some of a plurality of acquired image frames.

For example, when the third time-series data is acquired based on a G–R value and a G–B value acquired for a third image frame, the third time-series data may be acquired for a third image frame group including the third image frame, but the present invention is not limited thereto.

Also, the third time-series data may be acquired based on a characteristic value acquired for the second ROI. For example, the third time-series data may be acquired based on a characteristic value acquired based on the G–R value acquired for the second ROI and a characteristic value acquired based on the G–B value acquired for the second ROI, but the present invention is not limited thereto.

Also, at least one piece of time-series data may be acquired for the third ROI for acquiring a blood pressure. For example, fourth time-series data may be acquired for the third ROI for acquiring a blood pressure.

In this case, the fourth time-series data may be acquired based on a color channel value acquired for the third ROI. For example, when the color channel value acquired for the third ROI for acquiring a blood pressure includes a G–R value and a G–B value, the fourth time-series data may be acquired based on the G–R value and the G–B value, but the present invention is not limited thereto.

Also, the fourth time-series data may be acquired for an image frame group including at least some of a plurality of acquired image frames.

For example, when the fourth time-series data is acquired based on a G–R value and a G–B value acquired for a fourth image frame, the fourth time-series data may be acquired for a fourth image frame group including the fourth image frame, but the present invention is not limited thereto.

Also, the fourth time-series data may be acquired based on a characteristic value acquired for the third ROI. For example, the fourth time-series data may be acquired based on a characteristic value acquired based on the G–R value acquired for the third ROI and a characteristic value acquired based on the G–B value acquired for the third ROI, but the present invention is not limited thereto.

Also, the first, second, third, and fourth image frame groups may be the same. However, the present invention is not limited thereto, and these image frame groups may differ from each other or at least partially overlap each other.

Also, referring to FIG. 31, at least one physiological parameter acquisition model 3251 may be used to acquire a plurality of physiological parameters according to an embodiment.

However, the physiological parameter acquisition model 3251 has been described, and thus a redundant description thereof will be omitted.

Also, the physiological parameter acquisition model 3251 may be used to acquire a core temperature.

In detail, the physiological parameter acquisition model 3251 may have, as an input value, a color channel value acquired for the fourth ROI for acquiring a core temperature. For example, the physiological parameter acquisition model 3251 may have, as input values, a hue channel value and a saturation channel value acquired for the fourth ROI, but the present invention is not limited thereto.

Also, the input value of the physiological parameter acquisition model 3251 may include a color channel value, a characteristic value, the mean of color channel values for an image frame group, etc., but the present invention is not limited thereto.

Also, referring to FIG. 31, at least one feature 3260 may be acquired to acquire a plurality of physiological parameters according to an embodiment.

Also, the at least one feature 3260 may be acquired in consideration of a physiological parameter to be acquired.

In detail, at least one feature may be acquired for the first ROI for acquiring an oxygen saturation level. For example, a first feature may be acquired for the first ROI for acquiring an oxygen saturation level.

In this case, the first feature may be acquired based on a color channel value or time-series data acquired for the first ROI. For example, when the color channel value acquired for the first ROI includes a red channel value and a blue channel value, the first feature may be acquired based on the red channel value and the blue channel value, but the present invention is not limited thereto.

Also, for example, the first feature may be acquired based on first time-series data and second time-series data acquired for the first ROI, but the present invention is not limited thereto.

Also, the first feature may be a feature for acquiring an oxygen saturation level. For example, the first feature may include an AC value and a DC value acquired based on the first time-series data and an AC value and a DC value acquired based on the second time-series data, but the present invention is not limited thereto.

Also, for example, the first feature may include at least one of a difference between the mean of local maximum values and the mean of the local minimum values acquired based on the first time-series data, an average value acquired based on the first time-series data, a difference between the mean of local maximum values and the mean of the local minimum values acquired based on the second time-series data, and an average value acquired based on the second time-series data, but the present invention is not limited thereto.

Also, the first feature may include a plurality of features. For example, the first feature may include at least two of a difference between the mean of local maximum values and the mean of the local minimum values acquired based on the first time-series data, an average value acquired based on the first time-series data, a difference between the mean of local maximum values and the mean of the local minimum values acquired based on the second time-series data, and an average value acquired based on the second time-series data, but the present invention is not limited thereto.

Also, at least one feature may be acquired for the second ROI for acquiring a heart rate. For example, a second feature may be acquired for the second ROI for acquiring a heart rate.

In this case, the second feature may be acquired based on a color channel value or time-series data acquired for the second ROI. For example, when the color channel value acquired for the second ROI includes a G–R value and a G–B value, the second feature may be acquired based on the G–R value and the G–B value, but the present invention is not limited thereto.

Also, for example, the second feature may be acquired based on third time-series data acquired for the second ROI, but the present invention is not limited thereto.

Also, the second feature may be a feature for acquiring a heart rate. For example, the second feature may include a frequency value, a wavelength value, and a value for the number of cycle repetitions during a measurement time, which are acquired based on the third time-series data, but the present invention is not limited thereto.

Also, at least one feature may be acquired for the third ROI for acquiring a blood pressure. For example, a third feature may be acquired for the third ROI for acquiring a blood pressure.

In this case, the third feature may be acquired based on a color channel value or time-series data acquired for the third ROI. For example, when the color channel value acquired for the third ROI includes a G–R value and a G–B value, the third feature may be acquired based on the G–R value and the G–B value, but the present invention is not limited thereto.

Also, for example, the third feature may be acquired based on fourth time-series data acquired for the third ROI, but the present invention is not limited thereto.

Also, the third feature may be a feature for acquiring a blood pressure. For example, the third feature may include a slope value, a maximum value, a minimum value, the mean of local maximum values, the mean of local minimum values, a difference between the mean of local maximum values and the mean of local minimum values, etc., which are acquired based on the fourth time-series data, but the present invention is not limited thereto.

Also, the third feature may include a plurality of features. For example, the third feature may include at least two of a slope value, a maximum value, a minimum value, the mean of local maximum values, the mean of local minimum values, a difference between the mean of local maximum values and the mean of local minimum values, etc., which are acquired based on the fourth time-series data, but the present invention is not limited thereto.

Also, at least one feature may be acquired for the fourth ROI for acquiring a core temperature. For example, a fourth feature may be acquired for the fourth ROI for acquiring a core temperature.

In this case, the fourth feature may be acquired based on an output value of a physiological parameter acquisition model or a color channel value acquired for the fourth ROI. For example, when the color channel value acquired for the fourth ROI includes a hue channel value and a saturation channel value, the fourth feature may be acquired based on the hue channel value and the saturation channel value, but the present invention is not limited thereto.

Also, for example, the fourth feature may be acquired based on the output value of the physiological parameter acquisition model, but the present invention is not limited thereto.

Also, the fourth feature may be a feature for acquiring a core temperature. For example, the fourth feature may be a skin portion, a skin temperature, etc., but the present invention is not limited thereto.

Also, referring to FIG. 31, at least one physiological parameter 3270 may be acquired to acquire a plurality of physiological parameters according to an embodiment.

In detail, each of the physiological parameters may be acquired based on a corresponding feature. For example, an oxygen saturation level may be acquired based on the first feature, a heart rate may be acquired based on the second feature, a blood pressure may be acquired based on the third feature, and a core temperature may be acquired based on the fourth feature, but the present invention is not limited thereto.

In this case, the above equations may be used to acquire an oxygen saturation level on the basis of the first feature, and thus a redundant description thereof will be omitted.

Also, the above equations may be used to acquire a heart rate on the basis of the second feature, and thus a redundant description thereof will be omitted.

Also, the above equations may be used to acquire a blood pressure on the basis of the third feature, and thus a redundant description thereof will be omitted.

Also, the above equations may be used to acquire a core temperature on the basis of the fourth feature, and thus a redundant description thereof will be omitted.

Also, when the physiological parameter 3270 includes a plurality of physiological parameters, the physiological parameters may be acquired at the same time. However, the present invention is not limited thereto, and the physiological parameters may be acquired at different times. For example, an oxygen saturation level and a heart rate may be acquired six seconds after measurement, and a blood pressure may be acquired eight seconds after measurement, but the present invention is not limited thereto.

Also, when the physiological parameter 3270 includes a plurality of physiological parameters, each of the physiological parameters may be acquired based on a corresponding image frame group. For example, an oxygen saturation level may be acquired based on a fifth image frame group, a heart rate may be acquired based on a sixth image frame group, and a blood pressure may be acquired based on a seventh image frame group.

Also, the image frame groups for acquiring the physiological parameter 3270 may be the same. However, the present invention is not limited thereto, and these image frame groups may differ from each other or at least partially overlap each other. For example, the fifth, sixth, and seventh image frame groups may be the same, different, or at least partially overlapped with each other.

Also, at least one preliminary physiological parameter may be acquired to acquire the physiological parameter 3270. For example, at least four preliminary heart rates may be acquired to acquire a heart rate.

However, the above description is applicable to a method of acquiring a heart rate or a physiological parameter using a preliminary heart rate or a preliminary physiological parameter, and thus a redundant description thereof will be omitted.

Also, the number of preliminary physiological parameters for acquiring the physiological parameter 3270 may be the same or different for each physiological parameter. For example, the number of preliminary heart rates for acquiring the heart rate may be at least four, and the number of preliminary saturation levels for acquiring the oxygen saturation level and the number of preliminary blood pressures for acquiring the blood pressure may be at least two, but the present invention is not limited thereto.

Figure 32:
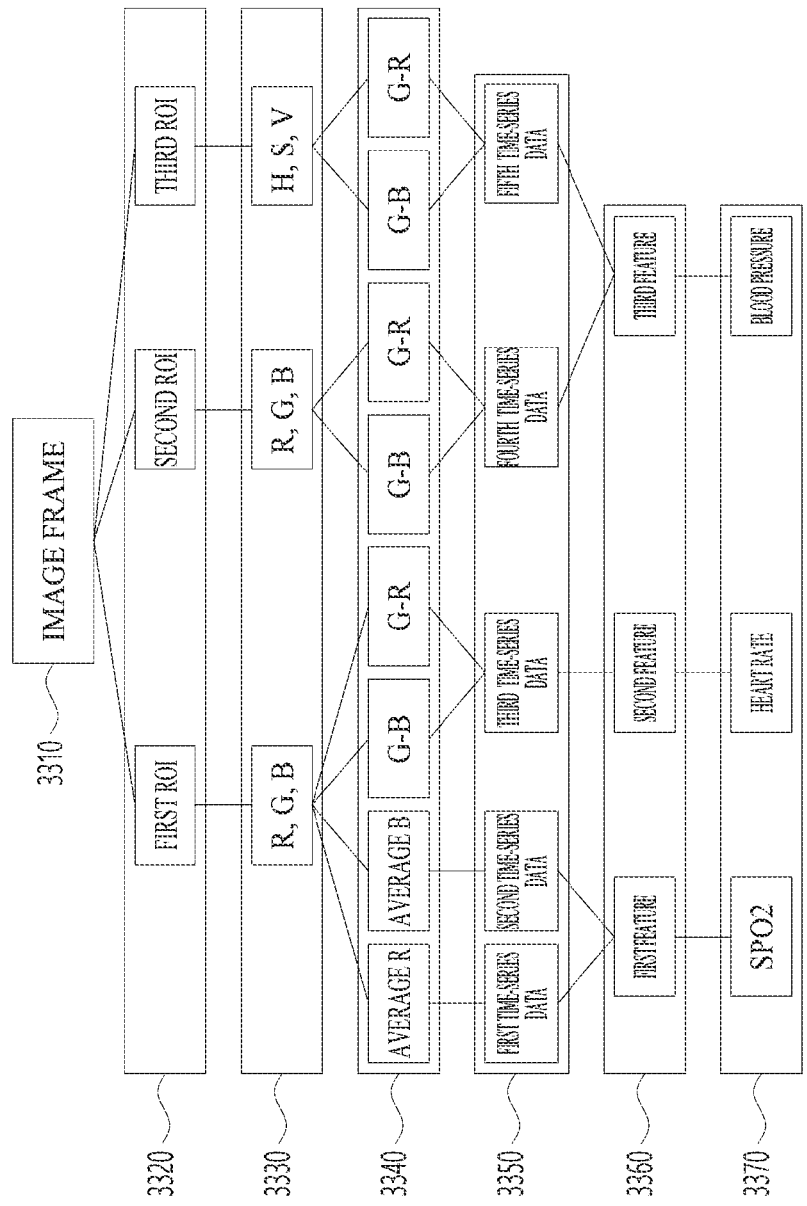
FIG. 32 is a diagram illustrating a method of acquiring a plurality of physiological parameters according to an embodiment.

7.2 Method of Acquiring Plurality of Physiological Parameters According to Embodiment FIG. 32 is a diagram illustrating a method of acquiring a plurality of physiological parameters according to an embodiment.

Referring to FIG. 32, an image frame 3310 may be acquired to acquire a plurality of physiological parameters according to an embodiment.

In this case, the image frame 3310 may be an image frame acquired from a visible light image, an infrared image, etc., but the present invention is not limited thereto.

Also, the image frame 3310 may include a plurality of image frames, but the present invention is not limited thereto.

Also, referring to FIG. 32, at least one ROI 3320 may be set to acquire a plurality of physiological parameters according to an embodiment. In detail, a first ROI, a second ROI, and a third ROI may be set.

In this case, the first ROI may be an ROI for acquiring an oxygen saturation level and a heart rate, and the second ROI and the third ROI may be ROIs for acquiring a blood pressure.

Also, the first to third ROIs may be the same or different from each other.

Also, the first to third ROIs may at least partially overlap each other.

Also, the sizes and areas of the first to third ROIs may be set based on a physiological parameter to be acquired. For example, the size of the first ROI for acquiring a heart rate and an oxygen saturation level may be set so that the first ROI includes a cheek region of a subject so as to detect a change in blood caused by a heartbeat well, and the areas of the second and third ROIs for acquiring a blood pressure may be set according to the direction of blood flow so as to reflect the blood pressure well. However, the present invention is not limited thereto, and the first to third ROIs may be set in various sizes and various areas.

Also, referring to FIG. 32, at least one pixel value 3330 may be acquired to acquire a plurality of physiological parameters according to an embodiment.

Also, the pixel value 3330 may be acquired for at least one of the plurality of acquired image frames.

In detail, at least some of a red channel pixel value, a green channel pixel value, and a blue channel pixel value, which correspond to an RGB color space, may be acquired for the first ROI, at least some of a red channel pixel value, a green channel pixel value, and a blue channel pixel value, which correspond to an RGB color space, may be acquired for the second. ROI, and at least some of a red channel pixel value, a green channel pixel value, and a blue channel pixel value, which correspond to an RGB color space, may be acquired for the third ROI, but the present invention is not limited thereto.

Also, referring to FIG. 32, at least one color channel value 3340 may be acquired to acquire a plurality of physiological parameters according to an embodiment.

In this case, the color channel value 3340 may refer to the mean of color channel pixel values and also may refer to a processed value. However, this has been described in detail above, and thus a redundant description thereof will be omitted.

Also, the color channel value 3340 may be acquired in consideration of a physiological parameter to be acquired.

In detail, at least two color channel values may be acquired for the first ROI for acquiring an oxygen saturation level and a heart rate.

For example, at least two of a red channel value, a green channel value, and a blue channel value, which correspond to an RGB color space, a hue channel value, a saturation channel value, and a value channel value, which correspond to an HSV color space, and the like may be acquired for the first ROI, but the present invention is not limited thereto.

Also, for example, at least two of a G–R value, which is a difference between a red channel value and a green channel value, a G–B value, which is a difference between a green channel value and a blue channel value, an value, which is a difference between a hue channel value and a value channel value, and the like may be acquired for the first ROI, but the present invention is not limited thereto.

Also, the at least two color channel values may be selected to acquire an oxygen saturation level in consideration of the absorbance of hemoglobin and oxyhemoglobin.

For example, a blue channel in which the absorbance of oxyhemoglobin is higher than the absorbance of hemoglobin and a red channel in which the absorbance of oxyhemoglobin is lower than the absorbance of hemoglobin may be selected, and thus the at least two color channel values may be selected as a red channel value and a blue channel value, but the present invention is not limited thereto.

Also, the at least two color channel values may be selected to reduce noise caused by motion and noise caused by external light or the like in order to acquire a heart rate.

For example, a G–R value, which is a difference between a green channel value absorbed relatively more by hemoglobin and oxyhemoglobin and a red channel value absorbed relatively less by hemoglobin and oxyhemoglobin, and a G–B value, which is a difference between a green channel value absorbed relatively more by hemoglobin and oxyhemoglobin and a blue channel value absorbed relatively less by hemoglobin and oxyhemoglobin, may be selected to reduce the noise, but the present invention is not limited thereto.

Also, for example, a G–R value and a G–B value, which are differences between a green channel value reflecting relatively more of a change caused by a heartbeat and red and blue channel values reflecting relatively less of a change caused by a heartbeat, may be selected to reduce the noise, but the present invention is not limited thereto.

Also, at least two color channel values may be acquired for the second and third ROIs for acquiring a blood pressure.

For example, at least two of a red channel value, a green channel value, and a blue channel value, which correspond to an RGB color space, a hue channel value, a saturation channel value, and a value channel value, which correspond to an HSV color space, and the like may be acquired for the second and third ROIs for acquiring a blood pressure, but the present invention is not limited thereto.

Also, for example, at least two of a G–R value, which is a difference between a red channel value and a green channel value, a G–B value, which is a difference between a green channel value and a blue channel value, an H–V value, which is a difference between a hue channel value and a value channel value, and the like may be acquired for the second and third ROIs for acquiring a blood pressure, but the present invention is not limited thereto.

Also, the at least two color channel values may be selected to reduce noise caused by motion and noise caused by external light or the like.

For example, a G–R value, which is a difference between a green channel value absorbed relatively more by hemoglobin and oxyhemoglobin and a red channel value absorbed relatively less by hemoglobin and oxyhemoglobin, and a G–B value, which is a difference between a green channel value absorbed relatively more by hemoglobin and oxyhemoglobin and a blue channel value absorbed relatively less by hemoglobin and oxyhemoglobin, may be selected to reduce the noise, but the present invention is not limited thereto.

Also, for example, a G–R value and a G–B value, which are differences between a green channel value reflecting relatively more of a change caused by a heartbeat and red and blue channel values reflecting relatively less of a change caused by a heartbeat, may be selected to reduce the noise, but the present invention is not limited thereto.

Also, referring to FIG. 32, at least one piece of time-series data 3350 may be acquired to acquire a plurality of physiological parameters according to an embodiment.

Also, the time-series data 3350 may be acquired in consideration of a physiological parameter to be acquired.

In detail, at least two pieces of time-series data may be acquired for the first ROI for acquiring an oxygen saturation level and a heart rate. For example, for the first ROI, first time-series data and second time-series data may be acquired to acquire an oxygen saturation level, and third time-series data may be acquired to acquire a heart rate.

In this case, the first time-series data may be acquired based on a color channel value acquired for the first ROI. For example, when the color channel value acquired for the first ROI is a red channel value, the first time-series data may be acquired based on the red channel value, but the present invention is not limited thereto.

Also, the first time-series data may be acquired for an image frame group including at least some of a plurality of acquired image frames.

For example, when the first time-series data is acquired based on a red channel value acquired for a first image frame, the first time-series data may be acquired for a first image frame group including the first image frame, but the present invention is not limited thereto.

Also, the second time-series data may be acquired based on a color channel value acquired for the first ROI. For example, when the color channel value acquired for the first ROI is a blue channel value, the second time-series data may be acquired based on the blue channel value, but the present invention is not limited thereto.

Also, the second time-series data may be acquired for an image frame group including at least some of a plurality of acquired image frames.

For example, when the second time-series data is acquired based on a blue channel value acquired for a second image frame, the second time-series data may be acquired for a second image frame group including the second image frame, but the present invention is not limited thereto.

Also, the third time-series data may be acquired based on a color channel value acquired for the first ROI. For example, when the color channel value acquired for the first ROI includes a G–R value and a G–B value, the third time-series data may be acquired based on the G–R value and the G–B value, but the present invention is not limited thereto.

Also, the third time-series data may be acquired for an image frame group including at least some of a plurality of acquired image frames.

For example, when the third time-series data is acquired based on a G–R value and a G–B value acquired for a third image frame, the third time-series data may be acquired for a third image frame group including the third image frame, but the present invention is not limited thereto.

Also, the third time-series data may be acquired based on a characteristic value acquired for the first ROI. For example, the third time-series data may be acquired based on a characteristic value acquired based on the G–R value acquired for the first ROI and a characteristic value acquired based on the G–B value acquired for the first ROI.

Also, the first, second, and third image frame groups may be the same. However, the present invention is not limited thereto, and these image frame groups may differ from each other or at least partially overlap each other.

Also, at least one piece of time-series data may be acquired for each of the second ROI and the third ROI to acquire a blood pressure. For example, fourth time-series data may be acquired for the second ROI, and fifth time-series data may be acquired for the third ROI, but the present invention is not limited thereto.

In this case, the fourth time-series data may be acquired based on a color channel value acquired for the second ROI. For example, when the color channel value acquired for the second ROI includes a G–R value and a G–B value, the fourth time-series data may be acquired based on the G–R value and the G–B value, but the present invention is not limited thereto.

Also, the fourth time-series data may be acquired for an image frame group including at least some of a plurality of acquired image frames.

For example, when the fourth time-series data is acquired based on a G–R value and a G–B value acquired for a fourth image frame, the fourth time-series data may be acquired for a fourth image frame group including the fourth image frame, but the present invention is not limited thereto.

Also, the fourth time-series data may be acquired based on a characteristic value acquired for the second ROI. For example, the fourth time-series data may be acquired based on a characteristic value acquired based on the G–R value acquired for the second ROI and a characteristic value acquired based on the G–B value acquired for the second ROI, but the present invention is not limited thereto.

Also, the fifth time-series data may be acquired based on a color channel value acquired for the third ROI. For example, when the color channel value acquired for the third ROI includes a G–R value and a G–B value, the fifth time-series data may be acquired based on the G–R value and the G–B value, but the present invention is not limited thereto.

Also, the fifth time-series data may be acquired for an image frame group including at least some of a plurality of acquired image frames.

For example, when the fifth time-series data is acquired based on a G–R value and a G–B value acquired for a fifth image frame, the fifth time-series data may be acquired for a fifth image frame group including the fifth image frame, but the present invention is not limited thereto.

Also, the fifth time-series data may be acquired based on a characteristic value acquired for the third ROI. For example, the fifth time-series data may be acquired based on a characteristic value acquired based on the G–R value acquired for the third ROI and a characteristic value acquired based on the G–B value acquired for the third ROI, but the present invention is not limited thereto.

Also, the first, second, third, fourth, and fifth image frame groups may be the same. However, the present invention is not limited thereto, and these image frame groups may differ from each other or at least partially overlap each other.

Also, referring to FIG. 32, at least one feature 3360 may be acquired to acquire a plurality of physiological parameters according to an embodiment.

Also, the at least one feature 3360 may be acquired in consideration of a physiological parameter to be acquired.

In detail, at least one feature may be acquired for the first ROI for acquiring an oxygen saturation level and a heart rate. For example, a first feature for the first ROI may be acquired to acquire an oxygen saturation level, and a second feature for the first ROI may be acquired to acquire a heart rate.

In this case, the first feature may be acquired based on a color channel value or time-series data acquired for the first ROI. For example, when the color channel value acquired for the first ROI includes a red channel value and a blue channel value, the first feature may be acquired based on the red channel value and the blue channel value, but the present invention is not limited thereto.

Also, for example, the first feature may be acquired based on first time-series data and second time-series data acquired for the first ROI, but the present invention is not limited thereto.

Also, the first feature may be a feature for acquiring an oxygen saturation level. For example, the first feature may include an AC value and a DC value acquired based on the first time-series data and an AC value and a DC value acquired based on the second time-series data, but the present invention is not limited thereto.

Also, for example, the first feature may include at least one of a difference between the mean of local maximum values and the mean of the local minimum values acquired based on the first time-series data, an average value acquired based on the first time-series data, a difference between the mean of local maximum values and the mean of the local minimum values acquired based on the second time-series data, and an average value acquired based on the second time-series data, but the present invention is not limited thereto.

Also, the first feature may include a plurality of features. For example, the first feature may include at least two of a difference between the mean of local maximum values and the mean of the local minimum values acquired based on the first time-series data, an average value acquired based on the first time-series data, a difference between the mean of local maximum values and the mean of the local minimum values acquired based on the second time-series data, and an average value acquired based on the second time-series data, but the present invention is not limited thereto.

Also, the second feature may be acquired based on a color channel value or time-series data acquired for the first ROI. For example, when the color channel value acquired for the first ROI includes a G–R value and a G–B value, the second feature may be acquired based on the G–R value and the G–B value, but the present invention is not limited thereto.

Also, for example, the second feature may be acquired based on third time-series data acquired for the first ROI, but the present invention is not limited thereto.

Also, the second feature may be a feature for acquiring a heart rate. For example, the second feature may include a frequency value, a wavelength value, and a value for the number of cycle repetitions during a measurement time, which are acquired based on the third time-series data, but the present invention is not limited thereto.

Also, at least one feature may be acquired for the second and third ROIs for acquiring a blood pressure. For example, a third feature may be acquired for the second and third ROIs to acquire a blood pressure.

In this case, the third feature may be acquired based on color channel values or time-series data acquired for the second and third ROIs. For example, when the color channel values acquired for the second and third ROIs include a G–R value and a G–B value, the third feature may be acquired based on the G–R value and the G–B value, but the present invention is not limited thereto.

Also, for example, the third feature may be acquired based on fourth time-series data acquired for the second ROI and fifth time-series data acquired for the third ROI, but the present invention is not limited thereto.

Also, the third feature may be a feature for acquiring a blood pressure. For example, the third feature may include a slope value, a maximum value, a minimum value, the mean of local maximum values, the mean of local minimum values, and a difference between the mean of local maximum values and the mean of local minimum values, etc., which are acquired based on the fourth and fifth time-series data, but the present invention is not limited thereto.

Also, for example, the third feature may include a time difference between the fourth and fifth time-series data, a time difference between local maximum values, a time difference between local minimum values, a time difference between inflection points, etc. but the present invention is not limited thereto.

Also, the third feature may include a plurality of features. For example, the third feature may include at least two of the above-described features, but the present invention is not limited thereto.

Also, referring to FIG. 32, at least one physiological parameter 3370 may be acquired to acquire a plurality of physiological parameters according to an embodiment.

In detail, each of the physiological parameters may be acquired based on a corresponding feature. For example, an oxygen saturation level may be acquired based on the first feature, a heart rate may be acquired based on the second feature, and a blood pressure may be acquired based on the third feature, but the present invention is not limited thereto.

In this case, the above equations may be used to acquire an oxygen saturation level on the basis of the first feature, and thus a redundant description thereof will be omitted.

Also, the above equations may be used to acquire a heart rate on the basis of the second feature, and thus a redundant description thereof will be omitted.

Also, the above equations may be used to acquire a blood pressure on the basis of the third feature, and thus a redundant description thereof will be omitted.

Also, when the physiological parameter 3370 includes a plurality of physiological parameters, the physiological parameters may be acquired at the same time. However, the present invention is not limited thereto, and the physiological parameters may be acquired at different times. For example, an oxygen saturation level and a heart rate may be acquired six seconds after measurement, and a blood pressure may be acquired eight seconds after measurement, but the present invention is not limited thereto.

Also, when the physiological parameter 3370 includes a plurality of physiological parameters, each of the physiological parameters may be acquired based on a corresponding image frame group. For example, an oxygen saturation level may be acquired based on a sixth image frame group, a heart rate may be acquired based on a seventh image frame group, and a blood pressure may be acquired based on an eighth image frame group.

Also, the image frame groups for acquiring the physiological parameter 3370 may be the same. However, the present invention is not limited thereto, and these image frame groups may differ from each other or at least partially overlap each other. For example, the sixth, seventh, and eighth image frame groups may be the same, different, or at least partially overlapped with each other.

Also, at least one preliminary physiological parameter may be acquired to acquire the physiological parameter 3370. For example, at least four preliminary heart rates may be acquired to acquire a heart rate.

However, the above description is applicable to a method of acquiring a heart rate or a physiological parameter using a preliminary heart rate or a preliminary physiological parameter, and thus a redundant description thereof will be omitted.

Also, the number of preliminary physiological parameters for acquiring the physiological parameter 3370 may be the same or different for each physiological parameter. For example, the number of preliminary heart rates for acquiring the heart rate may be at least four, and the number of preliminary saturation levels for acquiring the oxygen saturation level and the number of preliminary blood pressures for acquiring the blood pressure may be at least two, but the present invention is not limited thereto.

Figure 33:
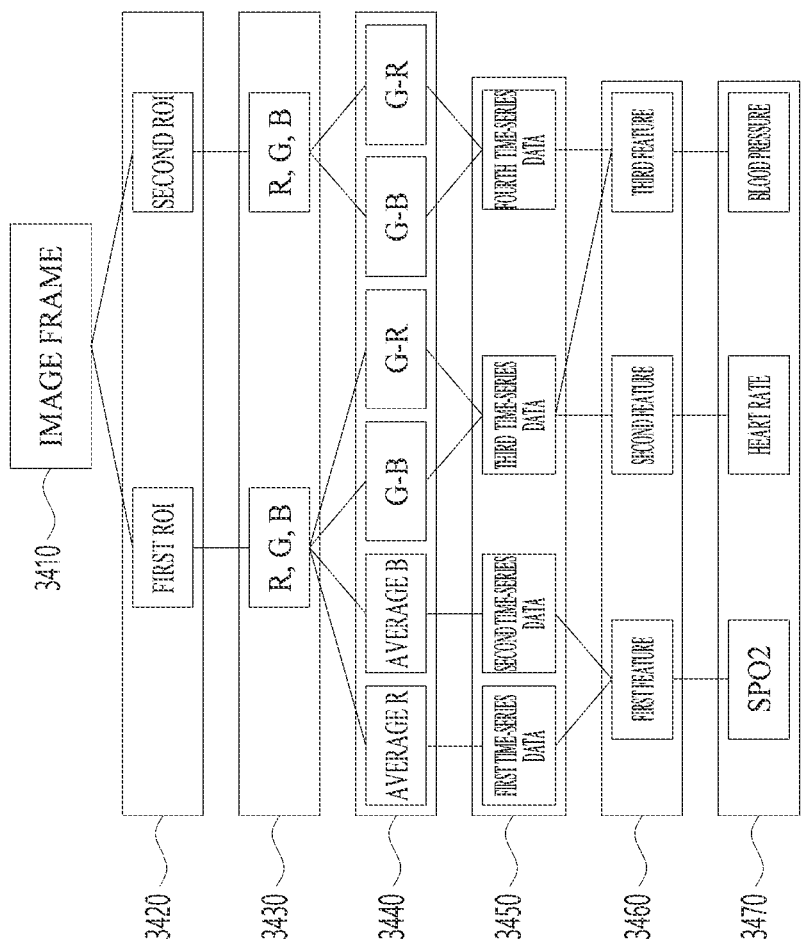
FIG. 33 is a diagram illustrating a method of acquiring a plurality of physiological parameters according to an embodiment.

7.3 Method of Acquiring Plurality of Physiological Parameters According to Embodiment FIG. 33 is a diagram illustrating a method of acquiring a plurality of physiological parameters according to an embodiment.

Referring to FIG. 33, an image frame 3410 may be acquired to acquire a plurality of physiological parameters according to an embodiment.

In this case, the image frame 3410 may be an image frame acquired from a visible light image, an infrared image, etc., but the present invention is not limited thereto.

Also, the image frame 3410 may include a plurality of image frames, but the present invention is not limited thereto.

Also, referring to FIG. 33, at least one ROI 3420 may be set to acquire a plurality of physiological parameters according to an embodiment. In detail, a first ROI and a second ROI may be set.

In this case, the first ROI may be an ROI for acquiring an oxygen saturation level, a heart rate, and a blood pressure, and the first and second. ROIs may be ROIs for acquiring a blood pressure.

Also, the first and second ROIs may be the same or different from each other.

Also, the first and second ROIs may at least partially overlap each other.

Also, the sizes and areas of the first and second ROIs may be set based on a physiological parameter to be acquired. For example, the size of the first ROI for acquiring a heart rate and an oxygen saturation level may be set so that the first ROI includes a cheek region of a subject so as to detect a change in blood caused by a heartbeat well, and the areas of the first and second ROIs for acquiring a blood pressure may be set according to the direction of blood flow so as to reflect the blood pressure well. However, the present invention is not limited thereto, and the first and second ROIs may be set in various sizes and various areas.

Also, referring to FIG. 33, at least one pixel value 3430 may be acquired to acquire a plurality of physiological parameters according to an embodiment.

Also, the pixel value 3430 may be acquired for at least one of the plurality of acquired image frames.

In detail, at least some of a red channel pixel value, a green channel pixel value, and a blue channel pixel value, which correspond to an RGB color space, may be acquired for the first ROI, and at least some of a red channel pixel value, a green channel pixel value, and a blue channel pixel value, which correspond to an RGB color space, may be acquired for the second ROI, but the present invention is not limited thereto.

Also, referring to FIG. 33, at least one color channel value 3440 may be acquired to acquire a plurality of physiological parameters according to an embodiment.

In this case, the color channel value 3440 may refer to the mean of color channel pixel values and also may refer to a processed value. However, this has been described in detail above, and thus a redundant description thereof will be omitted.

Also, the color channel value 3440 may be acquired in consideration of a physiological parameter to be acquired.

In detail, at least two color channel values may be acquired for the first ROI for acquiring an oxygen saturation level, a heart rate, and a blood pressure.

For example, at least two of a red channel value, a green channel value, and a blue channel value, which correspond to an RGB color space, a hue channel value, a saturation channel value, and a value channel value, which correspond to an HSV color space, and the like may be acquired for the first ROI, but the present invention is not limited thereto.

Also, for example, at least two of a G–R value, which is a difference between a red channel value and a green channel value, a G–B value, which is a difference between a green channel value and a blue channel value, an H–V value, which is a difference between a hue channel value and a value channel value, and the like may be acquired for the first ROI, but the present invention is not limited thereto.

Also, the at least two color channel values may be selected to acquire an oxygen saturation level in consideration of the absorbance of hemoglobin and oxyhemoglobin.

For example, a blue channel in which the absorbance of oxyhemoglobin is higher than the absorbance of hemoglobin and a red channel in which the absorbance of oxyhemoglobin is lower than the absorbance of hemoglobin may be selected, and thus the at least two color channel values may be selected as a red channel value and a blue channel value, but the present invention is not limited thereto.

Also, the at least two color channel values may be selected to reduce noise caused by motion and noise caused by external light or the like in order to acquire a heart rate.

For example, a G-R value, which is a difference between a green channel value absorbed relatively more by hemoglobin and oxyhemoglobin and a red channel value absorbed relatively less by hemoglobin and oxyhemoglobin, and a G-B value, which is a difference between a green channel value absorbed relatively more by hemoglobin and oxyhemoglobin and a blue channel value absorbed relatively less by hemoglobin and oxyhemoglobin, may be selected to reduce the noise, but the present invention is not limited thereto.

Also, for example, a G-R value and a G-B value, which are differences between a green channel value reflecting relatively more of a change caused by a heartbeat and red and blue channel values reflecting relatively less of a change caused by a heartbeat, may be selected to reduce the noise, but the present invention is not limited thereto.

Also, at least two color channel values may be acquired for the first and second ROIs for acquiring a blood pressure.

For example, at least two of a red channel value, a green channel value, and a blue channel value, which correspond to an RGB color space, a hue channel value, a saturation channel value, and a value channel value, which correspond to an HSV color space, and the like may be acquired for the first and second ROIs for acquiring a blood pressure, but the present invention is not limited thereto.

Also, for example, at least two of a G-R value, which is a difference between a red channel value and a green channel value, a G-B value, which is a difference between a green channel value and a blue channel value, an H-V value, which is a difference between a hue channel value and a value channel value, and the like may be acquired for the first and second ROIs for acquiring a blood pressure, but the present invention is not limited thereto.

Also, the at least two color channel values may be selected to reduce noise caused by motion and noise caused by external light or the like.

For example, a G-R value, which is a difference between a green channel value absorbed relatively more by hemoglobin and oxyhemoglobin and a red channel value absorbed relatively less by hemoglobin and oxyhemoglobin, and a G-B value, which is a difference between a green channel value absorbed relatively more by hemoglobin and oxyhemoglobin and a blue channel value absorbed relatively less by hemoglobin and oxyhemoglobin, may be selected to reduce the noise, but the present invention is not limited thereto.

Also, for example, a G-R value and a G-B value, which are differences between a green channel value reflecting relatively more of a change caused by a heartbeat and red and blue channel values reflecting relatively less of a change caused by a heartbeat, may be selected to reduce the noise, but the present invention is not limited thereto.

Also, referring to FIG. 33, at least one piece of time-series data 3450 may be acquired to acquire a plurality of physiological parameters according to an embodiment.

Also, the time-series data 3450 may be acquired in consideration of a physiological parameter to be acquired.

In detail, at least two pieces of time-series data may be acquired for the first ROI. For example, for the first ROI, first time-series data and second time-series data may be acquired to acquire an oxygen saturation level, and third time-series data may be acquired to acquire a heart rate and a blood pressure.

In this case, the first time-series data may be acquired based on a color channel value acquired for the first ROI. For example, when the color channel value acquired for the first ROI is a red channel value, the first time-series data may be acquired based on a red channel value, but the present invention is not limited thereto.

Also, the first time-series data may be acquired for an image frame group including at least some of a plurality of acquired image frames.

For example, when the first time-series data is acquired based on a red channel value acquired for a first image frame, the first time-series data may be acquired for a first image frame group including the first image frame, but the present invention is not limited thereto.

Also, the second time-series data may be acquired based on a color channel value acquired for the first ROI. For example, when the color channel value acquired for the first ROI is a blue channel value, the second time-series data may be acquired based on the blue channel value, but the present invention is not limited thereto.

Also, the second time-series data may be acquired for an image frame group including at least some of a plurality of acquired image frames.

For example, when the second time-series data is acquired based on a blue channel value acquired for a second image frame, the second time-series data may be acquired for a second image frame group including the second image frame, but the present invention is not limited thereto.

Also, the third time-series data may be acquired based on a color channel value acquired for the first ROI. For example, when the color channel value acquired for the first ROI includes a G-R value and a G-B value, the third time-series data may be acquired based on the G-R value and the G-B value, but the present invention is not limited thereto.

Also, the third time-series data may be acquired for an image frame group including at least some of a plurality of acquired image frames.

For example, when the third time-series data is acquired based on a G-R value and a G-B value acquired for a third image frame, the third time-series data may be acquired for a third image frame group including the third image frame, but the present invention is not limited thereto.

Also, the third time-series data may be acquired based on a characteristic value acquired for the first ROI. For example, the third time-series data may be acquired based on a characteristic value acquired based on the G-R value acquired for the first ROI and a characteristic value acquired based on the G-B value acquired for the first ROI.

Also, at least one piece of time-series data may be acquired for the second ROI to acquire a blood pressure, and the blood pressure may be acquired based on the third time-series data acquired for the first ROI and fourth time-series data acquired for the second ROI.

In this case, the fourth time-series data may be acquired based on a color channel value acquired for the second ROI.

For example, when the color channel value acquired for the second ROI includes a G–R value and a G–B value, the fourth time-series data may be acquired based on the G–R value and the G–B value, but the present invention is not limited thereto.

Also, the fourth time-series data may be acquired for an image frame group including at least some of a plurality of acquired image frames.

For example, when the fourth time-series data is acquired based on a G–R value and a G–B value acquired for a fourth image frame, the fourth time-series data may be acquired for a fourth image frame group including the fourth image frame, but the present invention is not limited thereto.

Also, the fourth time-series data may be acquired based on a characteristic value acquired for the second ROI. For example, the fourth time-series data may be acquired based on a characteristic value acquired based on the G–R value acquired for the second ROI and a characteristic value acquired based on the G–B value acquired for the second ROI, but the present invention is not limited thereto.

Also, the first, second, third, and fourth image frame groups may be the same. However, the present invention is not limited thereto, and these image frame groups may differ from each other or at least partially overlap each other.

Also, referring to FIG. 33, at least one feature 3460 may be acquired to acquire a plurality of physiological parameters according to an embodiment.

Also, the at least one feature 3460 may be acquired in consideration of a physiological parameter to be acquired.

In detail, at least one feature may be acquired for the first ROI. For example, a first feature for the first ROI may be acquired to acquire an oxygen saturation level, and a second feature for the first ROI may be acquired to acquire a heart rate.

In this case, the first feature may be acquired based on a color channel value or time-series data acquired for the first ROI. For example, when the color channel value acquired for the first ROI includes a red channel value and a blue channel value, the first feature may be acquired based on the red channel value and the blue channel value, but the present invention is not limited thereto.

Also, for example, the first feature may be acquired based on first time-series data and second time-series data acquired for the first ROI, but the present invention is not limited thereto.

Also, the first feature may be a feature for acquiring oxygen saturation level. For example, the first feature may include an AC value and a DC value acquired based on the first time-series data and an AC value and a DC value acquired based on the second time-series data, but the present invention is not limited thereto.

Also, for example, the first feature may include at least one of a difference between the mean of local maximum values and the mean of the local minimum values acquired based on the first time-series data, an average value acquired based on the first time-series data, a difference between the mean of local maximum values and the mean of the local minimum values acquired based on the second time-series data, and an average value acquired based on the second time-series data, but the present invention is not limited thereto.

Also, the first feature may include a plurality of features. For example, the first feature may include at least two of a difference between the mean of local maximum values and the mean of the local minimum values acquired based on the first time-series data, an average value acquired based on the first time-series data, a difference between the mean of local maximum values and the mean of the local minimum values acquired based on the second time-series data, and an average value acquired based on the second time-series data, but the present invention is not limited thereto.

Also, the second feature may be acquired based on a color channel value or time-series data acquired for the first ROI. For example, when the color channel value acquired for the first ROI includes a G–R value and a G–B value, the second feature may be acquired based on the G–R value and the G–B value, but the present invention is not limited thereto.

Also, for example, the second feature may be acquired based on third time-series data acquired for the first ROI, but the present invention is not limited thereto.

Also, the second feature may be a feature for acquiring a heart rate. For example, the second feature may include a frequency value, a wavelength value, and a value for the number of cycle repetitions during a measurement time, which are acquired based on the third time-series data, but the present invention is not limited thereto.

Also, at least one feature may be acquired for the first and second ROIs for acquiring a blood pressure. For example, a third feature may be acquired for the first and second ROIs to acquire a blood pressure.

In this case, the third feature may be acquired based on color channel values or time-series data acquired for the first and second ROIs. For example, when the color channel values acquired for the first and second ROIs include a G–R value and a G–B value, the third feature may be acquired based on the G–R value and the G–B value, but the present invention is not limited thereto.

Also, for example, the third feature may be acquired based on third time-series data acquired for the first ROI and fourth time-series data acquired for the second ROI, but the present invention is not limited thereto.

Also, the third feature may be a feature for acquiring a blood pressure. For example, the third feature may include a slope value, a maximum value, a minimum value, the mean of local maximum values, the mean of local minimum values, a difference between the mean of local maximum values and the mean of local minimum values, etc., which are acquired based on the third and fourth time-series data, but the present invention is not limited thereto.

Also, for example, the third feature may include a time difference between the third and fourth time-series data, a time difference between local maximum values, a time difference between local minimum values, a time difference between inflection points, etc, but the present invention is not limited thereto.

Also, the third feature may include a plurality of features. For example, the third feature may include at least two of the above-described features, but the present invention is not limited thereto.

Also, referring to FIG. 33, at least one physiological parameter 3470 may be acquired to acquire a plurality of physiological parameters according to an embodiment.

In detail, each of the physiological parameters may be acquired based on a corresponding feature. For example, an oxygen saturation level may be acquired based on the first feature, a heart rate may be acquired based on the second feature, and a blood pressure may be acquired based on the third feature, but the present invention is not limited thereto.

In this case, the above equations may be used to acquire an oxygen saturation level on the basis of the first feature, and thus a redundant description thereof will be omitted.

Also, the above equations may be used to acquire a heart rate on the basis of the second feature, and thus a redundant description thereof will be omitted.

Also, the above equations may be used to acquire a blood pressure on the basis of the third feature, and thus a redundant description thereof will be omitted.

Also, when the physiological parameter 3470 includes a plurality of physiological parameters, the physiological parameters may be acquired at the same time. However, the present invention is not limited thereto, and the physiological parameters may be acquired at different times. For example, an oxygen saturation level and a heart rate may be acquired six seconds after measurement, and a blood pressure may be acquired eight seconds after measurement, but the present invention is not limited thereto.

Also, when the physiological parameter 3470 includes a plurality of physiological parameters, each of the physiological parameters may be acquired based on a corresponding image frame group. For example, an oxygen saturation level may be acquired based on a fifth image frame group, a heart rate may be acquired based on a sixth image frame group, and a blood pressure may be acquired based on a seventh image frame group.

Also, the image frame groups for acquiring the physiological parameter 3470 may be the same. However, the present invention is not limited thereto, and these image frame groups may differ from each other or at least partially overlap each other. For example, the fifth, sixth, and seventh image frame groups may be the same, different, or at least partially overlapped with each other.

Also, at least one preliminary physiological parameter may be acquired to acquire the physiological parameter 3470. For example, at least four preliminary heart rates may be acquired to acquire a heart rate.

However, the above description is applicable to a method of acquiring a heart rate or a physiological parameter using a preliminary heart rate or a preliminary physiological parameter, and thus a redundant description thereof will be omitted.

Also, the number of preliminary physiological parameters for acquiring the physiological parameter 3470 may be the same or different for each physiological parameter. For example, the number of preliminary heart rates for acquiring the heart rate may be at least four, and the number of preliminary saturation levels for acquiring the oxygen saturation level and the number of preliminary blood pressures for acquiring the blood pressure may be at least two, but the present invention is not limited thereto.

Figure 34:
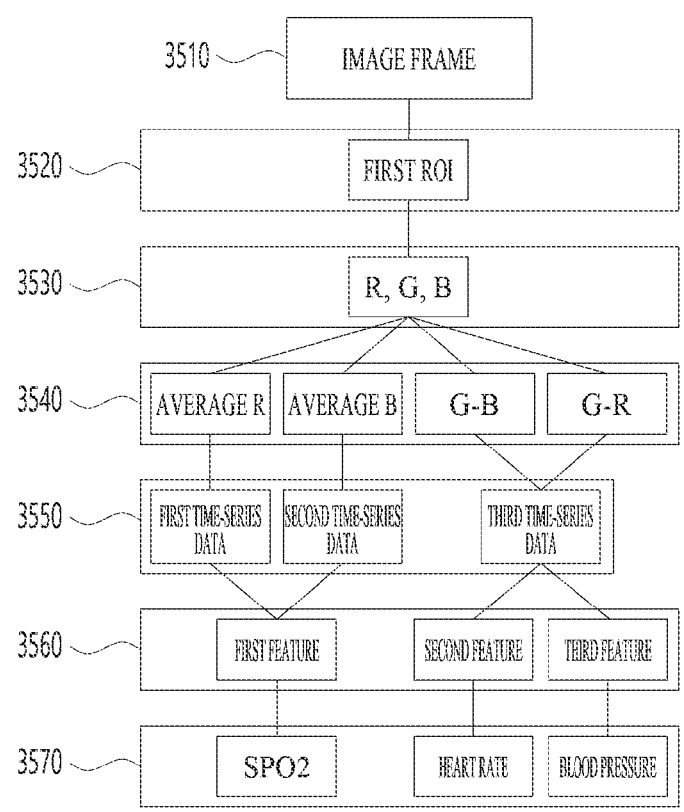
FIG. 34 is a diagram illustrating a method of acquiring a plurality of physiological parameters according to an embodiment.

7.4 Method of Acquiring Plurality of Physiological Parameters According to Embodiment FIG. 34 is a diagram illustrating a method of acquiring a plurality of physiological parameters according to an embodiment.

Referring to FIG. 34, an image frame 3510 may be acquired to acquire a plurality of physiological parameters according to an embodiment.

In this case, the image frame 3510 may be an image frame acquired from a visible light image, an infrared image, etc., but the present invention is not limited thereto.

Also, the image frame 3510 may include a plurality of image frames, but the present invention is not limited thereto.

Also, referring to FIG. 34, at least one ROI 3520 may be set to acquire a plurality of physiological parameters according to an embodiment. In detail, a first ROI may be set.

In this case, the first ROI may be an ROI for acquiring an oxygen saturation level, a heart rate, and a blood pressure.

Also, the size and area of the first ROI may be set based on a physiological parameter to be acquired. For example, the size of the first ROI for acquiring a heart rate and an oxygen saturation level may be set so that the first ROI includes a cheek region of a subject so as to detect a change in blood caused by a heartbeat well. However, the present invention is not limited thereto, and the first ROI may be set in various sizes and various areas.

Also, referring to FIG. 34, at least one pixel value 3530 may be acquired to acquire a plurality of physiological parameters according to an embodiment.

Also, the pixel value 3530 may be acquired for at least one of the plurality of acquired image frames.

In detail, at least some of a red channel pixel value, a green channel pixel value, and a blue channel pixel value, which correspond to an RGB color space, may be acquired for the first ROI, but the present invention is not limited thereto.

Also, referring to FIG. 34, at least one color channel value 3540 may be acquired to acquire a plurality of physiological parameters according to an embodiment.

In this case, the color channel value 3540 may refer to the mean of color channel pixel values and also may refer to a processed value. However, this has been described in detail above, and thus a redundant description thereof will be omitted.

Also, the color channel value 3540 may be acquired in consideration of a physiological parameter to be acquired.

In detail, at least, two color channel values may be acquired for the first ROI for acquiring an oxygen saturation level, a heart rate, and a blood pressure.

For example, at least two of a red channel value, a green channel value, and a blue channel value, which correspond to an RGB color space, a hue channel value, a saturation channel value, and a value channel value, which correspond to an HSV color space, and the like may be acquired for the first ROI, but the present invention is not limited thereto.

Also, for example, at least two of a G–R value, which is a difference between a red channel value and a green channel value, a G–B value, which is a difference between a green channel value and a blue channel value, an H–V value, which is a difference between a hue channel value and a value channel value, and the like may be acquired for the first ROI, but the present invention is not limited thereto.

Also, the at least two color channel values may be selected to acquire an oxygen saturation level in consideration of the absorbance of hemoglobin and oxyhemoglobin.

For example, a blue channel in which the absorbance of oxyhemoglobin is higher than the absorbance of hemoglobin and a red channel in which the absorbance of oxyhemoglobin is lower than the absorbance of hemoglobin may be selected, and thus the at least two color channel values may be selected as a red channel value and a blue channel value, but the present invention is not limited thereto.

Also, the at least two color channel values may be selected to reduce noise caused by motion and noise caused by external light or the like in order to acquire a heart rate and a blood pressure.

For example, a G–R value, which is a difference between a green channel value absorbed relatively more by hemoglobin and oxyhemoglobin and a red channel value absorbed relatively less by hemoglobin and oxyhemoglobin, and a G–B value, which is a difference between a green channel value absorbed relatively more by hemoglobin and oxyhemoglobin and a blue channel value absorbed relatively less by hemoglobin and oxyhemoglobin, may be selected to reduce the noise, but the present invention is not limited thereto.

Also, for example, a G–R value and a G–B value, which are differences between a green channel value reflecting relatively more of a change caused by a heartbeat and red and blue channel values reflecting relatively less of a change caused by a heartbeat, may be selected to reduce the noise, but the present invention is not limited thereto.

Also, referring to FIG. 34, at least one piece of time-series data 3550 may be acquired to acquire a plurality of physiological parameters according to an embodiment.

Also, the time-series data 3550 may be acquired in consideration of a physiological parameter to be acquired.

In detail, at least two pieces of time-series data may be acquired for the first ROI. For example, for the first ROI, first time-series data and second time-series data may be acquired to acquire an oxygen saturation level, and third time-series data may be acquired to acquire a heart rate and a blood pressure.

In this case, the first time-series data may be acquired based on a color channel value acquired for the first ROI. For example, when the color channel value acquired for the first ROI is a red channel value, the first time-series data may be acquired based on a red channel value, but the present invention is not limited thereto.

Also, the first time-series data may be acquired for an image frame group including at least some of a plurality of acquired image frames.

For example, when the first time-series data is acquired based on a red channel value acquired for a first image frame, the first time-series data may be acquired for a first image frame group including the first image frame, but the present invention is not limited thereto.

Also, the second time-series data may be acquired based on a color channel value acquired for the first ROI. For example, when the color channel value acquired for the first ROI is a blue channel value, the second time-series data may be acquired based on the blue channel value, but the present invention is not limited thereto.

Also, the second time-series data may be acquired for an image frame group including at least some of a plurality of acquired image frames.

For example, when the second time-series data is acquired based on a blue channel value acquired for a second image frame, the second time-series data may be acquired for a second image frame group including the second image frame, but the present invention is not limited thereto.

Also, the third time-series data may be acquired based on a color channel value acquired for the first ROI. For example, when the color channel value acquired for the first ROI includes a G–R value and a G–B value, the third time-series data may be acquired based on the G–R value and the G–B value, but the present invention is not limited thereto.

Also, the third time-series data may be acquired for an image frame group including at least some of a plurality of acquired image frames.

For example, when the third time-series data is acquired based on a G–R value and a G–B value acquired for a third image frame, the third time-series data may be acquired for a third image frame group including the third image frame, but the present invention is not limited thereto.

Also, the third time-series data may be acquired based on a characteristic value acquired for the first ROI. For example, the third time-series data may be acquired based on a characteristic value acquired based on the G–R value acquired for the first ROI and a characteristic value acquired based on the G–B value acquired for the first ROI.

Also, the first, second, and third image frame groups may be the same. However, the present invention is not limited thereto, and these image frame groups may differ from each other or at least partially overlap each other.

Also, referring to FIG. 34, at least one feature 3560 may be acquired to acquire a plurality of physiological parameters according to an embodiment.

Also, the at least one feature 3560 may be acquired in consideration of a physiological parameter to be acquired.

In detail, at least one feature may be acquired for the first ROI. For example, a first feature for the first ROI may be acquired to acquire an oxygen saturation level, a second feature for the first ROI may be acquired to acquire a heart rate, and a third feature for the first ROI may be acquired to acquire a blood pressure, but the present invention is not limited thereto.

In this case, the first feature may be acquired based on a color channel value or time-series data acquired for the first ROI. For example, when the color channel value acquired for the first ROI includes a red channel value and a blue channel value, the first feature may be acquired based on the red channel value and the blue channel value, but the present invention is not limited thereto.

Also, for example, the first feature may be acquired based on first time-series data and second time-series data acquired for the first ROI, but the present invention is not limited thereto.

Also, the first feature may be a feature for acquiring an oxygen saturation level. For example, the first feature may include an AC value and a DC value acquired based on the first time-series data and an AC value and a DC value acquired based on the second time-series data, but the present invention is not limited thereto.

Also, for example, the first feature may include at least one of a difference between the mean of local maximum values and the mean of the local minimum values acquired based on the first time-series data, an average value acquired based on the first time-series data, a difference between the mean of local maximum values and the mean of the local minimum values acquired based on the second time-series data, and an average value acquired based on the second time-series data, but the present invention is not limited thereto.

Also, the first feature may include a plurality of features. For example, the first feature may include at least two of a difference between the mean of local maximum values and the mean of the local minimum values acquired based on the first time-series data, an average value acquired based on the first time-series data, a difference between the mean of local maximum values and the mean of the local minimum values acquired based on the second time-series data, and an average value acquired based on the second time-series data, but the present invention is not limited thereto.

Also, the second feature may be acquired based on a color channel value or time-series data acquired for the first ROI. For example, when the color channel value acquired for the first ROI includes a G–R value and a G–B value, the second feature may be acquired based on the G–R value and the G–B value, but the present invention is not limited thereto.

Also, for example, the second feature may be acquired based on third time-series data acquired for the first ROI, but the present invention is not limited thereto.

Also, the second feature may be a feature for acquiring a heart rate. For example, the second feature may include a frequency value, a wavelength value, and a value for the number of cycle repetitions during a measurement time, which are acquired based on the third time-series data, but the present invention is not limited thereto.

Also, the third feature may be acquired based on a color channel value or time-series data acquired for the first ROI. For example, when the color channel value acquired for the first ROI includes a G-R value and a G-B value, the third feature may be acquired based on the G-R value and the G-B value, but the present invention is not limited thereto.

Also, for example, the third feature may be acquired based on third time-series data acquired for the first ROI, but the present invention is not limited thereto.

Also, the third feature may be a feature for acquiring a blood pressure. For example, the third feature may include a slope value, a maximum value, a minimum value, the mean of local maximum values, the mean of local minimum values, a difference between the mean of local maximum values and the mean of local minimum values, etc., which are acquired based on the third time-series data, but the present invention is not limited thereto.

Also, the third feature may include a plurality of features. For example, the third feature may include at least two of a slope value, a maximum value, a minimum value, the mean of local maximum values, the mean of local minimum values, a difference between the mean of local maximum values and the mean of local minimum values, etc., which are acquired based on the third time-series data, but the present invention is not limited thereto.

Also, referring to FIG. 34, at least one physiological parameter 3570 may be acquired to acquire a plurality of physiological parameters according to an embodiment.

In detail, each of the physiological parameters may be acquired based on a corresponding feature. For example, an oxygen saturation level may be acquired based on the first feature, a heart rate may be acquired based on the second feature, and a blood pressure may be acquired based on the third feature, but the present invention is not limited thereto.

In this case, the above equations may be used to acquire an oxygen saturation level on the basis of the first feature, and thus a redundant description thereof will be omitted.

Also, the above equations may be used to acquire a heart rate on the basis of the second feature, and thus a redundant description thereof will be omitted.

Also, the above equations may be used to acquire a blood pressure on the basis of the third feature, and thus a redundant description thereof will be omitted.

Also, when the physiological parameter 3570 includes a plurality of physiological parameters, the physiological parameters may be acquired at the same time. However, the present invention is not limited thereto, and the physiological parameters may be acquired at different times. For example, an oxygen saturation level and a heart rate may be acquired six seconds after measurement, and a blood pressure may be acquired eight seconds after measurement, but the present invention is not limited thereto.

Also, when the physiological parameter 3570 includes a plurality of physiological parameters, each of the physiological parameters may be acquired based on a corresponding image frame group. For example, an oxygen saturation level may be acquired based on a fourth image frame group, a heart rate may be acquired based on a fifth image frame group, and a blood pressure may be acquired based on a sixth image frame group.

Also, the image frame groups for acquiring the physiological parameter 3570 may be the same. However, the present invention is not limited thereto, and these image frame groups may differ from each other or at least partially overlap each other. For example, the fourth, fifth, and sixth image frame groups may be the same, different, or at least partially overlapped with each other.

Also, at least one preliminary physiological parameter may be acquired to acquire the physiological parameter 3570. For example, at least four preliminary heart rates may be acquired to acquire a heart rate.

However, the above description is applicable to a method of acquiring a heart rate or a physiological parameter using a preliminary heart rate or a preliminary physiological parameter, and thus a redundant description thereof will be omitted.

Also, the number of preliminary physiological parameters for acquiring the physiological parameter 3570 may be the same or different for each physiological parameter. For example, the number of preliminary heart rates for acquiring the heart rate may be at least four, and the number of preliminary saturation levels for acquiring the oxygen saturation level and the number of preliminary blood pressures for acquiring the blood pressure may be at least two, but the present invention is not limited thereto.

Figure 35:
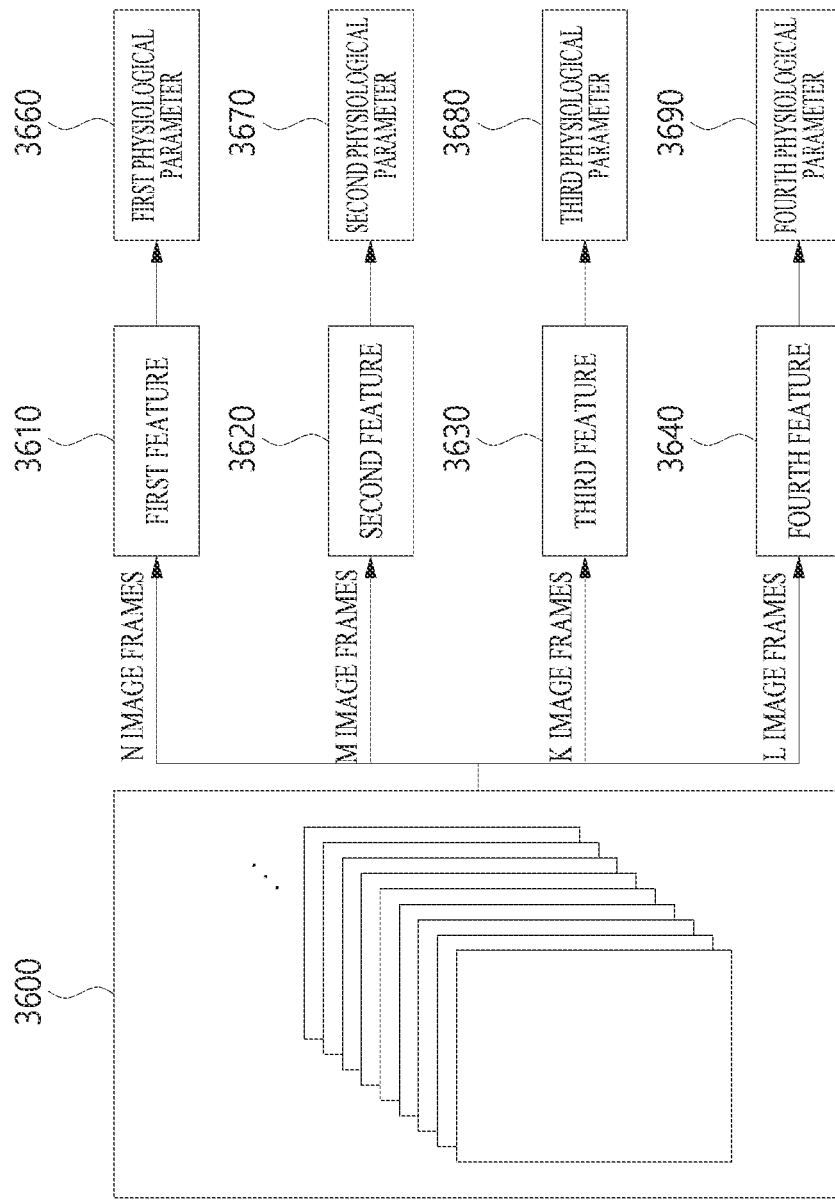
FIG. 35 is a diagram illustrating a method of acquiring a plurality of physiological parameters according to an embodiment.

7.5 Method of Acquiring Plurality of Physiological Parameters According to Embodiment FIG. 35 is a diagram illustrating a method of acquiring a plurality of physiological parameters according to an embodiment.

Referring to FIG. 35, a plurality of image frames 3600 may be acquired to acquire a plurality of physiological parameters according to an embodiment.

In this case, the image frame 3600 may be an image frame acquired from a visible light image, an infrared image, etc., but the present invention is not limited thereto.

Also, referring to FIG. 35, at least one physiological parameter may be acquired based on at least one feature.

For example, as shown in FIG. 35, a first physiological parameter 3660 may be acquired based on a first feature 3610, a second physiological parameter 3670 may be acquired based on a second feature 3620, a third physiological parameter 3680 may be acquired based on a third feature 3630, and a fourth physiological parameter 3690 may be acquired based on a fourth feature 3640, but the present invention is not limited thereto. One physiological parameter may be acquired based on a plurality of features, and a plurality of physiological parameters may be acquired based on one feature.

In this case, the first to fourth features may include at least one of an AC value, a DC value, a difference between the mean of local maximum values and the mean of local minimum values, an average value, a frequency component value, a wavelength component value, a value for the number of cycle repetitions during measurement, a slope value, a maximum value, a minimum value, the mean of local maximum values, the mean of local minimum values, an acquisition time difference, a time difference between local maximum values, a time difference between local minimum values, a time difference between inflection points, a skin temperature, and the like which are acquired based on at least one piece of time-series data, but the present invention is not limited thereto.

Also, the first to fifth physiological parameters may include at least one of a heart rate, an oxygen saturation level, a blood pressure, a core temperature, and a blood flow, but the present invention is not limited thereto.

However, the features and physiological parameters have been described in detail above, and thus a redundant description thereof will be omitted.

Also, the first to fourth features and/or the first to fourth physiological parameters may be acquired based on an image frame group including at least some of a plurality of image frames.

For example, the first feature and/or the first physiological parameter may be acquired based on a first image frame group, the second feature and/or the second physiological parameter may be acquired based on a second image frame group, the third feature and/or the third physiological parameter may be acquired based on a third image frame group, and the fourth feature and/or the fourth physiological parameter may be acquired based on a fourth image frame group, but the present invention is not limited thereto.

In this case, each of the first to fourth image frames may include at least two image frames.

For example, as shown in FIG. 35, the first image frame group may include N image frames, the second image frame group may include M image frames, the third image frame group may include K image frames, and the fourth image frame group may include L image frames, but the present invention is not limited thereto.

Also, the numbers of image frames included in the first to fourth image frame groups may be the same.

For example, the first image frame group may include 180 image frames, the second image frame group may include 180 image frames, the third image frame group may include 180 image frames, and the fourth image frame group may include 180 image frames, but the present invention is not limited thereto.

In this case, the first to fourth physiological parameters may be acquired or output at the same time. However, the present invention is not limited thereto, and these physiological parameters may be acquired or output at different times.

Also, in this case, the first to fourth physiological parameters may be acquired from the same condition of a subject and may be associated with each other.

Also, the number of image frames included in the first to fourth image frame groups may be different from each other.

For example, the first image frame group may include 180 image frames, the second image frame group may include 90 image frames, the third image frame group may include 240 image frames, and the fourth image frame group may include 360 image frames, but the present invention is not limited thereto.

In this case, the first to fourth physiological parameters may be acquired or output at different times. However, the present invention is not limited thereto, and these physiological parameters may be acquired or output at the same time.

Also, the numbers of image frames included in the first to fourth image frame groups may differ depending on a physiological parameter to be acquired.

For example, when it is assumed that the first physiological parameter is a heart rate, that the second physiological parameter is an oxygen saturation level, that the third physiological parameter is a blood pressure, and that the fourth physiological parameter is a core temperature, the first image frame group may include 180 image frames, the second image frame group may include 120 image frames, the third image frame group may include 60 image frames, and the fourth image frame group may include 60 image frames, but the present invention is not limited thereto. The number of image frames included in an image frame group may be set in consideration of a physiological parameter to be acquired.

Figure 36:
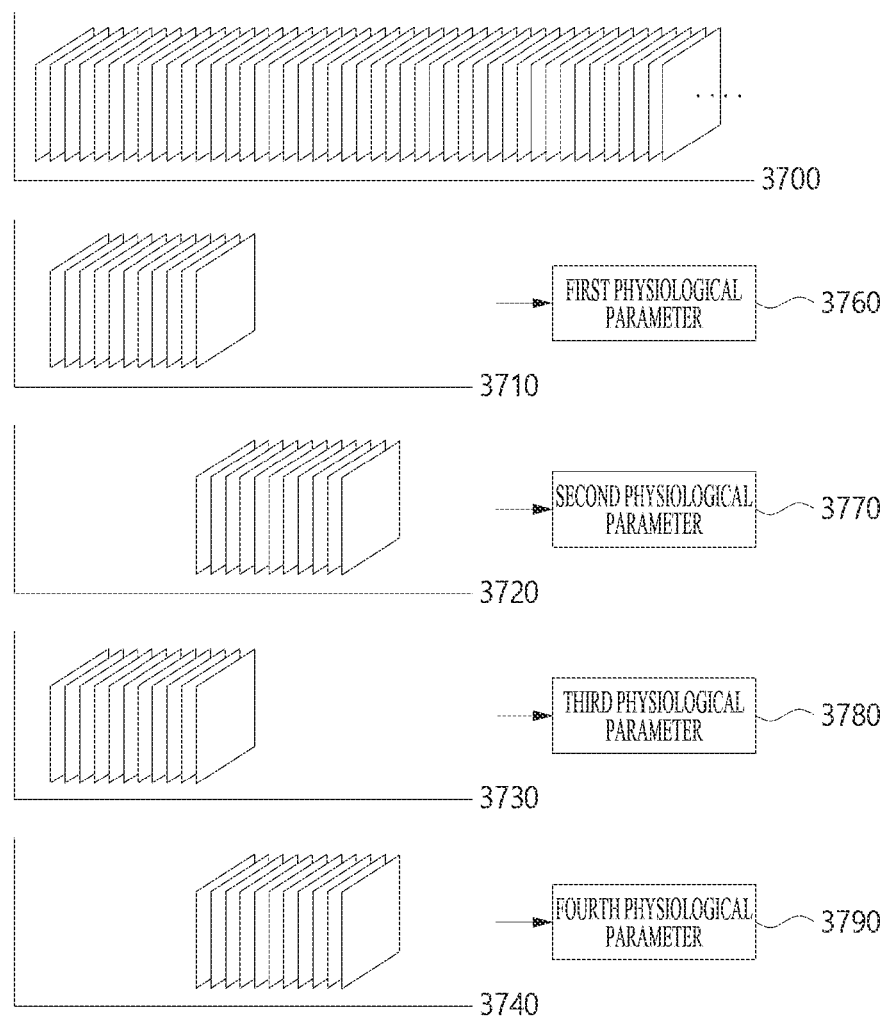
FIG. 36 is a diagram illustrating a method of acquiring a plurality of associated physiological parameters according to an embodiment.

FIG. 36 is a diagram illustrating a method of acquiring a plurality of associated physiological parameters according to an embodiment.

Referring to FIG. 36, a plurality of image frames 3700 may be acquired to acquire a plurality of associated physiological parameters according to an embodiment.

In this case, the image frames 3700 may be image frames acquired from a visible light image, an infrared image, etc., but the present invention is not limited thereto.

Also, referring to FIG. 36, at least one physiological parameter may be acquired based on at least one image frame group.

In detail, as shown in FIG. 36, a first physiological parameter 3760 may be acquired based on a first image frame group 3710, a second physiological parameter 3770 may be acquired based on a second image frame group 3720, a third physiological parameter 3780 may be acquired based on a third image frame group 3730, and a fourth physiological parameter 3790 may be acquired based on a fourth image frame group 3740.

In this case, the above description is applicable to each image frame group acid each physiological parameter, and thus a redundant description thereof will be omitted.

Referring to FIG. 36, the first physiological parameter 3760, the second physiological parameter 3770, the third physiological parameter 3780, and the fourth physiological parameter 3790 may at least partially overlap each other to acquire the first image frame group 3710, the second image frame group 3720, the third image frame group 3730, and the fourth image frame group 3740 in association with each other.

For example, as shown in FIG. 36, the first image frame group 3710 may include $1^{st}$ to $13^{th}$ image frames, the second image frame group 3720 may include $6^{th}$ to $19^{th}$ image frames, the third image frame group 3730 may include $4^{th}$ to $17^{th}$ image frames, and the fourth image frame group 3740 may include $9^{th}$ to $23^{rd}$ image frames, but the present invention is not limited thereto.

Accordingly, the first to fourth image frame groups 3710, 3720, 3730, and 3740 may include $9^{th}$ to $13^{th}$ image frames in common.

Also, as described above, the first to fourth image frame groups at least partially overlap each other, and thus the first to fourth physiological parameters may be acquired in association with each other.

For example, since the first to fourth image frame groups include the $9^{th}$ to $13^{th}$ image frames in common, the first to fourth physiological parameters may be acquired in the same state of a subject, and thus the first to fourth physiological parameters may be acquired in association with each other.

In detail, for example, when the state of the subject at a time at which the $9^{th}$ image frame is acquired is a first state, the first to fourth physiological parameters may be acquired by reflecting the first state of the subject in common, and thus the first to fourth physiological parameters may be acquired in association with each other.

Also, when the first to fourth physiological parameters 3760, 3770, 3780, and 3790 are acquired in association with each other, it is possible to accurately obtain the physiological parameters of the subject.

Also, at least one piece of physiological information may be acquired based on the first to fourth physiological parameters 3760, 3770, 3780, and 3790.

Also, when the physiological information is acquired based on associated physiological parameters, it is possible to improve the accuracy of the physiological information. For example, when a heart rate and a blood pressure to be included in the first to fourth physiological parameters are used to acquire hypertension information to be included in the physiological information, the hypertension information may be more accurate when the heart rate and the blood pressure are associated with each other.

In detail, when it is assumed that a blood pressure is measured when a subject is exercising or excited, that a heart rate is measured when the subject is stable, and that hypertension information is acquired based on the blood pressure and the heart rate, the subject may be detected as having hypertension even if the subject is not hypertensive. However, on the contrary, when it is assumed that a blood pressure and a heart rate are measured when a subject is exercising or excited and that hypertension information is acquired based on the blood pressure and the heart rate, the hypertension information may be accurately acquired.

Figure 37:
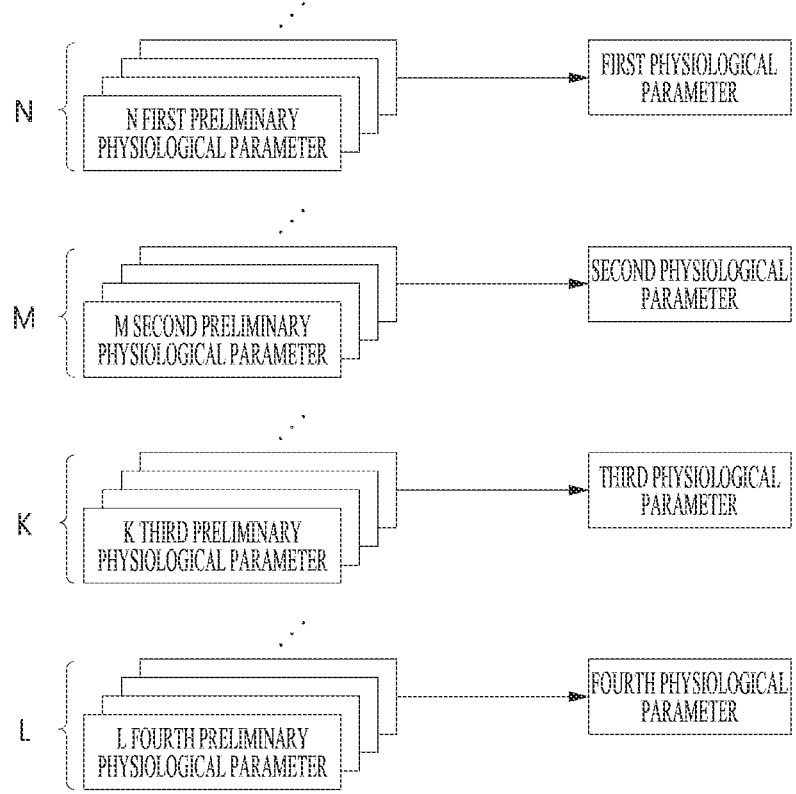
FIG. 37 is a diagram illustrating a method of acquiring a plurality of physiological parameters according to an embodiment.

FIG. 37 is a diagram illustrating a method of acquiring a plurality of physiological parameters according to an embodiment.

Referring to FIG. 37, at least one physiological parameter may be acquired based on at least one preliminary physiological parameter.

For example, as shown in FIG. 37, a first physiological parameter may be acquired based on N first preliminary physiological parameters, a second physiological parameter may be acquired based on M second preliminary physiological parameters, a third physiological parameter may be acquired based on K third preliminary physiological parameters, and a fourth physiological parameter may be acquired based on L fourth preliminary physiological parameters.

However, the above description is applicable to a method of acquiring a physiological parameter using a preliminary physiological parameter, and thus a redundant description thereof will be omitted.

The numbers of first to fourth preliminary physiological parameters for acquiring the first to fourth physiological parameters may be the same.

For example, the number of first preliminary physiological parameters for acquiring the first physiological parameter may be four, the number of second preliminary physiological parameters for acquiring the second physiological parameter may be four, the number of third preliminary physiological parameters for acquiring the third physiological parameter may be four, and the number of fourth preliminary physiological parameters for acquiring the fourth physiological parameter may be four, but the present invention is not limited thereto.

Also, the numbers of first to fourth preliminary physiological parameters for acquiring the first to fourth physiological parameters may be different from each other.

For example, the number of first preliminary physiological parameters for acquiring the first physiological parameter may be four, the number of second preliminary physiological parameters for acquiring the second physiological parameter may be two, the number of third preliminary physiological parameters for acquiring the third physiological parameter may be two, and the number of fourth preliminary physiological parameters for acquiring the fourth physiological parameter may be one, but the present invention is not limited thereto.

Also, the numbers of first to fourth preliminary physiological parameters for acquiring the first to fourth physiological parameters may differ depending on a physiological parameter to be acquired.

For example, when it is assumed that the first physiological parameter is a heart rate, that the second physiological parameter is an oxygen saturation level, that the third physiological parameter is a blood pressure, and that the fourth physiological parameter is a core temperature, the number of first preliminary physiological parameters for acquiring the heart rate may be four, the number of second preliminary physiological parameters for acquiring the oxygen saturation level may be two, the number of third preliminary physiological parameters for acquiring the blood pressure may be two, and the number of fourth preliminary physiological parameters for acquiring the core temperature may be one. However, the present invention is not limited thereto, and the number of preliminary physiological parameters that are to be used as a basis may be set in consideration of a physiological parameter to be acquired.

8. Drowsiness Detection Device and Method 8.1 Drowsiness Detection Device

A drowsiness detection device described herein may refer to a device for detecting a subject's drowsiness-related state. In detail, the drowsiness detection device may detect whether the subject is drowsy, the degree of drowsiness, and the like.

People may feel drowsy during daily life. In some cases, the drowsiness may pose a safety hazard. For example, when a driver feels drowsy while driving, he or she cannot concentrate on driving, which can lead to a traffic accident. In this case, the drowsiness detection device may prevent a situation which poses a threat to a driver, such as a traffic accident, by detecting the driver's drowsiness-related state and notifying the driver of the drowsiness-related state. It will be appreciated that the drowsiness detection device may be used in places and fields where drowsiness serves as important information, such as reading rooms and infant monitoring, as well as in situations in which drowsiness poses a safety hazard.

The drowsiness detection device may detect a drowsiness-related state by using a contact-type device that involves physical contact with a subject, such as an attachable electrode sensor or a wearable device. Also, the drowsiness detection device may detect a subject's drowsiness-related state in a contactless manner by using a camera. When the drowsiness-related state is detected in the contactless manner, the subject's drowsiness may be detected without the subject being constrained by a contact-type device, and thus the drowsiness detection device may have increased user convenience and may also be used in various places and fields.

The contactless drowsiness detection device may detect a drowsiness-related state by detecting a subject's abnormal state exposed to the outside, for example, by measuring the number of eye blinks of a subject or tracking the position of the pupil of a subject. However, when a subject consciously controls eye blinks or the position of the pupil, it is difficult to accurately detect a drowsiness-related state. When information that appears in a subject's body when the subject feels drowsy is used to compensate for the accuracy, it is possible to accurately detect a drowsiness-related state. Also, when physiological information that appears in a situation in which a subject does not feel drowsy but will soon become drowsy is further used, a drowsiness-related state may be detected in advance in an initial stage.

Due to these advantages, a drowsiness detection device 6000 described herein provided in the specification may detect whether a subject is in a drowsiness-related state and the degree of drowsiness using a subject's physiological parameter acquired in a contactless manner.

Figure 38:
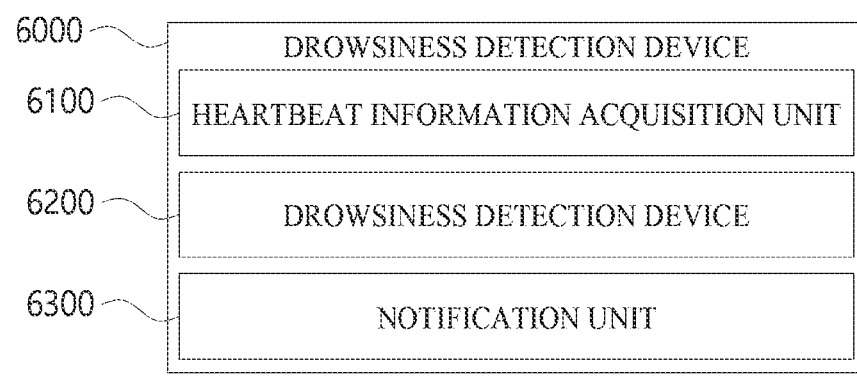
FIG. 38 is a block diagram of a drowsiness detection device on the basis of a heart rate.
Figure 39:
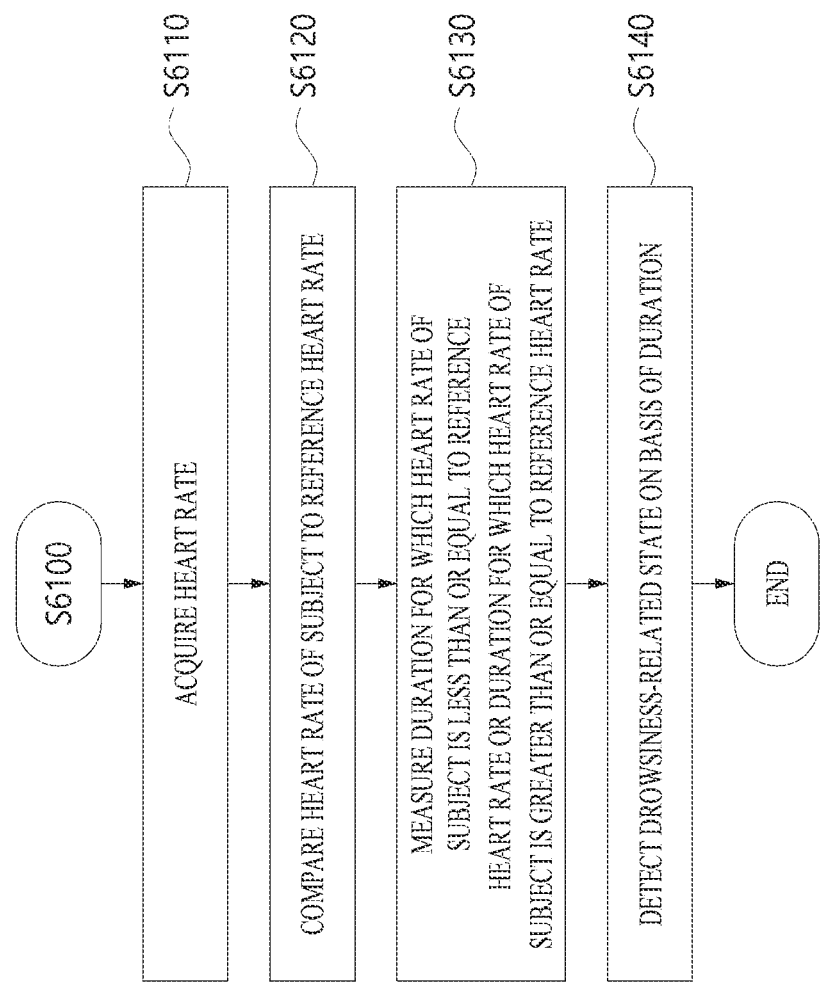
FIG. 39 is a flowchart of a method of detecting drowsiness on the basis of a heart rate.

According to an embodiment, referring to FIG. 38, the drowsiness detection device 6000 may include a heartbeat information acquisition unit 6100 configured to acquire a heart rate from a subject and a drowsiness detection unit 6200 configured to detect the subject's drowsiness on the basis of the acquired heart rate of the subject.

It will be appreciated that the drowsiness detection device 6000 of the present invention may further include elements other than the heartbeat information acquisition unit 6100 and the drowsiness detection unit 6200. For example, the drowsiness detection device 6000 may further include a notification unit 6300 in addition to the heartbeat information acquisition unit 6100 and the drowsiness detection unit 6200. Here, the notification unit 6300 may provide a notification for waking up a drowsy subject to the subject or an entity other than the subject on the basis of a detection result of the drowsiness detection unit 6200. Here, the entity other than the subject may refer to an administrator who manages the subject or a third party who is positioned around the subject.

In an embodiment, the drowsiness detection device 6000 may detect a subject's drowsiness at various time points. That is, some or all of the elements included in the drowsiness detection device 6000 may operate at various time points, and each operation or all operations of various drowsiness detection methods to be described below may be implemented at various time points.

For example, the drowsiness detection device 6000 may detect a subject's drowsiness at predetermined intervals (e.g., every minute, every hour, etc.). As another example, the drowsiness detection device 6000 may detect a subject's drowsiness without following predetermined intervals. As an example, the drowsiness detection device 6000 may detect a subject's drowsiness whenever acquiring information on a subject's heartbeat, i.e., in real time. Also, the drowsiness detection device 6000 may detect a subject's drowsiness in succession or when a signal for triggering drowsiness detection is input or when a request to detect drowsiness is received.

In another embodiment, the drowsiness detection device 6000 may start drowsiness detection when a heart rate is acquired for the first time. For example, the heartbeat information acquisition unit 6100 may acquire a heartbeat for the first time a few seconds or minutes after measurement to acquire a subject's heart rate is started. In this case, the drowsiness detection device 6000 may start to detect the subject's drowsiness when a heart rate is acquired for the first time.

Elements included in the drowsiness detection device 6000 according to an embodiment will be described in detail below with reference to FIG. 38.

8.1.1 Heartbeat Information Acquisition Unit

In an embodiment, a heartbeat information acquisition unit 6100 may acquire information on a subject's heart rate, for example, at least one of a subject's heart rate or a subject's ratio of sympathetic activity to parasympathetic activity.

Here, a heart rate may refer to the number of times a heart beats during a reference time. Generally, a heart rate may refer to the number of heartbeats during a reference time of one minute, but the reference time may be arbitrarily set. For example, the reference time may be set to 30 seconds, etc. Also, the ratio of sympathetic activity to parasympathetic activity is due to a heartbeat signal, where the heartbeat signal may refer to a signal that can vary depending on a heartbeat or a signal that can be estimated to vary depending on a heartbeat. Generally, sympathetic activity and parasympathetic activity are highly associated with a subject's drowsiness state. Accordingly, the drowsiness detection device 6000 may detect a subject's drowsiness using the ratio of sympathetic activity to parasympathetic activity which is due to a heartbeat signal.

Also, the feature of the sympathetic activity may appear in low frequency bands of the heartbeat signal, and the feature of the parasympathetic activity may appear in high frequency bands of the heartbeat signal. Herein, accordingly, the ratio of sympathetic activity to parasympathetic activity may be expressed as an LF/HF ratio. LF may refer to a characteristic value in a low frequency (LF) band of a heartbeat signal, and HF may refer to a characteristic value in a high frequency (HF) band of a heartbeat signal.

In an embodiment, a low frequency band and a high frequency band may be classified based on a reference frequency. As an example, the low frequency band and the high frequency band may be classified based on a reference frequency of 0.15 Hz. The low frequency band may include a signal with a frequency ranging from 0.04 Hz to 0.15 Hz, and the high frequency band may include a signal with a frequency ranging from 0.15 Hz to 0.4 Hz. It will be appreciated that the reference frequency may be set to frequencies other than 0.15 Hz.

In an embodiment, the heartbeat information acquisition unit 6100 may transform a heartbeat signal into a signal in a frequency domain by various methods such as the Fourier transform. The heartbeat information acquisition unit 6100 may acquire an LF/HF ratio by extracting a low-frequency band (0.04 to 0.15 Hz) signal and a high-frequency band (0.15 to 0.4 Hz) from the heartbeat signal through the transformation.

In an embodiment, the heartbeat information acquisition unit 6100 may acquire heart rate information in an invasive or non-invasive manner.

Also, according to another embodiment, the heartbeat information acquisition unit 6100 may acquire information regarding a heartbeat rate in a contact or contactless manner.

In detail, the heartbeat information acquisition unit 6100 may acquire heart rate information in a contactless manner using a device that does not come into physical contact with a subject. For example, the heartbeat information acquisition unit 6100 may acquire an image of a subject using a camera, analyze the acquired image, and acquire information on the subject's heart rate. A method and device for acquiring heart rate information in a contactless manner using a camera have been described above, and thus a detailed description thereof will be omitted.

Also, it will be appreciated that the heartbeat information acquisition unit 6100 may acquire heart rate information in a contact manner using a device that comes into physical contact with a subject. For example, the heartbeat information acquisition unit 6100 may acquire heart rate information using an attachable sensor for heartbeat measurement or a wearable device including various attachable sensors and optical sensors. For convenience of description, the elements of the drowsiness detection device and the drowsiness detection method will be described below, focusing on an example in which heart rate information is acquired in a contactless manner.

In an embodiment, the heartbeat information acquisition unit 6100 may acquire heart rate information by directly measuring the heart rate. In detail, the heartbeat information acquisition unit 6100 may include a heartbeat measuring device and may acquire heart rate information measured by the heartbeat measuring device. For example, the heartbeat information acquisition unit 6100 may include a camera and may directly measure heart rate information by analyzing an image acquired from the camera.

Also, the heartbeat information acquisition unit 6100 may acquire heart rate information by receiving heart rate information measured by an external device. For example, the heart rate information may be measured by a device including an electrode sensor for heartbeat measurement, and the heartbeat information acquisition unit 6100 may receive the measured heart rate information. Also, the heartbeat information acquisition unit 6100 may receive the measured heart rate information through a device (e.g., a server) for relaying the heartbeat information acquisition unit 6100 and an external device.

In an embodiment, when the drowsiness detection device 6000 is included in the physiological parameter acquisition device 10, the heartbeat information acquisition unit 6100 may read and acquire a heart rate stored in a memory of the physiological parameter acquisition device 10. In another embodiment, when the drowsiness detection device 6000 is not included in the physiological parameter acquisition device 10, the heartbeat information acquisition unit 6100 may receive a heart rate measured by the physiological parameter acquisition device 10 through a communication unit (not shown) included in the drowsiness detection device 6000. It will be appreciated that the drowsiness detection device 6000 may acquire a heart rate from a device other than the physiological parameter acquisition device 10.

8.1.2 Drowsiness Detection Unit

In an embodiment, a drowsiness detection unit 6200 may detect whether a subject is drowsy or the degree of drowsiness felt by a subject on the basis of heart rate information. In detail, the drowsiness detection unit 6200 may detect a drowsiness state and a normal state of a subject on the basis of the heart rate information. Here, the drowsiness state may be divided into a plurality of levels.

Herein, the drowsiness state may refer to a state in which a subject is temporarily sleeping or a state in which a subject is not sleeping but is likely to sleep within a predetermined period, and the normal state, which is not the drowsiness state, may refer to a state in which a subject is unlikely to fall asleep within a predetermined time.

In an embodiment, the drowsiness state may be divided into a plurality of levels according to the degree of drowsiness. In some cases, the drowsiness state may be divided into first to $N^{th}$ levels. Herein, for convenience of description, the lowest level of the degree of drowsiness is expressed as the first level, and the highest level of the degree of drowsiness is expressed as the $N^{th}$ level. For example, the drowsiness state may be divided into first to third levels. In this case, the first level may refer to the lowest level of the degree of drowsiness, and the third level may refer to the highest level of the degree of drowsiness.

In an embodiment, a first-level drowsiness state may refer to a state in a subject physically enters a drowsiness state but is not aware of drowsiness. For example, in the first-step drowsiness state, heartbeat information of a subject objectively indicates that the subject is drowsy, but the subject himself or herself may not feel drowsy. Herein, this drowsiness state may be expressed as an unconscious drowsiness state or an unaware drowsiness state.

In an embodiment, a second-level drowsiness state and a third-level drowsiness state may refer to states in which a subject physically enters a drowsiness state and also is aware of drowsiness. Herein, these drowsiness states may be expressed as a conscious drowsiness state or an aware drowsiness state.

Generally, a subject enters the unconscious drowsiness state before entering the conscious drowsiness state. When a subject receives a notification about drowsiness after entering the conscious drowsiness state, there is a high likelihood that a situation dangerous to the subject will occur because the subject is already drowsy. Also, even if a notification about the drowsiness state is received before a dangerous situation occurs, it may take a great deal of time for the subject to come out of the drowsiness state.

In order to prevent such a dangerous situation, the drowsiness detection device 6000 may detect the unconscious drowsiness state before a subject enters the conscious drowsiness state and may provide a notification based on the detection result to the outside. The drowsiness detection device 6000 may make the subject become aware of the drowsiness state through the notification when the subject is in the unconscious drowsiness state in which the subject does not feel drowsy.

Accordingly, the detection and notification of the unconscious drowsiness state can increase the likelihood that the subject will come out of the drowsiness state before a dangerous situation occurs and can more reliably protect the subject from the dangerous situation due to the drowsiness state.

In an embodiment, the drowsiness detection unit 6200 may measure a subject's drowsiness state using heartbeat information. Herein, a drowsiness state is a state in which a subject is temporarily sleeping or a state in which a subject is likely to sleep within a predetermined period of time immediately before he or she falls asleep. In the drowsiness state, a parasympathetic nervous system is relatively more activated compared to the normal state, and when the parasympathetic nervous system is activated, a heart rate decreases. That is, a change in heart rate may serve as a biomarker capable of estimating the drowsiness state of the subject. As an example, when a subject enters the drowsiness state, the heart rate of the subject is decreased below a certain level, and the decreased heart rate may continue for a certain time. In some cases, the drowsiness detection unit 6200 may estimate the drowsiness state of the subject through the duration of the decreased heart rate.

In an embodiment, the drowsiness detection unit 6200 may measure a subject's normal state using heartbeat information. As an example, when a subject enters the normal state, the heart rate of the subject is increased above a certain level due to the activation of a sympathetic nerve, and the increased heart rate may also continue for a certain time. In this case, the drowsiness detection unit 6200 may estimate the subject's normal state through the duration of the increased heart rate.

Also, in another embodiment, the drowsiness detection unit 6200 may measure a subject's drowsiness state and normal state using an LF/HF ratio. When the subject enters the drowsiness state, the parasympathetic nervous system of the subject may be activated, and the LF value of the heartbeat signal may be decreased relative to the HF value.

Also, when the subject enters the normal state, the sympathetic nervous system of the subject may be activated, and the LF value may be increased relative to the HF value. Accordingly, the drowsiness detection unit 6200 may estimate the subject's drowsiness state and normal state through an LF/HF ratio.

In still another embodiment, the drowsiness detection unit 6200 may estimate the subject's drowsiness state or normal state in consideration of both of the change in heart rate and the LF/HF ratio.

The drowsiness detection method will be described in detail below.

8.1.3 Notification Unit

In an embodiment, a notification unit 6300 may provide detected drowsiness-state-related information to the outside. In detail, the notification unit 6300 may provide information on whether a subject is drowsy, a drowsiness level, and also various pieces of detected drowsiness-state-related information. For example, the notification unit 6300 may provide a duration for which the drowsiness state is maintained, a time at which each level of the drowsiness state is entered, a time at which the drowsiness state is exited, and the like to the outside.

In an embodiment, the notification unit 6300 may provide drowsiness-state-related information to a subject. For example, the notification unit 6300 may notify a subject at an intensity corresponding to the level of the drowsiness state. The notification may induce recovery from the drowsiness state by applying a certain stimulus to a drowsy subject.

In another embodiment, the notification unit 6300 may provide the drowsiness-state-related information to an entity other than the subject. For example, the notification unit 6300 may provide drowsiness-state-related information to an administrator or a server. Here, an administrator may refer to an administrator of a subject or an entity who manages a drowsiness state of a subject. The provision of such information can help the administrator to effectively manage the safety of the subject on the basis of the drowsiness-state-related information.

In an embodiment, the notification unit 6300 may provide information on drowsiness states detected at all the levels to the outside. For example, the notification unit 6300 may provide drowsiness-state-related information regarding first-level drowsiness state, second-level drowsiness state, and third-level drowsiness state to a subject.

Also, in another embodiment, the notification unit 6300 may provide information on only at least some of the drowsiness states detected at all the levels to the outside.

For example, the notification unit 6300 may provide an administrator with information regarding a time and a level at which the third-level drowsiness state is detected only when the third-level drowsiness state is detected. When notifications about the drowsiness states at all the levels interfere with the subject, the notification unit 6300 can increase the work efficiency of the subject by providing only information on a high-risk drowsiness level (e.g., information on a third-level drowsiness state) and not providing information on a low-risk drowsiness level (e.g., information on a first-level drowsiness state).

Also, in an embodiment, when a subject is detected as being in a normal state, the notification unit 6300 may provide information on the detected normal state. In detail, the notification unit 6300 may provide various pieces of information associated with the detected normal state, including whether the subject is in the normal state. For example, the notification unit 6300 may provide a duration for which the normal state is maintained, a time at which the normal state is entered, etc.

In an embodiment, the notification unit 6300 may provide normal-state-related information to the subject. For example, when a drowsy subject has recovered to the normal state, the notification unit 6300 may output a message for notifying the subject that he or she has recovered to the normal state.

In another embodiment, the notification unit 6300 may provide the normal-state-related information to an entity other than the subject. For example, the notification unit 6300 may provide the normal-state-related information to an administrator or a server. The provision of such information can help the administrator to effectively recognize that the subject is in a safe situation.

In an embodiment, the notification unit 6300 may generate a notification signal indicating the drowsiness-state-related information and provide the notification signal to an output unit (not shown) so that the normal-state-related information and the drowsiness-state-related information are output to the outside of the drowsiness detection device.

Here, the output unit is a device configured to provide information to the outside. For example, the output unit may include at least one of a display unit configured to display information to the outside in a visual manner, an audio unit configured to provide information in an auditory manner, and a tactile stimulation unit configured to provide information in a tactile manner. The output unit may be included in the drowsiness detection device 6000 or an external device of the drowsiness detection device 6000.

When the output unit is included in a device outside the drowsiness detection device 6000, the drowsiness detection device 6000 may further include a communication unit (not shown), and the notification unit 6300 may provide a notification signal to the output unit through the communication unit. The output unit may receive the notification signal provided by the notification unit 6300 and output drowsiness-related information to the outside according to the notification signal.

For example, the notification unit 6300 may provide an auditory notification through the audio unit. Such an auditory notification is effective because it can give an immediate stimulus to a notification recipient and change the intensity of the stimulus according to sound intensity.

As another example, the notification unit 6300 may provide a notification by displaying a message on a display through the display unit. Such a visual notification can minimize a situation in which the notification interferes with an entity other than the notification recipient.

As another example, the notification unit 6300 may provide a notification through the tactile stimulation unit, for example, vibration, electric stimulus, a thermal element, or a cooling element. Such a tactile notification is effective because it may not interfere with an entity other than the notification recipient, can provide an immediate stimulus, and change the intensity of the stimulus according to stimulus intensity.

Also, in an embodiment, the notification unit 6300 may provide a subject with notifications of different types and/or intensities depending on the detected level of the drowsiness state. In this case, the notification unit 6300 may provide a notification of a type suitable for recognizing that the subject is in the drowsiness state and/or of an intensity necessary for the subject to come out of the drowsiness state.

For example, when the first-level drowsiness state, which is the low degree of drowsiness state, is detected, the notification unit 6300 may make the subject recognize that he or she is drowsy by notifying him or her using a visual message. Also, when the third-level drowsiness state, which is the high degree of drowsiness state, is detected, the notification unit 6300 may make the subject come out of the drowsiness state by notifying; him or her using electrical stimulation.

As another example, the notification unit 6300 may provide a low intensity alarm to the subject when the first-level drowsiness state, which is the low degree of drowsiness state, is detected, and the notification unit 6300 may provide a high intensity alarm to the subject when the third-level drowsiness state is detected.

It will be appreciated that, in some embodiments, the notification unit 6300 may provide a notification of the same type and/or intensity regardless of the level of the drowsiness state detected by the subject.

Also, the notification unit 6300 may notify at least one of a subject and an entity other than the subject according to the detected level of the drowsiness state.

In an embodiment, the notification unit 6300 may notify the subject when the first-level drowsiness state and the second-level drowsiness state are detected. In this case, the notification unit 6300 may provide the subject with at least one of an auditory notification, a visual notification, and a tactile notification.

Also, when the third-level drowsiness state is detected, the notification unit 6300 may notify an entity other than a subject as well as the subject. In detail, the notification unit 6300 may notify the entity other than the subject through a device or server for relaying the notification unit 6300 and the entity other than the subject. For example, when the entity other than the subject is an administrator who manages the subject, such a notification may be effective in a situation in which the subject turns off or ignores a notification provided through an output unit. A drowsiness detection method performed by the drowsiness detection device 6000 will be described in detail below.

8.2 Heart Rate-Based Drowsiness Detection Method

A heart rate-based drowsiness detection method according to an embodiment will be described below with reference to FIGS. 39 to 43.

In an embodiment, the heart rate-based drowsiness detection method may include a heart rate acquisition operation (S6110), an operation of comparing an acquired heart rate of a subject to a reference heart rate (S6120), a duration measurement operation for measuring a duration for which a heart rate is changed according to a result of the comparison (S6130), and a level-specific drowsiness detection operation for detecting drowsiness for each level on the basis of the measured duration of the change in heart rate (S6140).

In the heart rate acquisition operation (S6110), a drowsiness detection device 6000 may acquire a subjects heart rate using a heartbeat information acquisition unit 6100.

In an embodiment, the drowsiness detection device 6000 may acquire a subject's heart rate at predetermined intervals. Here, the predetermined interval may include various intervals such as one second, one minute, and five minutes. Also, it will be appreciated that the predetermined interval may be fixed or variable.

In another embodiment, the drowsiness detection device 6000 may acquire a subject's heart rate without following predetermined intervals. For example, the drowsiness detection device 6000 may detect a subject's heart rate whenever the physiological parameter acquisition device 10 or the like measures the subject's heart rate, i.e., in real time.

It will be appreciated that when a subject's heart rate is measured by the physiological parameter acquisition device 10 or the like at predetermined intervals, the drowsiness detection device 6000 may acquire the subject's heart rate on the basis of the predetermined intervals at which the physiological parameter acquisition device 10 or the like measure the heart rate.

As another example, the drowsiness detection device 6000 may request the physiological parameter acquisition device 10 or the like to provide a heart rate upon an external input or request and may acquire a subject's heart rate each time the request is made.

In an embodiment, the drowsiness detection device 6000 may acquire a subject's average heart rate corresponding to a certain time period. The time period may be arbitrarily determined. Here, the drowsiness detection device 6000 may calculate an average heart rate corresponding to a certain time period using the subject's heart rate received from an external device. Also, the drowsiness detection device 6000 may receive the subject's average heart rate corresponding to a certain time period from an external device.

An effect that can be obtained when an average heart rate is acquired as a subject's heart rate will be described below with reference to FIG. 40.

Figure 40:
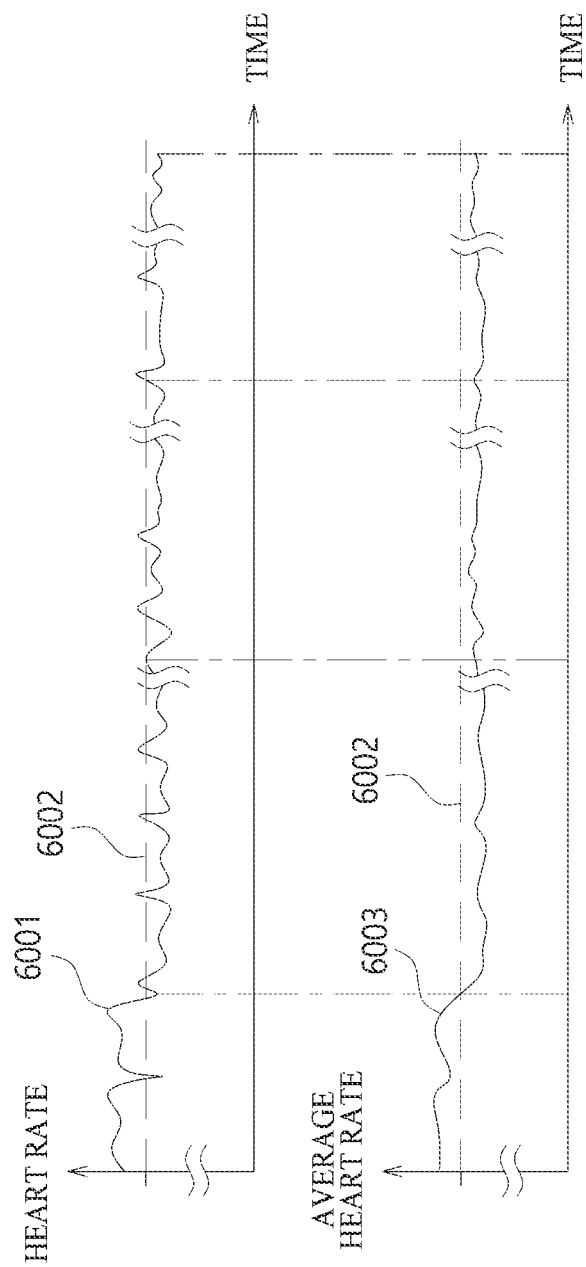
FIG. 40 is a graph of an average heart rate of a subject on the basis of a heart rate of the subject of the measurement.

In an embodiment, referring to FIG. 40, the drowsiness detection device 6000 may acquire heart rate from which noise is removed by acquiring an average heart rate 6003.

Here, noise represents errors caused by various causes such as a subject's motion or external light. When noise is contained in a heart rate, it may be difficult for the corresponding heart rate to accurately reflect the subject's state.

For example, it is assumed that the heartbeat information acquisition unit 6100 acquires a heart rate every second from one second to ten seconds. When noise occurs after a lapse of five seconds, the drowsiness detection device 6000 may not accurately detect drowsiness. However, when the heartbeat information acquisition unit 6100 acquires the average heart rate 6003, the drowsiness detection device 6000 may more accurately detect drowsiness because deviations between noise and other values can be corrected while the average heart rate 6003 is calculated.

A method of the heartbeat information acquisition unit 6100 acquiring a subject's heart rate has been described in Section 8.1.1, and thus a detailed description thereof will be omitted.

The operation of comparing a subject's heart rate to a reference heart rate (S6120) and the duration measurement operation for measuring a duration for which the acquired heart rate of the subject is decreased or increased and then maintained will be described below with reference to FIG. 41.

Figure 41:
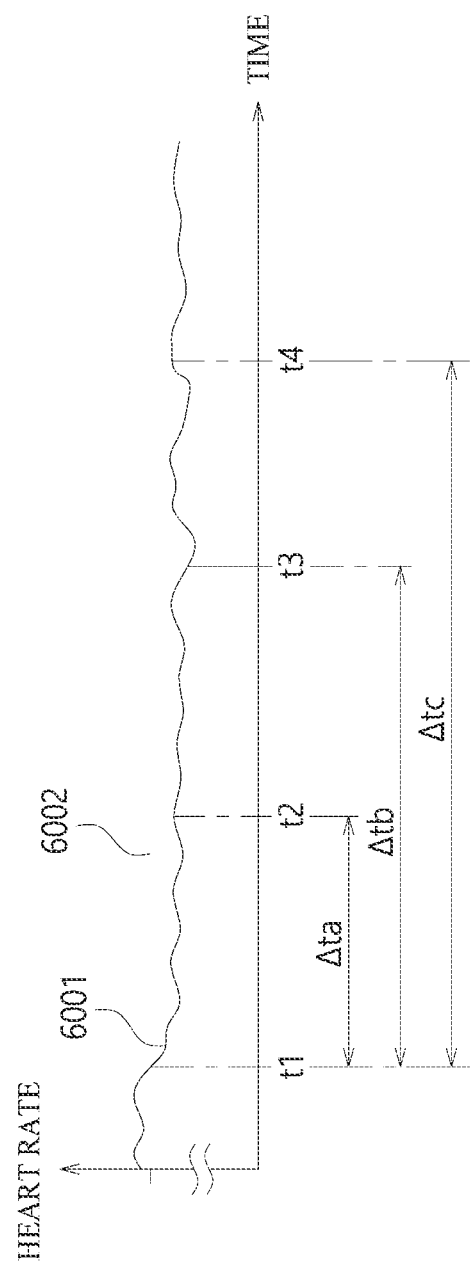
FIG. 41 is a graph of a heart rate of a subject for explaining a situation in which the subject is detected to be in a drowsiness state on the basis of a heart rate.

According to an embodiment, referring to FIG. 41, the drowsiness detection device 6000 may compare a subject's heart rate 6001 acquired by the heartbeat information acquisition unit 6100 to a reference heart rate 6002 in the operation of comparing the subject's heart rate to the reference heart rate (S6120).

Here, the reference heart rate 6002 may refer to a heart rate that is set as a reference for distinguishing between a drowsiness state and a normal state. As described above, due to the activation of a parasympathetic nervous system, a heart rate in the drowsiness state decreases below a heart rate in the normal state. Accordingly, in order to distinguish between the drowsiness state and the normal state, a heart rate which is the same or similar to the decreased heart rate may be set as the reference heart rate 6002. In this case, when the heart rate of the subject is equal to or below the reference heart rate 6002, the drowsiness detection device 6000 may determine that the subject is in the drowsiness state. When the heart rate 6001 of the subject is equal to or above the reference heart rate 6002, the drowsiness detection device 6000 may determine that the subject is in the normal state.

Various methods for setting the reference heart rate 6002 will be described below.

In an embodiment, the drowsiness detection device 6000 may set the reference heart rate 6002 using the mean of heart rates acquired during a certain time after the heart rate is acquired for the first time. The certain time may be set to various values such as one minute or five minutes. Generally, there is a high possibility that the subject is not in the drowsiness state but in the normal state during a certain time after the subject's heart rate is acquired for the first time. Accordingly, the drowsiness detection device 6000 may acquire the average heart rate of the subject acquired during the certain time and may acquire a value obtained by multiplying the average heart rate by a predetermined value a (e.g., a indicates a real number less than or equal to 1 and, as a specific example, is 0.9) as the reference heart rate 6002. The predetermined value a is not limited to the above example.

In another embodiment, the drowsiness detection device 6000 may set the reference heart rate 6002 using a resting heart rate and/or an active heart rate. In detail, the resting heart rate may refer to a heart rate when the subject is not moving (or when the amount of movement is small). Herein, a heart rate when a subject is awake but not moving (or the amount of movement is small) is defined as a first resting heart rate, and a heart rate when a subject is sleeping is defined as a second resting heart rate.

Also, the active heart rate may refer to a heart rate when the subject is actively moving.

In an embodiment, the drowsiness detection device 6000 may acquire a heart rate measured in a situation in which the subject is awake but not moving (or the amount of movement is small) as a first resting heart rate. For example, when a subject is in an environment in which he or she cannot be actively moving (e.g., the subject seats on the driver seat), the drowsiness detection device 6000 may assume that the subject is awake but not moving during a certain time after a heart rate is acquired for the first time, and then may set a heart rate measured during the certain time as a first resting heart rate.

Also, the drowsiness detection device 6000 may acquire, as a second resting heart rate, a heart rate measured in a situation in which the subject is recognized as being sleeping and may acquire, as an active heart rate, a heart rate measured in a situation in which the subject is recognized as being actively moving.

Also, the drowsiness detection device 6000 may acquire the first resting heart rate, the second resting heart rate, and the active heart rate using a camera or a wearable device.

For example, the drowsiness detection device 600 may use a camera to acquire information on whether a subject is moving and whether the pupil of a subject is being tracked. As an example, the drowsiness detection device 6000 may acquire, as the active heart rate, a heart rate measured when a subject is moving. Also, by using a camera, the drowsiness detection device 6000 may acquire, as the first resting heart rate, a heart rate measured when the pupil of a subject is continuously tracked even if the subject does not move and may acquire, as the second resting heart rate, a heart rate measured when the pupil of a subject is not continuously tracked while the subject does not move.

As another example, the drowsiness detection device 600 may use a wearable device to acquire information on whether a subject is moving and whether a body part (e.g., a wrist) on which the wearable device is worn is being moved. As an example, the drowsiness detection device 6000 may use a wearable device to acquire, as the active heart rate, a heart rate measured when the movement of a subject is detected. Also, the drowsiness detection device 6000 may acquire, as the first resting heart rate, a heart rate measured when the movement of the body part on which the wearable device is worn is detected even if the movement of the subject is not detected and may acquire, as the second resting heart rate, a heart rate measured when the movement of the body part is not detected during a certain time while the movement of the subject is not detected.

Also, the drowsiness detection device 6000 may preset the first resting heart rate, the second resting heart rate, and the active heart rate before starting drowsiness detection or may receive the first resting heart rate, the second resting heart rate, and the active heart rate from the outside before or after starting drowsiness detection.

According to an embodiment, the reference heart rate 6002 may be set based on the first resting heart rate. In detail, the reference heart rate 6002 may be set to a certain proportion of the first resting heart rate. For example, the reference heart rate 6002 may be calculated by multiplying the first resting heart rate, by a predetermined value a (e.g., a indicates a real number less than or equal to 1 and, as a specific example, is 0.9). It will be appreciated that the predetermined value a is not limited to the above example.

According to another embodiment, the reference heart rate 6002 may be set based on the second resting heart rate. In detail, the reference heart rate 6002 may be set to be the same as the second resting heart rate or may be calculated by multiplying the second resting heart rate by a predetermined value b (e.g., b indicates a real number greater than one, and as a specific example, is 1.1). It will be appreciated that the predetermined value b is not limited to the above example.

Also, according to another embodiment, the reference heart rate 6002 may be set based on the active heart rate. In detail, the reference heart rate 6002 may be calculated by multiplying the active heart rate by a predetermined value c (e.g., c is a real number less than or equal to 1 and, as a specific example, is 0.8). Also, the predetermined value c may be set to be lower than the predetermined value a, considering that generally, the active heart rate is higher than the first resting heart rate. It will be appreciated that the predetermined value c is not limited to the above example.

It will also be appreciated that a method of setting the reference heart rate 6002 is not limited to a method of calculating the reference heart rate 6002 as a certain proportion of the first resting heart rate, the second resting heart rate, or the active heart rate and that various mathematical operations such as addition and subtraction are applicable.

In detail, in an embodiment, the drowsiness detection device 6000 may set the reference heart rate 6002 by adding or subtracting a predetermined value to or from the first resting heart rate, the second resting heart rate, or the active heart rate. For example, when the first resting heart rate is 75, the drowsiness detection device 6000 may set the reference heart rate 6002 to 65 (=first resting heart rate−10) (beats per minute) on the basis of the first resting heart rate. For example, when the second resting heart rate is 65, the drowsiness detection device 6000 may set the reference heart rate 6002 to 75 (=second resting heart rate+10) (heats per minute) on the basis of the second resting heart rate.

Also, in another embodiment, the drowsiness detection device 600 may change the previous reference heart rate 6002 to a new reference heart rate 6002. That is, the drowsiness detection device 6000 may update the previous reference heart rate 6002 to set the new reference heart rate 6002.

For example, the drowsiness detection device 6000 may set the reference heart rate 6002 on the basis of heart rates acquired during a certain time after the heart rate of the subject is acquired for the first time as described above. The drowsiness detection device 6000 may detect the normal state on the basis of the subject's heart rates acquired after the certain time and may change an average heart rate in a time interval in which the normal state is detected to a new reference heart rate 6002. Also, the drowsiness detection device 6000 may change the average heart rate to the new reference heart rate 6002 on the basis of the first resting heart rate, the second resting heart rate, and the active heart rate acquired for the same subject after the certain time. Thus, the drowsiness detection device 6000 may set a reference heart rate 6002 reflecting the latest state of the subject and thus may detect the drowsiness of the subject on the basis of the more accurate reference heart rate 6002.

As another example, the drowsiness detection device 6000 may preset the reference heart rate 6002 on the basis of the first resting heart rate, the second resting heart rate, and the active heart rate as described above. In this case, after the reference heart rate 6002 is set based on the first resting heart rate, the second resting heart rate, or the active heart rate, the drowsiness detection device 6000 may newly acquire a first resting heart rate, a second resting heart rate, or an active heart rate during a predetermined time. The drowsiness detection device 6000 may set a new reference heart rate 6002 using the newly acquired first resting heart rate, second resting heart rate, or active heart rate according to the above-described method of setting the reference heart rate 6002.

According to an embodiment, referring to FIG. 41, in the operation of comparing the subject's heart rate 6001 to the reference heart rate 6002 (S6120), the drowsiness detection device 6000 may compare the subject's heart rate 6001 to the reference heart rate 6002.

In an embodiment, the drowsiness detection device 6000 may compare the subject's heart rate 6001 to the reference heart rate 6002 to detect a time point t1 at which the subject's heart rate 6001 is less than (or greater than) or equal to the reference heart rate 6002. The detected time point t1 may be a starting point for measuring a drowsiness state and normal state for each level.

That is, in the above embodiment, the detection of the time point t1 at which the subject's heart rate 6001 is less than (or greater than) or equal to the reference heart rate 6002 may act as a trigger for measuring the drowsiness state and the normal state for each level.

In the duration measurement operation S6130, the drowsiness detection device 6000 may measure a duration for which the subject's heart rate 6001 is less than or equal to the reference heart rate 6002 with respect to a time point when the subject's heart rate 6001 becomes less than or equal to the reference heart rate 6002. Also, the drowsiness detection device 6000 may measure a duration for which the subject's heart rate 6001 is greater than or equal to the reference heart rate 6002 with respect to a time point when the subject's heart rate 6001 is greater than or equal to the reference heart rate 6002.

A heart rate may vary due to several physical factors in addition to drowsiness. Among various physical factors, the decrease or increase in heart rate due to drowsiness is maintained. Thus, the decreased or increased heart rate being maintained for several seconds to minutes may be a good biomarker indicating a drowsiness state.

For example, when a person's tension is relieved, a heart rate is temporarily decreased, but the decreased heart rate can be easily recovered to normal. When the drowsiness detection device 600 detects a drowsiness state on the basis of a duration for which the heart rate is decreased and maintained, the drowsiness detection device 6000 may avoid detecting, as the drowsiness state, a situation in which the heart rate is temporarily decreased due to the tension relief. Thus, the drowsiness detection device 6000 may more accurately detect the drowsiness state.

Also, as the subject enters a higher degree of drowsiness state, the duration of the heart rate being decreased due to drowsiness may be increased. Accordingly, by measuring a duration for which the decreased heart rate is maintained, the drowsiness detection device 6000 may determine which level of the drowsiness state the subject has entered. That is, by classifying the level of the drowsiness state according to the length of the duration, the drowsiness detection device 6000 may more specifically detect the subject's drowsiness state.

According to an embodiment, referring to FIG. 41, the drowsiness detection device 6000 may measure a duration for which the subject's heart rate 6001 is less than or equal to the reference heart rate 6002 with respect to a time point t1 at which the subject's heart rate 6001 becomes less than or equal to the reference heart, rate 6002.

For example, the reference heart rate 6002 may be set to 72 (beats per minute) corresponding to 90% of the first resting heart rate. Here, when the heart rate of the subject is 74 (beats per minute) at a first time point and is 72 (beats per minute) at a second time point immediately after the first time point, the drowsiness detection device 6000 may measure a duration for which the heart rate of the subject at the second time point is less than or equal to 72 (beats per minute).

It will be appreciated that, according to another embodiment, the drowsiness detection device 6000 may measure a duration for which the subject's heart rate is greater than or equal to the reference heart rate with respect to a time point at which the subject's heart rate becomes greater than or equal to the reference heart rate.

For example, the reference heart rate 6002 may be set to 72 (beats per minute) corresponding to 90% of the first resting heart rate. Here, when the heart rate 6001 of the subject is 70 (beats per minute) at a third time point and is 72 (beats per minute) at a fourth time point immediately after the third time point, the drowsiness detection device 6000 may measure a duration for which the heart rate 6001 of the subject is greater than or equal to 72 (beats per minute) after the fourth time point.

Figure 42:
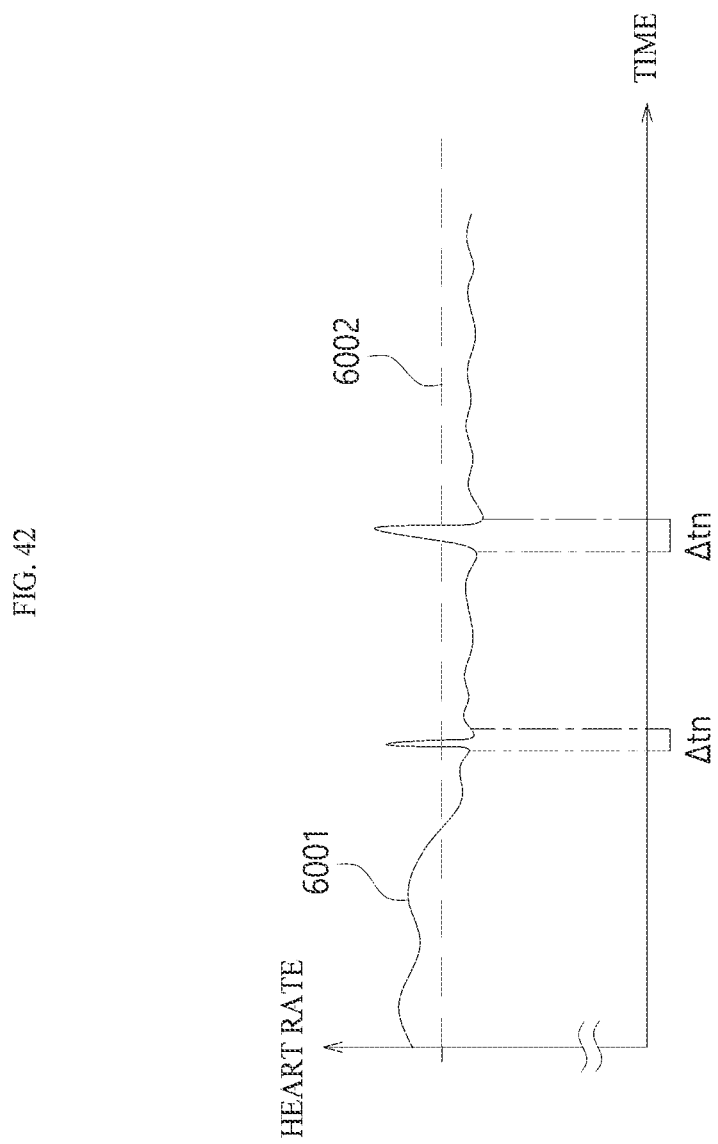
FIG. 42 is a graph of a heart rate including noise.

According to an embodiment, referring to FIG. 42, when measuring a duration for which the subject's heart rate 6001 is less than (or greater than) or equal to the reference heart rate 6002, the drowsiness detection device 6000 may correct a time interval Δtn in which a heart rate containing noise is measured and then may measure the duration. As an example, the drowsiness detection device 6000 may correct a heart rate detected as noise on the basis of previously measured heart rates. As another example, the time interval Δtn in which the heart rate containing noise is measured may be excluded when the duration is measured.

Here, noise represents errors caused by various causes such as a subject's motion or external light, and it may be difficult for a heart rate containing noise to reflect the subject's state. Generally, a heart rate containing noise may be temporarily acquired and greatly different from a previously acquired heart rate of the subject and a subsequently acquired heart rate of the subject.

Based on this fact, according to an embodiment, when an acquired heart rate has a deviation greater than or equal to a certain value from the previously acquired heart rate 6001 of the subject and/or the subsequently acquired heart rate 6001 of the subject, the drowsiness detection device 6000 may detect the subjects heart rate 6001 as a heart rate containing noise. For example, when acquiring a heart rate having a deviation of 20 or more from a previously detected heart rate and/or a subsequently acquired heart rate during a time interval of 3 seconds or less, the drowsiness detection device 600 may detect the subject's heart rate 6001 acquired for three seconds as a heart rate containing noise. Here, a time at which the heart rate containing noise is acquired and a deviation between the heart rate containing noise and other heart rates are not limited to specific values.

According to an embodiment, although the heart rate containing noise is a heart rate greater than or equal to the reference heart rate 6002, when measuring a duration for which the subject's heart rate 6001 is less than or equal to the reference heart rate 6002, the drowsiness detection device 6000 may regard the noise as a heart rate less than or equal to the reference heart rate and then measure the duration.

According to an embodiment, although the heart rate containing noise is a heart rate less than or equal to the reference heart rate, when measuring a duration for which the subject's heart rate is greater than or equal to the reference heart rate, the drowsiness detection device 6000 may regard the noise as a heart rate less than or equal to the reference heart rate and then measure the duration.

According to an embodiment, although the heart rate containing noise is a heart rate less than or equal to the reference heart rate, when measuring a duration for which the subject's heart rate is less than or equal to the reference heart rate, the drowsiness detection device 6000 may exclude the time interval $\Delta tn$ in which the heart rate containing noise is measured from the measurement.

According to an embodiment, although the heart rate containing noise is a heart rate less than or equal to the reference heart rate, when measuring a duration for which the subject's heart rate is greater than or equal to the reference heart rate, the drowsiness detection device 6000 may exclude the time interval $\Delta tn$ in which the heart rate containing noise is measured from the measurement.

According to an embodiment, referring to FIG. 41, in the level-specific drowsiness state detection operation S6140, the drowsiness detection device 6000 may detect a drowsiness state or a normal state through a comparison between a measured duration and a reference duration.

The drowsiness detection device 6000 may measure a duration for which the subject's heart rate 6001 is less than or equal to the reference heart rate and may detect a drowsiness state when the measured duration reaches a reference duration $\Delta ta$, $\Delta tb$, or $\Delta tc$. In this case, the reference duration $\Delta ta$, $\Delta tb$, or $\Delta tc$ may include a plurality of reference durations. For example, the number of reference durations $\Delta ta$, $\Delta tb$, and $\Delta tc$ may be three. In this case, a first reference duration $\Delta ta$ may be set to 30 seconds, a second reference duration $\Delta tb$ may be set to 60 seconds, and a third reference duration $\Delta tc$ may be set to 90 seconds.

In this case, when the duration for which the subject's heart rate 6001 is less than or equal to the reference heart rate 6002 reaches 30 seconds, the drowsiness detection device 6000 may detect that the subject is in the first-level drowsiness state.

In this case, when the duration for which the subject's heart rate 6001 is less than or equal to the reference heart rate 6002 reaches 60 seconds, the drowsiness detection device 6000 may detect that the subject is in the second-level drowsiness state.

In this case, when the duration for which the subject's heart rate 6001 is less than or equal to the reference heart rate 6002 reaches 90 seconds, the drowsiness detection device 6000 may detect that the subject is in the third-level drowsiness state.

Also, before detecting a different-level drowsiness state or a normal state for a subject detected as being in a drowsiness state, the drowsiness detection device 6000 may maintain the detected drowsiness state.

In another embodiment, when the duration for which the subject's heart rate 6001 is less than or equal to the reference heart rate 6002 does not reach the first reference duration $\Delta ta$, the drowsiness detection device 6000 may detect that the subject is in the normal state.

For example, when it is assumed that the first reference duration $\Delta ta$ is 30 seconds and that the subject's heart rate 6001 has recovered to a heart rate greater than or equal to the reference heart rate after the heart rate 6001 is maintained less than or equal to the reference heart rate for 10 seconds, the drowsiness detection device 6000 may detect that the subject is in the normal state.

Figure 43:
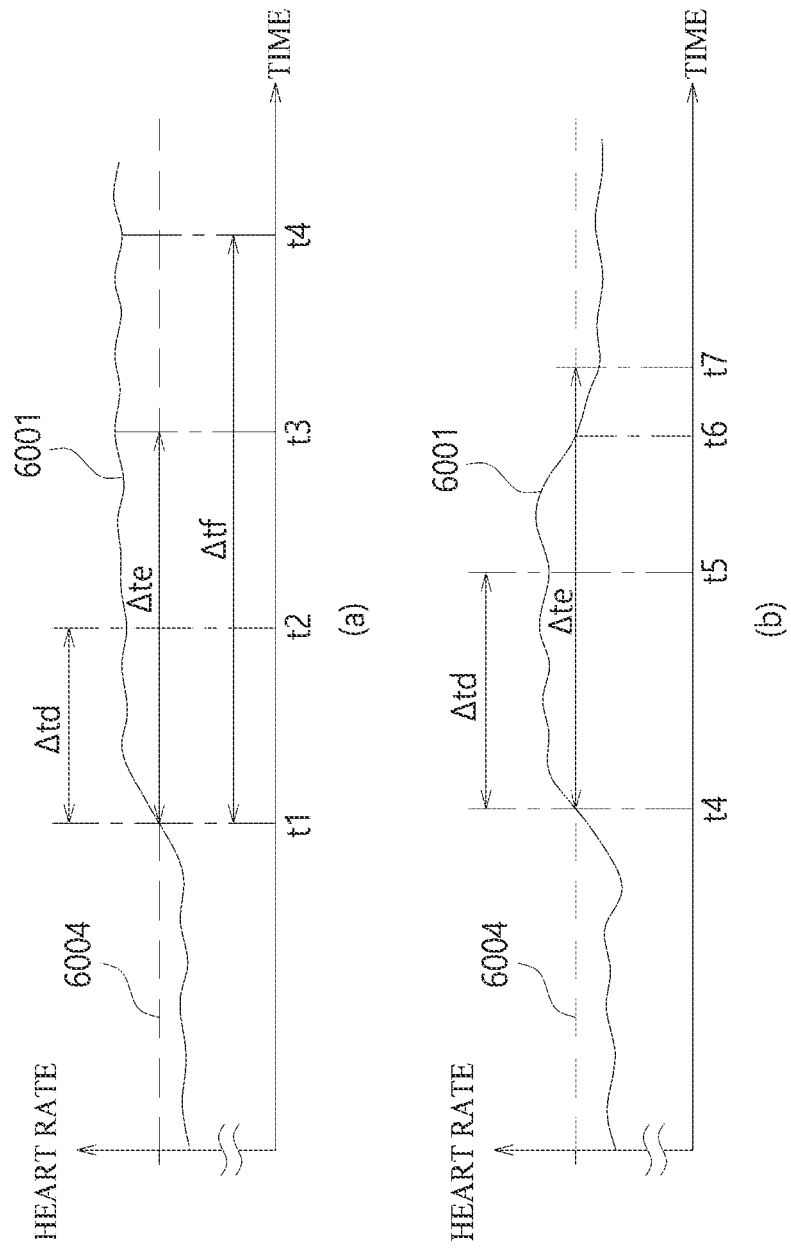
FIG. 43 is a graph illustrating a situation in which a subject has recovered to a normal state.
Figure 44:
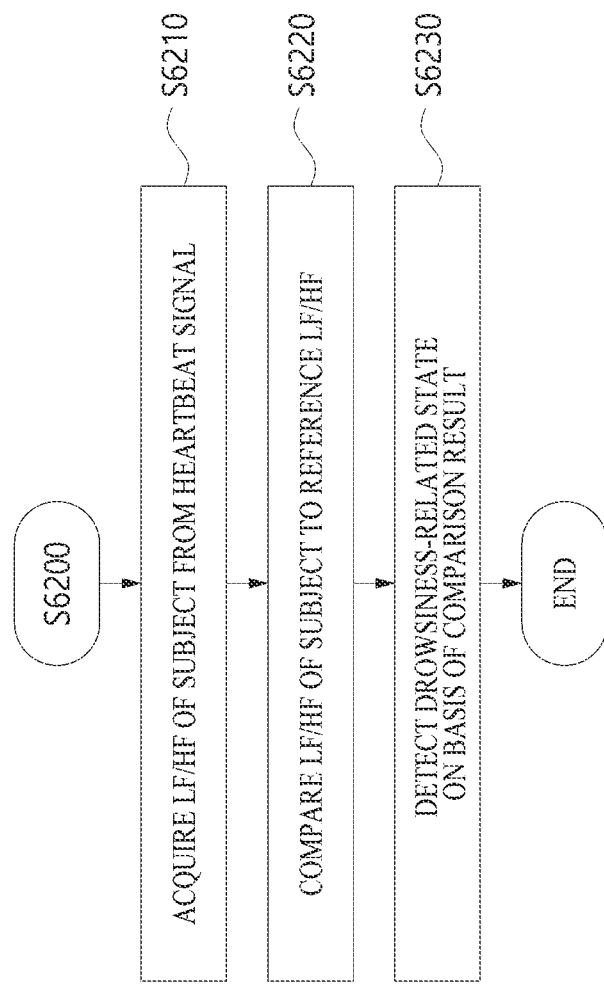
FIG. 44 is a flowchart of a method of detecting drowsiness on the basis of a low frequency (LF)/high frequency (HF) ratio.

A method of detecting recovery from a drowsiness state on the basis of a heart rate will be described below with reference to FIG. 43.

Also, in the drowsiness-related state detection operation (S6140), the drowsiness detection device 6000 may detect that the subject has recovered from the drowsiness state when the measured duration reaches a recovery reference duration $\Delta td$, $\Delta te$, or $\Delta tf$.

The recovery from the drowsiness state may refer to a state in which a subject comes out of a detected drowsiness state after entering the drowsiness state. In detail, the recovery from the drowsiness state may refer to a situation in which a drowsiness state at a level lower than a predetermined level is detected after a drowsiness state at the predetermined level is detected. Also, the recovery from the drowsiness state may refer to a situation in which the normal state is detected after the drowsiness state is detected.

According to an embodiment, when a duration, for which the heart rate 6001 of a drowsy subject is greater than or equal to a recovery reference heart rate 6004, reaches a recovery reference duration $\Delta td$, $\Delta te$, or $\Delta tf$, the drowsiness detection device 6000 may detect the recovery of the subject from the drowsiness state.

In detail, according to an embodiment, referring to FIG. 46A, the drowsiness detection device 6000 may measure a duration for which the subject's heart rate 6001 is greater than or equal to the recovery reference heart rate 6004 from the time point t1 and may detect that the subject has recovered from the drowsiness state at time points t1, t2, and t3 at which the duration reaches the recovery reference duration.

Here, the recovery reference duration may be set to various values. For example, the recovery reference duration may be set to various units such as several seconds, tens of seconds, several minutes, and tens of minutes.

For example, the recovery reference duration may be set to 30 seconds. In this case, when a duration, for which a heart rate of a subject detected as being in a third-level drowsiness state is greater than or equal to the recovery reference heart rate 6004, reaches 30, the drowsiness detection device 6000 may detect that the subject has recovered to the normal state.

Here, there may be a plurality of recovery reference durations. For example, there are three recovery reference durations. A first recovery reference duration may be set to 20 seconds, a second recovery reference duration may be set to 40 seconds, and a third recovery reference duration may be set to 60 seconds. Here, the first to third recovery reference durations are limited to the values proposed in the above example.

According to an embodiment, referring to FIG. 43A, the drowsiness detection device 6000 may measure a duration, for which a subject's heart rate 6001 detected as being in the third-level drowsiness state is greater than or equal to the recovery reference heart rate 6004, from a time point t1 at which the subject's heart rate 6001 becomes greater than or equal to the recovery reference heart rate 6004 and may detect that the subject has recovered to the second-level drowsiness state at a time point t2 at which the duration reaches the first recovery reference duration.

Also, after the subject has recovered from the third-level drowsiness state to the second-level drowsiness state, the drowsiness detection device 6000 may measure a duration for which a heart rate 6001 of a subject is greater than or equal to the recovery reference heart rate 6004 from a time point t1 at which the subject's heart rate 6001 becomes greater than or equal to the recovery reference heart rate 6004 and may detect that the subject has recovered to the first-level drowsiness state at a time point t3 at which the duration reaches the second recovery reference duration.

However, according to an embodiment, referring to FIG. 43B, after the subject has recovered from the third-level drowsiness state to the second-level drowsiness state and before a duration, for which the subject's heart rate 6001 is greater than or equal to the recovery reference heart rate 6004 from a time point t4 at which the subject's heart rate 6001 is greater than or equal to the recovery reference heart rate 6004, reaches the second recovery duration, the drowsiness detection device 6000 may detect a time point t6 at which the heart rate 6001 of the subject is less than or equal to the recovery reference heart rate 6004. In this case, the drowsiness detection device 6000 may maintain the drowsiness state of the subject in the second-level drowsiness state and also reset the drowsiness state of the subject to the third-level drowsiness state.

It will be appreciated that the drowsiness detection device 6000 may detect recovery from the drowsiness state on the basis of a duration for which an average heart rate 6003 of the subject is greater than or equal to the recovery reference heart rate 6004.

The recovery reference heart rate 6004 may be the same as or different from the reference heart rate 6002 for detecting a drowsiness state.

The recovery reference duration may be the same as or different from a duration for detecting a drowsiness state.

8.3 LF/HF Ratio-Based Drowsiness Detection Method

An LF/HF ratio-based drowsiness detection method according to an embodiment will be described below with reference to FIGS. 44 to 47.

In an embodiment, the LF/FH-based drowsiness detection method may include an operation of acquiring a subject's LF/HF ratio 6005 (S6210), an operation of comparing the subject's LF/HF ratio 6005 to a reference LF/HF ratio (S6220), and an operation of detecting drowsiness for each level on the basis of a result of the comparison (S6230).

In some embodiments, the drowsiness detection method may further include providing a notification corresponding to a drowsy level to the outside.

In the operation of acquiring an LF/HF ratio (S6210), the heartbeat information acquisition unit 6100 may acquire the subject's LF/HF ratio 6005.

In an embodiment, the drowsiness detection device 6000 may acquire the subject's LF/HF ratio 6005 at predetermined intervals. In another embodiment, the drowsiness detection device 6000 may acquire the subject's LF/HF ratio 6005 without following predetermined intervals.

It will be appreciated that when a subject's LF/HF ratio 6005 is measured by the physiological parameter acquisition device 10 or the like at predetermined intervals, the drowsiness detection device 6000 may acquire the subject's LF/HF ratio 6005 on the basis of the predetermined intervals at which the physiological parameter acquisition device 10 or the like measure the LF/HF ratio.

As another example, the drowsiness detection device 6000 may request the physiological parameter acquisition device 10 or the like to provide an LF/HF ratio upon an external input or request and may acquire a subject's LF/HF ratio each time the request is made.

In an embodiment, the drowsiness detection device 6000 may acquire a subject's average LF/HF ratio for a certain time period.

The drowsiness detection device 6000 can correct noise by acquiring the average LF/HF ratio, and thus can have an effect of accurately detecting drowsiness. This effect is the same as an effect obtainable when an average heart rate is acquired and thus a detailed description thereof will be omitted.

Figure 45:
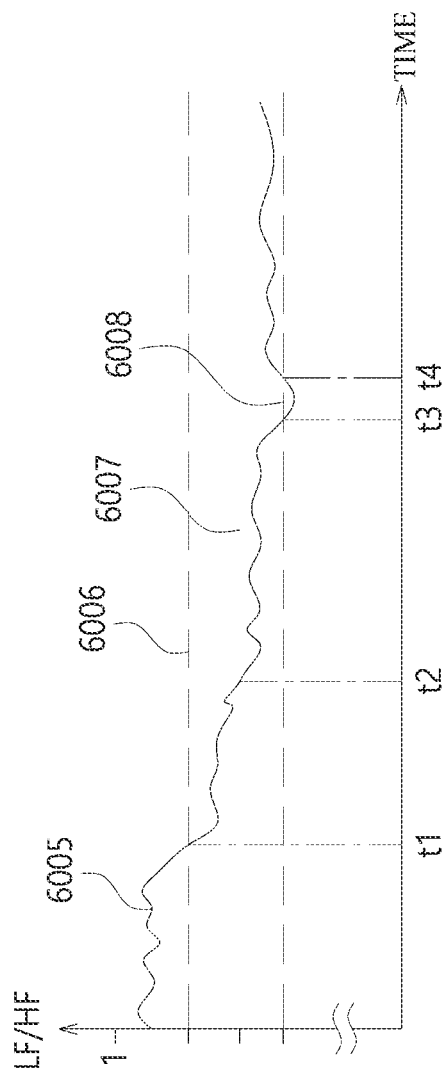
FIG. 45 is a graph of an LF/HF ratio of a subject for explaining a situation in which the subject is detected to be in a drowsiness state on the basis of an LF/HF ratio.

According to an embodiment, referring to FIG. 45, in the operation of comparing an acquired LF/HF ratio 6005 of a subject to reference LF/HF ratios 6006, 6007, and 6008 (S6220), the drowsiness detection device 6000 may compare the acquired LF/HF ratio 6005 of the subject to a reference LF/HF ratio.

Here, the reference LF/HF ratios 6006, 6007, and 6008 may refer to values that are set as a reference for distinguishing between a drowsiness state and a normal state. As described above, an LF/HF ratio in the drowsiness state may be smaller than an LF/HF ratio in the normal state according to the activation of a parasympathetic nervous system.

In an embodiment, the drowsiness detection device 6000 may set the reference LF/HF ratios 6006, 6007, and 6008 using the mean of LF/HF ratios of a heartbeat signal acquired during a certain time from a time point at which the LF/HF ratio of the heartbeat signal is acquired for the first time. The certain time may be set to various values such as one minute or five minutes. Generally, there is a high possibility that the subject is in the normal state during a certain time after the subject's LF/HF ratio 6005 is acquired for the first time. Accordingly, the drowsiness detection device 6000 may acquire an average LF/HF ratio of the subject acquired during the certain time and may acquire a value obtained by multiplying the average LF/HF ratio by a predetermined value a (e.g., a indicates a real number less than or equal to one and, as a specific example, is 0.9) as a reference LF/HF ratio. Also, the drowsiness detection device 6000 may set a plurality of reference LF/HF ratios using different predetermined real numbers. The predetermined value a is not limited to the above example.

In another embodiment, the drowsiness detection device 6000 may set a reference LF/HF ratio 6006, 6007, or 6008 using a resting LF/HF ratio and/or an active LF/HF ratio. In this case, there may be a plurality of reference LF/HF ratios 6006, 6007, and 6008.

In detail, the drowsiness detection device 6000 may use a camera or a wearable device to obtain a first resting LF/HF ratio based on a first resting heart rate, a second resting LF/HF ratio based on a second resting heart rate, and an active LF/HF ratio based on an active heart rate.

According to an embodiment, the reference LF/HF ratios 6006, 6007, and 6008 may be set based on the first resting LF/HF ratio. In detail, the reference LF/HF ratios 6006, 6007, and 6008 may be set to certain proportions of the first resting LF/HF ratio. For example, the reference LF/HF ratios 6006, 6007, and 6008 may include a first reference LF/HF ratio 6006 obtained by multiplying the first resting LF/HF ratio by 0.9, which is a predetermined value, a second reference LF/HF ratio 6007 obtained by multiplying the first resting LF/HF ratio by 0.8, and a third reference LF/HF ratio 6008 obtained by multiplying the first resting LF/HF ratio by 0.7. It will be appreciated that the predetermined value is not limited to the above example.

According to another embodiment, the reference LF/HF ratios 6006, 6007, and 6008 may be set based on the second resting LF/HF ratio. In detail, the reference LF/HF ratios 6006, 6007, and 6008 may be set to certain proportions of the second resting LF/HF ratio. For example, the reference LF/HF ratios 6006, 6007, and 6008 may include a first reference LF/HF ratio 6006 obtained by multiplying the second resting LF/HF ratio by 1.5, which is a predetermined value, a second reference LF/HF ratio 6007 obtained by multiplying the second resting LF/HF ratio by 1.3, and a third reference LF/HF ratio 6008 obtained by multiplying the second resting LF/HF ratio by 1.1. It will be appreciated that the predetermined value is not limited to the above example.

Also, according to another embodiment, the reference LF/HF ratios 6006, 6007, and 6008 may be set based on the active LF/HF ratio. In detail, the reference LF/HF ratios 6006, 6007, and 6008 may include a first reference LF/HF ratio 6006 obtained by multiplying the active LF/HF ratio by 0.8, which is a predetermined value, a second reference LF/HF ratio 6007 obtained by multiplying the active LF/HF ratio by 0.7, and a third reference LF/HF ratio 6008 obtained by multiplying the active LF/HF ratio by 0.6. It will be appreciated that the predetermined value is not limited to the above example.

It will also be appreciated that a method of setting the reference LF/HF ratios 6006, 6007, and 6008 is not limited to a method of calculating the reference LF/HF ratios 6006, 6007, and 6008 as certain proportions of the first resting LF/HF ratio, the second resting LF/HF ratio, and the active LF/HF ratio and various mathematical operations such as addition and subtraction are applicable. Also, in another embodiment, the drowsiness detection device 600 may change the previous reference LF/HF ratios 6006, 6007, and 6008 to new reference LF/HF ratios 6006, 6007, and 6008.

For example, the drowsiness detection device 6000 may set the reference LF/HF ratios 6006, 6007, and 6008 on the basis of LF/HF ratios acquired during a certain time after the LF/HF ratio 6005 of the subject is acquired for the first time as described above. The drowsiness detection device 6000 may detect a normal state on the basis of the subject's LF/HF ratios 6005 acquired after the certain time and may change an average LF/HF ratio in a time interval in which the normal state is detected to a new reference LF/HF ratio 6006, 6007, or 6008. Also, the drowsiness detection device 6000 may change the average LF/HF ratio to the new reference LF/HF ratio 6006, 6007, or 6008 on the basis of a first resting LF/HF ratio, a second resting LF/HF ratio, and an active LF/HF ratio which are acquired for the same subject after the certain time.

As another example, the drowsiness detection device 6000 may preset reference LF/HF ratios 6006, 6007, and 6008 on the basis of the first resting LF/HF ratio, the second resting LF/HF ratio, and the active LF/HF ratio as described above. In this case, after the reference LF/HF ratios 6006, 6007, and 6008 are set based on the first resting LF/HF ratio, the second resting LF/HF ratio, and the active resting LF/HF ratio, the drowsiness detection device 6000 may set new reference LF/HF ratios 6006, 6007, and 6008 on the basis of a first resting LF/HF ratio, a second resting LF/HF ratio, and an active resting LF/HF ratio which are newly set for the same subject in the same manner.

Also, the drowsiness detection device 6000 may set new reference LF/HF ratios 6006, 6007, and 6008 on the basis of LF/HF ratios acquired during a certain time after an LF/HF ratio is acquired for the first time.

Also, the drowsiness detection device 6000 may set new reference LF/HF ratios 6006, 6007, and 6008 on the basis of an average LF/HF ratio in a time interval in which the subject is detected as being in the normal state.

According to an embodiment, referring to FIG. 45, the drowsiness detection device 6000 may detect time points t1, t2, t3, and t4 at which the LF/HF ratio 6005 of the subject becomes greater than (or less than) or equal to one of the plurality of reference LF/HF ratios 6006, 6007, and 6008. The detected time points may be time points for measuring level-specific drowsiness states and a normal state.

In an embodiment, the drowsiness detection device 6000 may detect a drowsiness state at time points t1, t2, and t3 at which the LF/HF ratio 6005 of the subject becomes less than or equal to the reference LF/HF ratios 6006, 6007, and 6008.

In an embodiment, at a time point t1, t2, or t3 at which the LF/HF ratio 6005 of the subject becomes one of the plurality of reference LF/HF ratios 6006, 6007, and 6008, the drowsiness detection device 6000 may detect a drowsiness state with a level corresponding to the reference LF/HF ratio. Here, the drowsiness detection device 6000 may detect a drowsiness state on the basis of a result of additionally comparing the LF/HF ratio 6005 of the subject to another reference LF/HF ratio as well as the corresponding reference LF/HF ratio.

In detail, the plurality of reference LF/HF ratios 6006, 6007, and 6008 may include a first reference LF/HF ratio 6006, a second reference LF/HF ratio 6007, and a third reference LF/HF ratio 6008. For convenience of description, the first reference LF/HF ratio 6006 is defined as a reference LF/HF ratio for detecting the lowest-level drowsiness state.

For example, when the LF/HF ratio 6005 of the subject is less than or equal to the first reference LF/HF ratio 6006 and greater than or equal to the second reference LF/HF ratio 6007 at a first time point, the drowsiness detection device 6000 may determine that the drowsiness state of the subject is a first-level drowsiness state.

Also, when the LF/HF ratio 6005 of the subject is less than or equal to the second reference LF/HF ratio 6007 and greater than or equal to the third reference LF/HF ratio 6008 at a first time point, the drowsiness detection device 6000 may determine that the drowsiness state of the subject is a second-level drowsiness state.

Also, when the LF/HF ratio 6005 of the subject is less than or equal to the third reference LF/HF ratio 6088 at a first time point, the drowsiness detection device 6000 may determine that the drowsiness state of the subject is a third-level drowsiness state.

Figure 46:
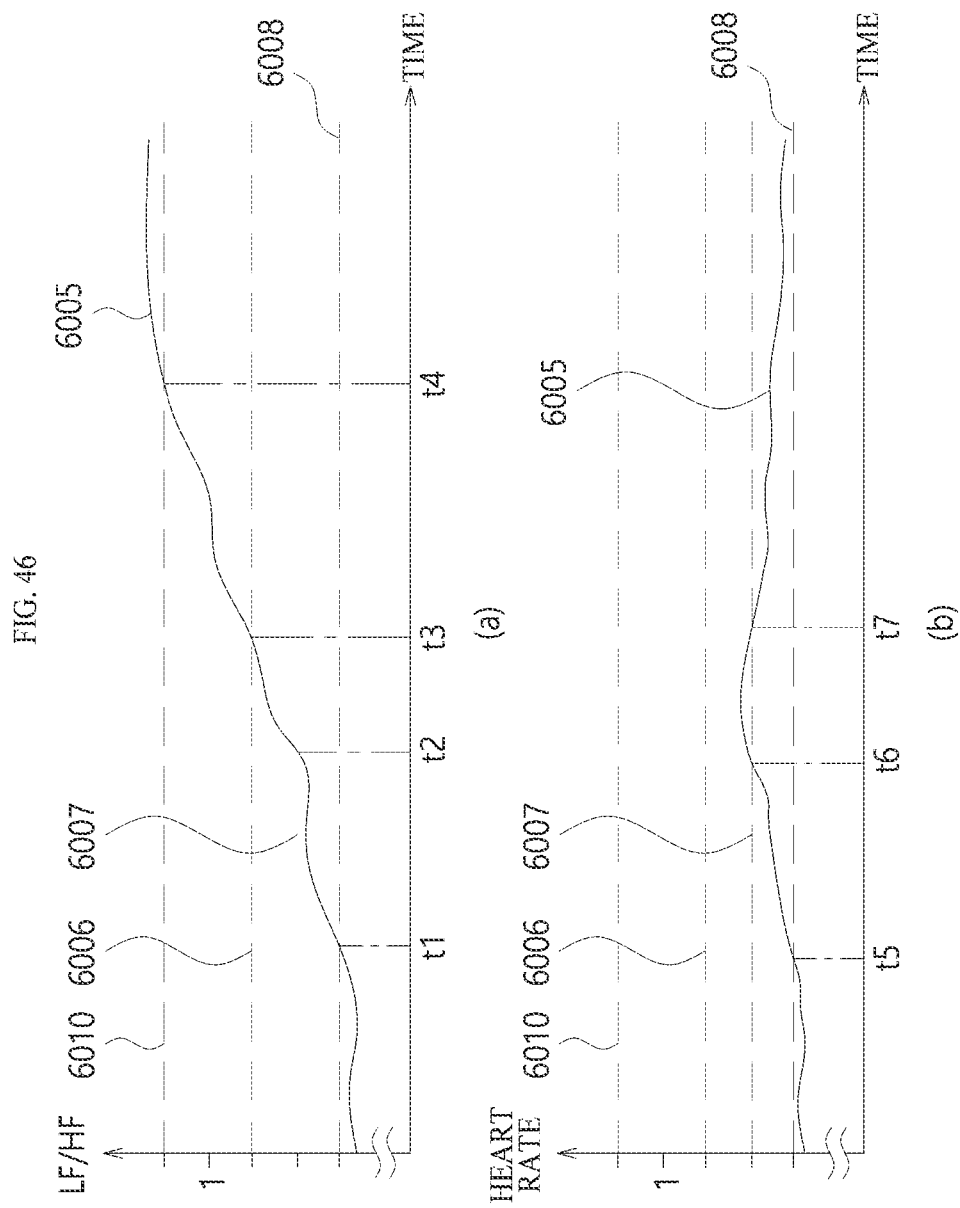
FIG. 46 is a graph of an LF/HF ratio of a subject in order to represent a situation in which the subject has recovered from a drowsiness state on the basis of an LF/HF ratio.

A method of detecting recovery from a drowsiness state on the basis of an LF/HF ratio will be described below with reference to FIG. 46.

According to an embodiment, referring to FIG. 46A, in the operation of detecting a drowsiness-related state (S6230), the drowsiness detection device 6000 may detect that the subject has recovered from a drowsiness state at time points t1, t2, t3, and t4 at which the measured LF/HF ratio 6005 of the subject becomes greater than or equal to recovery reference LF/HF ratios 6006, 6007, 6008, and 6010. Here, the drowsiness detection device 6000 may detect recovery from the drowsiness state on the basis of a result of additionally comparing the LF/HF ratio 6005 of the subject to another reference LF/HF ratio as well as the corresponding reference LF/HF ratio.

In an embodiment, the plurality of reference LF/HF ratios 6006, 6007, 6008, and 6010 may include a first recovery reference LF/HF ratio 6006, a second recovery reference LF/HF ratio 6007, and a third recovery reference LF/HF ratio 6008. For convenience of description, the first recovery reference LF/HF ratio 6006 may be set as a recovery reference LF/HF ratio which is largest among recovery reference LF/HF ratios of 1 or less. For example, when the LF/HF ratio 6005 of the subject is less than or equal to the third recovery reference LF/HF ratio 6008 at a first time point and is greater than or equal to the third recovery reference LF/HF ratio 6008 and less than or equal to the second recovery reference LF/HF ratio 6007 at a second time point subsequent to the first time point, the drowsiness detection device 6000 may determine that the drowsiness state of the subject is changed from the third-level drowsiness state to the second-level drowsiness state at the second time point. Also, when the LF/HF ratio 6005 of the subject is greater than or equal to the second recovery reference LF/HF ratio 6007 and less than or equal to the first recovery reference LF/HF ratio 6006 at a third time point after the subject has recovered from the third-level drowsiness state to the second-level drowsiness state, the drowsiness detection device 6000 may determine that the drowsiness state of the subject is changed from the second-level drowsiness state to the first-level drowsiness state at the third time point.

In an embodiment, when the LF/HF ratio 6005 of the subject is less than or equal to the third recovery reference LF/HF ratio 6008 at a first time point and is greater than or equal to the second recovery reference LF/HF ratio 6007 and less than or equal to the first recovery reference LF/HF ratio 6006 at a second time point subsequent to the first time point, the drowsiness detection device 6000 may determine that the drowsiness state of the subject is changed from the third-level drowsiness state to the first-level drowsiness state at the second time point.

However, according to an embodiment, referring to FIG. 46B, when the drowsiness detection device 6000 detects a time point t7 at which the LF/HF ratio 6005 of the subject is decreased to the second recovery reference LF/HF ratio 6007 within a certain time after a time point t6 at which the subject has recovered from the third-level drowsiness state to the first-level drowsiness state, the drowsiness detection device 6000 may detect that the subject is in the second-level drowsiness state. Also, the drowsiness detection device 6000 may detect that the subject is reset to the third-level drowsiness state.

The first recovery reference LF/HF ratio 6006 may be the same as or different from the first reference LF/HF ratio 6006 shown in FIG. 45, the second recovery reference LF/HF ratio 6007 may be the same as or different from the second reference LF/HF ratio 6007 shown in FIG. 45, and the third recovery reference LF/HF ratio 6008 may be the same as or different from the third reference LF/HF ratio 6008 shown in FIG. 45.

Also, in order for the drowsiness detection device 6000 to detect recovery from the drowsiness state to the normal state, a fourth recovery reference LF/HF ratio 6010, which is greater than the first to third recovery reference LF/HF ratios, may be set. For example, when detecting a time point at which the LF/HF ratio 6005 of a subject detected as being in the drowsiness state becomes greater than or equal to the fourth recovery reference LF/HF ratio 6010, the drowsiness detection device 6000 may determine that the subject has recovered from the drowsiness state to the normal state. Generally, when a subject is in the normal state, the LF/HF ratio is measured in the range of 0.9 to 1. Accordingly, even if a subject is detected as being in a very low-level drowsiness state, it may be difficult for the LF/HF of the subject to have a value of 1 or more. That is, by setting the fourth recovery reference LF/HF ratio 6010 greater than or equal to one as a recovery reference LF/HF ratio, the drowsiness detection device 6000 may determine that a subject is in the normal state only when the subject completely recovers from the drowsiness state.

8.4 Heart Rate and LF/HF-Based Drowsiness Detection Method

Figure 47:
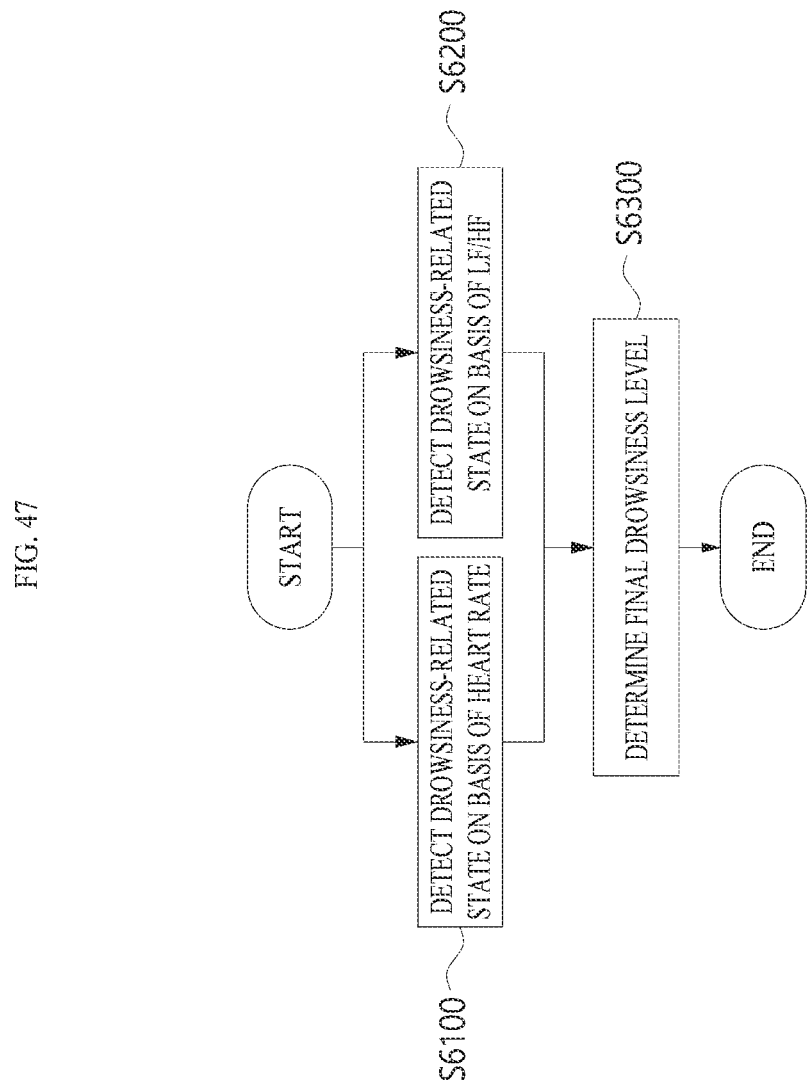
FIG. 47 is a flowchart of a method of detecting drowsiness on the basis of a heart rate and an LF/HF ratio.

A method of detecting drowsiness on the basis of a heart rate and an LF/HF ratio will be described below with reference to FIG. 47.

In an embodiment, the method may include level-specific drowsiness detection operations based on a heart rate and an LF/HF ratio (S6100 and S6200) and an operation of determining a final drowsiness state (S6300).

In some embodiments, the drowsiness detection method may further include notifying a subject or an entity other than the subject according to the level of the drowsiness state.

In this section, a drowsiness detection method to which the heart rate-based drowsiness detection method which has been described in Section 8.3 and the LF/HF ratio based drowsiness detection method which has been described in Section 8.4 are applied will be described.

The heart rate and the LF/HF ratio are due to information on heartbeats acquired from the same subject, but in some cases, the level of the drowsiness state determined based on the heart rate and the level of the drowsiness state determined based on the LF/HF ratio may be different from each other. For example, the drowsiness detection device may detect the third-level drowsiness state on the basis of the heart rate and detect the second-level drowsiness state on the basis of the LF/HF ratio in the same subject at the same time. As described above, different drowsy levels being determined depending on the drowsy detection methods although the drowsiness detection device performs the drowsy-state determination on the same subject at the same time may mean that the result of the drowsy-state determination performed by one of the drowsy detection methods may be wrong.

Therefore, in order to reduce such errors and more accurately detect drowsiness, a drowsiness detection method based on a heart rate and an LF/HF ratio will be described below.

In an embodiment, a drowsiness-related state detected in the heart rate and LF/HF ratio-based drowsiness detection method may be expressed as a final drowsiness state and a final normal state. In an embodiment, the final drowsiness state may be divided into a plurality of levels according to the degree of drowsiness. For example, the final drowsiness state may be divided into a first final drowsiness state, a second final drowsiness state, and a third final drowsiness state. Here, the first final drowsiness state may refer to the lowest-level final drowsiness state, and the third final drowsiness state may refer to the highest-level final drowsiness state.

In an embodiment, the final drowsiness state and the final normal state may refer to states corresponding to the drowsiness state and the normal state which are detected on the basis of each of the heart rate-based drowsiness detection method and the LF/HF ratio-based drowsiness detection method, respectively. That is, the final drowsiness state may refer to a state in which a subject is temporarily sleeping or a state in which a subject is not sleeping but is likely to sleep within a predetermined period, and the final normal state, which is not the final drowsiness state, may refer to a state in which a subject is unlikely to fall asleep within a predetermined time.

As described above, the drowsiness detection method based on a change in heart rate and an LF/HF ratio may be divided into a total of four levels, i.e., a normal state, a first-level drowsiness state, a second-level drowsiness state, and a third-level drowsiness state according to the degree of drowsiness. Here, the first-level drowsiness state may refer to an unconscious/unaware drowsiness state, and the second-level drowsiness state and the third-level drowsiness state may refer to conscious/aware drowsiness states.

In an embodiment, the final drowsiness state divided into a plurality of levels according to the degree of drowsiness may refer to the first-level drowsiness state, the second-level drowsiness state, and the third-level drowsiness state, which are detected based on each of the heart rate-based drowsiness detection method and the LF/HF ratio-based drowsiness detection method. Accordingly, the first final drowsiness state may refer to an unconscious/unaware drowsiness state. Also, the second final drowsiness state and the third final drowsiness state may refer to conscious/aware drowsiness states. In an embodiment, the drowsiness detection device may acquire a subject's final drowsiness state at predetermined intervals. It will be appreciated that the predetermined interval may be fixed or variable.

In another embodiment, the drowsiness detection device may acquire a subject's final drowsiness state without following predetermined intervals. For example, the drowsiness detection device may detect a subject's drowsiness state each time the physiological parameter acquisition device 10 or the like measures the subject's heart rate and/or LF/HF ratio, i.e., in real time.

It will be appreciated that when a subject's heart rate or LF/HF ratio is measured by the physiological parameter acquisition device 10 or the like at predetermined intervals, the drowsiness detection device may acquire the subject's final drowsiness state on the basis of the predetermined intervals at which the physiological parameter acquisition device 10 or the like measure the heart rate or LF/HF ratio.

As another example, the drowsiness detection device may request the physiological parameter acquisition device 10 or the like to provide an LF/HF ratio and a heart rate upon an external input or request and may acquire a subject's final drowsiness state each time the request is made.

In an embodiment, the drowsiness detection device may acquire a subject's average heart rate and average LF/HF for a certain time period.

The drowsiness detection device can correct noise by acquiring the average heart rate and the average LF/HF ratio, and thus can have an effect of accurately detecting drowsiness. This effect is the same as an effect obtainable when the average heart rate or the average LF/HF ratio is acquired, and thus a detailed description thereof will be omitted.

In an embodiment, the drowsiness detection device may determine the level of the final drowsiness state according to the level of the drowsiness state detected based on the heart rate and the level of the drowsiness state detected based on the LF/HF ratio. In some cases, the level of the drowsiness state detected based on the heart rate and the level of the drowsiness state detected based on the LF/HF ratio may or may not match each other.

For convenience of description, the normal state detected based on a heart rate is defined as a drowsiness state lower than the first-level drowsiness state. Also, the normal state detected based on an LF/HF ratio is defined as a drowsiness state lower than the first-level drowsiness state.

When the level of the drowsiness state detected based on the heart rate and the level of the drowsiness state detected based on the LF/HF ratio match each other, the drowsiness detection device may determine the matching level as the level of the final drowsiness state. For example, when, for the subject, the drowsiness detection device detects the first-level drowsiness state on the basis of the heart rate and detects the first-level drowsiness state on the basis of the LF/HF ratio, the drowsiness detection device may determine the first-level final drowsiness state as the final drowsiness state. Also, when, for the subject, the drowsiness detection device detects the second-level drowsiness state on the basis of the heart rate and detects the second-level drowsiness state on the basis of the LF/HF ratio, the drowsiness detection device may determine the second-level final drowsiness state as the final drowsiness state. Also, when, for the subject, the drowsiness detection device detects the third-level drowsiness state on the basis of the heart rate and detects the third-level drowsiness state on the basis of the LF/HF ratio, the drowsiness detection device may determine the third-level final drowsiness state as the final drowsiness state.

When the level of the drowsiness state detected based on the heart rate and the level of the drowsiness state detected based on the LF/HF ratio do not match each other, the drowsiness detection device may determine the final drowsiness level in consideration of various situations.

In an embodiment, when the level of the drowsiness state detected based on the heart rate and the level of the drowsiness state detected based on the LF/HF ratio do not match each other, the drowsiness detection device may determine the higher one of the two levels as the level of the final drowsiness state. For example, when, for the subject, the drowsiness detection device detects the first-level drowsiness state on the basis of the heart rate and detects the second-level drowsiness state on the basis of the LF/HF ratio, the drowsiness detection device may determine the second-level final drowsiness state as the final drowsiness state.

In another embodiment, when the level of the drowsiness state detected based on the heart rate and the level of the drowsiness state detected based on the LF/HF ratio do not match each other, the drowsiness detection device may determine the lower one of the two levels as the level of the final drowsiness state. For example, when, for the subject, the drowsiness detection device detects the first-level drowsiness state on the basis of the heart rate and detects the second-level drowsiness state on the basis of the LF/HF ratio, the drowsiness detection device may determine the first-level final drowsiness state as the final drowsiness state.

In another embodiment, when the level of the drowsiness state detected based on the heart rate and the level of the drowsiness state detected based on the LF/HF ratio do not match each other, the drowsiness detection device may determine the average of the two levels as the level of the final drowsiness state. Here, when the average is not an integer, the average may be rounded up or down to the first decimal place. For example, when, for the subject, the drowsiness detection device detects the first-level drowsiness state on the basis of the heart rate and detects the third-level drowsiness state on the basis of the LF/HF ratio, the drowsiness detection device may determine the second-level final drowsiness state, which is the average of the two levels, as the final drowsiness state. As another example, when the first-level drowsiness state is detected on the basis of the heart rate and the second-level drowsiness state is detected on the basis of the LF/HF ratio, the drowsiness detection device may determine the first-level final drowsiness state as the final drowsiness state by rounding 1.5, which is the average of the two levels, down to the first decimal place. Also, the drowsiness detection device may determine the second-level final drowsiness state as the final drowsiness state by rounding 1.5, which is the average of the two levels, up to the first decimal place.

It will be appreciated that, in some cases, the drowsiness detection device may define a new drowsiness level between the level of the drowsiness state detected based on the heart rate and the level of the drowsiness state detected based on the LF/HF ratio and determine the new level as the final drowsiness level. For example, when the first-level drowsiness state is detected based on the heart rate and the second-level drowsiness state is detected based on the LF/HF ratio, the drowsiness detection device may define an intermediate level drowsiness state indicating the degree of drowsiness between the first-level drowsiness state and the second-level drowsiness state and determine the intermediate level drowsiness state as the final drowsiness level.

In another embodiment, when the level of the drowsiness state detected based on the heart rate and the level of the drowsiness state detected based on the LF/HF ratio do not match each other, the drowsiness detection device may maintain the previously determined final drowsiness state or final normal state as the drowsiness-related state. For example, when, for the subject, the drowsiness detection device detects the first-level drowsiness state on the basis of the heart rate and detects the third-level drowsiness state on the basis of the LF/HF ratio after detecting the first-level drowsiness state, the drowsiness detection device may maintain the first-level final drowsiness state, which is the previously determined final drowsiness state, as the drowsiness-related state. For example, when, for the subject, the drowsiness detection device detects the first-level drowsiness state on the basis of the heart rate and detects the third-level drowsiness state on the basis of the LF/HF ratio while detecting the final normal state, the drowsiness detection device may maintain the previously determined final normal state as the drowsiness-related state.

The following detailed description will focus on a case in which the level of the drowsiness state detected based on the heart rate and the level of the drowsiness state detected based on the LF/HF ratio do not match each other.

8.4.1 Specific Embodiment

In an embodiment, when the level of the drowsiness state detected based on the heart rate and the level of the drowsiness state detected based on the LF/HF ratio match each other and both are the normal state, the drowsiness detection device may determine that the subject is in the final normal state.

In an embodiment, when the level of the drowsiness state detected based on the heart rate and the level of the drowsiness state detected based on the LF/HF ratio match each other and both are the first-level drowsiness state, the drowsiness detection device may determine that the subject is in the first-level final drowsiness state.

In an embodiment, when the level of the drowsiness state detected based on the heart rate and the level of the drowsiness state detected based on the LF/HF ratio match each other and both are the second-level drowsiness state, the drowsiness detection device may determine that the subject is in the second-level final drowsiness state.

In an embodiment, when the level of the drowsiness state detected based on the heart rate and the level of the drowsiness state detected based on the LF/HF ratio match each other and both are the third-level drowsiness state, the drowsiness detection device may determine that the subject is in the third-level final drowsiness state.

In an embodiment, a method of determining the lower one of the level of the drowsiness state detected based on the heart rate and the level of the drowsiness state detected based on the LF/HF ratio as the level of the final drowsiness state when the level of the drowsiness state detected based on the heart rate and the level of the drowsiness state detected based on the LF/HF ratio do not match each other (hereinafter referred to a first method) may be applied to detect a level that needs to be less sensitively detected.

For example, a notification may be issued when the first-level drowsiness state, the second-level drowsiness state, and the third-level drowsiness state are detected. In some cases, the first-level drowsiness state and the second-level drowsiness state may have little effect on the safety of the subject. In this case, if the notification is frequently given, the subject may feel uncomfortable or may not operate the drowsiness detection device. Also, by determining the lower one of the level of the drowsiness state detected based on the heart rate and the level of the drowsiness state detected based on the LF/HF ratio as the level of the final drowsiness state, the drowsiness detection device may more accurately detect the drowsiness-related state. That is, determining the final drowsiness state using the drowsiness detection device according to the first method may be advantageous in improving user convenience and accuracy.

In an embodiment, when the level of the drowsiness state detected based on the heart rate and the level of the drowsiness state detected based on the LF/HF ratio do not match each other, one of which indicates the normal state, and the other of which is detected as a drowsiness state that is one or two levels higher than the normal state, the drowsiness detection device may determine that the subject is in the final normal state on the basis of the normal state, which has a lower level.

For example, when the drowsiness detection device detects the normal state on the basis of the heart rate and detects the first-level drowsiness state on the basis of the LF/HF ratio, the drowsiness detection device may determine that the subject is in the final normal state.

In an embodiment, when the level of the drowsiness state detected based on the heart rate and the level of the drowsiness state detected based on the LF/HF ratio do not match each other, one of which indicates the first-level drowsiness state, and the other of which is detected as a drowsiness state that is one level higher than the normal state, the drowsiness detection device may determine that the subject is in the first-level drowsiness state on the basis of the first-level drowsiness state, which has a lower level.

For example, when the drowsiness detection device detects the first-level drowsiness state on the basis of the heart rate and detects the second-level drowsiness state on the basis of the LF/HF ratio, the drowsiness detection device may determine that the subject is in the first-level drowsiness state.

In an embodiment, when the level of the drowsiness state detected based on the heart rate and the level of the drowsiness state detected based on the LF/HF ratio do not match each other, one of which indicates the second-level drowsiness state, and the other of which is detected as a drowsiness state that is higher than the normal state, the drowsiness detection device may determine that the subject is in the second-level drowsiness state on the basis of the second-level drowsiness state, which has a lower level. On the other hand, a method of determining the higher one of the level of the drowsiness state detected based on the heart rate and the level of the drowsiness state detected based on the LF/HF ratio as the level of the final drowsiness state when the level of the drowsiness state detected based on the heart rate and the level of the drowsiness state detected based on the LF/HF ratio do not match each other (hereinafter referred to a second method) may be applied to detect a level that needs to be more sensitively detected.

For example, a notification may be issued when the first-level drowsiness state, the second-level drowsiness state, and the third-level drowsiness state are detected. In some cases, the third-level drowsiness state is the highest degree of drowsiness state and may directly affect the safety of the subject. In this case, when the drowsiness detection device does not give a strong notification to the subject as soon as the third-level drowsiness state is detected, the subject may be in a seriously dangerous situation. Also, by determining the higher one of the level of the drowsiness state detected based on the heart rate and the level of the drowsiness state detected based on the LF/HF ratio as the level of the final drowsiness state, the drowsiness detection device may determine a level to be detected in various situations as the level of the final drowsiness state. That is, determining the final drowsiness state using the drowsiness detection device according to the second method may be advantageous in reducing user risk.

In an embodiment, when the level of the drowsiness state detected based on the heart rate and the level of the drowsiness state detected based on the LF/HF ratio do not match each other, one of which indicates the third-level drowsiness state, and the other of which is detected as a drowsiness state that is one, two, or three levels lower than the third-level drowsiness state, the drowsiness detection device may determine that the subject is in the third-level final drowsiness state on the basis of the third-level drowsiness state, which has a higher level.

For example, when the drowsiness detection device detects the third-level drowsiness state on the basis of the heart rate and detects the first-level drowsiness state on the basis of the LF/HF ratio, the drowsiness detection device may determine that the subject is in the third-level drowsiness state.

In another embodiment, the drowsiness detection device may follow the second method in order to detect the second final drowsiness state. This is because in some cases, the drowsiness detection device may need to detect not only the third-level drowsiness state but also the second-level drowsiness state in more various situations. In detail, when the subject is a freight vehicle driver or a public transport vehicle driver and is in danger of a traffic accident, the drivers and passengers of nearby vehicles may be in serious danger in addition to the driver. Accordingly, when the level of the drowsiness state detected based on the heart rate and the level of the drowsiness state detected based on the LF/HF ratio do not match each other, one of which indicates the second-level drowsiness state, and the other of which is detected as a drowsiness state that is one or two levels lower than the second-level drowsiness state, the drowsiness detection device may determine that the subject is in the second-level final drowsiness state on the basis of the second-level drowsiness state, which has a higher level.

For example, when the drowsiness detection device detects the second-level drowsiness state on the basis of the heart rate and detects the first-level drowsiness state on the basis of the LF/HF ratio, the drowsiness detection device may determine that the subject is in the second-level drowsiness state.

9. Various Applications Using Physiological Parameter Acquisition Device

9.1 Various Embodiments of Display Device

The above-described physiological parameter acquisition method or drowsiness detection method may be used in various applications. For example, the physiological parameter acquisition method or drowsiness detection method may be used in a display device.

In this case, the display device may include a smart mirror including a mirror display, but the present invention is not limited thereto. The display device may refer to a device with a display, such as a smartphone, a tablet, and the like.

Also, a physiological parameter or physiological information acquired according to the physiological parameter acquisition method may be output through the display, and also drowsiness information acquired according to the drowsiness detection method may be output through the display.

Also, the display device may perform an operation corresponding to the physiological parameter of physiological information acquired according to the physiological parameter acquisition method.

Also, the display device may perform an operation corresponding to the drowsiness information acquired according to the drowsiness detection method.

Also, a user of the display device may set a physiological parameter of interest, and when a physiological parameter of interest is set, only the physiological parameter of interest may be acquired or output. For example, when a first user sets a heart rate and a second user sets a blood pressure, the first user may acquire only a heart rate, and the second user may acquire only a blood pressure, but the present invention is not limited thereto.

Also, the display device may be installed in a public place such as a hotel lobby, a hotel front desk, and a public restroom and used to measure physiological parameters of incoming or outgoing people, but the present invention is not limited thereto.

Also, the operation of the physiological parameter measurement device will be described below, but the operation to be described may be performed even by other processors such as an electronic control unit (ECU) mounted on a vehicle or may be performed even by a processor included in a server.

Also, a device that will be described as the physiological parameter measurement device may refer to an image acquisition device. In this case, the operation to be described may be performed by other processors such as an ECU or a processor included in a server.

Figure 48:
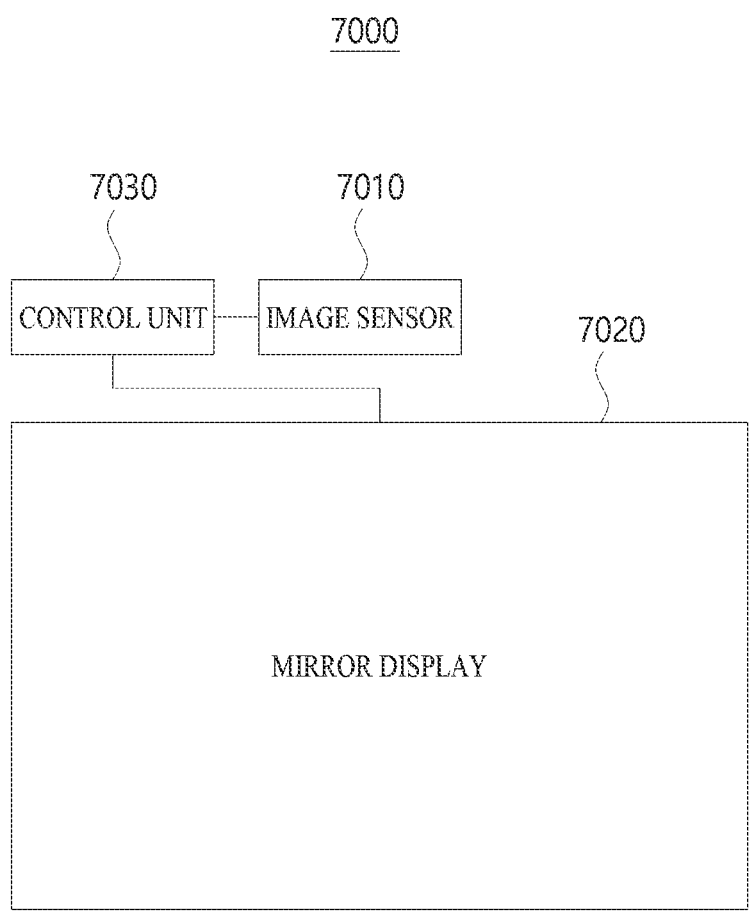
FIG. 48 is a diagram illustrating a smart mirror device according to an embodiment.

FIG. 48 is a diagram illustrating a smart mirror device according to an embodiment.

Referring to FIG. 48, a smart mirror device 7000 according to an embodiment may include at least one of an image sensor 7010, a mirror display 7020, and a control unit 7030. For example, the smart mirror device 7000 may include the mirror display 7020 and the control unit 7030, but the present invention is not limited thereto.

In this case, the image sensor 7010 may be provided as a visible camera for acquiring a visible light image, an infrared (IR) camera for acquiring an infrared image, and the like. However, the present invention is not limited thereto, and a hybrid-type camera for acquiring a visible light image and an infrared image may be provided.

Also, the image sensor 7010 may be provided as one package with the mirror display 7020. However, the present invention is not limited thereto, and the image sensor 7010 may be provided as a separate unit distinct from the mirror display 7020.

Also, the image sensor 7010 may acquire a plurality of image frames and transmit an acquired image frame to the control unit 7030.

Also, the mirror display 7020 may refer to a means for forwarding information while functioning as a looking glass, but the present invention is not limited thereto.

Also, the mirror display 7020 may include a mirror configured to function as a looking glass and a display configured to forward information and may be provided in a form in which a mirror film is added to the display, but the present invention is not limited thereto.

Also, the mirror display 7020 may include a half mirror that may refer to a translucent looking glass configured to transmit light in one direction but reflect light in another direction, but the present invention is not limited thereto.

Also, the mirror display 7020 may include a polarizing plate, but the present invention is not limited thereto.

Also, the mirror display 7020 may include a mirror display that can be commonly understood in addition to the above-described exemplary principles and exemplary elements. In detail, the mirror display 7020 may be understood as a device configured to forward information while functioning as a mirror.

Also, the control unit 7030 may acquire a physiological parameter and physiological information on the basis of a plurality of image frames acquired from the image sensor 7010.

In this case, the above description is applicable to a method of acquiring a physiological parameter and physiological information on the basis of a plurality of image frames acquired from the image sensor 7010, and thus a redundant description thereof will be omitted.

Also, the control unit 7030 may acquire a physiological parameter and physiological information from an external sensor (not shown). For example, the control unit 7030 may acquire heartbeat information through an ECG sensor attached to a subject or the like, but the present invention is not limited thereto.

Also, the control unit 7030 may acquire personal statistical data through an input device (not shown). For example, the control unit 7030 may acquire personal statistical data such as a subject's height, age, and weight through a keyboard, but the present invention is not limited thereto.

In this case, the input device may be a keyboard, a mouse, a keypad, a dome switch, a touchpad (e.g., a static pressure/capacitance), a jog wheel, or a jog switch, but the present invention is not limited thereto.

Also, the control unit 7030 may acquire personal statistical data through an external device (not shown). For example, the control unit 7030 may acquire personal statistical data such as a subject's height, age, and weight through the subject smartphone, but the present invention is not limited thereto.

In this case, the external device may include a mobile terminal, such as a cellular phone, a smartphone, a laptop computer, a digital broadcasting terminal, a personal digital assistant (PDA), portable multimedia player (PMP), and a navigation device, and also a stationary terminal, such as a digital TV and a desktop computer, but the present invention is not limited thereto.

Also, the control unit 7030 may control the operation of the mirror display 7020. For example, the control unit 7030 may control the operation of the mirror display 7020 so that the physiological parameter or physiological information acquired based on the image frames is output, but the present invention is not limited thereto.

Also, the control unit 7030 may control the operation of the mirror display 7020 so that various pieces of information are output. For example, the control unit 7030 may control the operation of the mirror display 7020 so that various pieces of information such as weather information, date information, calendar information, internal humidity information, and internal temperature information are output, but the present invention is not limited thereto.

Also, the control unit 7030 may control the operation of the mirror display 7020 so that various pieces of personal information are output. For example, the control unit 7030 may control the operation of the mirror display 7020 so that various pieces of personal information such as a subject's schedule information and medication information are output, but the present invention is not limited thereto.

Figure 49:
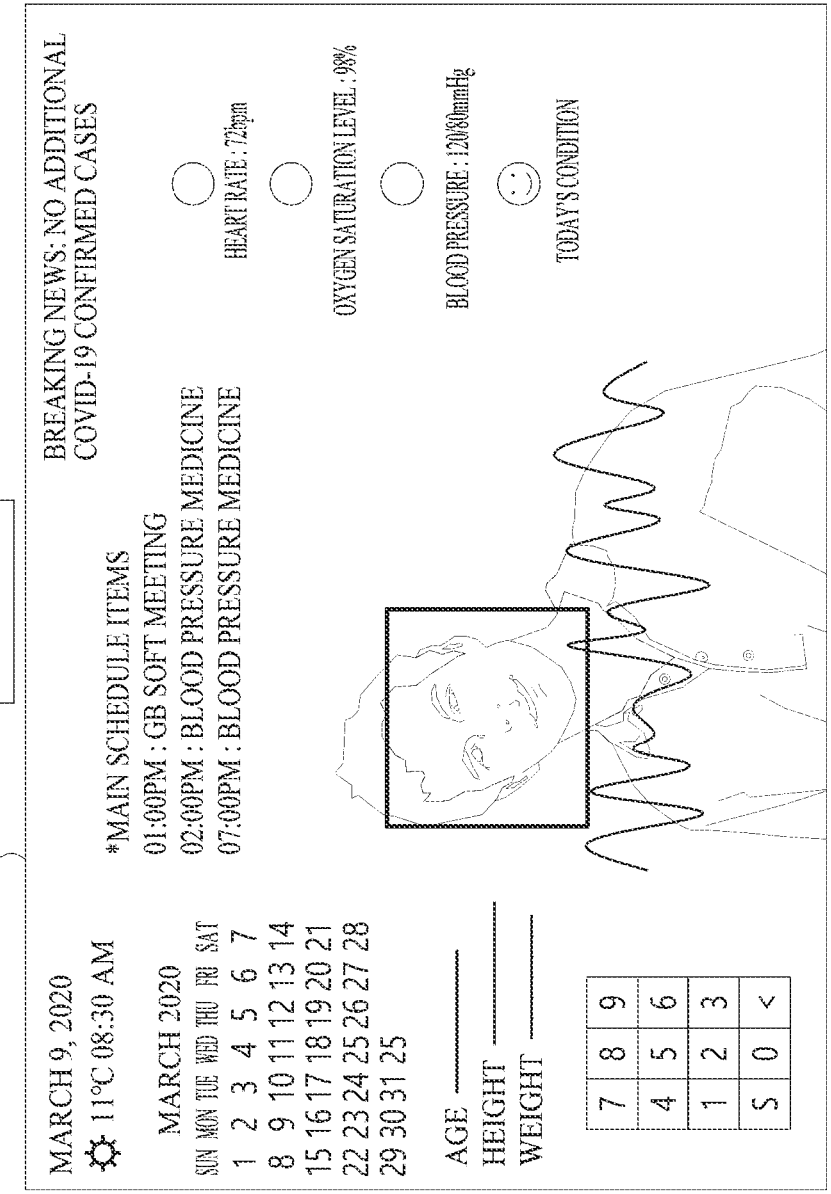
FIG. 49 is a diagram illustrating a smart mirror device according to an embodiment.

FIG. 49 is a diagram illustrating a smart mirror device according to an embodiment.

Referring to FIG. 49, a smart mirror device 7100 according to an embodiment may include an image sensor 7110 and a mirror display 7120.

In this case, the above-described operations are applicable to the image sensor 7110 and the mirror display 7120, and thus a redundant description thereof will be omitted.

According to an embodiment, basic information may be output to the mirror display 7120. For example, as shown in FIG. 49, at least one piece of the basic information such as date information, time information, external temperature information, weather information, calendar information, and news information may be output, but the present invention is not limited thereto.

Also, personal information may be output to the mirror display 7120. For example, as shown in FIG. 49, at least one piece of the personal information such as a subject's age, height, and weight may be output to the mirror display 7120, but the present invention is not limited thereto.

Also, for example, as shown in FIG. 49, at least one piece of the personal information such as a subject's schedule information and medication information may be output to the mirror display 7120, but the present invention is not limited thereto.

Also, a subject's physiological parameters may be output to the mirror display 7120. For example, as shown in FIG. 49, at least one of the physiological parameters, such as a heart rate, an oxygen saturation level, and a blood pressure, may be output to the mirror display 7120, but the present invention is not limited thereto.

In this case, the physiological parameter may be acquired based on an image frame acquired from the image sensor 7110. However, the present invention is not limited thereto, and the physiological parameter may be acquired by an external sensor or the like.

Also, a subject's physiological information may be output to the mirror display 7120. For example, as shown in FIG. 49, at least one piece of the physiological information such as condition information may be output to the mirror display 7120, but the present invention is not limited thereto.

In this case, the physiological information may be acquired based on an image frame acquired from the image sensor 7110. However, the present invention is not limited thereto, and the physiological information may be acquired by an external sensor or the like.

Also, the physiological information may be acquired based on at least one piece of the physiological information, but the present invention is not limited thereto.

Also, a subject's physiological signals may be output to the mirror display 7120. For example, as shown in FIG. 49, at least one of the physiological signals such as a heartbeat signal may be output to the mirror display 7120, but the present invention is not limited thereto.

In this case, the physiological signal may be acquired based on an image frame acquired from the image sensor 7110. However, the present invention is not limited thereto, and the physiological signal may be acquired based on an external sensor or the like.

Also, the mirror display 7120 may include an input device. For example, as shown in FIG. 49, the mirror display 7120 may include at least one input device such as a touch panel, but the present invention is not limited thereto.

Also, for example, although not shown in FIG. 49, the smart mirror device 7100 may track a user's pupil or the like or recognize a user's gesture to receive an input from the user, but the present invention is not limited thereto.

Also, the mirror display 7120 may acquire information regarding a subject through the input device, and the acquired information regarding the subject may be output to the mirror display 7120.

Also, the above drawing and description of the mirror display 7120 are merely an example, and it is obvious that various pieces of information may be output in various ways without being limited to FIG. 49 and a related description.

9.1.1 Various Embodiments of Display Device in which Guide Region is Output

Figure 50:
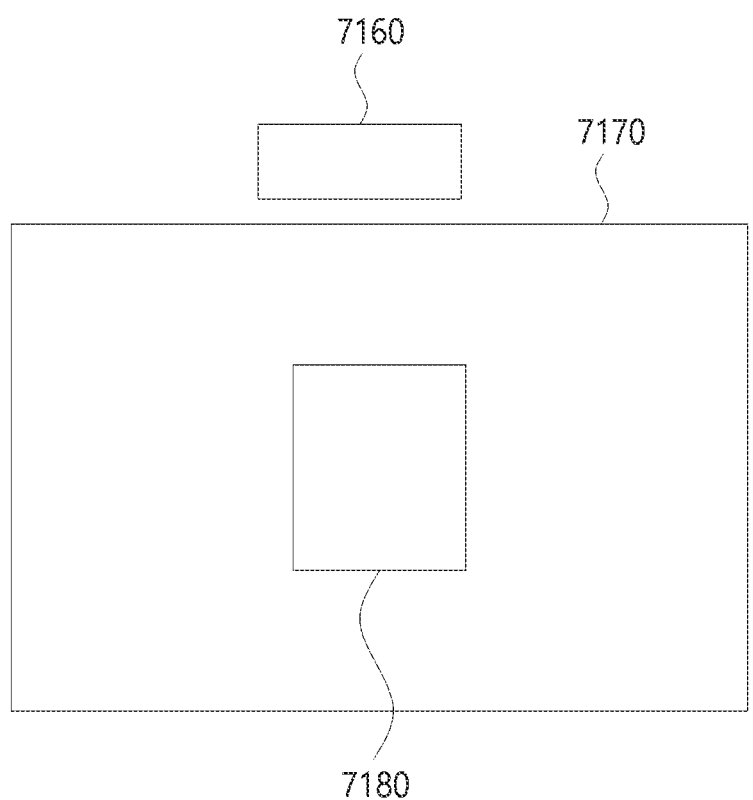
FIG. 50 is a diagram illustrating a smart mirror device in which a guide region is output according to an embodiment.

FIG. 50 is a diagram illustrating a smart mirror device in which a guide region is output according to an embodiment.

Referring to FIG. 50, a smart mirror device 7150 according to an embodiment may include an image sensor 7160 and a mirror display 7170. The above description is applicable to the image sensor 7160 and the mirror display 7170, and thus a redundant description thereof will be omitted.

Also, a guide region 7180 may be displayed in the mirror display 7170 according to an embodiment. In this case, the guide region 7180 may function to approximate a measurement position of a subject.

When a physiological parameter is acquired using an image sensor, measurement accuracy may vary depending on the measurement position of the subject. Thus, when the guide region 7180 for guiding the measurement position of the subject is utilized, it is possible to improve the accuracy of the measurement of the subject's physiological parameter.

Also, the guide region 7180 may be displayed in a rectangular shape as shown in FIG. 50. The present invention is not limited thereto, and the guide region 7180 may be displayed in various shapes such as a human face contour, a circle, and an ellipse.

Also, a position at which the guide region 7180 is displayed may vary depending on the subject. For example, a guide region 7180 for a tall subject may be relatively positioned in an upper portion of the mirror display 7108, and a guide region 7180 for a short subject is relatively positioned in a lower portion of the mirror display 7170, but the present invention is not limited thereto.

Also, the position of the guide region 7180 may be changed in real time. For example, when a subject moves during measurement, the position of the guide region 7180 may be changed in real time in response to the movement of the subject, but the present invention is not limited thereto.

Also, the guide region 7180 may be displayed before a subject's physiological parameter is measured. For example, before a subject enters a measurement region, the guide region 7180 may be displayed to notify the subject of an approximate measurement position, but the present invention is not limited thereto.

Also, when there are a plurality of people to be measured, the guide region 7180 may function to provide a notification about a subject to be measured. For example, when person A and person B enter a measurement region and only person B is a subject, the guide region 7180 may be displayed to correspond to person B, but the present invention is not limited thereto.

9.1.2 Various Embodiments of Display Device in which Predetermined Information is Displayed During Physiological Parameter Measurement When a physiological parameter is acquired using an image sensor, measurement accuracy may vary depending on subject movement, and thus a function for minimizing subject movement may be required during physiological parameter measurement.

Accordingly, when a display device in which predetermined information is displayed during physiological parameter measurement is used, it is possible to induce subject movement to be minimized using the displayed information.

Figure 51:
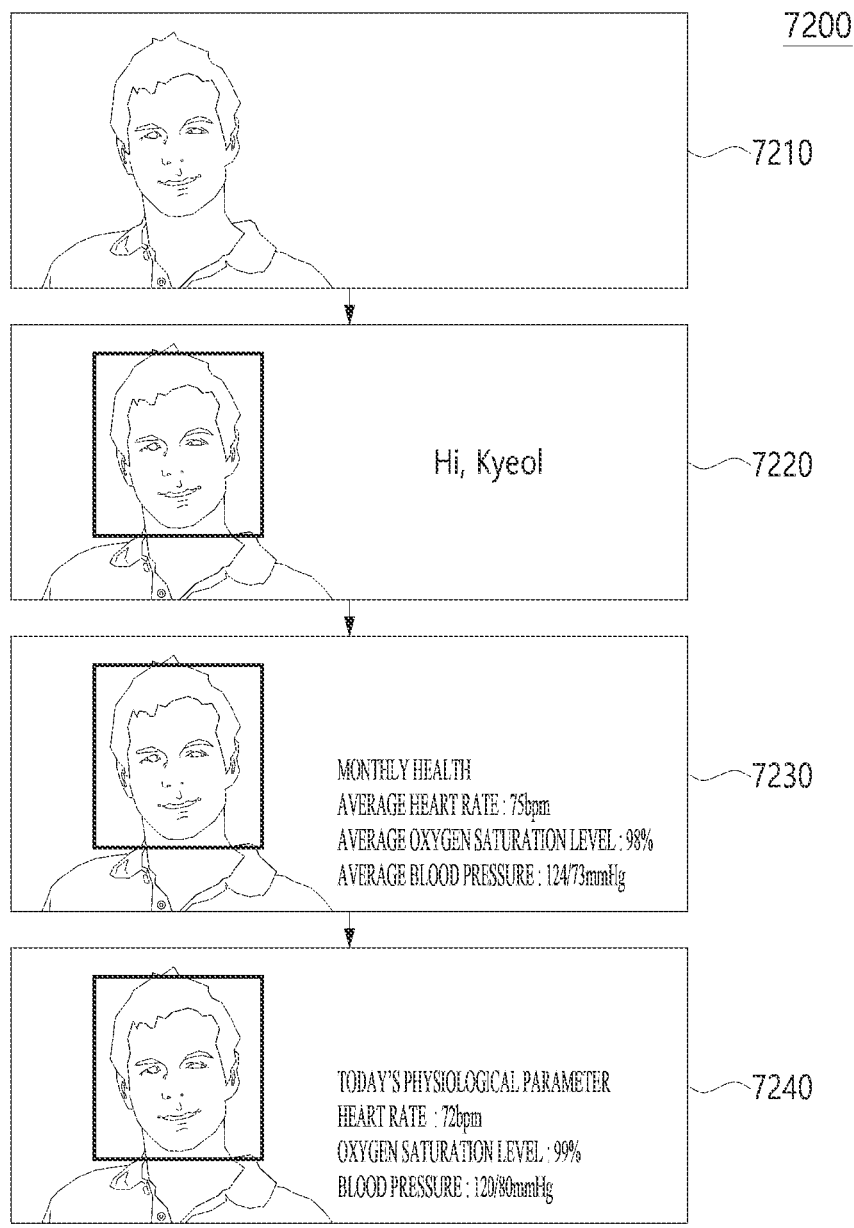
FIG. 51 is a diagram illustrating a smart mirror device in which predetermined information is output according to an embodiment.

FIG. 51 is a diagram illustrating a smart mirror device in which predetermined information is output according to an embodiment.

Referring to FIG. 51, depending on the physiological parameter measurement time, different information may be displayed in the smart mirror device 7200 according to an embodiment.

In detail, physiological parameter measurement for a subject may be started at a first time point 7210.

In this case, the first time point 7210 may be a time point at which a measurement target region of the subject is positioned in a measurement region. However, the present invention is not limited thereto, and the first time point 7210 may be a time point at which a person to which the measurement is to be performed is positioned within the angle of view of an image sensor.

Also, the first time point 7210 may be a time point at which a subject enters an intention for measurement. For example, the first time point 7210 may be a time point at which the subject touches a measurement button, but the present invention is not limited thereto.

Also, first information may be displayed at a second time point 7220.

In this case, the second time point 7220 may be a time point at which a facial recognition for the subject is completed, but the present invention is not limited thereto.

Also, the second time point 7220 may refer to a predetermined time after the physiological parameter measurement for the subject is started, but the present invention is not limited thereto.

Also, the first information may be recognition information of the subject. For example, as shown in FIG. 51, the first information displayed at the second tune point 7220 may be greeting information of the subject whose face has been recognized, but the present invention is not limited thereto.

Also, the first information may be information regarding a measurement processing time. For example, when the second tune point 7220 is two seconds after the measurement is started, information corresponding to two seconds may be displayed.

Also, the first information may be information regarding the time remaining until the end of the measurement. For example, it takes six seconds to measure a physiological parameter. When the second time point 7220 is two seconds after the measurement is started, information corresponding to the remaining four seconds may be displayed.

Also, second information may be displayed at a third time point 7230.

In this case, the third time point 7230 may refer to a predetermined time after the facial recognition for the subject is completed, but the present invention is not limited thereto.

Also, the third time point 7230 may refer to a predetermined time after the physiological parameter measurement for the subject is started, but the present invention is not limited thereto.

Also, the second information may be health information of the subject. For example, as shown in FIG. 51, the second information displayed at the third time point 7230 may be a monthly average physiological parameter of the subject, but the present invention is not limited thereto.

Also, the second information may be information regarding a measurement processing time. For example, when the third time point 7230 is four seconds after the measurement is started, information corresponding to four seconds may be displayed.

Also, the second information may be information regarding the time remaining until the end of the measurement. For example, it takes six seconds to measure a physiological parameter. When the third time point 7230 is four seconds after the measurement is started, information corresponding to the remaining two seconds may be displayed.

Also, third information may be displayed at a fourth time point 7240.

In this case, the fourth time point 7240 may be a time point at which the physiological parameter measurement for the subject is completed, but the present invention is not limited thereto.

Also, the third information may be information related to a physiological parameter of the subject. For example, as shown in FIG. 51, the third information displayed at the fourth time point 7240 may be a heart rate, an oxygen saturation level, and a blood pressure of the subject, but the present invention is not limited thereto.

Also, the third information may be information related to physiological information of the subject. For example, although not shown in FIG. 51, the fourth information displayed at the fourth time point 7240 may be physiological information such as a condition index of the subject, but the present invention is not limited thereto.

Figure 52:
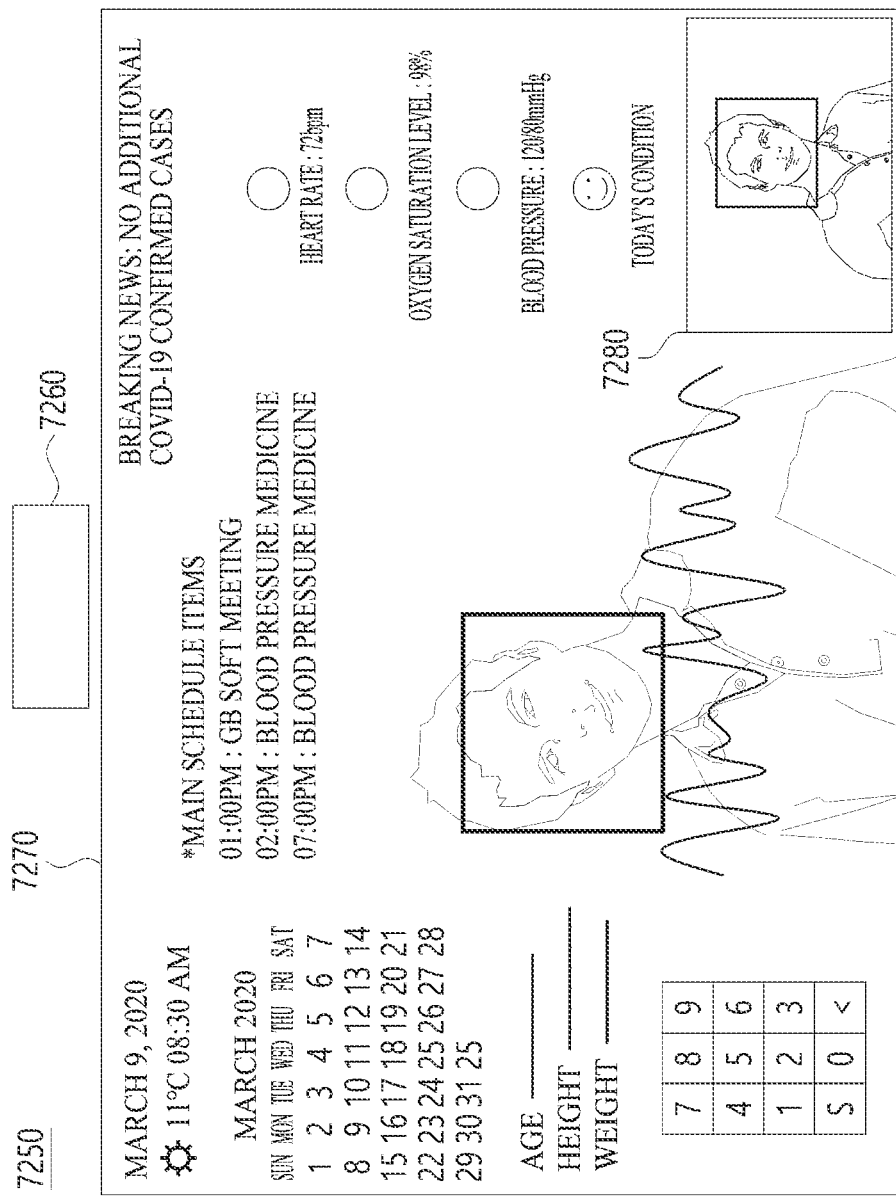
FIG. 52 is a diagram illustrating a smart mirror device according to an embodiment.

9.1.3 Various Embodiments of Smart Mirror Device in which Image Acquired Through Image Sensor is Displayed FIG. 52 is a diagram illustrating a smart mirror device according to an embodiment.

Referring to FIG. 52, a smart mirror device 7250 according to an embodiment may include an image sensor 7260 and a mirror display 7270.

In this case, the above-described operations are applicable to the image sensor 7260 and the mirror display 7270, and thus a redundant description thereof will be omitted.

According to an embodiment, an image may be displayed on the mirror display 7270. For example, as shown in FIG. 52, an image acquired through the image sensor 7260 may be displayed on the mirror display 7270, but the present invention is not limited thereto.

Also, information regarding a subject to be measured may be shown in the displayed image. For example, a region included in the image to display a measurement target may be showed, but the present invention is not limited thereto.

As described above, by additionally displaying the image even though the subject can see himself or herself through the mirror display 7270, a subject whose physiological parameter is to be measured may be definitely shown when there are a plurality of measurement targets, and thus it is possible to prevent confusion among a plurality of people who may be the measurement targets.

Also, the displayed image of the subject and the shape of the subject reflected through the mirror display 7270 may be positioned at different places. However, the present invention is not limited thereto, and the displayed image of the subject and the shape of the subject may overlap each other.

Figure 53:
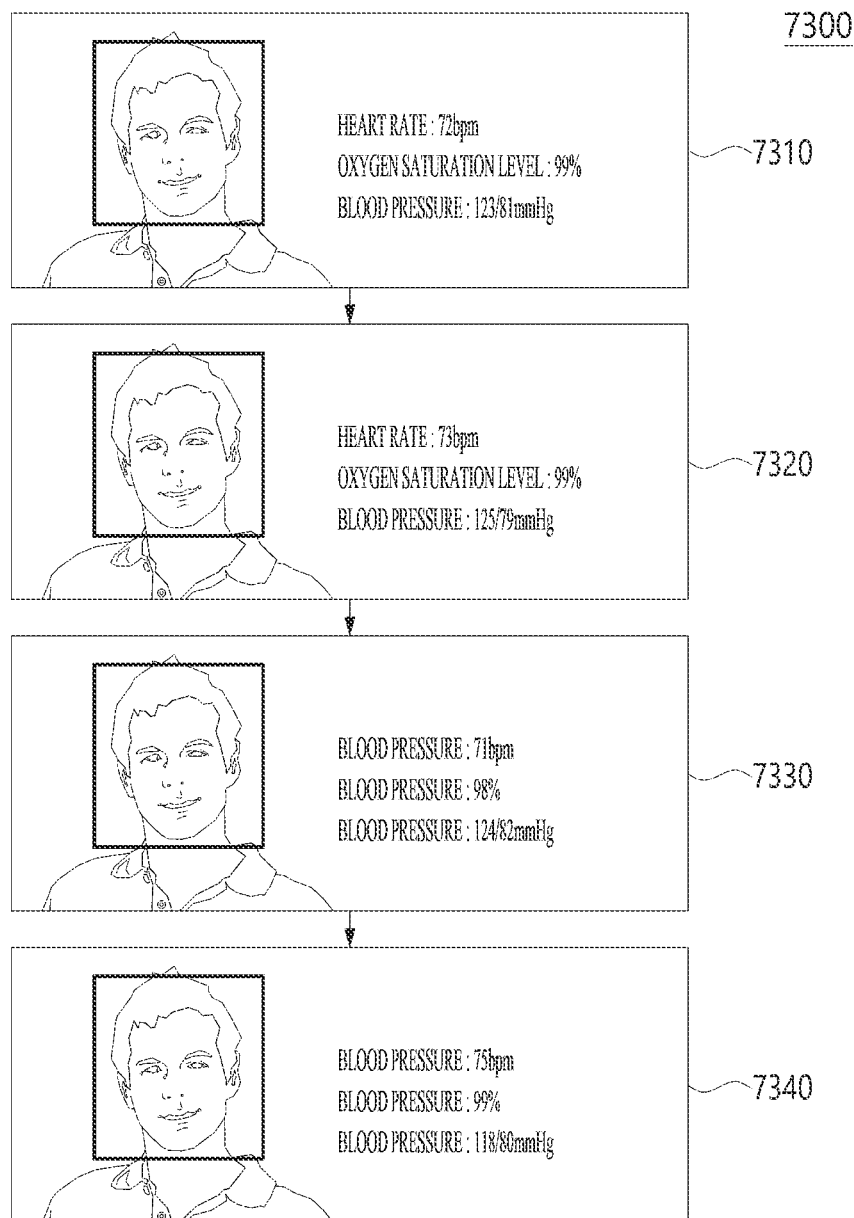
FIG. 53 is a diagram illustrating a display device configured to measure a physiological parameter in real time according to an embodiment.

9.1.4 Various Embodiments of Display Device Configured to Measure Physiological Parameter in Real Time FIG. 53 is a diagram illustrating a display device configured to measure a physiological parameter in real time according to an embodiment.

Referring to FIG. 53, a display device 7300 according to an embodiment may measure a physiological parameter in real time, and a physiological parameter may be displayed on the display device 7300 in real time.

In detail, a physiological parameter of a subject acquired in a first time period may be displayed at a first time point 7310.

In this case, the first time point 7310 may be a time point after the physiological parameter of the subject is acquired in the first time period.

In detail, a physiological parameter of a subject acquired in a second time period may be displayed at a second time point 7320.

In this case, the second time point 7320 may be a time point after the physiological parameter of the subject is acquired in the second time period.

Also, the second time period and the first time period may differ from each other and may at least partially overlap each other.

Also, the second time point 7320 may be later than the first time point 7310.

Also, a physiological parameter of a subject acquired in a third time period may be displayed at a third time point 7330.

In this case, the third time point 7330 may be a time point after the physiological parameter of the subject is acquired in the third time period.

Also, the third time period may differ from the first and second time periods and may at least partially overlap the first and second time periods.

Also, the third time point 7330 may be later than the first time point 7310 and the second time point 7320.

Also, a physiological parameter of a subject acquired in a fourth time period may be displayed at a fourth time point 7340.

In this case, the fourth time point 7340 may be a time point after the physiological parameter of the subject is acquired in the fourth time period.

Also, the fourth time period may differ from the first, second, and third time periods and may at least partially overlap the first, second, and third time periods.

Also, the fourth time point 7340 may be later than the first, second, and third time points 7310, 7320, and 7330.

Also, as described above, when a physiological parameter is acquired in real time, a physiological parameter acquired at a specific time point may be used to store a final physiological parameter. For example, a physiological parameter acquired for the first time may be stored, but the present invention is not limited thereto. A physiological parameter acquired for the last time may be stored, and a physiological parameter acquired during physiological parameter measurement may be stored.

Also, as described above, when a physiological parameter is acquired in real time, a plurality of physiological parameters may be used to store a final physiological parameter. For example, the average of a plurality of physiological parameters acquired during a certain time period may be stored as a final physiological parameter, but the present invention is not limited thereto.

Also, as described above, when a physiological parameter is acquired in real time, a plurality of physiological parameters are acquired even when noise due to subject movement occurs during the physiological parameter measurement. Thus, it is possible to acquire a more accurate physiological parameter.

Also, as described above, when a physiological parameter is acquired in real time, an update period may be set to display the physiological parameter. For example, a user may set an update period to display the physiological parameter, and the physiological parameter may be updated according to the set period, but the present invention is not limited thereto.

Figure 54:
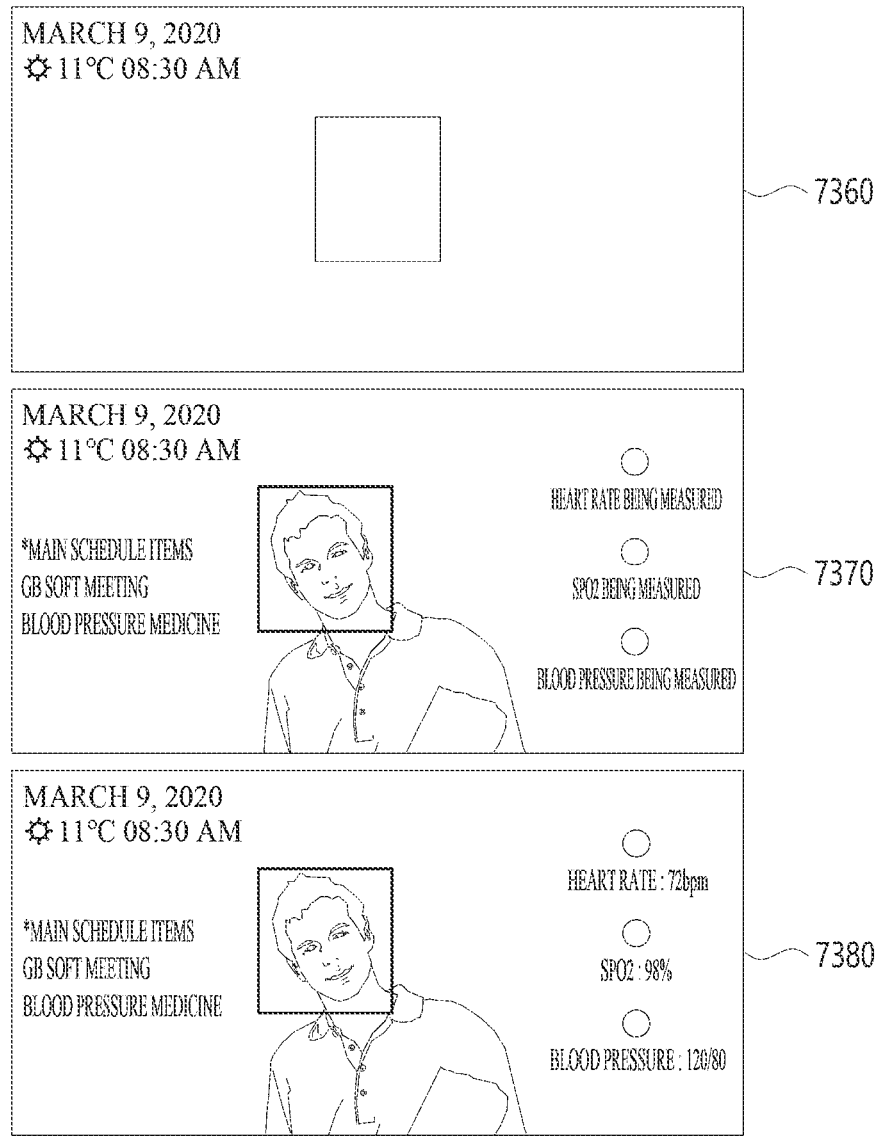
FIG. 54 is a diagram illustrating a smart mirror device in which predetermined information is output according to an embodiment.

9.1.5 Various Embodiments of Display Device in which Predetermined Information is Displayed During Physiological Parameter Measurement FIG. 54 is a diagram illustrating a smart mirror device in which predetermined information is output according to an embodiment.

Referring to FIG. 54, depending on the physiological parameter measurement time, different information may be displayed in the smart mirror device 7350 according to an embodiment.

In detail, a first time point 7360 may be a time point at which or before physiological parameter measurement for a subject is started.

In this case, the first time point 7360 may be a time point at which a measurement target region of the subject is positioned in a measurement region. However, the present invention is not limited thereto, and the first time point 7360 may be a time point at which a person, on which the measurement is to be performed, is positioned within the angle of view of an image sensor.

Also, first information may be displayed at the first time point 7360.

In this case, the first information may include basic information. For example, as shown in FIG. 54, the first information may include basic information such as date information, time information, and weather information, but the present invention is not limited thereto.

Also, the first information may include information regarding a guide region. For example, as shown in FIG. 54, a guide region may be displayed at the first time point 7360, but the present invention is not limited thereto.

Also, second information may be displayed at a second time point 7370.

In this case, the second time point 7370 may be a time point at which the physiological parameter of the subject is being measured, but the present invention is not limited thereto.

Also, the second time point 7370 may refer to a predetermined time after the physiological parameter measurement for the subject is started, but the present invention is not limited thereto.

Also, the second information may be personal information of the subject. For example, as shown in FIG. 54, the second information displayed at the second time point 7370 may include personal information, such as the subject's main schedule items and medication information, but the present invention is not limited thereto.

Also, the second information may include information related to physiological parameter measurement. For example, as shown in FIG. 54, the second information displayed at the second time point 7370 may include information indicating that the subject's physiological parameter is being measured, but the present invention is not limited thereto.

Also, third information may be displayed at a third time point 7380.

In this case, the third time point 7380 may be a time point at which the physiological parameter measurement for the subject is completed. However, the present invention is not limited thereto, and when measurement is made in real time, the third time point 7380 may be a time point at which the measurement is completed at least once.

Also, the third information may include the measured physiological parameter. For example, as shown in FIG. 54, the third information displayed at the third time point 7380 may include a measured heart rate, oxygen saturation level, and blood pressure, but the present invention is not limited thereto.

Also, as shown in FIG. 54, the first information and the second information may be simultaneously displayed at the second time point 7370, and the first information, the second information, and the third information may be simultaneously displayed at the third time point 7380.

9.1.6 Various Embodiments of Smart Mirror Device Including Switching Device

Figure 55:
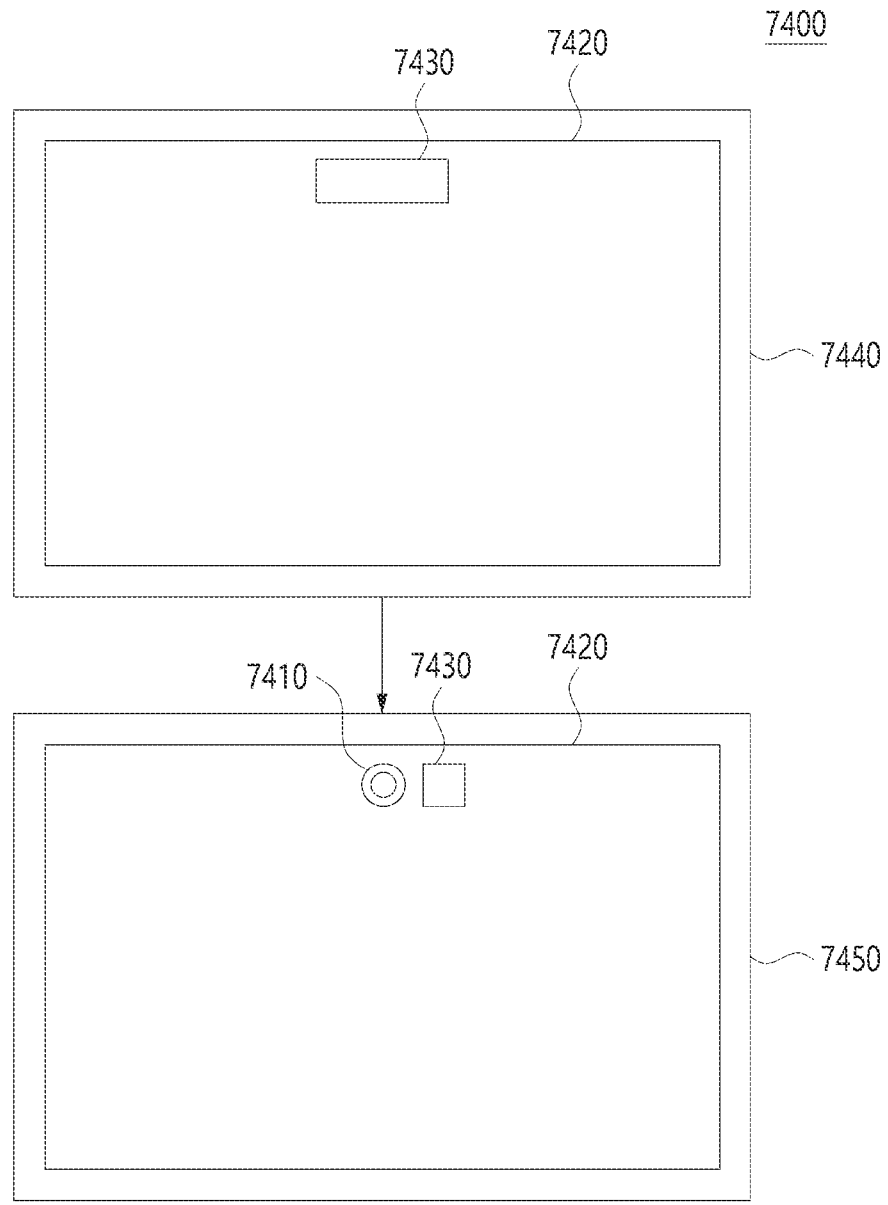
FIG. 55 is a diagram illustrating a smart mirror device including a switching device according to an embodiment.

FIG. 55 is a diagram illustrating a smart mirror device including a switching device according to an embodiment.

Referring to FIG. 55, a smart mirror device 7400 according to an embodiment may include an image sensor 7410, a mirror display 7420, and a switching device 7430.

In this case, the above description is applicable to the image sensor 7410 and the mirror display 7420, and thus a redundant description thereof will be omitted.

Also, herein, an open state of the switching device 7430 may refer to a state in which a window for the image sensor 7410 acquiring an image is obtained, and a closed state of the switching device 7430 may refer to a state in which a window for the image sensor 7410 acquiring an image is not obtained.

Also, the image sensor 7410 may be used to detect the open state and the closed state. For example, the closed state may be detected when illumination detected by the image sensor 7410 is less than or equal to a reference value, and the open state may be detected when the illumination is greater than or equal to the reference value. However, the present invention is not limited thereto, and the open state and the closed state may be detected using the image sensor 7410 in various ways.

Also, an external sensor may be used to detect the open state and the closed state. For example, the open state may be detected when the external sensor detects the degree to which the switching device 7430 is open, and the closed state may be detected when the external sensor detects the degree to which the switching device 7430 is closed. However, the present invention is not limited thereto, and the open state and the closed state may be detected using the external sensor in various ways.

According to an embodiment, the switching device 7430 may open or close the image sensor 7410. For example, the switching device 7430 may open or close the front of the image sensor 7410 housed in an internal housing space to adjust an image acquired by the image sensor 7410 or prevent the image sensor 7410 from being visible from the outside.

In detail, at a first time point 7440 at which the switching device 7430 is positioned in the closed state, the image sensor 7410 may not be visible from the outside due to the switching device 7430.

Also, the image sensor 7410 may acquire no image at the first time point 7440. For example, the image sensor 7410 may be powered off through the closing operation of the switching device 7430, but the present invention is not limited thereto.

Also, at a second time point at which the switching device 7430 is positioned in the open state, the image sensor 7410 may be visible from the outside.

Also, the image sensor 7410 may acquire an image at the second time point 7450. For example, the image sensor 7410 may be powered on through the opening operation of the switching device 7430, but the present invention is not limited thereto.

Also, the surface of the switching device 7430 may be formed as a mirror and may be formed of the same material as that of the external surface of the mirror display 7420, but the present invention is not limited thereto.

Also, the switching device 7430 may function to protect the image sensor 7410 from external dust or the like. For example, when the switching device 7430 is in the closed state, it is possible to prevent external dust or the like from coming into contact with the image sensor 7410, but the present invention is not limited thereto.

9.1.7 Various Embodiments of Smart Mirror Device Placed on Shoe Rack

A smart mirror device placed above a shoe rack of a house or at the entrance of a building may measure physiological parameters for people who come in or go out. Usually, a shoe rack of a house or the entrance of a building is a place where people wear clothes, and has few privacy issues when an image sensor is used. Thus, it may be easy to install an image sensor for measuring a physiological parameter.

A smart mirror device placed at the entrance of a building or the like, which may be represented with a shoe rack, will be described below, and for convenience of description, a smart mirror device placed above a shoe rack will be described.

Figure 56:
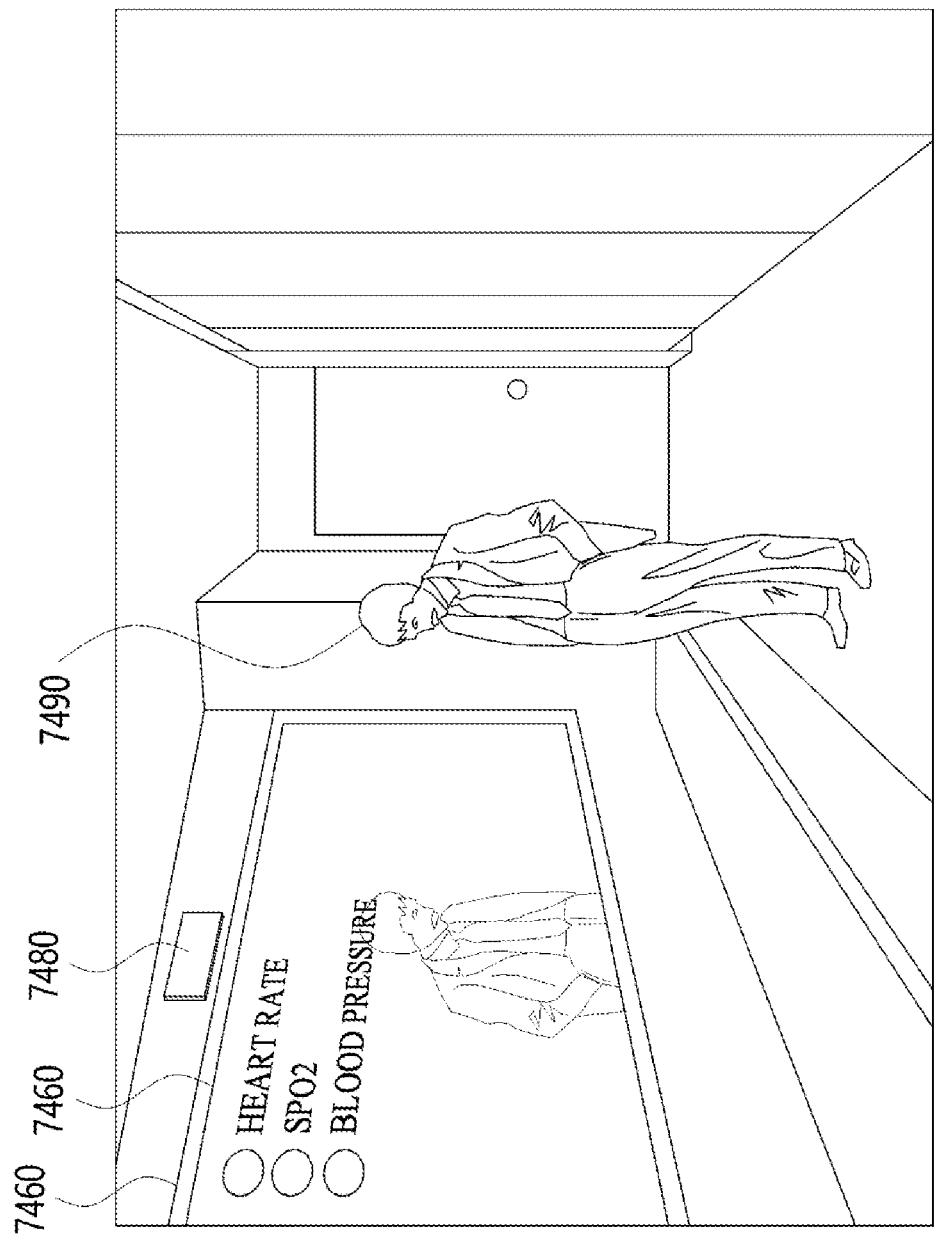
FIG. 56 is a diagram illustrating a smart mirror device placed above a shoe rack according to an embodiment.

FIG. 56 is a diagram illustrating a smart mirror device placed above a shoe rack according to an embodiment.

Referring to FIG. 56, a smart mirror device 7460 according to an embodiment may include an image sensor 7470 and a mirror display 7480.

In this case, the above description is applicable to the image sensor 7470 and the mirror display 7480, and thus a redundant description thereof will be omitted.

The image sensor 7470 according to an embodiment may acquire an image of a subject 7490. For example, the image sensor 7470 may acquire an image of a subject 7490 who passes by a shoe rock on which the smart mirror device 7460 is placed Also, the smart mirror device 7460 may acquire a physiological parameter on the basis of an image frame acquired from the image sensor 7470.

Also, the mirror display 7480 may reflect and provide the shape of the subject 7490. For example, the subject 7490 may observe himself or herself through the mirror display.

Also, the mirror display 7480 may display a physiological parameter of the subject 7490. For example, the mirror display 7480 may display a physiological parameter acquired based on an image frame acquired from the image sensor 7470, but the present invention is not limited thereto.

Also, the mirror display 7480 may display physiological information of the subject 7490. For example, the mirror display 7480 may display physiological information acquired based on the acquired physiological parameter, but the present invention is not limited thereto.

Also, the mirror display 7480 may be formed on at least a portion of the smart mirror device 7460. For example, as shown in FIG. 56, the mirror display 7480 may be placed in a central part of the smart mirror device 7460 to occupy a certain area.

Also, although not shown in FIG. 56, it is obvious that the mirror display 7480 may display basic information, personal information, and the like.

9.1.7.1 Various Embodiments of Smart Mirror Device Using Trigger Signal

When a smart mirror device for measuring a physiological parameter operates continuously, power may continue to be consumed in order to acquire and analyze an image. Accordingly, a trigger signal may be used to provide a smart mirror device capable of saving energy and operating more smartly.

Figure 57:
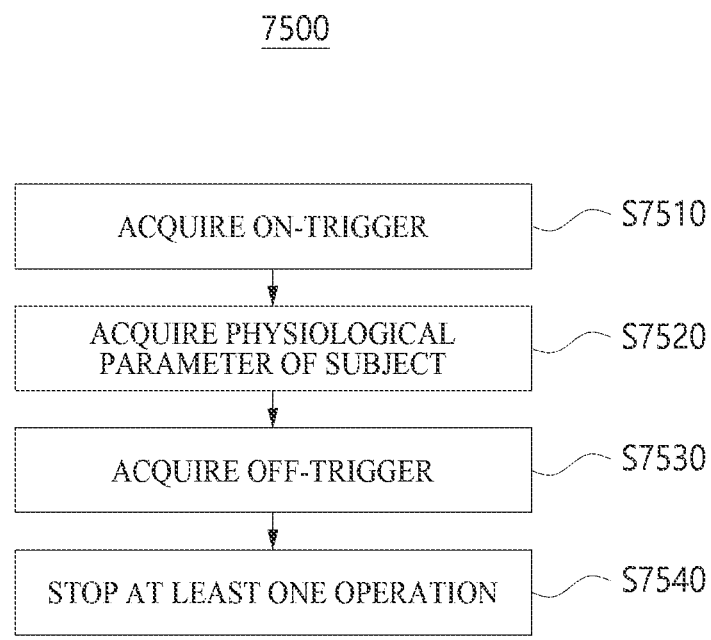
FIG. 57 is a flowchart illustrating a smart mirror device operating method according to an embodiment.

FIG. 57 is a flowchart illustrating a smart mirror device operating method according to an embodiment.

Referring to FIG. 57, a smart mirror device operating method 7500 according to an embodiment may include at least one of an operation of acquiring an on-trigger (S7510), an operation of acquiring a physiological parameter of a subject (S7520), an operation of acquiring an off-trigger (S7530), and an operation of stopping at least one operation of a smart mirror device (S7540), but the present invention is not limited thereto.

In detail, the smart mirror device operating method 7500 according to an embodiment may include an operation of acquiring the on-trigger (S7510).

In this case, the on-trigger may be a trigger signal for starting at least one operation of the smart mirror device. For example, the on-trigger may be a trigger signal for performing an operation of an image sensor acquiring an image. However, the present invention is not limited thereto, and the on-trigger may be a trigger signal for starting at least one operation of the smart mirror device, e.g., an operation of powering the smart mirror device on.

Also, the on-trigger may be provided in various ways.

For example, when the smart mirror device includes a motion detection sensor, the on-trigger may be acquired from the motion detection sensor. In detail, when a predetermined motion is detected by the motion detection sensor, the smart mirror device may acquire a corresponding trigger signal, and the trigger signal may become the on-trigger, but the present invention is not limited thereto.

Also, in this case, the motion detection sensor may be placed inside the smart mirror device. However, the present invention is not limited thereto, and the motion detection sensor may be placed outside the smart mirror device.

Also, for example, when the smart mirror device includes an input device such as a touch panel, the on-trigger may be acquired from the input device. In detail, when a predetermined input is acquired from the input device, the smart mirror device may acquire a corresponding trigger signal, and the trigger signal may become the on-trigger, but the present invention is not limited thereto.

Also, for example, when the smart mirror device includes an image sensor, the on-trigger may be acquired from the image sensor. In detail, a lighting device placed above a shoe rack detects a predetermined motion and emits light, and the image sensor may detect light emitted from the lighting device. In this case, the smart mirror device may acquire a corresponding trigger signal, and the trigger signal may become the on-trigger, but the present invention is not limited thereto.

Also, for example, when an entrance door is included within the angle of view of the image sensor, the on-trigger may be acquired based on a change in the entrance door. In detail, the image sensor may determine that the entrance door is open, the smart mirror device may acquire a corresponding trigger signal, and the trigger signal may become the on-trigger, but the present invention is not limited thereto.

Also, the smart mirror device operating method 7500 according to an embodiment may include an operation of acquiring a physiological parameter of a subject (S7520).

In this case, a physiological signal for the subject may be acquired based on an image frame acquired through the image sensor. However, this has been described above, and thus a redundant description thereof will be omitted.

Also, the smart mirror device operating method 7500 according to an embodiment may include acquiring the off-trigger (S7530).

In this case, the off-trigger may be a trigger signal for stopping at least one operation of the smart mirror device.

For example, the off-trigger may be a trigger signal for stopping an operation of an image sensor acquiring an image. However, the present invention is not limited thereto, and the off-trigger may be a trigger signal for stopping at least one operation of the smart mirror device, e.g., an operation of powering the smart mirror device off.

Also, the off-trigger may be provided in various ways.

For example, when the smart mirror device includes a motion detection sensor, the off-trigger may be acquired from the motion detection sensor. In detail, when a predetermined motion has not been detected by the motion detection sensor during a certain time, the smart mirror device may acquire a corresponding trigger signal, and the trigger signal may be the off-trigger, but the present invention is not limited thereto.

Also, for example, when the smart mirror device includes an input device such as a touch panel, the off-trigger may be acquired from the input device. In detail, when a predetermined input is acquired from the input device, the smart mirror device may acquire a corresponding trigger signal, and the trigger signal may become the off-trigger, but the present invention is not limited thereto.

Also, for example, when the smart mirror device includes an image sensor, the off-trigger may be acquired from the image sensor. In detail, a lighting device placed above a shoe rack has not detected a predetermined motion during a certain time and is turned off. The image sensor may detect the intensity of light to determine that the light device is turned off, the smart mirror device may acquire a corresponding trigger signal, and the trigger signal may become the off-trigger, but the present invention is not limited thereto.

Also, for example, the off-trigger may be acquired based on the acquisition of a physiological parameter by the smart mirror device. In detail, when a measurement target region is not present within the angle of view of the image sensor, no physiological parameter may be acquired. When no physiological parameter is detected during a certain time, the smart mirror device may acquire a corresponding trigger signal, and the trigger signal may become the off-trigger, but the present invention is not limited thereto.

Also, for example, when an entrance door is included within the angle of view of the image sensor, the off-trigger may be acquired based on a change in the entrance door. In detail, the image sensor may determine that the entrance door is open, the smart mirror device may acquire a corresponding trigger signal, and the trigger signal may become the off-trigger, but the present invention is not limited thereto.

Figure 58:
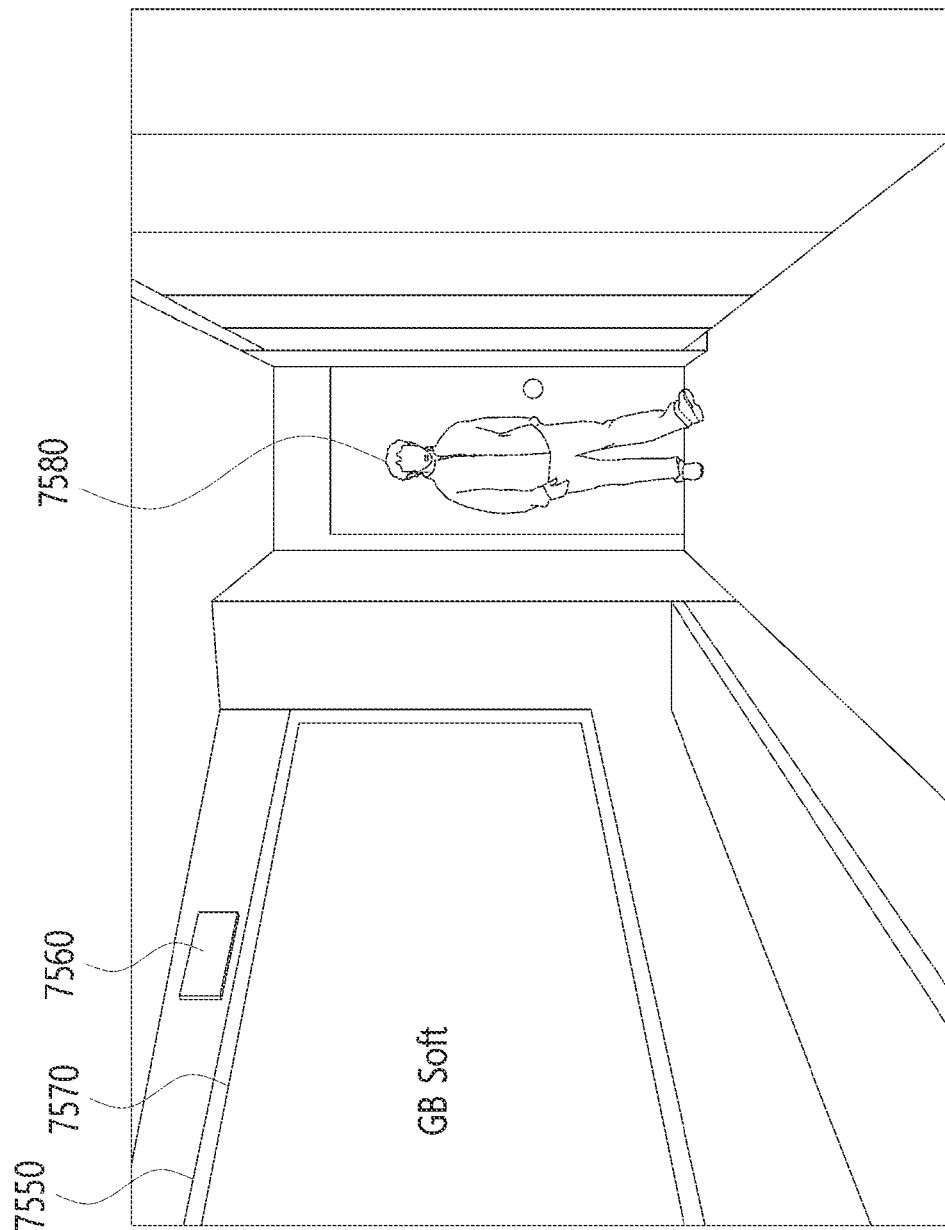
FIGS. 58 and 59 are diagrams illustrating an operation of a smart mirror device using a trigger signal according to an embodiment.
Figure 59:
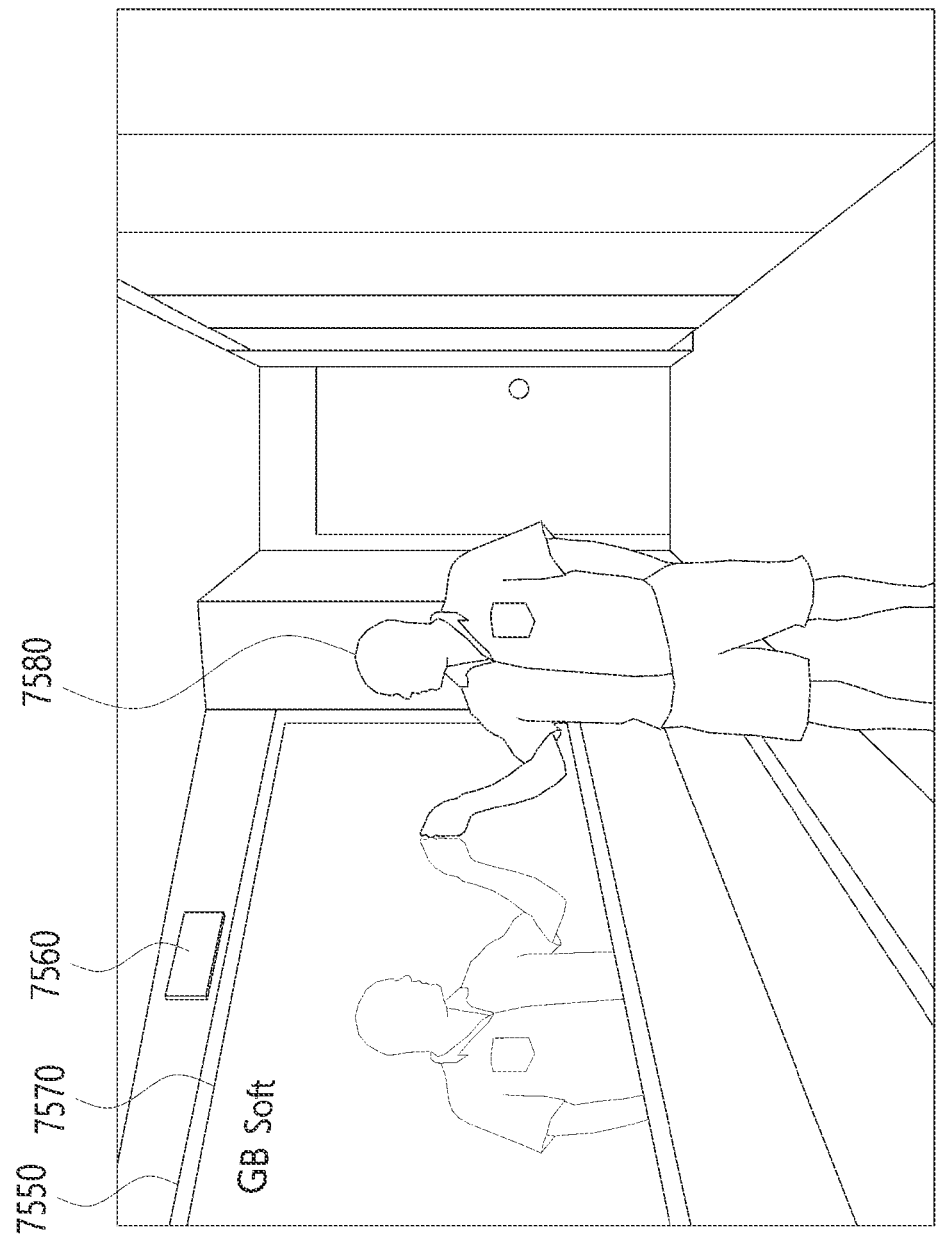

FIGS. 58 and 59 are diagrams illustrating an operation of a smart mirror device using a trigger signal according to an embodiment.

Referring to FIGS. 58 and 59, a smart mirror device 7550 according to an embodiment may include an image sensor 7560 and a mirror display 7570.

In this case, the above description is applicable to the image sensor 7560 and the mirror display 7570, and thus a redundant description thereof will be omitted.

According to an embodiment, referring to FIG. 58, when a subject 7580 is positioned in a predetermined on-trigger occurrence region, at least one operation of the smart mirror device may be started.

In this case, when the smart mirror device includes a motion detection sensor, the predetermined on-trigger occurrence region may be the detection range of the motion detection sensor and may be the detection range of the motion detection sensor of a lighting device installed on a shoe rack, but the present invention is not limited thereto.

Also, according to an embodiment, referring to FIG. 59, when the smart mirror device 7550 receives a predetermined input from the subject 7580, at least one operation of the smart mirror device 7550 may be started.

In this case, the predetermined input may be acquired through an input device such as a touch panel, but the present invention is not limited thereto.

9.1.7.2 Various Embodiments of Smart Mirror Device Configured to Measure Physiological Parameter According to Priority When a plurality of people are present in a physiological parameter measurement region of a smart mirror device, a physiological parameter may be measured according to priority.

Figure 60:
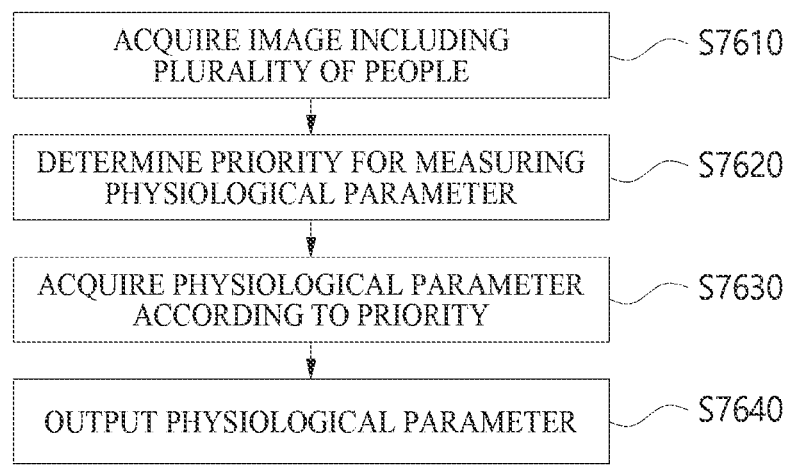
FIG. 60 is a diagram illustrating a smart mirror device operating method according to an embodiment.

FIG. 60 is a diagram illustrating a smart mirror device operating method according to an embodiment.

Referring to FIG. 60, a smart mirror device operating method 7600 according to an embodiment may include at least one of an operation of acquiring an image including a plurality of people (S7610), an operation of determining priority for physiological parameter measurement (S7620), an operation of acquiring a physiological parameter according to the priority (S7630), and an operation of outputting the acquired physiological parameter (S7640), but the present invention is not limited thereto.

In detail, the smart mirror device operating method 7600 according to an embodiment may include an operation of acquiring an image including a plurality of people (S7610). The above description about image acquisition is applicable to this operation, and thus a redundant description thereof will be omitted.

Also, the smart mirror device operating method 7600 according to an embodiment may include an operation of determining priority for physiological parameter measurement (S7620) and an operation of acquiring a physiological parameter according to the priority (S7630).

In this case, the ease of the physiological parameter measurement may be considered to determine the priority. For example, a physiological parameter of a person who occupies the largest area in the acquired image among the plurality of people may be measured, but the present invention is not limited thereto.

Also, for example, a physiological parameter of a person who is actually recognized as a person in the acquired image among the plurality of people may be measured, but the present invention is not limited thereto.

Also, for example, a physiological parameter of a person who occupies an area closet to the center in the acquired image among the plurality of people may be measured, but the present invention is not limited thereto.

Also, for example, a physiological parameter of a person who is positioned closest to the image sensor in the acquired image among the plurality of people may be measured, but the present invention is not limited thereto.

Also, prestored information may be utilized to determine the priority. For example, a physiological parameter of a person who is stored as a subject among the plurality of people may be measured, but the present invention is not limited thereto.

Also, for example, a physiological parameter may be acquired according to preset priority. In detail, when a child among family members is set to have high priority and a child and his or her father is positioned in the physiological parameter measurement region, a physiological parameter of the child may be measured, but the present invention is not limited thereto.

Also, physiological parameter measurement order information may be utilized to determine the priority. For example, when an image of a first subject is acquired first and then an image of a second subject is acquired, a physiological parameter of the first subject may be measured, but the present invention is not limited thereto.

Also, the smart mirror device operating method 7600 according to an embodiment may include an operation of outputting the acquired physiological parameter (S7640).

In this case, the physiological parameter may be a physiological parameter of a person determined according to the priority.

Also, while the physiological parameter is being output, an indicator for a person whose physiological parameter is measured may be output. For example, a guide region for a person who is determined according to the priority and whose physiological parameter is to be measured may be output, but the present invention is not limited thereto.

Figure 61:
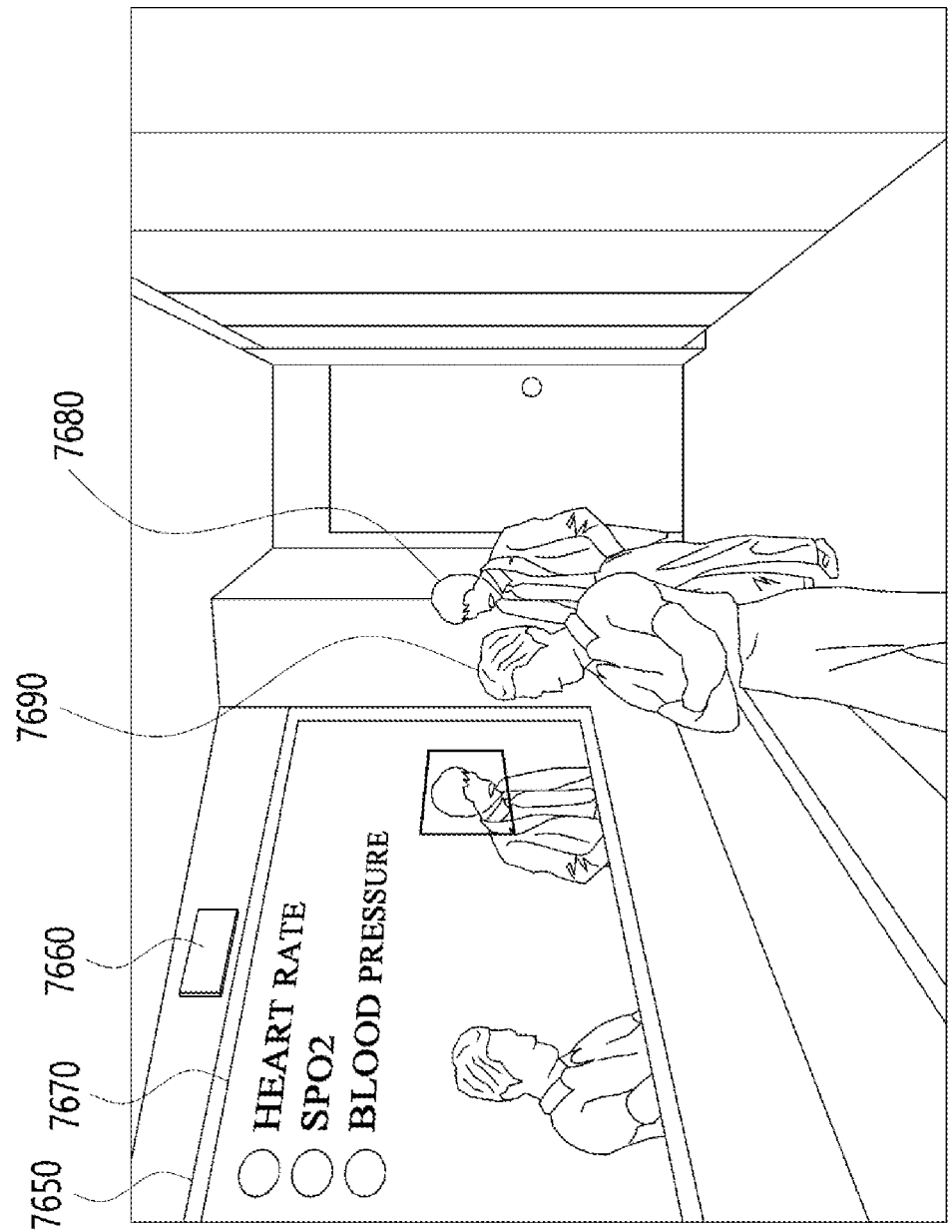
FIG. 61 is a diagram illustrating an operation of a smart mirror device according to an embodiment.

FIG. 61 is a diagram illustrating an operation of a smart mirror device according to an embodiment.

Referring to FIG. 61, a smart mirror device 7650 according to an embodiment may include an image sensor 7660 and a mirror display 7670.

In this case, the above description is applicable to the image sensor 7660 and the mirror display 7670, and thus a redundant description thereof will be omitted.

According to an embodiment, referring to FIG. 61, a first person 7680 and a second person 7690 may be positioned in the measurement range of the image sensor 7660.

Also, the first person 7680 may be subject to the physiological parameter measurement of the smart mirror device 7650.

For example, as shown in FIG. 61, when the first person 7680 is positioned closer to the image sensor 7660 than the second person 7690, the first person 7680 may be subject to the physiological parameter measurement, but the present invention is not limited thereto.

Also, for example, when in an image acquired by the image sensor 7660, an area occupied by an image of the first person 7680 is larger than an area occupied by an image of the second person 7690, the first person 7680 may be subject to the physiological parameter measurement, but the present invention is not limited thereto.

Also, for example, when only the first person 7680 is actually recognized as a person by the smart mirror device 7650, the first person 7680 may be subject to the physiological parameter measurement, but the present invention is not limited thereto.

Also, for example, when in an image acquired by the image sensor 7660, an area occupied by an image of the first person 7680 is closer to the center than an area occupied by an image of the second person 7690, the first person 7680 may be subject to the physiological parameter measurement, but the present invention is not limited thereto.

Also, for example, when the priority of the first person 7680 is stored to be higher than the priority of the second person 7690, the first person 7680 may be subject to the physiological parameter measurement, but the present invention is not limited thereto.

Also, for example, when the first person 7680 is stored as a subject, the first person 7680 may be subject to the physiological parameter measurement, but the present invention is not limited thereto.

Also, when a physiological parameter of the first person 7680 is measured, the physiological parameter of the first person 7680 may be output. For example, as shown in FIG. 61, a heart rate, an oxygen saturation level, and a blood pressure of the first person 7680 may be output, but the present invention is not limited thereto.

Also, when a physiological parameter of the first person 7680 is measured, an indicator for the first person 7680 may be output. For example, as shown in FIG. 61, a guide region for the first person 7680 may be output, but the present invention is not limited thereto.

9.1.7.3 Various Embodiments of Smart Mirror Device Configured to Measure Physiological Parameters of Plurality of Subjects When a plurality of people are present in a physiological parameter measurement region of a smart mirror device, a physiological parameter may be measured according to priority.

Figure 62:
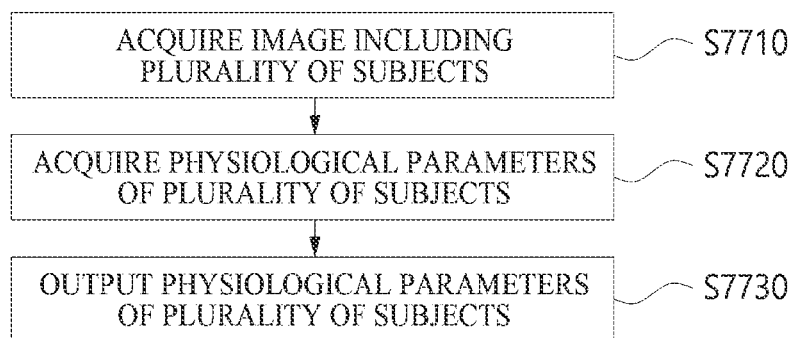
FIG. 62 is a diagram illustrating a smart mirror device operating method according to an embodiment.

FIG. 62 is a diagram illustrating a smart mirror device operating method according to an embodiment.

Referring to FIG. 62, a smart mirror device operating method 7700 according to an embodiment may include at least one of an operation of acquiring an image including a plurality of subjects (S7710), an operation of acquiring physiological parameters of the plurality of subjects (S7720), and an operation of outputting the physiological parameters of the plurality of subjects (S7730), but the present invention is not limited thereto.

In detail, the smart mirror device operating method 7700 according to an embodiment may include an operation of acquiring an image including a plurality of subjects (S7610). The above description about image acquisition is applicable to this operation, and thus a redundant description thereof will be omitted.

Also, the smart mirror device operating method 7700 according to an embodiment may include an operation of acquiring physiological parameters of the plurality of subjects (S7720). The above-described physiological parameter acquisition methods are applicable to this operation, and thus a redundant description thereof will be omitted.

According to an embodiment, a region for each of the plurality of subjects may be set to acquire the physiological parameters of the plurality of subjects. For example, when a first subject and a second subject are positioned within a physiological parameter measurement region, a region for the first subject and a region for the second subject may be set.

Also, a plurality of physiological parameters for each of a plurality of subjects may be acquired. For example, a heart rate, an oxygen saturation level, and a blood pressure of each of a plurality of subjects may be acquired, but the present invention is not limited thereto.

Also, different types of physiological parameters may be acquired for the plurality of subjects. For example, a heart rate of a first subject may be acquired, and an oxygen saturation level and a blood pressure of a second subject may be acquired, but the present invention is not limited thereto.

Also, a sub-region for each of the plurality of subjects may be set to acquire the plurality of physiological parameters of the plurality of subjects. For example, a region for a first subject, a first sub-region for measuring a heart rate of the first subject, a second sub-region for measuring an oxygen saturation level of the first subject, and a third sub-region for measuring a blood pressure of the first subject may be set, and a region for a second subject, a fourth sub-region for measuring a heart rate of the second subject, a fifth sub-region for measuring an oxygen saturation level of the second subject, and a sixth sub-region for measuring a blood pressure of the second subject may be set, but the present invention is not limited thereto.

Also, the first to sixth sub-regions may differ from each other and at least partially overlap each other.

Also, the smart mirror device operating method 7700 according to an embodiment may include an operation of outputting the physiological parameters of the plurality of subjects (S7730).

In this case, the physiological parameters may include at least one physiological parameter of each of the plurality of subjects.

Also, while the physiological parameters are being output, indicators for the plurality of subjects may be output. For example, when physiological parameters of the first subject and the second subject are acquired, guide regions for the first subject and the second subject may be output, but the present invention is not limited thereto.

Also, while the physiological parameters are being output, indicators indicating for which subjects the physiological parameters are acquired may be output. For example, an indicator for identifying a first subject may be output when a physiological parameter of the first subject is output, and an indicator for identifying a second subject may be output when a physiological parameter of the second subject is output.

Figure 63:
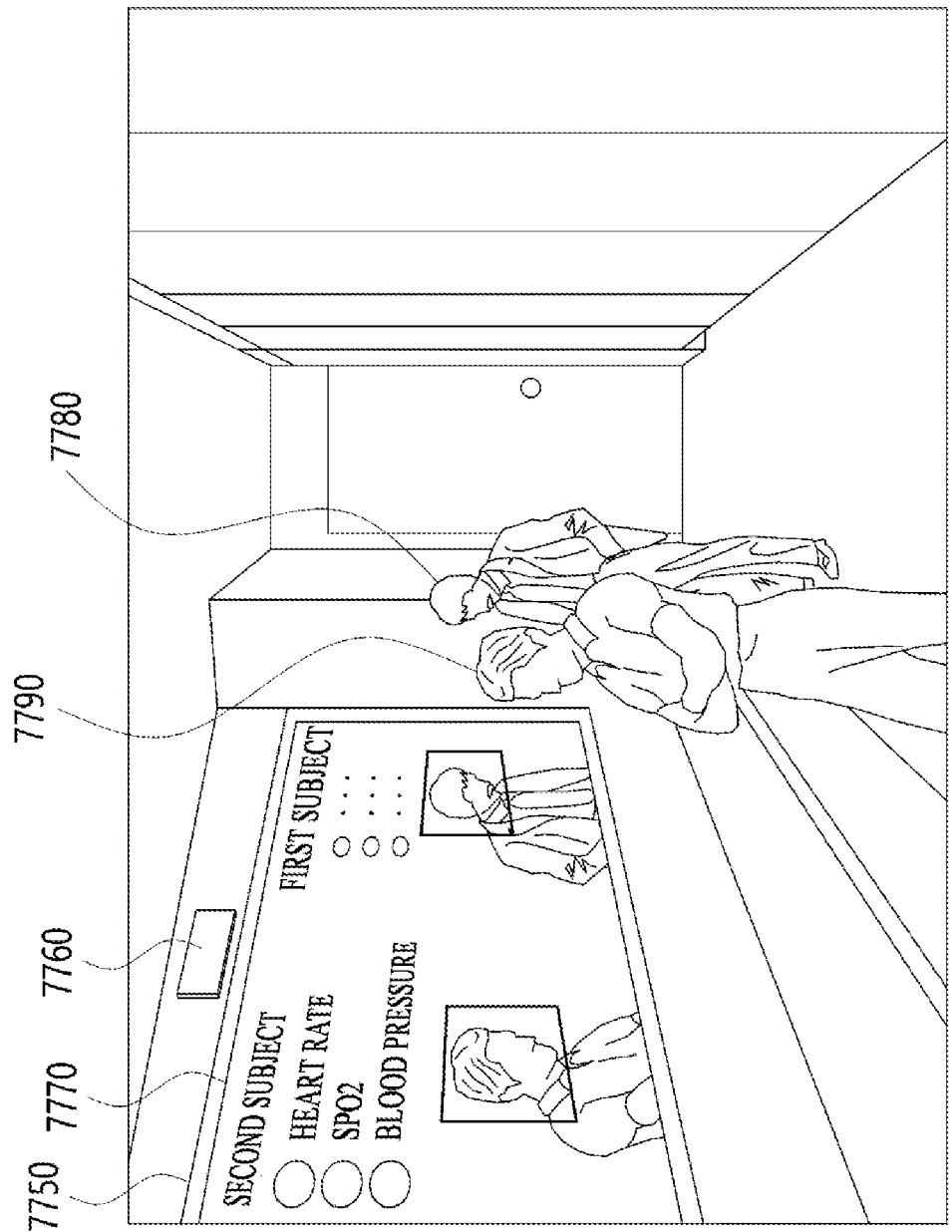
FIG. 63 is a diagram illustrating an operation of a smart mirror device according to an embodiment.

FIG. 63 is a diagram illustrating an operation of a smart mirror device according to an embodiment.

Referring to FIG. 63, a smart mirror device 7750 according to an embodiment may include an image sensor 7760 and a mirror display 7770.

In this case, the above description is applicable to the image sensor 7760 and the mirror display 7770, and thus a redundant description thereof will be omitted.

According to an embodiment, referring to FIG. 63, a first subject 7780 and a second subject 7790 may be positioned in the measurement range of the image sensor 7760.

Also, a region for each of a plurality of subjects may be set in an image frame acquired to acquire physiological parameters of the first subject 7780 and the second subject 7790.

Also, physiological parameters of the first subject 7780 and the second subject 7790 may be acquired. For example, heart rates of the first subject 7780 and the second subject 7790 may be acquired, but the present invention is not limited thereto.

Also, a plurality of physiological parameters for each of the first subject 7780 and the second subject 7790 may be acquired. For example, as shown in FIG. 63, a heart rate, an oxygen saturation level, and a blood pressure for the first subject 7780 may be acquired, and a heart rate, an oxygen saturation level, and a blood pressure for the second subject 7790 may be acquired, but the present invention is not limited thereto.

Also, for example, although not shown in FIG. 63, a heart rate of the first subject 7780 may be acquired, and an oxygen saturation level and a blood pressure of the second subject 7790 may be acquired, but the present invention is not limited thereto.

9.1.7.4 Various Embodiments of Smart Mirror Device Configured to Output Different Information Depending on Situation When a smart mirror device is placed at the entrance of a building, e.g., on a shoe rack, information a user needs in a situation of entering the building may be different from information a user needs in a situation of exiting the building.

Accordingly, the smart mirror device may output and provide different information to a user depending on the situation.

Also, the smart mirror device may output and provide a different physiological parameter to a user depending on the situation.

Figure 64:
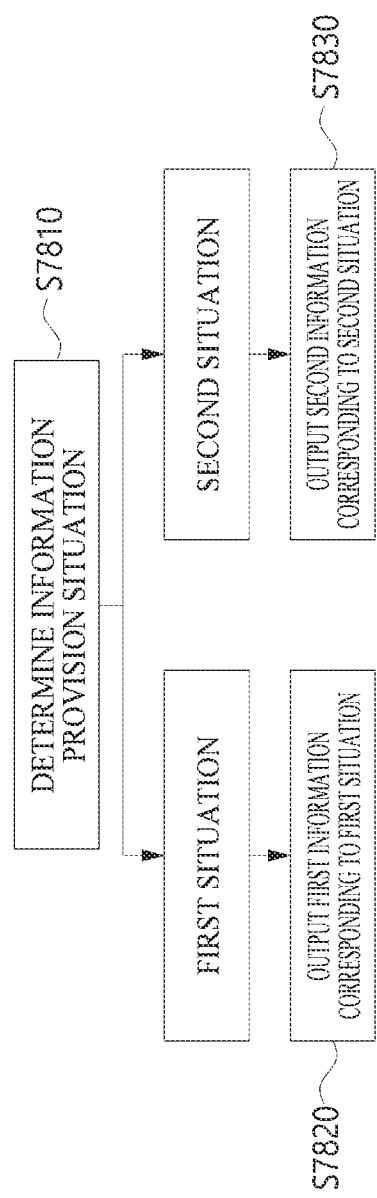
FIG. 64 is a diagram illustrating a smart mirror device operating method according to an embodiment.

FIG. 64 is a diagram illustrating a smart mirror device operating method according to an embodiment.

Referring to FIG. 64, a smart mirror device operating method 7800 according to an embodiment may include at least one of an operation of determining an information provision situation (S7810), an operation of outputting first information corresponding to a first situation (S7820), and an operation of outputting second information corresponding to a second situation (S7830), but the present invention is not limited thereto.

In detail, the smart mirror device operating method 7800 according to an embodiment may include an operation of determining an information provision situation (S7810).

In this case, the information provision situation may refer to a situation of a user of a smart mirror device. For example, the information provision situation may include a situation in which the user of the smart mirror device enters a building or a situation in which the user of the smart mirror device exits a building, but the present invention is not limited thereto.

Also, the information provision situation may simply refer to a situation determined to provide information. For example, the information provision situation may include a first situation or a second situation, but the present invention is not limited thereto.

Also, the information provision situation may simply refer to a situation associated with whether to determine a physiological parameter. For example, the information provision situation may include a situation in which there is no need to measure a physiological parameter and a situation in which there is a need to measure a physiological parameter, but the present invention is not limited thereto.

Also, the information provision situation may refer to a situation associated with time. For example, the information provision situation may include a before-noon situation or an after-noon situation, but the present invention is not limited thereto.

Also, the information provision situation may refer to a situation corresponding to an external environment. For example, the information provision situation may include a situation corresponding to an external situation such as an external epidemic situation, but the present invention is not limited thereto.

Also, the smart mirror device may include an additional sensor in order to determine the information provision situation. For example, the smart mirror device may additionally include a motion detection sensor in order to determine a user access situation, determine that the first situation is that a user's motion is detected first by a first motion detection sensor, and determine that the second situation is that a user's motion is detected first by a second motion detection sensor, but the present invention is not limited thereto.

Also, an image sensor included in the smart mirror device may be used to determine the information provision situation. For example, an image frame acquired through the image sensor may be used to determine the user access situation. In detail, in a plurality of image frames acquired in time-series, the smart mirror device may determine that the first situation is that a region corresponding to the user becomes close to a central part in a first aspect and may determine that the second situation is that the region corresponding to the user becomes close to the central part in a second aspect, but the present invention is not limited thereto.

Also, an image sensor included in the smart mirror device may be used to determine the information provision situation. For example, an image frame acquired through the image sensor may be used to determine whether there is a need for physiological parameter measurement and information provision. In detail, in a plurality of image frames acquired in time-series, the smart mirror device may determine that the first situation is that a movement speed of the region corresponding to the user exceeds a reference value and may determine that the second situation is that the movement speed is less than or equal to the reference value, but the present invention is not limited thereto.

Also, time information may be used to determine the information provision situation. For example, the smart mirror device may determine that the first situation is before a reference time and may determine that the second situation is after the reference time, but the present invention is not limited thereto.

Also, recognition information may be used to determine the information provision situation. For example, face recognition information of people may be used to determine whether physiological parameter measurement and information provision are necessary. In detail, according to a result of face recognition, the smart mirror device may determine that the first situation is that a user is registered and may determine that the second situation is that a user is not registered, but the present invention is not limited thereto.

Also, movement direction information of a subject may be used to determine the information provision situation. For example, movement direction information of a subject detected to determine the information provision situation or detected using an external sensor may be used. In detail, the smart mirror device may determine that the first situation is that the subject moves in a first direction and may determine that the second situation is that the subject moves in a second situation, but the present invention is not limited thereto.

Also, a smart mirror device operating method 7800 according to an embodiment may include an operation of outputting first information corresponding to the first situation (S7820) and an operation of outputting second information corresponding to the second situation (S7830), but the present invention is not limited thereto.

In this case, when the first situation includes a situation in which a building is exited and the second situation includes a situation in which a building is entered, the first information and the second information may be different from each other.

For example, the first information may include external weather information, today's schedule information, product information corresponding to external weather, and the like. However, the present invention is not limited thereto, and the first information may be information corresponding to the first situation.

Also, the second information may include internal temperature information, internal humidity information, security information, internal air quality information, and the like. However, the present invention is not limited thereto, and the second information may be information corresponding to the second situation.

Also, physiological parameter information may be included in at least one of the first information and the second information, but the present invention is not limited thereto.

Also, a physiological parameter included in the first information and a physiological parameter included in the second information may be different from each other. For example, a heart rate may be output when a physiological parameter of a first subject is provided, and a blood pressure may be output when a physiological parameter of a second subject is provided, but the present invention is not limited thereto.

Figure 65:
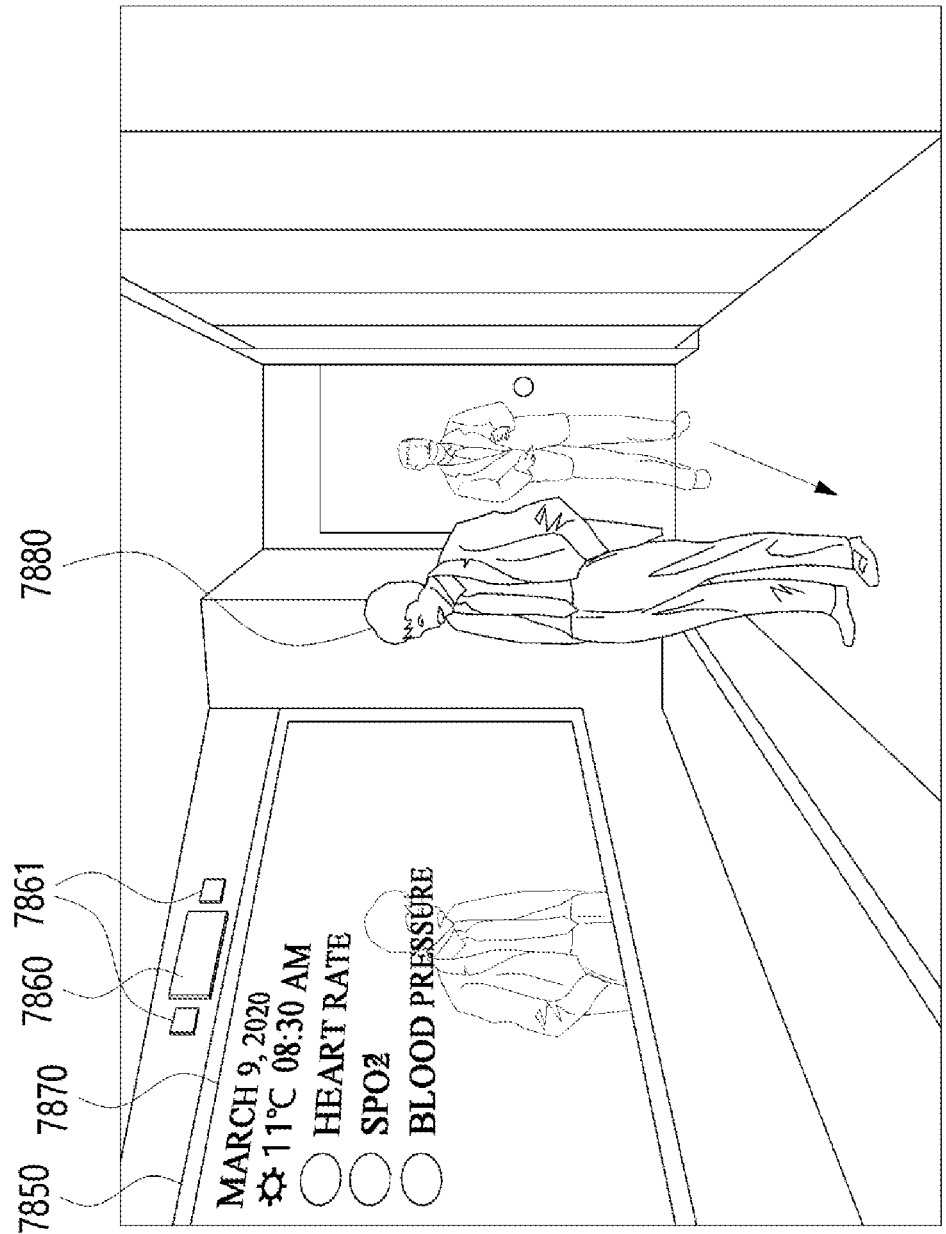
FIGS. 65 and 66 are diagrams illustrating an operation of a smart mirror device according to an embodiment.
Figure 66:
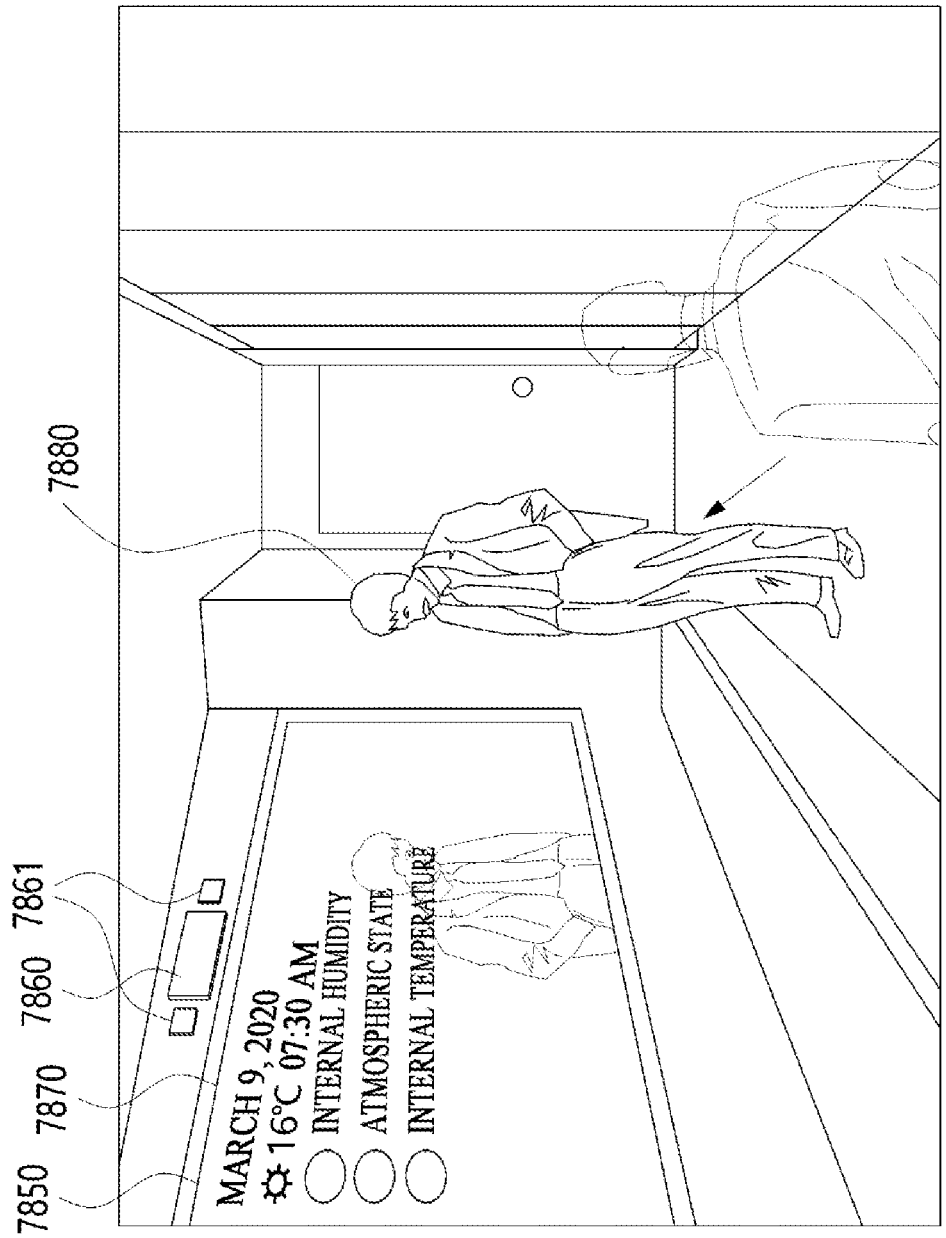

FIGS. 65 and 66 are diagrams illustrating an operation of a smart mirror device according to an embodiment.

Referring to FIGS. 65 and 66, a smart mirror device 7850 according to an embodiment may include an image sensor 7860 and a mirror display 7870.

In this case, the above description is applicable to the image sensor 7860 and the mirror display 7870, and thus a redundant description thereof will be omitted.

According to an embodiment, FIG. 65 may be a diagram illustrating the operation of the smart mirror device 7850 in a first situation, and FIG. 66 may be a diagram illustrating the operation of the smart mirror device 7850 in a second situation.

Also, information output in the first situation may be different from information output in the second situation. The above description is applicable to this situation, and thus a redundant description thereof will be omitted.

Also, an external sensor 7861 may be used to determine the first situation and the second situation. However, the present invention is not limited thereto, and the above examples may be applied to determine the first situation and the second situation.

Also, although not shown in FIGS. 65 and 66, the information output in the first situation and the information output in the second situation may at least partially overlap each other. For example, physiological parameters may be included in both of the information output in the first situation and the information output in the second situation, but the present invention is not limited thereto.

9.2 Various Embodiments of Physiological Parameter Measurement Device Placed in Vehicle The above-described physiological parameter acquisition method and drowsiness detection method may be used in various applications. For example, the physiological parameter acquisition method or drowsiness detection method may be used in a physiological parameter measurement device placed in a vehicle.

Also, the physiological parameter measurement device may perform an operation corresponding to a physiological parameter or physiological information acquired according to the physiological parameter acquisition method.

Also, the physiological parameter measurement device may perform an operation corresponding to drowsiness information acquired according to the drowsiness detection method.

Also, the operation of the physiological parameter measurement device will be described below, but the operation to be described may be performed even by other processors such as an ECU mounted on a vehicle or may be performed even by a processor included in a server.

Also, a device that will be described as the physiological parameter measurement device may refer to an image acquisition device. In this case, the operation to be described may be performed by other processors such as an ECU or a processor included in a server.

Figure 67:
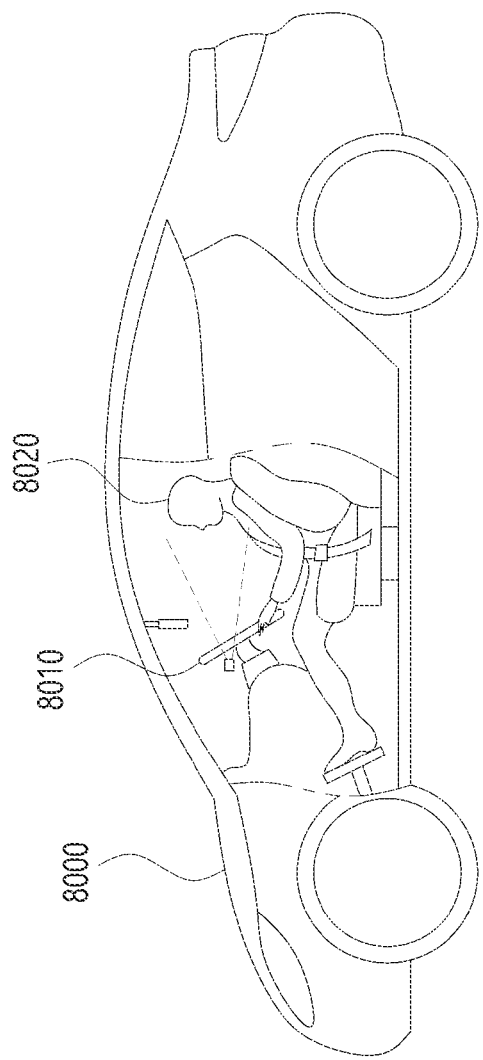
FIG. 67 is a diagram illustrating a physiological parameter measurement device according to an embodiment.

FIG. 67 is a diagram illustrating a physiological parameter measurement device according to an embodiment.

Referring to FIG. 67, a physiological parameter measurement device 8010 according to an embodiment may be placed in a vehicle 8000 and configured to measure a physiological parameter of an occupant 8020 in the vehicle 8000.

In this case, the physiological parameter measurement device 8010 may be placed at various positions of the vehicle 8000.

For example, the physiological parameter measurement device 8010 may be placed on an overhead console, a sun visor, a rearview mirror, a dashboard, an instrument panel, a steering wheel, a center fascia, a console box, etc. of the vehicle 8000, but the present invention is not limited thereto.

Also, the occupant 8020 may be a driver. However, the present invention is not limited thereto, and the occupant 8020 may be a person in a vehicle such as a passenger.

Also, when the occupant 8020 includes a plurality of people, the physiological parameter measurement device 8010 may measure physiological parameters of the plurality of people.

Also, the physiological parameter measurement device 8010 may include an image sensor and acquire a physiological parameter on the basis of an image frame acquired from the image sensor. However, the present invention is not limited thereto, and a contact-type sensor or the like may be used.

Also, when the physiological parameter measurement device 8010 includes an image sensor, the image sensor may be provided as a visible camera for acquiring a visible light image, an IR camera for acquiring an infrared image, and the like. However, the present invention is not limited thereto, and a hybrid-type camera for acquiring a visible light image and an infrared image may be provided.

Also, the physiological parameter measurement device 8010 may operate in a mode changed according to the amount of external light. For example, the physiological parameter measurement device 8010 may operate in a first mode during the daytime when there is a great deal of external light and may operate in a second mode during the night when there is little external light, but the present invention is not limited thereto.

Also, for example, the physiological parameter measurement device 8010 may operate in a first mode in which a physiological parameter is acquired based on an RGB image when the external light is higher than or equal to a reference value and may operate in a second mode in which a physiological parameter is acquired based on an IR image when the external light is lower than or equal to a reference value, but the present invention is not limited thereto.

Figure 68:
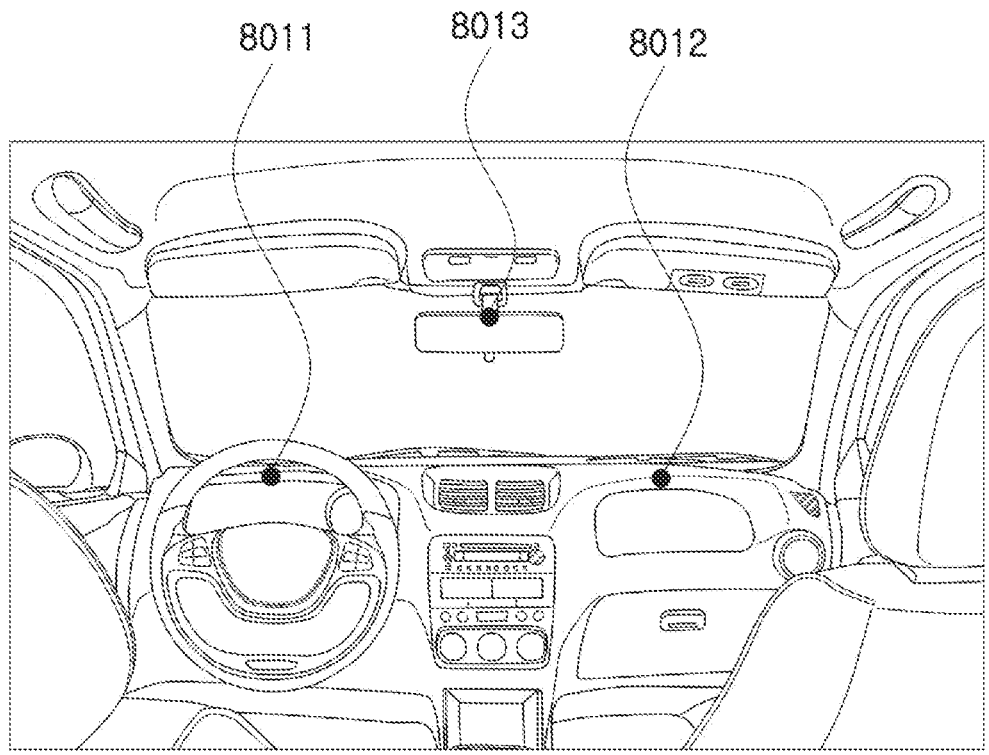
FIG. 68 is a diagram illustrating a physiological parameter measurement device according to an embodiment.

FIG. 68 is a diagram illustrating a physiological parameter measurement device according to an embodiment.

Referring to FIG. 68, a physiological parameter measurement device according to an embodiment may be placed at various positions of a vehicle.

For example, as shown in FIG. 68, a first physiological parameter measurement device 8011 may be placed on a driver seat dashboard, a second physiological parameter measurement device 8012 may be placed on a passenger seat dashboard, and a third physiological parameter measurement device 8013 may be placed on a rearview mirror, but the present invention is not limited thereto.

Also, at least one of the first to third physiological parameter measurement devices 8011, 8012, and 8013 may be placed inside the vehicle.

Also, at least one of the first to third physiological parameter measurement devices 8011, 8012, and 8013 may acquire a physiological parameter of the driver.

For example, at least one of the first to third physiological parameter measurement devices 8011, 8012, and 8013 may measure a physiological parameter, such as a heart rate, a blood pressure, an oxygen saturation level, and a core temperature, of the driver, but the present invention is not limited thereto.

Also, at least one of the first to third physiological parameter measurement devices 8011, 8012, and 8013 may perform an operation corresponding to the acquired physiological parameter of the driver.

For example, when the acquired physiological parameter of the driver is abnormal, at least one of the first to third physiological parameter measurement devices 8011, 8012, and 8013 may perform an operation of providing information about nearby hospitals, but the present invention is not limited thereto.

Also, for example, when the acquired physiological parameter of the driver is abnormal, at least one of the first to third physiological parameter measurement devices 8011, 8012, and 8013 may transmit relevant information to another mobile device, but the present invention is not limited thereto.

Also, for example, when the acquired physiological parameter of the driver is abnormal, at least one of the first to third physiological parameter measurement devices 8011, 8012, and 8013 may generate a hardware alarm such as sound and vibration, but the present invention is not limited thereto.

Also, for example, when the acquired physiological parameter of the driver is abnormal, at least one of the first to third physiological parameter measurement devices 8011, 8012, and 8013 performs an operation of changing a vehicle to an autonomous driving mode, but the present invention is not limited thereto.

Also, at least one of the first, second, and third physiological parameter measurement devices 8011, 8012, and 8013 may acquire physiological information of the driver.

For example, at least one of the first to third physiological parameter measurement devices 8011, 8012, and 8013 may acquire the physiological information of the driver, such as drowsiness information and condition information of the driver, but the present invention is not limited thereto.

Also, at least one of the first to third physiological parameter measurement devices 8011, 8012, and 8013 may perform an operation corresponding to the acquired physiological information of the driver.

For example, when the acquired drowsiness information of the driver is abnormal, at least one of the first to third physiological parameter measurement devices 8011, 8012, and 8013 may generate a hardware alarm such as sound and vibration, but the present invention is not limited thereto.

Also, for example, when the acquired drowsiness information of the driver is abnormal, at least one of the first to third physiological parameter measurement devices 8011, 8012, and 8013 may perform an operation of providing information about nearby rest areas, but the present invention is not limited thereto.

Also, for example, when the acquired drowsiness information of the driver is abnormal, at least one of the first to third physiological parameter measurement devices 8011, 8012, and 8013 may transmit relevant information to another mobile device, but the present invention is not limited thereto.

Also, for example, when the acquired drowsiness information of the driver is abnormal, at least one of the first to third physiological parameter measurement devices 8011, 8012, and 8013 performs an operation of changing a vehicle to an autonomous driving mode, but the present invention is not limited thereto.

Also, for example, at least one of the first to third physiological parameter measurement devices 8011, 8012, and 8013 may perform an operation of selecting an appropriate song according to the acquired condition information of the driver, but the present invention is not limited thereto.

Also, for example, at least one of the first to third physiological parameter measurement devices 8011, 8012, and 8013 may perform an operation of providing information about appropriate content according to the acquired condition information of the driver, but the present invention is not limited thereto.

Also, at least one of the first, second, and third physiological parameter measurement devices 8011, 8012, and 8013 may acquire a physiological parameter of a passenger.

For example, at least one of the first to third physiological parameter measurement devices 8011, 8012, and 8013 may measure a physiological parameter, such as a heart rate, a blood pressure, an oxygen saturation level, and a core temperature, of the passenger, but the present invention is not limited thereto.

Also, at least one of the first, second, and third physiological parameter measurement devices 8011, 8012, and 8013 may perform an operation corresponding to the acquired physiological parameter of the passenger.

For example, when the acquired physiological parameter of the passenger is abnormal, at least one of the first to third physiological parameter measurement devices 8011, 8012, and 8013 may perform an operation of providing an alarm to the driver, but the present invention is not limited thereto.

Also, for example, when the acquired physiological parameter of the passenger is abnormal, at least one of the first to third physiological parameter measurement devices 8011, 8012, and 8013 may perform an operation of providing information about nearby hospitals, but the present invention is not limited thereto.

Also, for example, when the acquired physiological parameter of the passenger is abnormal, at least one of the first to third physiological parameter measurement devices 8011, 8012, and 8013 may transmit relevant information to another mobile device, but the present invention is not limited thereto.

Also, for example, when the acquired physiological parameter of the passenger is abnormal, at least one of the first to third physiological parameter measurement devices 8011, 8012, and 8013 performs an operation of changing a vehicle to an autonomous driving mode, but the present invention is not limited thereto.

Also, at least one of the first to third physiological parameter measurement devices 8011, 8012, and 8013 may acquire physiological information of the passenger.

For example, at least one of the first to third physiological parameter measurement devices 8011, 8012, and 8013 may acquire the physiological information of the passenger, such as drowsiness information and condition information of the driver, but the present invention is not limited thereto.

Also, at least one of the first to third physiological parameter measurement devices 8011, 8012, and 8013 may perform an operation corresponding to the acquired physiological information of the passenger.

For example, when the acquired physiological information of the passenger is abnormal, at least one of the first to third physiological parameter measurement devices 8011, 8012, and 8013 may perform an operation of providing relevant information to the driver, but the present invention is not limited thereto.

Also, for example, when the acquired physiological information of the passenger is abnormal, at least one of the first to third physiological parameter measurement devices 8011, 8012, and 8013 may transmit relevant information to another mobile device, but the present invention is not limited thereto.

Figure 69:
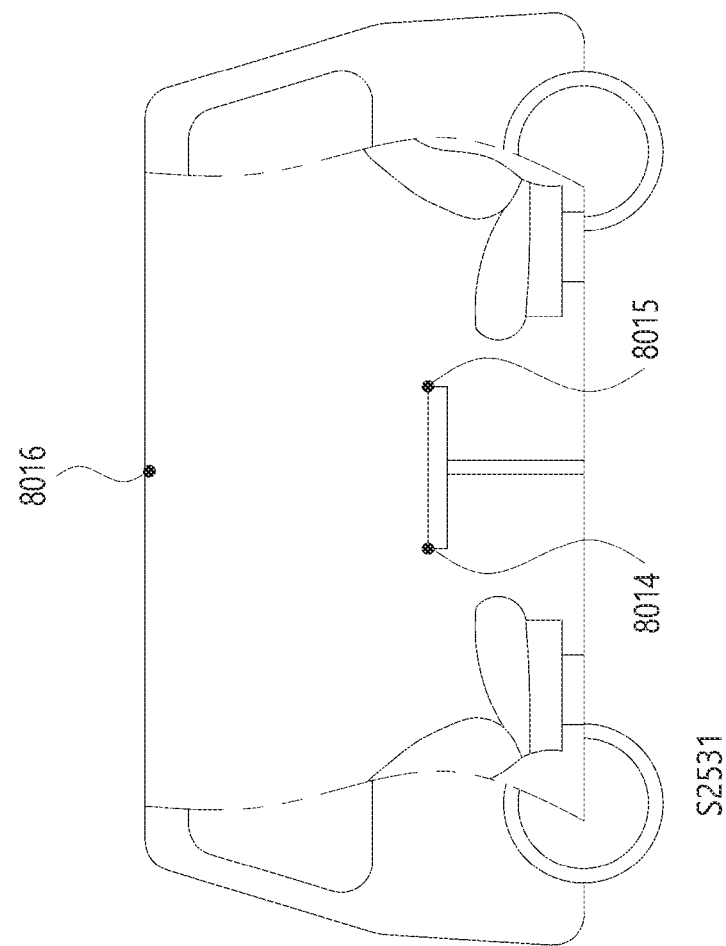
FIG. 69 is a diagram illustrating a physiological parameter measurement device placed on an autonomous vehicle according to an embodiment.

FIG. 69 is a diagram illustrating a physiological parameter measurement device placed on an autonomous vehicle according to an embodiment.

Referring to FIG. 69, a physiological parameter measurement device according to an embodiment may be placed at various positions of a vehicle.

For example, as shown in FIG. 69, a first physiological parameter measurement device 8014 may be placed on one side of a table, a second physiological parameter measurement device 8015 may be placed on the other side, and a third physiological parameter measurement device 8016 may be placed on the ceil of an autonomous vehicle, but the present invention is not limited thereto.

Also, at least one of the first to third physiological parameter measurement devices 8014, 8015, and 8016 may be placed inside the vehicle.

Also, at least one of the first to third physiological parameter measurement devices 8014, 8015, and 8016 may acquire a physiological parameter of an occupant.

For example, at least one of the first to third physiological parameter measurement devices 8014, 8015, and 8016 may measure a physiological parameter, such as a heart rate, a blood pressure, an oxygen saturation level, and a core temperature, of the occupant, but the present invention is not limited thereto.

Also, at least one of the first to third physiological parameter measurement devices 8014, 8015, and 8016 may perform an operation corresponding to the acquired physiological parameter of the occupant.

For example, when the acquired physiological parameter of the occupant is abnormal, at least one of the first to third physiological parameter measurement devices 8014, 8015, and 8016 may perform an operation of providing information about nearby hospitals, but the present invention is not limited thereto.

Also, for example, when the acquired physiological parameter of the occupant is abnormal, at least one of the first to third physiological parameter measurement devices 8014, 8015, and 8016 may perform an operation of driving to a nearby hospital, but the present invention is not limited thereto.

Also, for example, when the acquired physiological parameter of the occupant is abnormal, at least one of the first to third physiological parameter measurement devices 8014, 8015, and 8016 may transmit relevant information to another mobile device, but the present invention is not limited thereto.

Also, for example, when the acquired physiological parameter of the occupant is abnormal, at least one of the first to third physiological parameter measurement devices 8014, 8015, and 8016 may generate a hardware alarm such as sound and vibration, but the present invention is not limited thereto.

Also, for example, when the acquired physiological parameter of the occupant is abnormal, at least one of the first to third physiological parameter measurement devices 8014, 8015, and 8016 may display relevant information, but the present invention is not limited thereto.

Also, at least one of the first to third physiological parameter measurement devices 8014, 8015, and 8016 may perform an operation corresponding to a result of recognizing the occupant.

For example, at least one of the first to third physiological parameter measurement devices 8014, 8015, and 8016 may recognize the face of the occupant and display information of the occupant when the face is recognized, but the present invention is not limited thereto.

Also, for example, only when the face of the occupant is recognized and the physiological parameter is acquired, may at least one of the first to third physiological parameter measurement devices 8014, 8015, and 8016 display information of the occupant, but the present invention is not limited thereto.

Also, for example, at least one of the first to third physiological parameter measurement devices 8014, 8015, and 8016 may acquire physiological information of the occupant.

For example, at least one of the first to third physiological parameter measurement devices 8014, 8015, and 8016 may acquire the physiological information of the occupant, such as drowsiness information and condition information of the occupant, but the present invention is not limited thereto.

Also, at least one of the first to third physiological parameter measurement devices 8014, 8015, and 8016 may perform an operation corresponding to the acquired physiological information of the occupant.

For example, when the acquired physiological information of the occupant is abnormal, at least one of the first to third physiological parameter measurement devices 8014, 8015, and 8016 may generate a hardware alarm such as sound and vibration, but the present invention is not limited thereto.

Also, for example, when the acquired physiological information of the occupant is abnormal, at least one of the first to third physiological parameter measurement devices 8014, 8015, and 8016 may transmit relevant information to another mobile device, but the present invention is not limited thereto.

Also, although not shown FIGS. 68 and 69, the physiological parameter measurement device may be placed in an ambulance or the like and may be used to measure a patient's physiological parameter and acquire physiological information.

Figure 70:
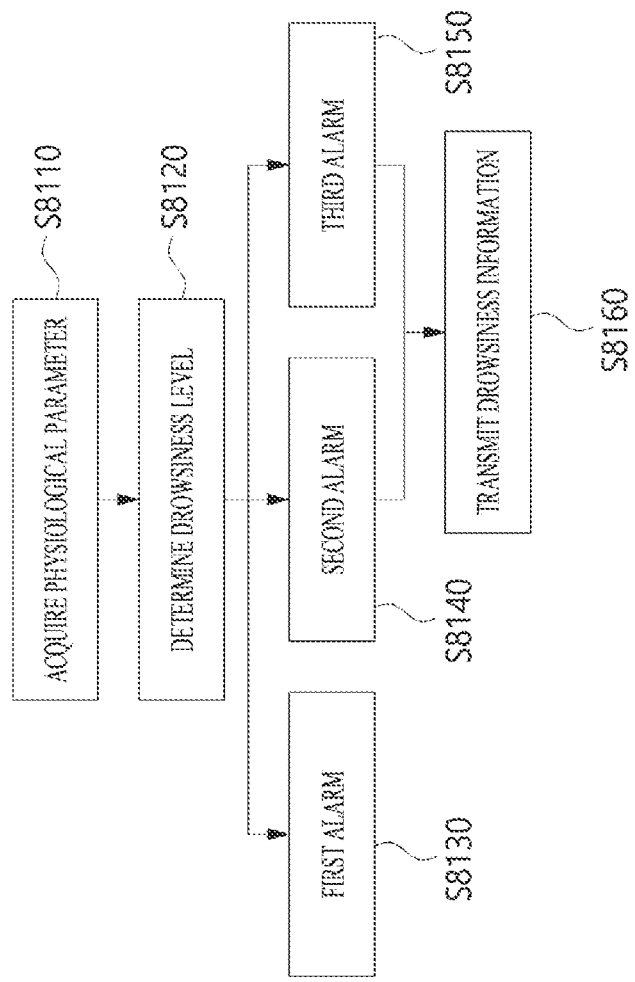
FIG. 70 is a flowchart illustrating a physiological parameter measurement device operating method according to an embodiment.

9.2.1 Various Embodiments of Physiological Parameter Measurement Device Performing Operation Corresponding to Drowsiness Information FIG. 70 is a flowchart illustrating a physiological parameter measurement device operating method according to an embodiment.

Referring to FIG. 70, a physiological parameter measurement device operating method 8100 according to an embodiment may include an operation of acquiring a physiological parameter (S8110) and an operation of determining a drowsiness level (S8120). An alarm may be output according to the determined drowsiness level. For example, as shown in FIG. 70, a first alarm S8130, a second alarm S8140, and a third alarm S8150 may be output, but the present invention is not limited thereto.

In this case, the above-described physiological parameter acquisition method or the like is applicable to the operation of acquiring a physiological parameter (S8110), and thus a redundant description thereof will be omitted.

Also, the above-described drowsiness detection method or the like is applicable to the operation of determining the drowsiness level (S8120), and thus a redundant description thereof will be omitted.

Also, the first alarm S8130 may be an alarm that is output at the lowest drowsiness level.

For example, the first alarm S8130 may include a visual alarm, but the present invention is not limited thereto.

Also, the second alarm S8140 may be an alarm that s output at a middle level.

For example, the second alarm S8140 may include an auditory alarm that has a weak intensity or a long cycle, but the present invention is not limited thereto.

Also, the third alarm S8150 may be an alarm that is output at the highest drowsiness level.

For example, the third alarm S8150 may include an auditory alarm that has a strong intensity or a short cycle, but the present invention is not limited thereto.

However, the above-described first to third alarms S8130, S8140, and S8150 are not limited to the above-described examples, and it is obvious that examples of outputting a different alarm depending on the drowsiness level are applicable.

Also, the physiological parameter measurement device operating method 8100 according to an embodiment may include an operation of transmitting drowsiness information (S8160).

Also, the operation of transmitting the drowsiness information (S8160) may be performed at only at least some drowsiness levels. For example, the operation of transmitting the drowsiness information (S8160) may not be performed at a first drowsiness level and may be performed at second and third drowsiness levels, but the present invention is not limited thereto.

Also, the operation of transmitting the drowsiness information (S8160) may include an operation of transmitting the drowsiness information to an administrator. For example, information regarding a drowsiness level of a driver of a vehicle may be transmitted to an administrator who performs vehicle dispatch and may be reflected in the vehicle dispatch.

Also, the operation of transmitting the drowsiness information (S8160) may include an operation of transmitting the drowsiness information to a driver's mobile terminal. For example, drowsiness information and information on a corresponding operating section may be transmitted to a driver's mobile terminal so that the driver can pay attention to the next operating.

Also, the operation of transmitting the drowsiness information (S8160) may include an operation of transmitting the drowsiness information to a road administrator. For example, information on a driver's drowsiness level and information on an operating section may be transmitted and used to produce a drowsiness map or the like.

Figure 71:
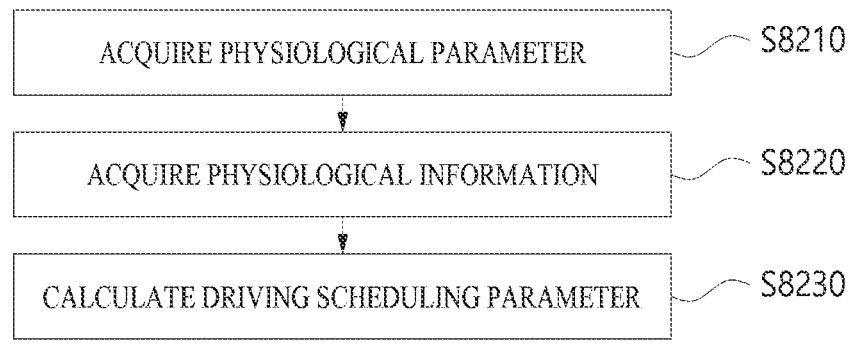
FIG. 71 is a flowchart illustrating a physiological parameter measurement device operating method according to an embodiment.

9.2.2 Various Embodiments of Driving Scheduling Method Using Physiological Parameter and Physiological Information FIG. 71 is a flowchart illustrating a physiological parameter measurement device operating method according to an embodiment.

Referring to FIG. 71, a physiological parameter measurement device operating method 8200 according to an embodiment may include at least some of an operation of acquiring a physiological parameter (S8210), an operation of acquiring physiological information (S8220), and calculating a driving scheduling parameter (S8230), but the present invention is not limited thereto.

In this case, the above-described physiological parameter acquisition method is applicable to the operation of acquiring a physiological parameter (S8210), and thus a redundant description thereof will be omitted.

Also, the above-described physiological information acquisition method is applicable to the operation of acquiring the physiological information (S8220), and thus a redundant description thereof will be omitted.

Also, the driving scheduling parameter may be a parameter for assisting in driving scheduling.

In this case, the driving scheduling parameter may be acquired based on the physiological parameter and the physiological information. For example, the driving scheduling parameter may be acquired based on heart rate information, drowsiness information, and the like of a driver, but the present invention is not limited thereto.

Also, the driving scheduling parameter may be acquired based on vehicle operating information. For example, the driving scheduling parameter may be acquired based on an operating distance, an operating time, the number of times of operating, and the like of a vehicle.

Also, the driving scheduling parameter may be acquired based on a physiological parameter and physiological information of a driver and vehicle operating information. For example, the driving scheduling parameter may be acquired based on drowsiness information of a driver, an operating distance and the number of times of operating of a vehicle, and the like, but the present invention is not limited thereto.

Figure 72:
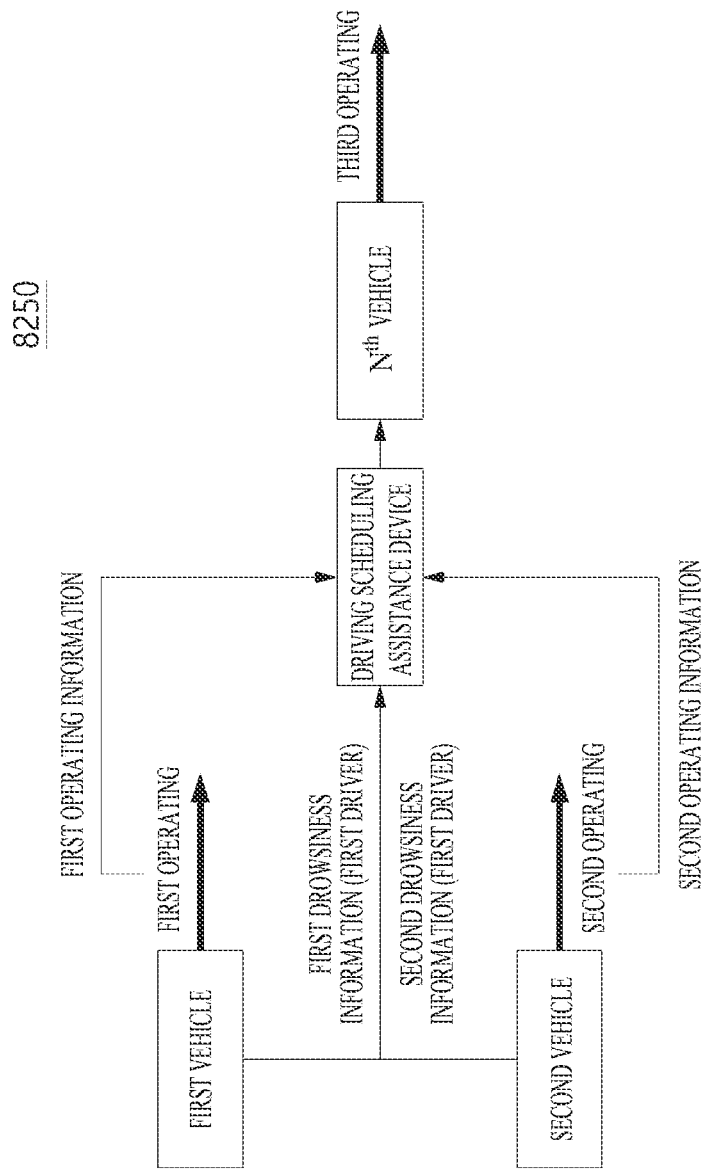
FIG. 72 is a diagram illustrating a driving scheduling assistance device operating method using a physiological parameter measurement device according to an embodiment.

FIG. 72 is a diagram illustrating a driving scheduling assistance device operating method using a physiological parameter measurement device according to an embodiment.

Referring to FIG. 72, a driving scheduling assistance device may acquire information from a first physiological parameter measurement device placed in a first vehicle and a second physiological parameter measurement device placed in a second vehicle.

In detail, the first physiological parameter measurement device may acquire a physiological parameter and physiological information of a first driver in the first vehicle. For example, the first physiological parameter measurement device may acquire a heart rate and drowsiness information of the first driver, but the present invention is not limited thereto.

Also, the second physiological parameter measurement device may acquire a physiological parameter and physiological information of a second driver in the second vehicle. For example, the second physiological parameter measurement device may acquire a heart rate and drowsiness information of the second driver, but the present invention is not limited thereto.

Also, as shown in FIG. 72, the driving scheduling assistance device may acquire the physiological parameter and physiological information of the first driver from the first physiological parameter measurement device and acquire the physiological parameter and physiological information of the second driver from the second physiological parameter measurement device, but the present invention is not limited thereto.

Also, as shown in FIG. 72, the driving scheduling assistance device may acquire first operating information for first operating of a first vehicle and second operating information for second operating of a second vehicle.

In this case, the first operating information and the second operating information may include an operating distance, the number of times of operating, an operating time, and the like, but the present invention is not limited thereto.

Also, the driving scheduling assistance device may calculate a driving scheduling parameter on the basis of the physiological parameter and physiological information of the first driver, the physiological parameter and physiological information of the second driver, the first operating information of the first vehicle, and the second operating information of the second vehicle.

For example, the driving scheduling assistance device may calculate a first driving scheduling parameter on the basis of first drowsiness information of the first driver and the first operating information of the first vehicle and calculate a second driving scheduling parameter on the basis of second drowsiness information of the second driver and the second operating information of the second vehicle, but the present invention is not limited thereto.

Also, for example, when a first operating distance included in the first operating information is equal to a second operating distance included in the second operating information, a driving scheduling parameter may be calculated so that one of the first driver and the second driver, who has a lower drowsiness parameter corresponding to drowsiness information, can perform third operating.

Also, for example, the first driving scheduling parameter may be calculated by adding different weights to the first drowsiness information and the first operating information, which are for calculating the first driving scheduling parameter.

In detail, the first driving scheduling parameter may be calculated by adding the larger weight to the first operating information, but the present invention is not limited thereto.

Also, for example, the second driving scheduling parameter may be calculated by adding different weights to the second drowsiness information and the second operating information, which are for calculating the second driving scheduling parameter.

In detail, the second driving scheduling parameter may be calculated by adding the larger weight to the second operating information, but the present invention is not limited thereto.

Also, the driving scheduling assistance device may use the calculated driving scheduling parameter to perform driving scheduling for the third operating, but the present invention is not limited thereto.

Also, the driving scheduling assistance device may display the calculated driving scheduling parameter, but the present invention is not limited thereto.

Figure 73:
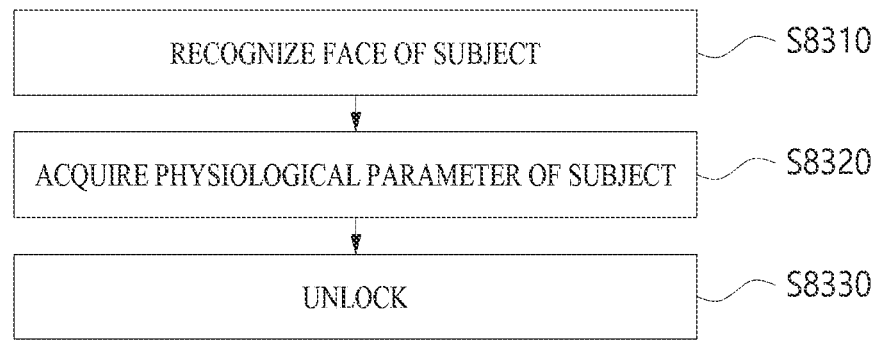
FIG. 73 is a flowchart illustrating a physiological parameter measurement device operating method according to an embodiment.

9.2.3 Various Embodiments of Physiological Parameter Measurement Device Used to Unlock Vehicle FIG. 73 is a flowchart illustrating a physiological parameter measurement device operating method according to an embodiment.

Referring to FIG. 73, a physiological parameter measurement device operating method 8300 according to an embodiment may include at least some of an operation of recognizing a subject's face (S8310), an operation of acquiring a physiological parameter of the subject (S8320), and an operation of unlocking at least some operations of a vehicle (S8330), but the present invention is not limited thereto.

In this case, the above description and a typical face recognition method are applicable to the operation of recognizing the subject's face (S8310), and thus a redundant description thereof will be omitted.

Also, the above-described physiological parameter acquisition method is applicable to the operation of acquiring a physiological parameter of the subject (S8320), and thus a redundant description thereof will be omitted.

Also, when the subject's face is recognized and the physiological parameter is acquired, the operation of unlocking at least some operations of the vehicle (S8330) may be performed.

For example, when the subject's face is recognized but the physiological parameter is not acquired, the operation of unlocking at least some operations of the vehicle (S8330) may not be performed, but the present invention is not limited thereto.

Also, in this case, it is possible to prevent unlocking caused by stolen photos or the like and strengthen vehicle security.

Also, when the recognized face of the subject matches an ID stored in a server and the physiological parameter is acquired, the operation of unlocking at least some operations of the vehicle (S8330) may be performed.

For example, when the subject's face is recognized and the physiological parameter is acquired but the recognized face of the subject does not match an ID stored in the server, the operation of unlocking at least some operations of the vehicle (S8330) may not be performed, but the present invention is not limited thereto.

Also, when the subject's face is recognized and the physiological parameter matches an ID stored in a server, the operation of unlocking at least some operations of the vehicle (S8330) may be performed.

For example, when the subject's face is recognized and the physiological parameter is acquired but the acquired physiological parameter of the subject does not match an ID stored in the server, the operation of unlocking at least some operations of the vehicle (S8330) may not be performed, but the present invention is not limited thereto.

Also, the locking of at least some operations of the vehicle may be the locking on the start-up of the vehicle, but the present invention is not limited thereto.

Figure 74:
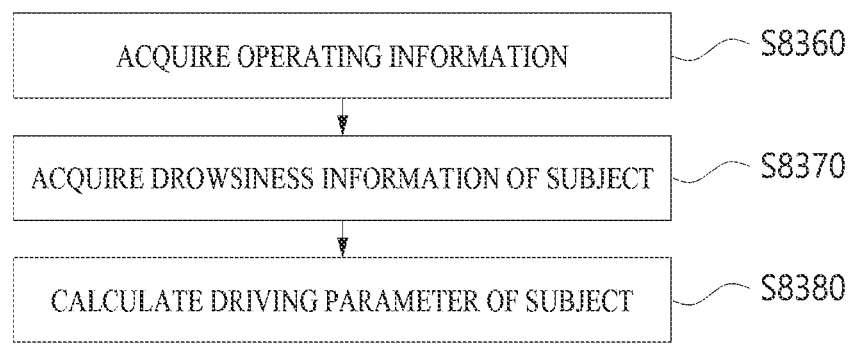
FIG. 74 is a flowchart illustrating a driving parameter calculation device operating method according to an embodiment.

9.2.4 Various Embodiments of Driving Parameter Calculation Device Operating Method Using Physiological Parameter Measurement Device FIG. 74 is a flowchart illustrating a driving parameter calculation device operating method according to an embodiment.

Referring to FIG. 74, a driving parameter calculation device operating method 8350 according to an embodiment may include at least some of an operation of acquiring operating information (S8360), an operation of acquiring drowsiness information of a subject (S8370), and an operation of calculating a driving parameter of the subject (S8380), but the present invention is not limited thereto.

In this case, the driving parameter may be a comprehensive evaluation parameter for a driver's operating or a numerical value calculated in comprehensive consideration of various pieces of information, but the present invention is not limited thereto.

Also, in this case, the operating information may include operating distance information, information on the number of times of operating, operating time information, operating section information, road information, and the like for an operating vehicle, but the present invention is not limited thereto.

Also, the above-described drowsiness detection method is applicable to the operation of acquiring the drowsiness information of the subject (S8370), and thus a redundant description thereof will be omitted.

Also, the operation of calculating the driving parameter of the subject (S8380) may include an operation of calculating a driving parameter on the basis of the operating information and the drowsiness information.

For example, the driving parameter may be calculated in comprehensive consideration of the number of times drowsiness occurs during a driving time, the degree of drowsiness, a method of coping with drowsiness, and the like, but the present invention is not limited thereto.

Also, a driver may be rewarded on the basis of the calculated driving parameter. For example, a driver may be rewarded on the basis of a driving parameter calculated based on driving time information of drivers who have been driving for a long time and drowsiness information indicating that drowsiness does not occur, but the present invention is not limited thereto.

Also, a driving parameter of a subject may be calculated in various ways on the basis of an operating time and drowsiness information in addition to the above examples.

9.3 Various Embodiments of Physiological Parameter Measurement Device Placed in Infant Monitoring Device Monitoring infants using image sensors such as a camera is becoming essential for their health and safety.

In addition, monitoring the health and safety of infants by measuring their physiological parameters is also becoming essential.

However, when a separate sensor is attached or a separate contact-type sensor is placed to monitor physiological parameters of infants, this may cause inconvenience to the infants, thereby limiting the role of a comfortable and safe shelter.

Accordingly, by monitoring infants using image sensors such as a camera and simultaneously monitoring their physiological parameters or the like using image sensors such as a camera, it is possible to protect the health and safety of the infants and provide a comfortable and safe shelter for the infants.

Figure 75:
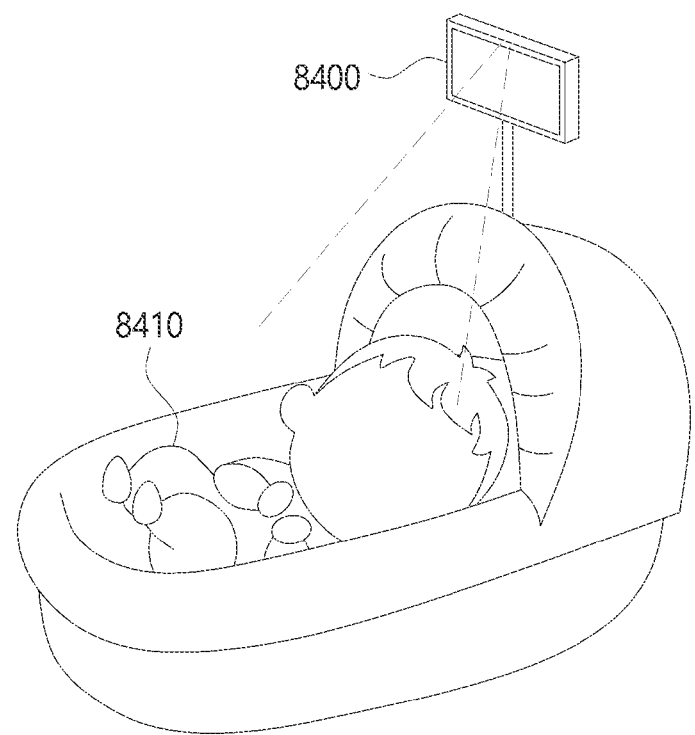
FIG. 75 is a diagram illustrating an infant monitoring device according to an embodiment.

FIG. 75 is a diagram illustrating an infant monitoring device according to an embodiment.

Referring to FIG. 75, an infant monitoring device 8400 according to an embodiment may acquire a physiological parameter of an infant 8410 in a contactless manner.

In detail, the infant monitoring device 8400 may include an image sensor and acquire a physiological parameter on the basis of an image frame acquired from the image sensor, but the present invention is not limited thereto.

Also, the above description is applicable to the infant monitoring device 8400 acquiring a physiological parameter on the basis of an image frame, and thus a redundant description thereof will be omitted.

Also, the infant monitoring device 8400 may store or transmit an image acquired through the image sensor.

For example, the infant monitoring device 8400 may acquire an image that at least partially includes an infant 8410 to be monitored and may store the acquired image or transmit the acquired image to a user's mobile phone.

Also, the infant monitoring device 8400 may detect motion of the infant 8410. For example, the infant monitoring device 8400 may detect whether the infant 8410 turns over, but the present invention is not limited thereto.

Also, the infant monitoring device 8400 may detect sound made by the infant 8410. For example, the infant monitoring device 8400 may detect the crying sound of the infant 8410, but the present invention is not limited thereto.

Also, the infant monitoring device 8400 may generate sound. For example, when an input for sound is received from an input device, the infant monitoring device 8400 may output sound corresponding to the input. In detail, when the voice of the parents of the infant 8410 is input, the infant monitoring device 8400 may output the voice, but the present invention is not limited thereto.

Also, the infant monitoring device 8400 may provide illumination. For example, when an input for illumination is received from an input device, the infant monitoring device 8400 may provide illumination corresponding to the input, but the present invention is not limited thereto.

Also, the infant monitoring device 8400 may control the movement of a cradle with the infant 8410. For example, when an input for a cradle is received from an input device, the infant monitoring device 8400 may allow the movement of the cradle corresponding to the input, but the present invention is not limited thereto.

Also, the infant monitoring device 8400 may output an alarm. For example, when an event occurs in relation to the infant 8410, the infant monitoring device 8400 may output an auditory alarm. However, the present invention is not limited thereto, and the infant monitoring device 8400 may output visual and tactile alarms and may transmit relevant information to a user's mobile terminal.

Also, the infant monitoring device 8400 may perform various operations for monitoring the infant 8410 in addition to the above-described examples.

9.3.1 Various Embodiments of Infant Monitoring Device Performing Operation Corresponding to Event Occurrence FIG. 76 is a diagram illustrating the occurrence of an event in relation to an infant.

Referring to FIG. 76, it can be seen that various events may occur in relation to an infant.

Referring to FIG. 76A, it can be seen that an event in which an infant turns over may occur.

Also, when an infant turns over, his or her breathing passage may be blocked, which can pose a great risk to the infant.

Also, referring to FIG. 76B, it can be seen that an event in which an infant moves out of a monitoring region may occur.

In this case, an infant may have been moved by a nurse at a postpartum care center or the like but may also have been moved by an unintended visitor.

Also, although not shown in FIG. 76, various events which can threaten the health and safety of an infant may occur.

Accordingly, there may be a need for an infant monitoring device capable of monitoring, tracking, and managing events.

Figure 77:
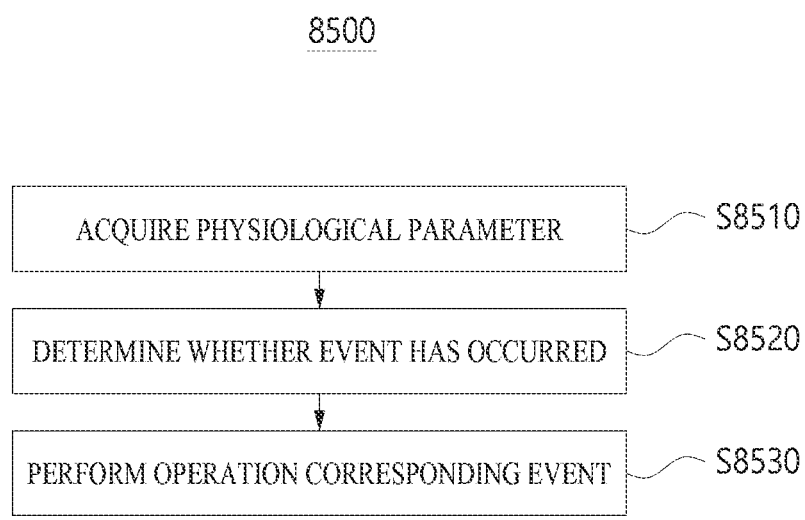
FIG. 77 is a flowchart illustrating an infant monitoring device operating method according to an embodiment.

FIG. 77 is a flowchart illustrating an infant monitoring device operating method according to an embodiment.

Referring to FIG. 77, an infant monitoring device operating method 8500 according to an embodiment may include at least some of an operation of acquiring a physiological parameter (S8510), an operation of determining whether an event has occurred (S8520), and an operation of performing an operation corresponding to the event (S8530), but the present invention is not limited thereto.

In this case, the above-described physiological parameter acquisition method is applicable to the operation of acquiring a physiological parameter (S8510), and thus a redundant description thereof will be omitted.

According to an embodiment, the operation of determining whether an event has occurred (S8520) may be performed based on the acquired physiological parameter.

For example, when no physiological parameter is acquired through the operation of acquiring a physiological parameter (S8510), it may be determined that an event has occurred. In detail, for example, when an infant whose physiological parameter is to be acquired turns over, no physiological parameter may be acquired, and in this case, it may be determined that an event has occurred, but the present invention is not limited thereto.

Also, for example, when the physiological parameter acquired through the operation of acquiring a physiological parameter (S8510) is abnormal, it may be determined that an event has occurred. In detail, for example, when a heart rate of an infant whose physiological parameter is to be acquired is abnormal, it may be determined that an event has occurred, but the present invention is not limited thereto.

Also, according to an embodiment, the operation of determining whether an event has occurred (S8520) may be performed based on a plurality of physiological parameters.

For example, it may be determined that a first event has occurred when at least one physiological parameter is not acquired through the operation of acquiring a physiological parameter (S8510), and it may be determined that a second event has occurred when all physiological parameters are not acquired, but the present invention is not limited thereto.

Also, for example, it may be determined that a first event has occurred when at least one physiological parameter acquired through the operation of acquiring a physiological parameter (S8510) is abnormal, and it may be determined that a second event has occurred when all physiological parameters are abnormal, but the present invention is not limited thereto.

Also, according to an embodiment, the operation of determining whether an event has occurred (S8520) may be performed based on a change in the physiological parameter.

For example, it may be determined that an event has occurred when a sudden change in the physiological parameter acquired through the operation of acquiring a physiological parameter (S8510) is detected. In detail, for example, when an infant whose physiological parameter is to be acquired changes from a sleep state to an awake state, the heart rate of the infant may increase, and in this case, it may be determined that an event has occurred, but the present invention is not limited thereto.

Also, according to an embodiment, the operation of performing the operation corresponding to the event (S8530) may include an operation of performing an operation corresponding to determined event information.

In this case, the operation corresponding to the event may include a hardware alarm such as visual, auditory, and tactile alarms. For example, when it is determined that an event has occurred, the infant monitoring device may output an auditory sound alarm, but the present invention is not limited thereto.

Also, the operation corresponding to the event may include an operation of recording an image. For example, when it is determined that an event has occurred, the infant monitoring device may operate to record an image, but the present invention is not limited thereto.

Also, the operation corresponding to the event may include an operation of transmitting information on the event. For example, when it is determined that an event has occurred, the infant monitoring device may transmit the information on the event to a user's mobile terminal, but the present invention is not limited thereto.

Also, the operation corresponding to the event may include an operation of storing information on an event occurrence time point. For example, when it is determined that an event has occurred, the infant monitoring device may store information on an event occurrence time point, but the present invention is not limited thereto.

Also, the operation corresponding to the event may include various operations corresponding to the event that has occurred other than the above examples.

Figure 78:
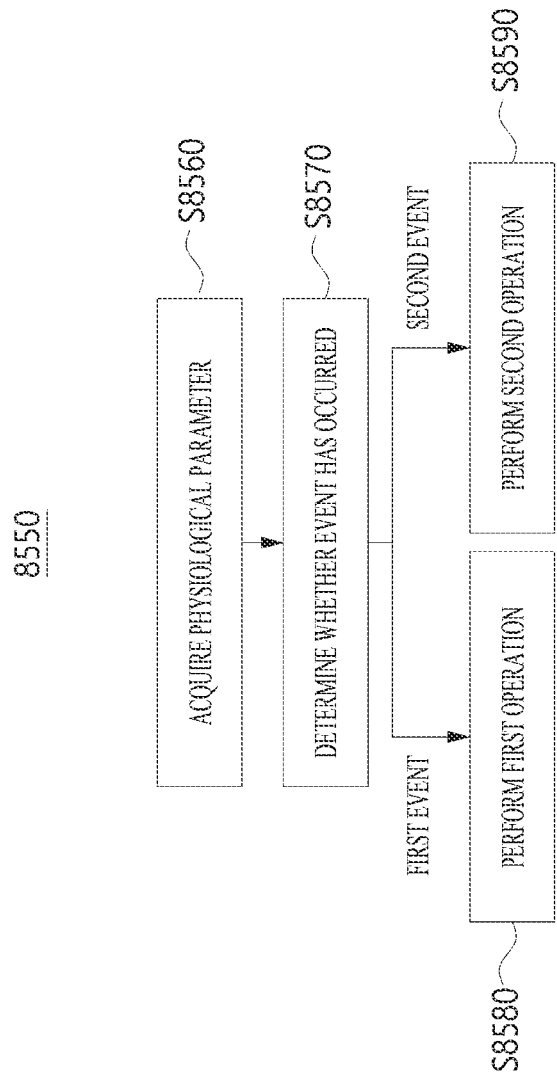
FIG. 78 is a flowchart illustrating an infant monitoring device operating method according to an embodiment.

FIG. 78 is a flowchart illustrating an infant monitoring device operating method according to an embodiment.

Referring to FIG. 78, an infant monitoring device operating method 8550 according to an embodiment may include at least some of an operation of acquiring a physiological parameter (S8560), an operation of determining whether an event has occurred (S8570), an operation of performing a first operation corresponding to a first event (S8580), and an operation of performing a second operation corresponding to a second event (S8590), but the present invention is not limited thereto.

In this case, the above-described physiological parameter acquisition method is applicable to the operation of acquiring a physiological parameter (S8560), and thus a redundant description thereof will be omitted.

According to an embodiment, the operation of determining whether an event has occurred (S8570) may be performed based on the acquired physiological parameter.

For example, when no physiological parameter is acquired through the operation of acquiring a physiological parameter (S8560), it may be determined that an event has occurred. In detail, for example, when an infant whose physiological parameter is to be acquired turns over, no physiological parameter may be acquired, and in this case, it may be determined that an event has occurred, but is not limited thereto.

Also, for example, when the physiological parameter acquired through the operation of acquiring the physiological parameter (S8560) is abnormal, it may be determined that an event has occurred. In detail, for example, when a heart rate of an infant whose physiological parameter is to be acquired is abnormal, it may be determined that an event has occurred, but the present invention is not limited thereto.

Also, according to an embodiment, the operation of determining whether an event has occurred (S8570) may be performed based on a plurality of physiological parameters.

For example, it may be determined that a first event has occurred when at least one physiological parameter is not acquired through the operation of acquiring the physiological parameter (S8560), and it may be determined that a second event has occurred when all physiological parameters are not acquired, but the present invention is not limited thereto.

Also, for example, it may be determined that a first event has occurred when at least one physiological parameter acquired through the operation of acquiring the physiological parameter (S8560) is abnormal, and it may be determined that a second event has occurred when all physiological parameters are abnormal, but the present invention is not limited thereto.

Also, according to an embodiment, the operation of determining whether an event has occurred (S8570) may be performed based on a change in the physiological parameter.

For example, it may be determined that an event has occurred when a sudden change in the physiological parameter acquired through the operation of acquiring the physiological parameter (S8560) is detected. In detail, for example, when an infant whose physiological parameter is to be acquired changes from a sleep state to an awake state, the heart rate of the infant may increase, and in this case, it may be determined that an event has occurred, but the present invention is not limited thereto.

Also, according to an embodiment, the operation of performing the first operation corresponding to the first event (S8580) and the operation of performing the second operation corresponding to the second event (S8590) may include an operation of performing an operation corresponding to determined event information.

In this case, the first operation and the second operation may include a hardware alarm such as visual, auditory, and tactile alarms. For example, when it is determined that an event has occurred, the infant monitoring device may output an auditory sound alarm, but the present invention is not limited thereto.

Also, the first operation and the second operation may include an operation of recording an image. For example, when it is determined that an event has occurred, the infant monitoring device may operate to record an image, but the present invention is not limited thereto.

Also, the first operation and the second operation may include an operation of transmitting information on the event. For example, when it is determined that an event has occurred, the infant monitoring device may transmit the information on the event to a user's mobile terminal, but the present invention is not limited thereto.

Also, the first operation and the second operation may include an operation of storing information on an event occurrence time. For example, when it is determined that an event has occurred, the infant monitoring device may store information on an event occurrence time point, but the present invention is not limited thereto.

Also, the first operation and the second operation may be different from each other. However, these operations may be entirely or at least partially the same.

Also, the first operation and the second operation may include various operations corresponding to the first event and the second event other than the above-described examples.

9.3.2 Various Embodiments of Infant Monitoring System

Figure 79:
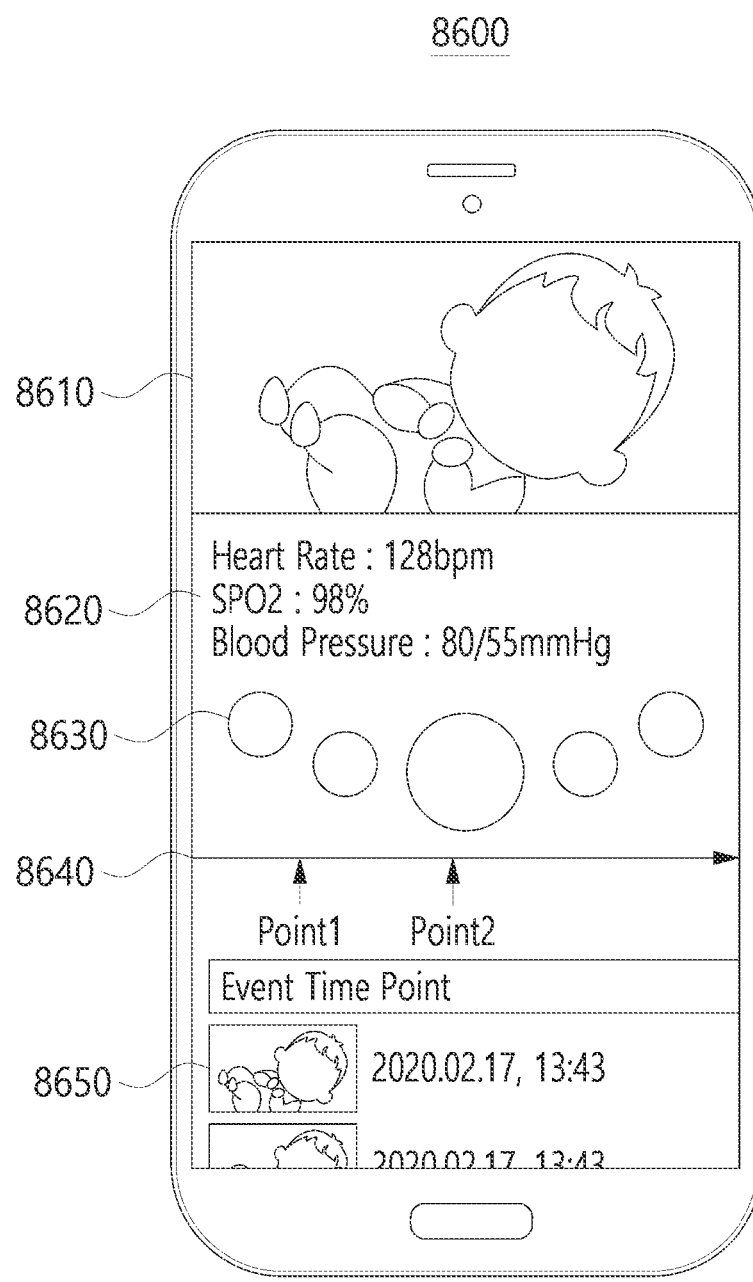
FIG. 79 is a diagram showing a mobile application for implementing an infant monitoring system according to an embodiment.

FIG. 79 is a diagram showing a mobile application for implementing an infant monitoring system according to an embodiment.

Referring to FIG. 79, a mobile application 8600 according to an embodiment may include at least some of a video display region 8610, a physiological parameter display region 8620, an input button display region 8630, a video time display region 8640, and a display region 8650 for a video recorded during an event time, but the present invention is not limited thereto.

In this case, a video displayed in the video display region 8610 may be a video or image acquired from the image monitoring device, but the present invention is not limited thereto.

Also, a physiological parameter displayed in the physiological parameter display region 8620 includes at least one physiological parameter. For example, as shown in FIG. 79, the physiological parameter may include a heart rate, an oxygen saturation level, a blood pressure, and the like, but the present invention is not limited thereto.

Also, a physiological parameter displayed in the physiological parameter display region 8620 may be a physiological parameter acquired from an infant monitoring device, but the present invention is not limited thereto.

Also, a physiological parameter displayed in the physiological parameter display region 8620 may be a physiological parameter acquired from at least one sensor, but the present invention is not limited thereto.

Also, a physiological parameter displayed in the physiological parameter display region 8620 may include physiological parameters acquired from different sensors. For example, a heart rate displayed in the physiological parameter display region 8620 may be a physiological parameter acquired from an infant monitoring device, and a blood pressure may be a physiological parameter acquired from an external blood pressure sensor, but the present invention is not limited thereto.

Also, an input button displayed in the input button display region 8630 may include at least one input button.

Also, the input button may include at least some of a video record button, an illumination button, a talk button, a cradle shaking button, and an alarm button, but the present invention is not limited thereto.

Also, a video time displayed in the video time display region 8640 may be time information of a recorded video.

Also, an event occurrence time point may be included in the video time displayed in the video time display region 8640. For example, as shown in FIG. 79, a first-event occurrence time point and a second-event occurrence time point may be included in the video time, but the present invention is not limited thereto.

Also, a thumbnail of the recorded video may be displayed in the display region 8650 for a video recorded during an event time.

Also, information on the recorded video may be displayed in the display region 8650 for a video recorded during an event time. For example, as shown in FIG. 79, time information of the recorded video or the like may be displayed, but the present invention is not limited thereto.

However, the above-described examples and drawings are for illustrative purposes only, and the present invention is not limited thereto. Various forms of applications may be provided as an application for implementing the infant monitoring system.

9.4 Various Embodiments of Physiological Parameter Measurement Device Placed in Reading Room By measuring a physiological parameter and physiological information in spaces for personal work and study, such as a reading room, it is possible to monitor individuals' concentration while continuously monitoring their health, thereby enabling efficient work or study.

Also, the concentration may be acquired based on a heart rate. For example, concentration information may be acquired based on a change, magnitude, and a change pattern of a heart rate, but the present invention is not limited thereto.

Figure 80:
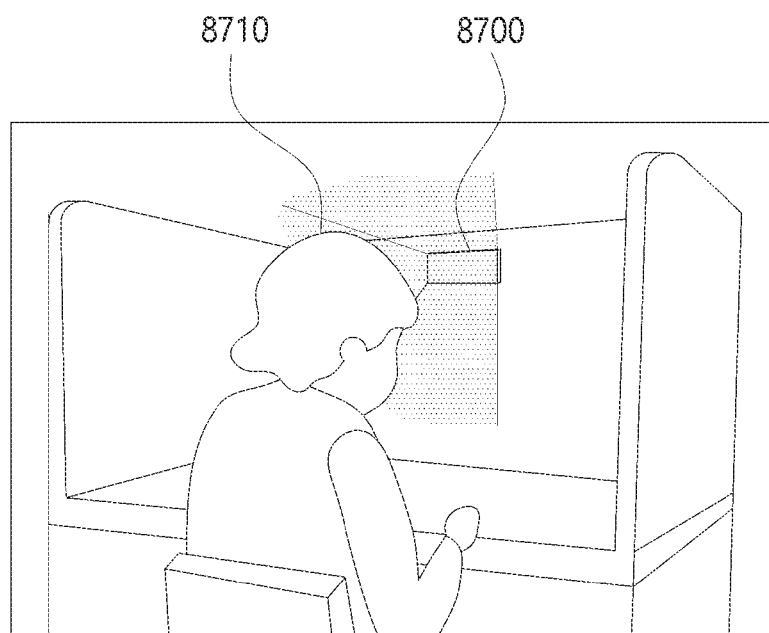
FIG. 80 is a diagram illustrating a physiological parameter measurement device placed in a reading room according to an embodiment.

FIG. 80 is a diagram illustrating a physiological parameter measurement device placed in a reading room according to an embodiment.

Referring to FIG. 80, a physiological parameter measurement device 8700 according to an embodiment may acquire a physiological parameter and physiological information of a subject 8710.

In this case, the physiological parameter may include a heart rate, an oxygen saturation level, a blood pressure, a core temperature, or the like, but the present invention is not limited thereto.

Also, the physiological information may include physiological information such as drowsiness information, condition information, and concentration information, but the present invention is not limited thereto.

Also, the above description is applicable to a method of acquiring the physiological parameter and the physiological information, and thus a redundant description thereof will be omitted.

Figure 81:
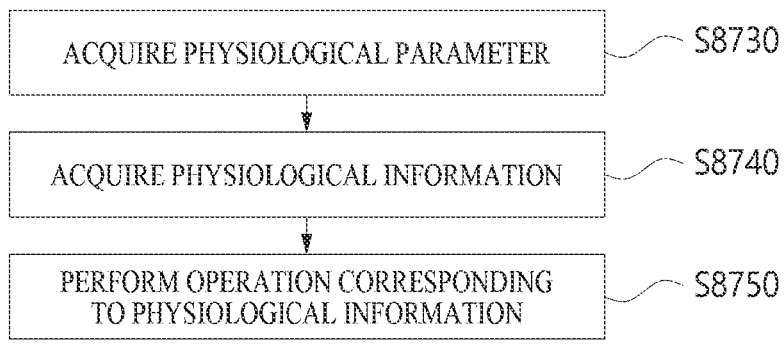
FIG. 81 is a flowchart illustrating a physiological parameter measurement device operating method according to an embodiment.

FIG. 81 is a flowchart illustrating a physiological parameter measurement device operating method according to an embodiment.

Referring to FIG. 81, a physiological parameter measurement device operating method 8720 according to an embodiment may include at least some of an operation of acquiring a physiological parameter (S8730), an operation of acquiring physiological information (S8740), and performing an operation corresponding to the physiological information (S8750).

In this case, the above description is applicable to the operation of acquiring the physiological parameter (S8730) and the operation of acquiring the physiological information (S8740), and thus a redundant description thereof will be omitted.

Also, the operation of performing the operation corresponding to the physiological information (S8750) may include an operation of performing various operations corresponding to various pieces of physiological information.

For example, when the physiological information is drowsiness information, the physiological parameter measurement device may perform an operation of outputting an alarm according to a drowsiness level, but the present invention is not limited thereto.

Also, for example, when the physiological information is drowsiness information, the physiological parameter measurement device may perform an operation of transmitting information to an administrator according to a drowsiness level, but the present invention is not limited thereto.

Also, for example, when the physiological information is drowsiness information, the physiological parameter measurement device may perform an operation of transmitting information to a user's terminal according to a drowsiness level, but the present invention is not limited thereto.

Also, for example, when the physiological information is drowsiness information, the physiological parameter measurement device may perform an operation of transmitting information to a scheduling device according to a drowsiness level, but the present invention is not limited thereto.

Also, for example, when the physiological information is drowsiness information, the physiological parameter measurement device may perform an operation of outputting an advisory text for taking a rest according to a drowsiness level, but the present invention is not limited thereto.

Also, for example, when the physiological information is condition information, the physiological parameter measurement device may perform an operation of outputting an alarm according to a condition, but the present invention is not limited thereto.

Also, for example, when the physiological information is condition information, the physiological parameter measurement device may perform an operation of transmitting information to an administrator according to a condition, but the present invention is not limited thereto.

Also, for example, when the physiological information is condition information, the physiological parameter measurement device may perform an operation of transmitting information to a user's terminal according to a condition, but the present invention is not limited thereto.

Also, for example, when the physiological information is condition information, the physiological parameter measurement device may perform an operation of transmitting information to a scheduling device according to a condition, but the present invention is not limited thereto.

Also, for example, when the physiological information is condition information, the physiological parameter measurement device may perform an operation of outputting an advisory text for taking a rest according to a condition, but the present invention is not limited thereto.

Also, for example, when the physiological information is concentration information, the physiological parameter measurement device may perform an operation of outputting an alarm according to a concentration, but the present invention is not limited thereto.

Also, for example, when the physiological information is concentration information, the physiological parameter measurement device may perform an operation of transmitting information to an administrator according to a concentration, but the present invention is not limited thereto.

Also, for example, when the physiological information is concentration information, the physiological parameter measurement device may perform an operation of transmitting information to a user's terminal according to a concentration, but the present invention is not limited thereto.

Also, for example, when the physiological information is concentration information, the physiological parameter measurement device may perform an operation of transmitting information to a scheduling device according to a concentration, but the present invention is not limited thereto.

Also, the physiological parameter measurement device may perform an operation corresponding to the physiological information and the physiological parameter.

Also, the physiological parameter measurement device may perform various operations corresponding to the physiological information and the physiological parameter other than the above-described examples.

Figure 82:
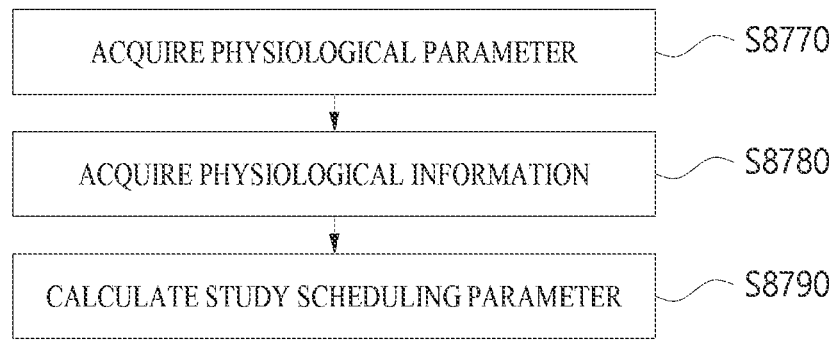
FIG. 82 is a flowchart illustrating a physiological parameter measurement device operating method according to an embodiment.

FIG. 82 is a flowchart illustrating a physiological parameter measurement device operating method according to an embodiment.

Referring to FIG. 82, a physiological parameter measurement device operating method 8760 according to an embodiment may include at least some of an operation of acquiring a physiological parameter (S8770), an operation of acquiring physiological information (S8780), and an operation of calculating a study or work scheduling parameter (S8790).

In this case, the above description is applicable to the operation of acquiring the physiological parameter (S8770) and the operation of acquiring the physiological information (S8780), and thus a redundant description thereof will be omitted.

Also, the operation of calculating the study or work scheduling parameter (S8790) may be performed based on the acquired physiological parameter and/or physiological information.

For example, the study or work scheduling parameter may be calculated based on an acquired heart rate and drowsiness information, but the present invention is not limited thereto.

Also, the operation of calculating the study or work scheduling parameter (S8790) may be performed based on the acquired physiological parameter or physiological information and/or study-related information.

For example, the study or work scheduling parameter may be calculated based on acquired drowsiness information and study time information, but the present invention is not limited thereto.

Also, scheduling may be carried out using the study or work scheduling parameter so that study or work is performed in a time period with high efficiency.

Also, scheduling may be carried out using the study or work scheduling parameter so that a rest is taken in a time period with low efficiency.

Accordingly, scheduling may be carried out so that study or work can be performed with the maximum efficiency in a limited time when the study or work scheduling parameter is used.

9.5 Various Embodiments of Physiological Parameter Measurement Device Used for Cognitive Rehabilitation Therapy In the case of patients who receive cognitive rehabilitation therapy, treatment effects can be maximized only when high-intensity treatment is performed during cognitive rehabilitation therapy.

However, supply of rehabilitation therapists to monitor individual patients' concentration may not meet demand, so it may be difficult to increase the individual patients' concentration to perform high-quality treatment.

Therefore, when a physiological parameter and physiological information are acquired using a physiological parameter measurement device in order to compensate for the difficulty, it is possible to monitor individual patients' concentration, and also it is possible to perform high-quality treatment using the monitoring.

Figure 83:
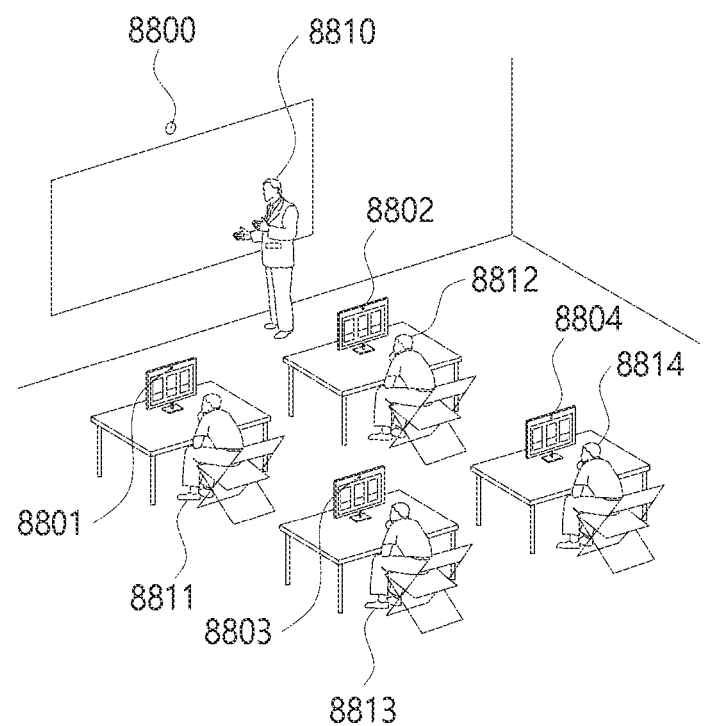
FIG. 83 is a diagram illustrating a physiological parameter measurement device used for cognitive rehabilitation therapy according to an embodiment.

FIG. 83 is a diagram illustrating a physiological parameter measurement device used for cognitive rehabilitation therapy according to an embodiment.

Referring to FIG. 83, a physiological parameter measurement device according to an embodiment may include at least one of a first physiological parameter measurement device 8800, a second physiological parameter measurement device 8801, a third physiological parameter measurement device 8802, a fourth physiological parameter measurement device 8803, and a fifth physiological parameter measurement device 8804.

Also, at least one of the first to fifth physiological parameter measurement devices 8800, 8801, 8802, 8803, and 8804 may measure a physiological parameter of at least one of first to fourth patients 8811, 8812, 8813, and 8814.

In this case, the above description is applicable to the physiological parameter measurement method, and thus a redundant description thereof will be omitted.

Also, at least one of the first to fifth physiological parameter measurement devices 8800, 8801, 8802, 8803, and 8804 may acquire physiological information of at least one of the first to fourth patients 8811, 8812, 8813, and 8814. For example, at least one of the first to fifth physiological parameter measurement devices 8800, 8801, 8802, 8803, and 8804 may acquire concentration information of at least one of the first to fourth patients 8811, 8812, 8813, and 8814.

Also, when physiological information of at least one of the first to fourth patients 8811, 8812, 8813, and 8814 is abnormal, at least one of the first to fifth physiological parameter measurement devices 8800, 8801, 8802, 8803, and 8804 may output an alarm so that a rehabilitation therapist 8810 can recognize the abnormality. For example, when physiological information of at least one of the first to fourth patients 8811, 8812, 8813, and 8814 is abnormal, at least one of the first to fifth physiological parameter measurement devices 8800, 8801, 8802, 8803, and 8804 may output an auditory alarm and transmit information related to the physiological information to a mobile terminal of the rehabilitation therapist 8810, but the present invention is not limited thereto.

Also, when physiological information of at least one of the first to fourth patients 8811, 8812, 8813, and 8814 is abnormal, at least one of the first to fifth physiological parameter measurement devices 8800, 8801, 8802, 8803, and 8804 may output an alarm so that the patient can recognize the abnormality of the physiological information. For example, when physiological information of at least one of the first to fourth patients 8811, 8812, 8813, and 8814 is abnormal, at least one of the first to fifth physiological parameter measurement devices 8800, 8801, 8802, 8803, and 8804 may output an auditory alarm and display information related to the physiological information through a display of the corresponding patient.

Also, as described above, by monitoring a patient's physiological parameter and physiological information in real time and maintaining his or her concentration during treatment, it is possible to maximize the effect of cognitive rehabilitation therapy.

Figure 84:
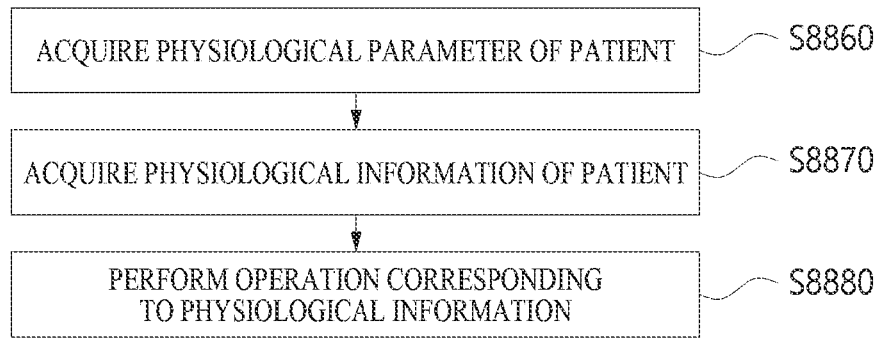
FIG. 84 is a flowchart illustrating a physiological parameter measurement device operating method according to an embodiment.

FIG. 84 is a flowchart illustrating a physiological parameter measurement device operating method according to an embodiment.

Referring to FIG. 84, a physiological parameter measurement device operating method 8850 according to an embodiment may include at least some of an operation of acquiring a physiological parameter of a patient (S8860), an operation of acquiring physiological information of the patient (S8870), and performing an operation corresponding to the physiological information of the patient (S8880).

In this case, the above description is applicable to the operation of acquiring the physiological parameter of the patient (S8860) and the operation of acquiring the physiological information of the patient (S8870), and thus a redundant description thereof will be omitted.

Also, the operation of performing the operation corresponding to the physiological information of the patient (S8880) may include an operation of performing various operations corresponding to various pieces of physiological information.

For example, when the physiological information is concentration information, the physiological parameter measurement device may perform an operation of outputting an alarm according to a concentration, but the present invention is not limited thereto.

Also, for example, when the physiological information is concentration information, the physiological parameter measurement device may perform an operation of transmitting information to be displayed on the patient's display according to a concentration, but the present invention is not limited thereto.

Also, for example, when the physiological information is concentration information, the physiological parameter measurement device may perform an operation of transmitting information to a rehabilitation therapist's mobile terminal according to a concentration, but the present invention is not limited thereto.

Also, for example, when the physiological information is concentration information, the physiological parameter measurement device may perform an operation of outputting an indication for increasing a concentration according to the concentration, but the present invention is not limited thereto.

Also, the physiological parameter measurement device may perform an operation corresponding to physiological information and a physiological parameter.

Also, the physiological parameter measurement device may perform various operations corresponding to the physiological information and the physiological parameter other than the above-described examples.

9.6 Various Embodiments of Physiological Parameter Measurement Device Used in Immigration Screening Inspection and quarantine at airports where people of various countries and races come and go can serve as an important gatekeeper to a national quarantine system.

However, it may be difficult to provide in-depth management for individuals due to a lack of management personnel compared to those who enter airports.

Therefore, when a physiological parameter is easily measured at a place where individuals are subjected to immigration screening, it is possible to more easily provide in-depth management for individuals.

Figure 85:
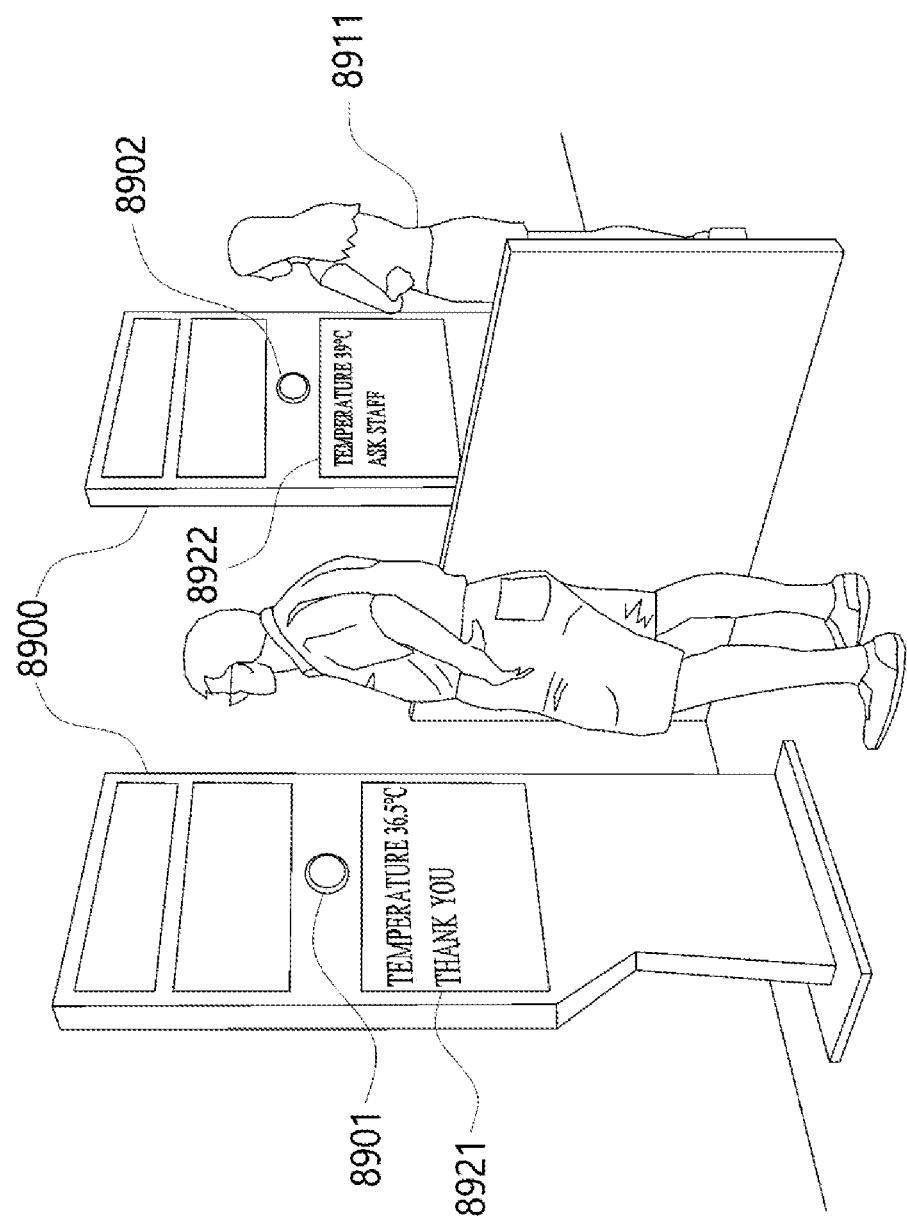
FIG. 85 is a diagram illustrating a physiological parameter measurement device used for immigration screening according to an embodiment.

FIG. 85 is a diagram illustrating a physiological parameter measurement device used for immigration screening according to an embodiment.

Referring to FIG. 85, physiological parameter measurement devices 8901 and 8902 according to an embodiment may be placed in an immigration kiosk 8900 and configured to measure physiological parameters of immigrants 8911 and 8912.

In this case, the physiological parameter measurement devices 8901 and 8902 may perform face recognition or the like used for immigration screening, but the present invention is not limited thereto.

Also, the physiological parameter may include at least one of a heart rate, an oxygen saturation level, a blood pressure, a core temperature, or the like, but the present invention is not limited thereto.

Also, the above description is applicable to a method of the physiological parameter measurement devices 8901 and 8902 measuring a physiological parameter, and thus a redundant description thereof will be omitted.

Also, the physiological parameter measurement devices 8901 and 8902 may perform an operation corresponding to a measured physiological parameter. For example, as shown in FIG. 85, the first physiological parameter measurement device 8901 may operate to display first information 8921 indicating entry allowance when a measured core temperature of a first immigrant 8911 is in a normal range, and the second physiological parameter measurement device 8902 may operate to display second information 8922 requiring more accurate core temperature measurement when a measured core temperature of a second immigrant 8912 deviates from a normal range, but the present invention is not limited thereto.

Also, as described above, by monitoring a physiological parameter of an immigrant screening during immigration to reinforce inspection and quarantine, it is possible to maximize the effect of national quarantine.

Figure 86:
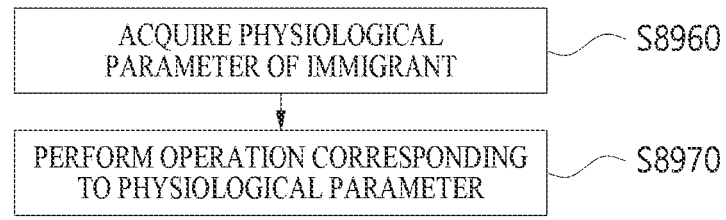
FIG. 86 is a flowchart illustrating a physiological parameter measurement device operating method according to an embodiment.

FIG. 86 is a flowchart illustrating a physiological parameter measurement device operating method according to an embodiment.

Referring to FIG. 86, a physiological parameter measurement device operating method 8950 according to an embodiment may include at least some of an operation of acquiring a physiological parameter of an immigrant (S8960) and an operation of performing an operation corresponding to the physiological parameter (S8970).

In this case, the above description is applicable to the operation of acquiring the physiological parameter of the immigrant (S8960), and thus a redundant description thereof will be omitted.

Also, the operation of performing the operation corresponding to the physiological parameter (S8970) may include an operation of performing various operations corresponding to various physiological parameters.

For example, when the physiological parameter is a heart rate, which is in a normal range, the physiological parameter measurement device may perform a corresponding operation, but the present invention is not limited thereto.

Also, for example, when the physiological parameter is a heart rate, which deviates from a normal range, the physiological parameter measurement device may perform a corresponding operation, but the present invention is not limited thereto.

Also, for example, when the physiological parameter is an oxygen saturation level, which is in a normal range, the physiological parameter measurement device may perform a corresponding operation, but the present invention is not limited thereto.

Also, for example, when the physiological parameter is an oxygen saturation level, which deviates from a normal range, the physiological parameter measurement device may perform a corresponding operation, but the present invention is not limited thereto.

Also, for example, when the physiological parameter is a blood pressure, which is in a normal range, the physiological parameter measurement device may perform a corresponding operation, but the present invention is not limited thereto.

Also, for example, when the physiological parameter is a blood pressure, which deviates from a normal range, the physiological parameter measurement device may perform a corresponding operation, but the present invention is not limited thereto.

Also, for example, when the physiological parameter is a core temperature, which is in a normal range, the physiological parameter measurement device may perform a corresponding operation, but the present invention is not limited thereto.

Also, for example, when the physiological parameter is a core temperature, which deviates from a normal range, the physiological parameter measurement device may perform a corresponding operation, but the present invention is not limited thereto.

Also, for example, the corresponding operation when the physiological parameter is in a normal range may include an operation of displaying entry allowance information, but the present invention is not limited thereto.

Also, for example, the corresponding operation when the physiological parameter deviates from a normal range may include an operation of displaying information indicating entry denial or information indicating a person subject to in-depth examination, but the present invention is not limited thereto.

Also, the physiological parameter measurement device may perform various operations corresponding to the physiological parameter other than the above-described examples.

9.7 Various Embodiments of Physiological Parameter Measurement Device Used in Security Device Security devices using physiological recognition such as face recognition, iris recognition, and fingerprint recognition are being widely used.

However, there is also a situation in which security devices are disabled through photos, fingerprint copying, and the like.

Accordingly, by using physiological parameters in addition to physiological recognition, it is possible to prevent a security device from being incapacitated and reinforce a security device.

Figure 87:
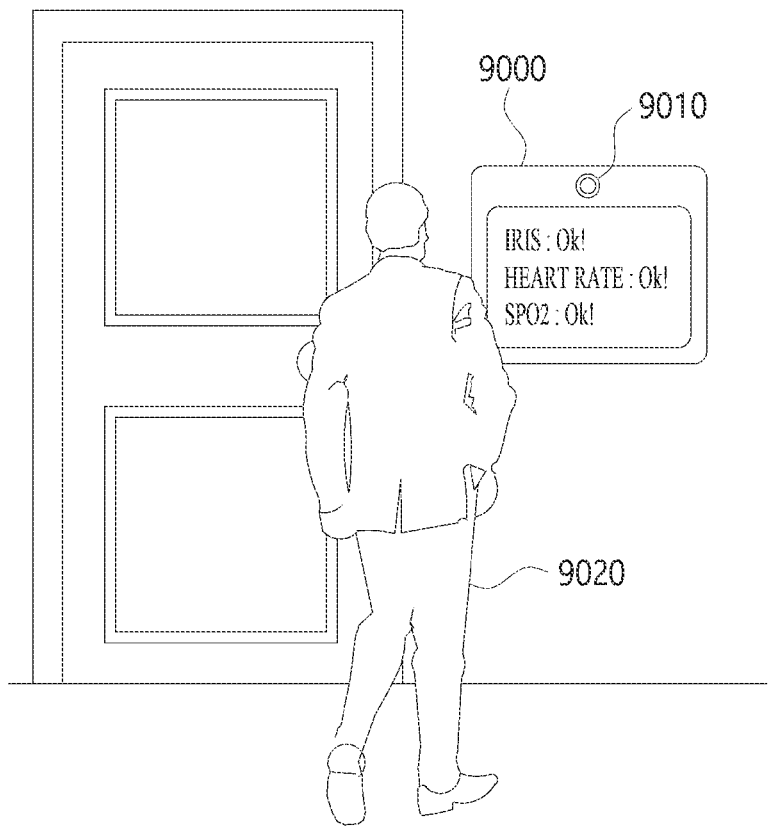
FIG. 87 is a diagram illustrating a physiological parameter measurement device used for a security device according to an embodiment.

FIG. 87 is a diagram illustrating a physiological parameter measurement device used for a security device according to an embodiment.

Referring to FIG. 87, a physiological parameter measurement device 9010 according to an embodiment may be placed in a security device 9000 and configured to measure a physiological parameter of a subject 9020.

In detail, the security device 9000 may perform physiological recognition, such as face recognition, fingerprint recognition, and iris recognition, on the subject 9020, but the present invention is not limited thereto.

Also, the physiological parameter measurement device 9010 may acquire the physiological parameter of the subject 9020, but the present invention is not limited thereto.

In this case, the physiological parameter may include at least one of a heart rate, an oxygen saturation level, a blood pressure, a core temperature, or the like, but the present invention is not limited thereto.

Also, the above description is applicable to a method of the physiological parameter measurement device 9010 measuring a physiological parameter, and thus a redundant description thereof will be omitted.

Also, the security device 9000 may release security on the basis of physiological recognition and a measured physiological parameter. For example, the security device 9000 may determine whether a user is designated through iris recognition first and then determine whether the user is a person through the acquisition of a physiological parameter to release security, but the present invention is not limited thereto.

Also, the security device 9000 may release security on the basis of a plurality of physiological parameters and a plurality of times of physiological recognition. For example, the security device 9000 may determine whether a user is designated through iris recognition and fingerprint recognition first and then determine whether the user is a person through the acquisition of a heart rate and an oxygen saturation level to release security, but the present invention is not limited thereto.

Also, the security device 9000 may release security on the basis of the physiological parameter. For example, when a signal related to an acquired heartbeat matches a signal related to the designated user's heartbeat, the security device 9000 may determine that the user is a designated user and release security, but the present invention is not limited thereto.

Also, as described above, by additionally utilizing the physiological parameter measurement device in the security device to reinforce security, it is possible to maximize the effect of security reinforcement.

Figure 88:
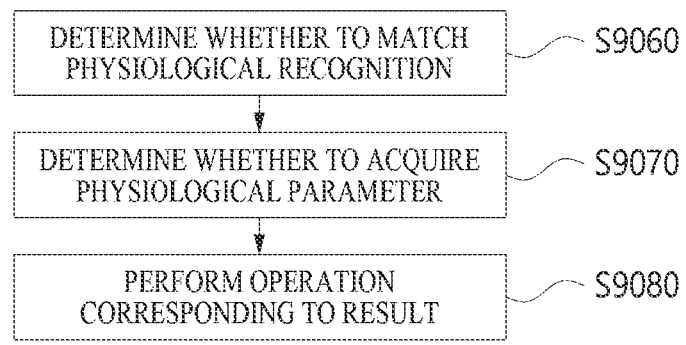
FIG. 88 is a flowchart illustrating a security device operating method according to an embodiment.

FIG. 88 is a flowchart illustrating a security device operating method according to an embodiment.

Referring to FIG. 88, a security device operating method 9050 according to an embodiment may include an operation of determining whether to match physiological recognition (S9060), an operation of determining whether to acquire a physiological parameter (S9070), and an operation of performing an operation corresponding to a result (S9080).

In this case, the physiological recognition may include at least one of fingerprint recognition, face recognition, iris recognition, and the like.

Also, the physiological parameter may include at least one of a heart rate, an oxygen saturation level, a blood pressure, a core temperature, or the like.

Also, a typical physiological recognition method is applicable to the operation of determining whether to match physiological recognition (S9060), but the present invention is not limited thereto.

Also, the above description is applicable to a method of acquiring the physiological parameter in order to determine whether to acquire the physiological parameter, and thus a redundant description thereof will be omitted.

Also, the operation of determining whether to acquire the physiological parameter (S9070) may include an operation of determining whether to acquire various physiological parameters. For example, the operation of determining whether to acquire the physiological parameter (S9070) may include an operation of determining whether a heart rate is to be acquired, but the present invention is not limited thereto.

Also, the operation of determining whether to acquire the physiological parameter (S9070) may include an operation of determining whether to match a physiological signal for acquiring the physiological parameter. For example, the operation of determining whether to acquire the physiological parameter (S9070) may include an operation of determining whether a heartbeat signal for acquiring a heart rate matches a heartbeat signal of the designated user, but the present invention is not limited thereto.

Also, the operation of determining whether to acquire the physiological parameter (S9070) may include an operation of determining whether to match the physiological parameter. For example, the operation of determining whether to acquire the physiological parameter (S9070) may include an operation of determining whether a currently measured heart rate is included in a pre-measured heart rate of the subject and a reference range based on the pre-measured heart rate, but the present invention is not limited thereto.

Also, the operation of performing the operation corresponding to the result (S9080) may include an operation of releasing security when all security release conditions are satisfied and an operation of maintaining security when all security release conditions are not satisfied, but the present invention is not limited thereto.

Also, the security device may perform various operations for reinforcing security using a physiological parameter other than the above-described examples.

9.8 Various Embodiments of Physiological Parameter Measurement Device Used in Kiosk When a physiological parameter measurement device capable of conveniently measuring a physiological parameter is placed in a kiosk for displaying information, it is possible to continuously monitor individual health by conveniently monitoring physiological parameters in everyday life.

Figure 89:
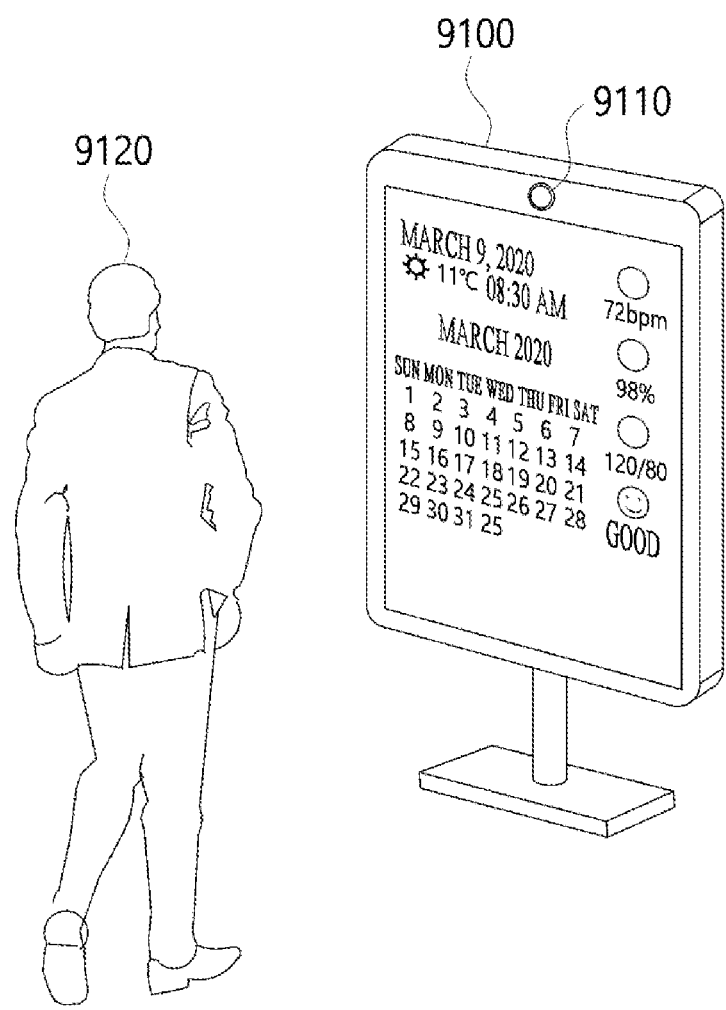
FIG. 89 is a diagram illustrating a physiological parameter measurement device used for a kiosk according to an embodiment.

FIG. 89 is a diagram illustrating a physiological parameter measurement device used for a kiosk according to an embodiment.

Referring to FIG. 89, a physiological parameter measurement device 9110 according to an embodiment may be placed in a kiosk 9100 and configured to measure a physiological parameter of a subject 9120.

In this case, the kiosk 9100 may include a display for displaying at least one piece of information. For example, as shown in FIG. 89, the kiosk 9100 may display date information and weather information, but the present invention is not limited thereto.

Also, the physiological parameter measurement device 9110 may acquire at least one physiological parameter. For example, the physiological parameter measurement device 9110 may acquire a heart rate. However, the present invention is not limited thereto, and the physiological parameter measurement device 9110 may acquire at least one physiological parameter among a heart rate, an oxygen saturation level, a blood pressure, and a core temperature.

Also, the physiological parameter measurement device 9110 may acquire at least one piece of physiological information. For example, the physiological parameter measurement device 9110 may acquire today's condition information. However, the present invention is not limited thereto, and the physiological parameter measurement device 9110 may acquire at least one piece of physiological information among drowsiness information, condition information, concentration information, health information, etc.

Also, the kiosk 9100 may display the acquired physiological parameter. For example, as shown in FIG. 89, the kiosk 9100 may display the acquired heart rate, oxygen saturation level, and blood pressure, but the present invention is not limited thereto.

Also, the kiosk 9100 may display the acquired physiological information. For example, as shown in FIG. 89, the kiosk 9100 may display the acquired today's condition information, but the present invention is not limited thereto.

Also, the kiosk 9100 may transmit the acquired physiological parameter and physiological information. For example, the kiosk 9100 may transmit the acquired physiological parameter and physiological information to a mobile terminal of the subject 9120, but the present invention is not limited thereto.

Also, the kiosk 9100 may transmit the acquired physiological parameter and physiological information. For example, the kiosk 9100 may transmit the acquired physiological parameter and physiological information to a terminal through which an administrator can check the physiological parameter and physiological information, but the present invention is not limited thereto.

Also, in this case, a patient with an abnormal physiological parameter may be detected in a building where the kiosk 9100 is placed, and thus it is possible to reinforce the quarantine and security of the building.

Also, by additionally using a physiological parameter measurement device in a kiosk as described above, individual health may be continuously monitored, and thus it is possible to reinforce the quarantine and security of a building where the kiosk is placed.

Also, the above-described physiological parameter measurement device may be used for human resource management. For example, the physiological parameter measurement device may be used in a kiosk for access of construction site workers to cope with construction site workers with abnormal physiological parameters, but the present invention is not limited thereto.

Figure 90:
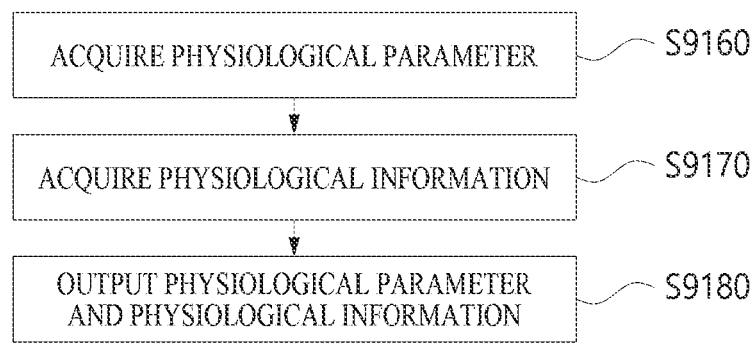
FIG. 90 is a flowchart illustrating a physiological parameter measurement device operating method according to an embodiment.

FIG. 90 is a flowchart illustrating a physiological parameter measurement device operating method according to an embodiment.

Referring to FIG. 90, a physiological parameter measurement device operating method 9150 according to an embodiment may include at least some of an operation of acquiring a physiological parameter (S9160), an operation of acquiring physiological information (S9170), and outputting the physiological parameter and the physiological information (S9180).

In this case, the above-described physiological parameter acquisition method is applicable to the operation of acquiring the physiological parameter (S9160), and thus a redundant description thereof will be omitted.

Also, the above-described physiological information acquisition method is applicable to the operation of acquiring the physiological information (S9170), and thus a redundant description thereof will be omitted.

Also, the operation of outputting the physiological parameter and the physiological information (S9180) may include an operation of displaying the physiological parameter and the physiological information. For example, the operation of outputting the physiological parameter and the physiological information (S9180) may include an operation of displaying a heart rate, an oxygen saturation level, a blood pressure, and today's condition information, but the present invention is not limited thereto.

Also, the operation of outputting the physiological parameter and the physiological information (S9180) may include an operation of transmitting the physiological parameter and the physiological information. For example, the operation of outputting the physiological parameter and the physiological information (S9180) may include an operation of transmitting a heart rate, an oxygen saturation level, a blood pressure, and today's condition information to another mobile terminal, but the present invention is not limited thereto.

Also, the operation of outputting the physiological parameter and the physiological information (S9180) may include an operation of printing the physiological parameter and the physiological information. For example, the operation of outputting the physiological parameter and the physiological information (S9180) may include an operation of printing a heart rate, an oxygen saturation level, a blood pressure, and today's condition information, but the present invention is not limited thereto.

Also, the physiological parameter acquisition device may perform various operations of acquiring and outputting physiological parameters and physiological information other than the above-described examples.

According to an embodiment of the present invention, it is possible to provide a method of acquiring a physiological parameter in a contactless manner.

According to another embodiment of the present invention, it is possible to provide a method of reducing noise caused by subject movement.

According to still another embodiment of the present invention, it is possible to provide a method of reducing noise caused by a change in intensity of external light.

According to still another embodiment of the present invention, it is possible to provide a method of acquiring various physiological parameters at the same time.

According to still another embodiment of the present invention, it is possible to provide a method of acquiring physiological information on the basis of various physiological parameters.

According to still another embodiment of the present invention, it is possible to provide a method of acquiring various physiological parameters in association with each other at the same time.

According to still another embodiment of the present invention, it is possible to provide a smart mirror device configured to acquire at least two associated physiological parameters.

According to still another embodiment of the present invention, it is possible to provide a smart mirror device operating method to acquire at least two associated physiological parameters.

According to still another embodiment of the present invention, it is possible to provide a method and device for detecting drowsiness on the basis of an LF/HF ratio of a heartbeat signal and a heart rate of a subject.

According to still another embodiment of the present invention, it is possible to provide a smart mirror device including a switch device.

The method according to an embodiment may be implemented in the form of program instructions executable by a variety of computer means and may be recorded on a computer-readable medium. The computer-readable medium may include program instructions, data files, data structures, and the like alone or in combination. The program instructions recorded on the medium may be designed and configured specifically for an embodiment or may be publicly known and usable by those who are skilled in the field of computer software. Examples of the computer-readable recording medium include a magnetic medium, such as a hard disk, a floppy disk, and a magnetic tape, an optical medium, such as a compact disc read-only memory (CD-ROM), a digital versatile disc (DVD), etc., a magneto-optical medium such as a floptical disk, and a hardware device specially configured to store and perform program instructions, for example, a read-only memory (ROM), a random access memory (RAM), a flash memory, etc. Examples of the computer instructions include not only machine language code generated by a compiler, but also high-level language code executable by a computer using an interpreter or the like. The hardware device may be configured to operate as one or more software modules in order to perform the operations of an embodiment, and vice versa.

Although the present invention has been described with reference to specific embodiments and drawings, it will be appreciated that various modifications and changes can be made from the disclosure by those skilled in the art. For example, appropriate results may be achieved although the described techniques are performed in an order different from that described above and/or although the described components such as a system, a structure, a device, or a circuit are combined in a manner different from that described above and/or replaced or supplemented by other components or their equivalents.

Therefore, other implementations, embodiments, and equivalents are within the scope of the following claims.

What is claimed is:

1. A method of operating an electronic device for measuring a physiological parameter of a subject in a contactless manner using a camera of the electronic device and one or more processors of the electronic device, the method comprising:

capturing, using the camera, a plurality of image frames for the subject;

defining, by the one or more processors, a first region for at least one image frame included in the plurality of image frames;

defining, by the one or more processors, a pre-set time period for the plurality of image frames;

identifying, by the one or more processors, first difference values by subtracting a red color channel value from a green color channel value for each of a first group of image frames related to the first region and the pre-set time period included in the plurality of image frames, the first difference values indicating a change of an amount of a blood;

obtaining, by the one or more processors, first characteristic values based on a standard deviation of the first difference values;

identifying, by the one or more processors, second difference values by subtracting a blue color channel value from the green color channel value for each of the first group of image frames related to the first region and the pre-set time period included in the plurality of image frames, the second difference values indicating a change of an amount of a blood;

obtaining, by the one or more processors, second characteristic values based on a standard deviation of the second difference values;

obtaining, by the one or more processors, third characteristic values indicating a photoplethysmography (PPG) based on a sum of the first characteristic values and the second characteristic values, for reducing an effect on the first group of image frames by an intensity related to at least one of the blue color channel or the red color channel of an external light source;

obtaining, by the one or more processors, a value of each of a plurality of frequency components about the third characteristic values based on a Fourier transform; and determining, by the one or more processors, a physiological parameter of the subject based on the value of each of the plurality of frequency components; and outputting, by the one or more processors, the physiological parameter, wherein the green color channel value represents average pixel value of a green color channel for the first region of each of the first group of image frames, wherein the red color channel value represents average pixel value of a red color channel for the first region of each of the first group of image frames, and wherein the blue color channel value represents average pixel value of a blue color channel for the first region of each of the first group of image frames.

2. The method of claim 1, wherein the third characteristic values are identified in order to reduce noise in consideration of absorbance of hemoglobin and oxyhemoglobin.

3. The method of claim 1, wherein the first characteristic values and the second characteristic values are normalized values.

4. The method of claim 1, further comprising:

outputting a second physiological parameter based on a second physiological parameter value, wherein the second physiological parameter is a physiological parameter of a same type as the physiological parameter, wherein the second physiological parameter is outputted after the physiological parameter, when a difference between the second physiological parameter value and the physiological parameter exceeds a reference value, the second physiological parameter is amended from the second physiological parameter value.

5. A non-transitory recording medium having a program recorded thereon for executing the method of claim 1.

6. A method of operating an electronic device for measuring a physiological parameter of a subject in a contactless manner, the method comprising:
receiving a plurality of image frames for the subject through a communication circuit, from an external electronic device;
defining, by one or more processors of the electronic device, a first region for at least one image frame included in the plurality of image frames;
defining, by the one or more processors, a pre-set time period for the plurality of image frames;
identifying, by the one or more processors, first difference values by subtracting a red color channel value from a green color channel value for each of a first group of image frames related to the first region and the pre-set time period included in the plurality of image frames, the first difference values indicating a change of an amount of a blood, and identifying first characteristic values based on a standard deviation of the first difference values;
identifying, by the one or more processors, second difference values by subtracting a blue color channel value from the green color channel value for each of the first group of image frames related to the first region and the pre-set time period included in the plurality of image frames, the second difference values indicating a change of an amount of a blood, and identifying second characteristic values based on a standard deviation of the second difference values;
identifying, by the one or more processors, third characteristic values related to a photoplethysmography (PPG) based on a sum of the first characteristic values and the second characteristic values, for reducing an effect on the first group of image frames by an intensity related to at least one of the blue color channel or the red color channel of an external light source;
obtaining, by the one or more processors, a value of each of a plurality of frequency components about the third characteristic values based on a Fourier transform;
determining, by the one or more processors, a physiological parameter of the subject based on the third characteristic values related to the first group of image frames included in the plurality of image frames value of each of the plurality of frequency components, and
outputting, by the one or more processors, the physiological parameter,
wherein the green color channel value represents average pixel value of a green color channel for the first region of each of the first group of image frames,
wherein the red color channel value represents average pixel value of a red color channel for the first region of each of the first group of image frames, and
wherein the blue color channel value represents average pixel value of a blue color channel for the first region of each of the first group of image frames.

7. The method of claim 6, wherein the first characteristic values and the second characteristic values are normalized values.

8. A non-transitory recording medium having a program recorded thereon for executing the method of claim 6.

9. The method of claim 1, further comprising extracting a portion of the third characteristic values corresponding to a specific wavelength range using a filter, wherein the specific wavelength range is determined based on a heart rate related to the subject.

10. The method of claim 9, further comprising identifying at least one highest value among the value of each of the plurality of frequency components, wherein the physiological parameter of the subject is determined based on the at least one highest value.

11. The method of claim 6, further comprising extracting a portion of the third characteristic values corresponding to a specific wavelength range using a filter, wherein the specific wavelength range is determined based on a heart rate related to the subject.

12. The method of claim 11, further comprising identifying at least one highest value among the value of each of the plurality of frequency components, wherein the physiological parameter of the subject is determined based on the at least one highest value.

* * * * *